US012807591B2

(12) United States Patent
Day et al.

(10) Patent No.: US 12,807,591 B2
(45) Date of Patent: Nov. 24, 2026

(54) SODIUM CHANNEL BLOCKERS

(71) Applicant: NOVARTIS AG, Basel (CH)

(72) Inventors: Robert Francis Day, Acton, MA (US); Michael Dore, St-Bruno-de-Montarville (CA); Adam Friedman, Cambridge, MA (US); Christian Michael Gampe, South San Francisco, CA (US); Xiang Gao, Cambridge, MA (US); Hatice Belgin Gulgeze Efthymiou, Cambridge, MA (US); Tyler Harrison, Burnaby (CA); Jay Francis Larrow, Wakefield, MA (US); Yunshan Peng, Arlington, MA (US); Nichola Smith, Burlington, MA (US)

(73) Assignee: NOVARTIS AG, Basel (CH)

( * ) Notice: Subject to any disclaimer, the term of this patent is extended or adjusted under 35 U.S.C. 154(b) by 285 days.

(21) Appl. No.: 18/764,471

(22) Filed: Jul. 5, 2024

(65) Prior Publication Data

US 2025/0034108 A1 Jan. 30, 2025

(30) Foreign Application Priority Data

Jul. 7, 2023 (WO) ................ PCT/CN2023/106400

(51) Int. Cl.

| | |
|---|---|
| ***C07D 401/04*** | (2006.01) |
| ***A61K 31/41*** | (2006.01) |
| ***A61K 31/4439*** | (2006.01) |
| ***C07D 257/04*** | (2006.01) |

(52) U.S. Cl.

CPC ............ *C07D 401/04* (2013.01); *A61K 31/41* (2013.01); *A61K 31/4439* (2013.01); *C07D 257/04* (2013.01)

(58) Field of Classification Search

CPC .... C07D 401/04; C07D 257/04; A61K 31/41; A61K 31/4439

See application file for complete search history.

(56) References Cited

U.S. PATENT DOCUMENTS

2013/0303526 A1 11/2013 Ni et al.

FOREIGN PATENT DOCUMENTS

| | | | |
|---|---|---|---|
| CN | 104024251 | A | 9/2014 |
| CN | 109526219 | A | 3/2019 |
| CN | 110325531 | A | 10/2019 |
| CN | 110885319 | A | 3/2020 |
| CN | 112368274 | A | 2/2021 |
| CN | 112638879 | A | 4/2021 |
| CN | 112638898 | A | 4/2021 |
| WO | 03029210 | A2 | 4/2003 |
| WO | 03077918 | A1 | 9/2003 |
| WO | 2004083189 | A1 | 9/2004 |
| WO | 2004089306 | A2 | 10/2004 |
| WO | 2004094395 | A2 | 11/2004 |
| WO | 2005020982 | A2 | 3/2005 |
| WO | 2007021941 | A2 | 2/2007 |
| WO | 2011053977 | A1 | 5/2011 |
| WO | 2013006596 | A1 | 1/2013 |
| WO | 2013131018 | A1 | 9/2013 |
| WO | 2015130905 | A1 | 9/2015 |
| WO | 2022226349 | A1 | 10/2022 |
| WO | 2023034946 | A1 | 3/2023 |

*Primary Examiner* — Kamal A Saeed
(74) *Attorney, Agent, or Firm* — Joohee Lee

(57) ABSTRACT

The present disclosure relates to sulfonamide compounds, the use thereof for modulating the sodium channel Nav1.5 and methods of treating or preventing diseases, disorders, or conditions using the same.

19 Claims, 9 Drawing Sheets

SODIUM CHANNEL BLOCKERS

CROSS-REFERENCE TO RELATED APPLICATIONS

The present application claims priority and benefit to the International Patent Application PCT/CN2023/106400 filed Jul. 7, 2023, the disclosure of which is incorporated herein by reference in its entirety.

TECHNICAL FIELD

The present disclosure relates to sulfonamide compounds, the use thereof for modulating activity of the sodium channel Nav1.5 and methods of treating disease using the same.

BACKGROUND

Cardiac arrhythmia is an abnormal heart rhythm and occurs when the normal sequence of electrical impulses in the heart changes. Atrial fibrillation (AF) is one type of arrhythmia, and can lead to stroke, heart failure and sudden cardiac death.

A normal cardiac cycle begins in the sino-atrial node, which produces an excitatory electrical stimulus that propagates in an orderly fashion throughout the atrial and ventricular myocardium to induce a contraction (systole). At the cellular level, the excitatory electrical impulse triggers the cardiac action potential. This is characterized by an initial, rapid membrane depolarization followed by a plateau phase and subsequent repolarization to return to resting membrane potential. The cardiac action potential governs signal propagation throughout the heart. For example, the rate of initial cellular depolarization determines the velocity at which excitatory stimuli propagate. The duration of the repolarization phase determines the action potential duration (APD) and the effective refractory period (ERP), or time in which a cardiomyocyte cannot respond to another electrical stimulus. Abnormalities in the cardiac action potential are associated with arrhythmia. For example, excessive reduction of action potential duration and the accompanying, shorter refractory period can provide a substrate for so-called re-entrant tachyarrhythmia. In this condition, instead of propagating normally, a cardiac impulse feeds back upon itself via excitable tissue to form a re-entrant circuit (Waldo and Wit, 1993, Mechanism of cardiac arrhythmias, Lancet 347, 1189-1193). When a trigger occurs in the atria with a re-entrant substrate, it can cause uncoordinated, fast, and often chaotic atrial contraction and manifests as atrial fibrillation (AF). The repetitive or lasting rapid activation can lead to electrical and structural remodeling that further abbreviates atrial APD/ERP to sustain the duration of AF and worsen the disease prognosis (also called as "AF begets AF") (Nattel S., Atrial electrophysiology and mechanisms of atrial fibrillation, Journal of Cardiovascular Pharmacology and Therapeutics, 2003, 8 (Suppl. 1), S5-S11).

One of the clinical strategies for rhythm control is prolonging the ERP. This approach increases the excitation threshold of atrial tissues and reduces the likelihood of a premature atrial beat, which can render the development or maintenance of AF harder or impossible (Antzelevitch C, Burashnikov A, Atrial-selective sodium channel block as a novel strategy for the management of atrial fibrillation, Ann N Y Acad Sci., 2010, 1188, 78-86). Two major rhythm control drug classes exist, termed Class III & I. Dofetilide, sotalol and ibutilide are Class III drugs and primarily target the human ether-a-go-go related gene potassium channels (hERG) involved in cardiac repolarization. hERG blockade prolongs atrial ERP (aERP) against AF by increasing atrial APD. Those drugs also affect ventricular hERG and can cause excessive prolongation of ventricular repolarization—so-called QT prolongation—and predispose to ventricular arrhythmias. Hence, in-hospital initiation of Class III drugs is mandated to mitigate excessive QT prolongation and prevent serious arrhythmia called Torsades de Pointes. Class Ic drugs are primarily sodium channel blockers and can prolong aERP by reducing excitability and promoting post-repolarization refractoriness (PRR) against AF. Flecainide, pilsicainide and propafenone belong to this class. Those drugs were originally developed for ventricular arrhythmias and can slow down ventricular conduction significantly via Nav1.5 blockade as manifested as QRS prolongation on the electrocardiogram (ECG) (Antzelevitch C. and Burashnikov A., cited hereinabove). QRS prolongation or ventricular conduction slowing has been associated with excess of deaths due to arrhythmia in myocardial infarction (MI) patients in the Cardiac Arrhythmia Suppression Trial (CAST) (Echt D S, Liebson P R, Mitchell L B, Peters R W, Obias-Manno D, Barker A H, Arensberg D, Baker A, Friedman L, Greene H L, et al. Mortality and morbidity in patients receiving encainide, flecainide, or placebo. The Cardiac Arrhythmia Suppression Trial, New England Journal of Medicine, 1991, 324(12), 781-788). As a result, QRS-prolonging Class I drugs are contraindicated for AF in the setting of structural heart disease, e.g., MI & heart failure.

The cardiac voltage-sensitive sodium channel (Nav1.5) is one of the ion-conducting membrane proteins, collectively known as ion channels, and is responsible for action potential initiation and electrical excitation in cardiac tissue. The SCN5A gene, located in the short (p) arm of chromosome 3 at position 22.2, encodes Nav1.5 protein (also often referred to as a subunit of Nav1.5), expressed predominantly in cardiac myocytes and in specialized conducting cells called Purkinje fibers. Nav1.5 consists of four homologous but non-identical domains (Domain I-IV), and each domain contains six segments (or a helices; S1-S6). The S1-S4 is the voltage-sensing domain (VSD) where the S4 functions as the voltage sensor that consists of positively charged arginine and lysine repeats and translocates across the lipid bilayer based on the state of the membrane potential. Depolarization (a positive change in the cellular membrane potential, VM) can displace the VSD and open Nav1.5, allowing sodium current to flow into a cell to further depolarize the membrane potential. When prolonged depolarization persists, Nav1.5 enters a distinct, non-conducting state called inactivation. Hyperpolarization (a negative change in the cellular membrane potential or diastolic potential) keeps Nav1.5 in the closed state and also facilitates channel recovery from the inactivation that occurs during systole (the period during cardiac contraction). There are different genes encoding non-pore forming subunits, collectively known as auxiliary R subunits, which can bind to Nav1.5 and modulate its trafficking and function (Yang, N. & Horn, R. Evidence for voltage-dependent S4 movement in sodium channels, Neuron, 1995, 15(1), 213-218; Ulbricht, W. Sodium Channel Inactivation: Molecular Determinants and Modulation, Physiol. Rev., 2005, 85(4), 1271-1301; Yarov-Yarovoy, V. et al. Structural basis for gating charge movement in the voltage sensor of a sodium channel, Proc. Natl. Acad. Sci., 2011, 109, E93-E102).

The sodium current associated with the slow inactivating component of Nav1.5 has been referred to as late or persistent $Na^+$ current (INa,late). An enhanced INa,late was shown to play an important pathophysiological role in cardiac conditions (Zaza, A., Pathophysiology and pharmacology of the cardiac "late sodium current", Pharmacol. Ther., 2008, 119(3), 326-339). Genetics also influences the level of INa,late. The defects in the inactivation of Nav1.5 can cause channels to stay open for an abnormal long period of time and elevate late $Na^+$ current. As a result, pathological late $Na^+$ current increases APD in the ventricles and manifests as a long QT (LQT) (or prolonged ventricular repolarization on an ECG) interval in affected individuals. The pathology is called long QT3 (LQT3) syndrome (abbreviated as LQTS in general, and LQTS3 in particular) and can predispose to dangerous arrhythmia called ventricular tachyarrhythmia or fibrillation. Both Class Ic and Class Ib Nav1.5 blockers (one example is mexiletine; Nav1.5 blocker) can inhibit pathological late $Na^+$ current in LQT3, thereby reducing the QT interval and ventricular arrhythmia risk. Recent clinical studies also have shown the benefit of Nav1.5 blockers in other LQT syndromes (LQTS) (caused by other genetic defects, e.g., KCNQ—LQTS1 & KCNH2—LQTS2) because reducing "endogenous" late $Na^+$ current decreases the QT interval and mitigates excessive QT intervals in high-risk patients for ventricular arrhythmias (Bos J M, Crotti L, Rohatgi R K, Castelletti S, Dagradi F, Schwartz P J, Ackerman M J. Mexiletine Shortens the QT Interval in Patients With Potassium Channel-Mediated Type 2 Long QT Syndrome, Circ. Arrhythm. Electrophysiol., 2019, 12(5)).

As reported by Antzelevitch C. and Burashnikov A., cited hereinabove, there has been new development towards making safer anti-AF drugs by avoiding ventricular side effects. One direction is to develop "atrial-selective" sodium channel blockers to enable a safer treatment in structural heart disease patients. Key biophysical properties of the sodium channel and cell type-associated electrophysiological properties have been found to confer atrial-selective peak Nav1.5 current blockade at high fibrillation rate mimicking AF. (1) Atrial-selective sodium channel blockers need to have been observed to have faster binding and unbinding rate than slow-unbinding Class Ic drugs. This property is essential to minimize or avoid inhibiting peak Nav1.5 current in the ventricles at sinus rate, thus mitigating QRS prolongation. (2) The fraction of inactivated sodium channels is greater in atrial myocytes because of a more negative inactivation curve or negative half-inactivation voltage. On average, the Nav1.5 inactivation curve is 7-14 mV more negative in atrial myocytes than in ventricular myocytes. (3) Atrial myocytes have more depolarized resting membrane potential (RMP), thus further reducing the availability of sodium channels and potentiating the effect of sodium channel blockers. (4) Recovery rate from inactivation of the sodium channel has been observed to be slower in atrial myocytes. Because Nav1.5 blockers unbind more slowly from the inactivated state than from the open state, properties (2) and (3) increase the population of the inactivated channels and render Nav1.5 blockade stronger in atrial myocytes than in ventricular myocytes.

Although blockers of Nav1.5 have been used extensively in treating cardiac arrhythmias (Srivatsa, U. et al., Mechanisms of antiarrhythmic drug actions and their clinical relevance for controlling disorders of cardiac rhythm, Current Cardiology Reports, 2002, 4(5), 401-410; Remme, C. A. and Bezzina, C. R., Sodium Channel (Dys)Function and Cardiac Arrhythmias, Cardiovascular Therapeutics, 2010, 28(5), 287-294; Roden, D. M., Pharmacology and Toxicology of Nav1.5-Class 1 anti-arrhythmic drugs, Card. Electrophysiol. Clin., 2014, 6(4), 695-704)), effective and safe treatment of atrial fibrillation (AF) remains a major unmet medical need. As such, there is a need for novel atrial-selective Nav1.5 blockers that can offer both efficacy and safety for the treatment of AF.

SUMMARY

There remains a need for new treatments and therapies for atrial fibrillation. This disclosure provides, inter alia, compounds, which compounds are modulators of the voltage-sensitive sodium channel Nav1.5, or pharmaceutically acceptable salts thereof.

Also, the disclosure provides crystalline forms of the compounds as described herein, including, in particular, co-crystalline form (e.g., proline co-crystalline). Further provided are pharmaceutical compositions including the compounds as described herein, and combinations including the compounds as described herein with one or more of therapeutically active agents. The disclosure further provides methods of treating, preventing, or ameliorating atrial fibrillation, and the methods include administering to a subject in need thereof an effective amount of the compounds, or pharmaceutically acceptable salts thereof as described herein.

In an aspect, provided herein is a compound having a structure of formula (I):

(I)

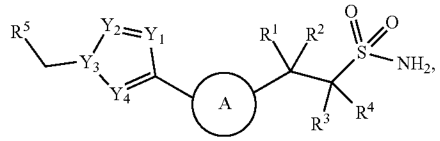

or a pharmaceutically acceptable salt thereof, wherein:

ring A is:

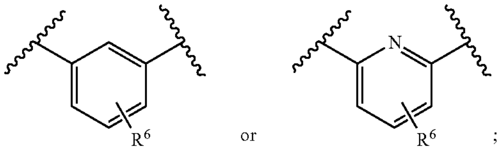

or

;

$R^1$ is selected from —OH and $C_{1-4}$-alkyl;

$R^2$ is selected from H and $C_{1-4}$-alkyl optionally substituted with one or more halogen atoms;

$R^3$ is selected from H and $C_{1-4}$-alkyl;

$R^4$ is selected from H and $C_{1-4}$-alkyl optionally substituted with —OH;

$R^5$ is phenyl substituted with (i) at least one group selected from halogen, $C_{1-4}$-alkyl, —O—$C_{1-4}$-alkyl, and O—$C_{3-6}$-cycloalkyl, wherein the $C_{1-4}$-alkyl is optionally substituted with one or more halogen atoms, or (ii) two adjacent groups bonded together to form a 4- to 7-membered heterocyclyl containing two or more heteroatoms selected from O, S and N, wherein the 4- to 7-membered heterocyclyl is optionally substituted with one or more halogen atoms;

$R^6$ is H or a halogen atom;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

In some embodiments, $R^1$ is selected from —OH, —$CH_3$ and —$CH_2CH_3$.

In some embodiments, $R^2$ is selected from H and $C_{1-4}$-alkyl optionally substituted with one or more halogen atoms selected from fluorine (F) and chlorine (Cl), preferably F.

In some embodiments, $R^3$ is selected from H, —$CH_3$ and —$CH_2CH_3$.

In some embodiments, $R^4$ is selected from H, —$CH_3$, —$CH_2CH_3$ and —$CH_2OH$.

In some embodiments, in the compound of formula (I) of the present disclosure ring A is:

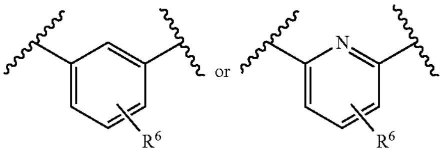

$R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

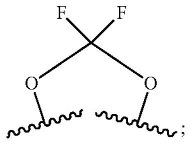 [SMILES: *OC(F)(F)O*]

$R^6$ is selected from H, F and Cl;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

In another aspect, this disclosure provides a crystalline form of a compound of the present disclosure or a pharmaceutically acceptable salt thereof.

In another aspect, this disclosure provides a pharmaceutical composition comprising a compound of the present disclosure, or a pharmaceutically acceptable salt thereof, and one or more pharmaceutically acceptable carriers.

In another aspect, this disclosure provides a combination, in particular a pharmaceutical combination, comprising a compound of the present disclosure, or a pharmaceutically acceptable salt thereof, and one or more therapeutically active agents.

DETAILED DESCRIPTION

Compounds

Figure 1:
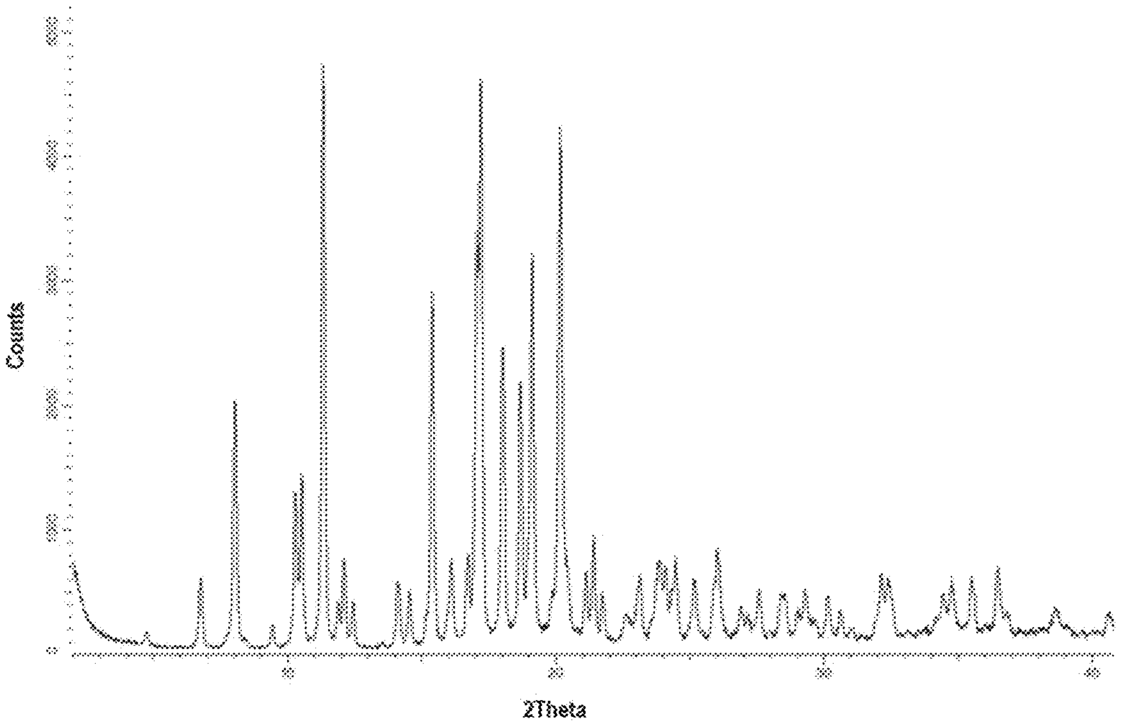
FIG. 1 shows the X-ray powder diffraction pattern of Modification A-1.

Provided herein, inter alia, sulfonamide compounds that can modulate or inhibit activity of the sodium channel Nav1.5.

In an aspect, the disclosure provides a compound having a structure of formula (I):

(I)

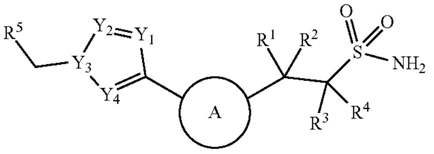

or a pharmaceutically acceptable salt thereof, wherein ring A is:

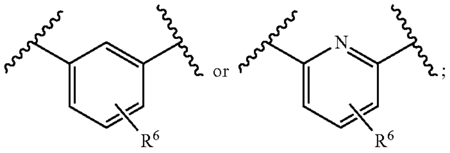

$R^1$ is selected from —OH and $C_{1-4}$-alkyl;

$R^2$ is selected from H and $C_{1-4}$-alkyl optionally substituted with one or more halogen atoms;

$R^3$ is selected from H and $C_{1-4}$-alkyl;

$R^4$ is selected from H and $C_{1-4}$-alkyl optionally substituted with —OH;

$R^5$ is phenyl substituted with (i) at least one group selected from halogen, $C_{1-4}$-alkyl, —O—$C_{1-4}$-alkyl, and O—$C_{3-6}$-cycloalkyl, wherein the $C_{1-4}$-alkyl is optionally substituted with one or more halogen atoms, or (ii) two adjacent groups bonded together to form a 4- to 7-membered heterocyclyl containing two or more heteroatoms selected from O, S and N, wherein the 4- to 7-membered heterocyclyl is optionally substituted with one or more halogen atoms;

$R^6$ is H or a halogen atom;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

In some embodiments, $R^1$ is —OH. In some embodiments, $R^1$ is $C_{1-4}$-alkyl. In some embodiments, $R^1$ is —$CH_3$. In some embodiments, $R^1$ is —$CH_2CH_3$. In some embodiments, $R^1$ is —$CH_2CH_2CH_3$. In some embodiments, $R^1$ is isopropyl. In some embodiments, $R^1$ is butyl. In some embodiments, $R^1$ is t-butyl.

In some embodiments, $R^2$ is —H. In some embodiments, $R^2$ is $C_{1-4}$-alkyl. In some embodiments, $R^2$ is —$CH_3$. In some embodiments, $R^2$ is —$CH_2CH_3$. In some embodiments, $R^2$ is —$CH_2CH_2CH_3$. In some embodiments, $R^2$ is isopropyl. In some embodiments, $R^2$ is $C_{1-4}$-haloalkyl. In some embodiments, $R^2$ is —$CH_2F$. In some embodiments, $R^2$ is —$CHF_2$. In some embodiments, $R^2$ is —$CF_3$.

In some embodiments, $R^3$ is —H. In some embodiments, $R^3$ is $C_{1-4}$-alkyl. In some embodiments, $R^3$ is —$CH_3$. In some embodiments, $R^3$ is —$CH_2CH_3$. In some embodiments, $R^3$ is —$CH_2CH_2CH_3$. In some embodiments, $R^3$ is isopropyl. In some embodiments, $R^3$ is butyl. In some embodiments, $R^3$ is t-butyl.

In some embodiments, $R^4$ is —H. In some embodiments, $R^4$ is $C_{1-4}$-alkyl. In some embodiments, $R^4$ is —$CH_3$. In some embodiments, $R^4$ is —$CH_2CH_3$. In some embodiments, $R^4$ is —$CH_2CH_2CH_3$. In some embodiments, $R^4$ is isopropyl. In some embodiments, $R^4$ is butyl. In some embodiments, $R^4$ is t-butyl. In some embodiments, $R^4$ is —$CH_2OH$. In some embodiments, $R^4$ is —$CH_2CH_2OH$. In some embodiments, $R^4$ is —$CHOHCH_3$. In some embodiments, $R^4$ is —$CH_2CH_2CH_2OH$.

In some embodiments, $R^5$ is a phenyl substituted with halogen (e.g., F, Cl, or Br). In some embodiments, $R^5$ is a phenyl substituted with —F. In some embodiments, $R^5$ is a phenyl substituted with —Cl. In some embodiments, $R^5$ is a phenyl substituted with —Br.

In some embodiments, $R^5$ is a phenyl substituted with $C_{1-4}$-alkyl. In some embodiments, $R^5$ is a phenyl substituted with —$CH_3$. In some embodiments, $R^5$ is a phenyl substituted with —$CH_2CH_3$. In some embodiments, $R^5$ is a phenyl substituted with —$CH(CH_3)_2$.

In some embodiments, $R^5$ is a phenyl substituted with —O—$C_{1-4}$-alkyl. In some embodiments, $R^5$ is a phenyl substituted with —$OCH_3$. In some embodiments, $R^5$ is a phenyl substituted with —$OCH_2CH_3$. In some embodiments, $R^5$ is a phenyl substituted with —$OCH(CH_3)_2$.

In some embodiments, the $C_{1-4}$-alkyl is optionally substituted with one or more halogen (e.g., F, Cl, or Br) atoms. In some embodiments, $R^5$ is a phenyl substituted with —$OCF_3$. In some embodiments, $R^5$ is a phenyl substituted with —$OCHF_2$. In some embodiments, $R^5$ is a phenyl substituted with —$OCH_2F$.

In some embodiments, $R^5$ is a phenyl substituted with O—$C_{3-6}$-cycloalkyl. In some embodiments, $R^5$ is a phenyl substituted with O-cyclopropyl. In some embodiments, $R^5$ is a phenyl substituted with O-cyclobutyl. In some embodiments, $R^5$ is a phenyl substituted with O-cyclopentyl. In some embodiments, $R^5$ is a phenyl substituted with O-cyclohexyl.

In some embodiments, $R^5$ is a phenyl substituted with at least one group selected from —F, —Cl, —Br, —$CH_3$, —$CH_2CH_3$, —$CH(CH_3)_2$, —$OCH_3$, —$CF_3$, —$OCF_3$, —$OCHF_2$, —$OCH_2F$, —$OCH_2CF_3$, and —O-cyclopropyl. In some embodiments, $R^5$ is a phenyl substituted with at least two groups selected from —F, —Cl, —Br, —$CH_3$, —$CH_2CH_3$, —$CH(CH_3)_2$, —$OCH_3$, —$CF_3$, —$OCF_3$, —$OCHF_2$, —$OCH_2F$, —$OCH_2CF_3$, and —O-cyclopropyl. In some embodiments, $R^5$ is a phenyl substituted with at least three groups selected from —F, —Cl, —Br, —$CH_3$, —$CH_2CH_3$, —$CH(CH_3)_2$, —$OCH_3$, —$CF_3$, —$OCF_3$, —$OCHF_2$, —$OCH_2F$, —$OCH_2CF_3$, and —O-cyclopropyl. In some embodiments, $R^5$ is a phenyl substituted with at least four group selected from —F, —Cl, —Br, —$CH_3$, —$CH_2CH_3$, —$CH(CH_3)_2$, —$OCH_3$, —$CF_3$, —$OCF_3$, —$OCHF_2$, —$OCH_2F$, —$OCH_2CF_3$, and —O-cyclopropyl.

In some embodiments, $R^5$ is a phenyl substituted with at least two group selected from —F, —Cl, —Br, —$CH_3$, —$CH_2CH_3$, —$CH(CH_3)_2$, —$OCH_3$, —$CF_3$, —$OCF_3$, —$OCH_2CF_3$, and —O-cyclopropyl. In some embodiments, $R^5$ is a phenyl substituted with at least three group selected from —F, —Cl, —$CH_3$, —$CF_3$, —$OCF_3$, —$OCH_2CF_3$, and —O-cyclopropyl.

In some embodiments, $R^5$ is a phenyl substituted with two adjacent groups bonded together to form a 4-membered heterocyclyl containing two or more heteroatoms selected from O, S and N. In some embodiments, $R^5$ is a phenyl substituted with two adjacent groups bonded together to form a 5-membered heterocyclyl containing two or more heteroatoms selected from O, S and N. In some embodiments, $R^5$ is a phenyl substituted with two adjacent groups bonded together to form a 6-membered heterocyclyl containing two or more heteroatoms selected from O, S and N. In some embodiments, $R^5$ is a phenyl substituted with two adjacent groups bonded together to form a 7-membered heterocyclyl containing two or more heteroatoms selected from O, S and N.

In some embodiments, the 4 to 7 membered heterocyclyl containing two or more heteroatoms selected from O, S and N are unsubstituted. In some embodiments, the 4 to 7 membered heterocyclyl containing two or more heteroatoms selected from O, S and N are substituted with one or more of halogen atoms. In some embodiments, the 4 to 7 membered heterocyclyl containing two or more heteroatoms selected from O, S and N are substituted with one or more of halogen (e.g., —F, —Cl, or —Br) atoms. In some embodiments, the 4 to 7 membered heterocyclyl containing two or more heteroatoms selected from O, S and N are substituted with at least one F. In some embodiments, the 4 to 7 membered heterocyclyl containing two or more heteroatoms selected from O, S and N are substituted with at least one Br. In some embodiments, the 4 to 7 membered heterocyclyl containing two or more heteroatoms selected from O, S and N are substituted with at least one Cl.

In some embodiments, $R^5$ is a phenyl substituted with two adjacent groups bonded together to form

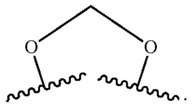 [SMILES: *OCO*]

In some embodiments, $R^5$ is a phenyl substituted with two adjacent groups bonded together to form

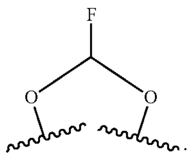 [SMILES: *OC(F)O*]

In some embodiments, $R^5$ is a phenyl substituted with two adjacent groups bonded together to form

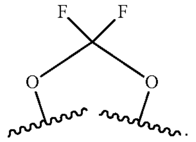 [SMILES: *OC(F)(F)O*]

In some embodiments, $R^6$ is —H. In some embodiments, $R^6$ is a halogen (e.g., —F, —Cl, or —Br). In some embodiments, $R^6$ is —F. In some embodiments, $R^6$ is Cl.

In some embodiments, ring A is

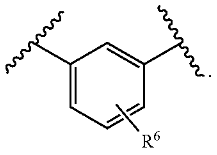

In some embodiments, ring A is

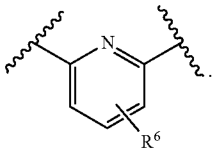

In certain aspect, the disclosure provides a compound having a structure of formula (I-A):

(I-A)

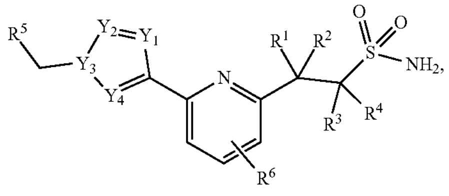

or a pharmaceutically acceptable salt thereof. $R^1$, $R^2$, $R^3$, $R^4$, $R^5$, $R^6$, $Y^1$, $Y^3$, and $Y^4$ are as describe above.

In certain aspect, the disclosure provides a compound having a structure of formula (I-B):

(I-B)

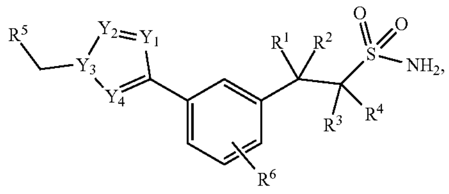

or a pharmaceutically acceptable salt thereof. $R^1$, $R^2$, $R^3$, $R^4$, $R^5$, $R^6$, $Y^1$, $Y^2$, $Y^3$, and $Y^4$ are as describe above.

In some embodiments, $R^6$ is H.

In certain aspect, the disclosure provides a compound having a structure of formula (II-A):

(II-A)

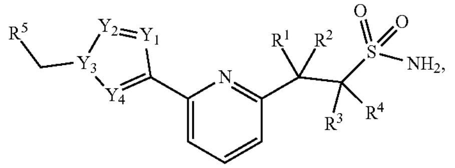

or a pharmaceutically acceptable salt thereof. $R^1$, $R^2$, $R^3$, $R^4$, $R^5$, $Y^1$, $Y^2$, $Y^3$, and $Y^4$ are as describe above.

In certain aspect, the disclosure provides a compound having a structure of formula (II-B).

(II-B)

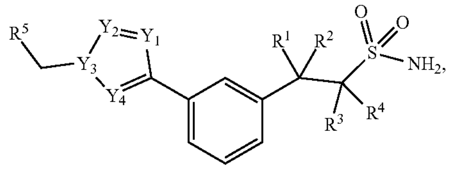

or a pharmaceutically acceptable salt thereof. $R^1$, $R^2$, $R^3$, $R^4$, $R^5$, $Y^1$, $Y^2$, $Y^3$, and $Y_4$ are as describe above.

In some embodiments, each of $Y_1$, $Y_2$, $Y_3$ and $Y_4$ are N. In some embodiments, $Y_2$ is CH and each of $Y_1$, $Y_3$ and $Y_4$ are N. In some embodiments, each of $Y_1$ and $Y_2$ are CH and each of $Y_3$ and $Y_4$ are N.

In certain aspect, the disclosure provides a compound having a structure of formula (III-A):

(III-A)

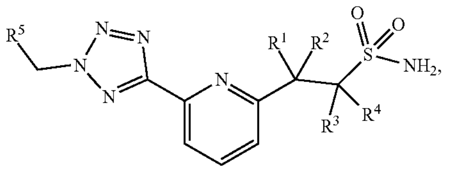

or a pharmaceutically acceptable salt thereof. $R^1$, $R^2$, $R^3$, $R^4$, and $R^5$ are as describe above.

In certain aspect, the disclosure provides a compound having a structure of formula (III-B):

(III-B)

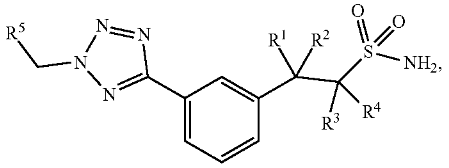

or a pharmaceutically acceptable salt thereof. $R^1$, $R^2$, $R^3$, $R^4$, and $R^5$ are as describe above.

In some embodiments, $R^1$ is —OH. In some embodiments, $R^2$ is H. In some embodiments, $R^2$ is —$CH_3$. In some embodiments, $R^2$ is —$CH_2CH_3$. In some embodiments, $R^2$ is —$CF_3$.

In some embodiments, $R^1$ is —OH and $R^2$ is H. In some embodiments, $R^1$ is —OH and $R^2$ is —$CH_3$. In some embodiments, $R^1$ is —OH and $R^2$ is —$CH_2CH_3$. In some embodiments, $R^1$ is —OH and $R^2$ is —$CF_3$.

In some embodiments, $R^1$ is —$CH_3$. In some embodiments, $R^2$ is H. In some embodiments, $R^2$ is —$CH_3$. In some embodiments, $R^2$ is —$CH_2CH_3$. In some embodiments, $R^2$ is —$CF_3$.

In some embodiments, $R^1$ is —$CH_3$ and $R^2$ is H. In some embodiments, $R^1$ is —$CH_3$ and $R^2$ is —$CH_3$. In some embodiments, $R^1$ is —$CH_3$ and $R^2$ is —$CH_2CH_3$. In some embodiments, $R^1$ is —$CH_3$ and $R^2$ is —$CF_3$.

In some embodiments, $R^3$ is H. In some embodiments, $R^4$ is H. In some embodiments, $R^4$ is —$CH_3$. In some embodiments, $R^4$ is —$CH_2CH_2OH$. In some embodiments, $R^3$ is H and $R^4$ is H. In some embodiments, $R^3$ is H and $R^4$ is —$CH_3$. In some embodiments, $R^3$ is H and $R^4$ is —$CH_2CH_2OH$.

In some embodiments, $R^3$ is —$CH_3$. In some embodiments, $R^4$ is H. In some embodiments, $R^4$ is —$CH_3$. In some embodiments, $R^3$ is —$CH_3$ and $R^4$ is H. In some embodiments, $R^3$ is —$CH_3$ and $R^4$ is —$CH_3$. In some embodiments, $R^3$ is H and $R^4$ is —$CH_2CH_2OH$.

In some embodiments, $R^1$ is —OH or —$CH_3$; $R^2$ is H, —$CH_3$, or —$CH_2CH_3$; $R^3$ is —H, or —$CH_3$; and $R^4$ is —H, —$CH_3$, or —$CH_2CH_2OH$. In some embodiments, $R^1$ is —OH; $R^2$ is —$CH_3$; $R^3$ is —H; and $R^4$ is —H.

In some embodiments, $R^5$ is a phenyl substituted with —F. In some embodiments, $R^5$ is a phenyl substituted with —Cl. In some embodiments, $R^5$ is a phenyl substituted with —Br. In some embodiments, $R^5$ is a phenyl substituted with $C_1$-$C_4$ alkyl, and the $C_{1-4}$-alkyl is optionally substituted with one or more halogen atoms. In some embodiments, $R^5$ is a phenyl substituted with —$CH_3$. In some embodiments, $R^5$ is a phenyl substituted with —$CH_2CH_3$. In some embodiments, $R^5$ is a phenyl substituted with —$CH(CH_3)_2$. In some embodiments, $R^5$ is a phenyl substituted with —$CF_3$. In some embodiments, $R^5$ is a phenyl substituted with —$CHF_2$. In some embodiments, $R^5$ is a phenyl substituted with —$CH_2F$. In some embodiments, $R^5$ is a phenyl substituted with —O—$C_{1-4}$-alkyl, and the $C_{1-4}$-alkyl is optionally substituted with one or more halogen atoms. In some embodiments, $R^5$ is a phenyl substituted with —$OCH_3$. In some embodiments, $R^5$ is a phenyl substituted with —$OCHF_2$. In some embodiments, $R^5$ is a phenyl substituted with —$OCF_3$. In some embodiments, $R^5$ is a phenyl substituted with —$OCH_2CF_3$. In some embodiments, $R^5$ is a phenyl substituted with —O-cyclopropyl. In some embodiments, $R^5$ is a phenyl substituted with at least one selected from —F, —Cl, —Br, —$CH_3$, —$CH_2CH_3$, —$CH(CH_3)_2$, —$CF_3$, —$OCH_3$, —$OCHF_2$, —$OCF_3$, —$OCH_2CF_3$ and —O-cyclopropyl. In some embodiments, $R^5$ is a phenyl substituted with at least two selected from —F, —Cl, —Br, —$CH_3$, —$CH_2CH_3$, —$CH(CH_3)_2$, —$CF_3$, —$OCH_3$, —$OCHF_2$, —$OCF_3$, —$OCH_2CF_3$ and —O-cyclopropyl. In some embodiments, $R^5$ is a phenyl substituted with at least one selected from —F, —Cl, —$CF_3$, —$OCF_3$ and —$OCH_2CF_3$. In some embodiments, $R^5$ is a phenyl substituted with at least two selected from —F, —Cl, —$CF_3$, —$OCF_3$ and —$OCH_2CF_3$.

In some embodiments, $R^5$ is

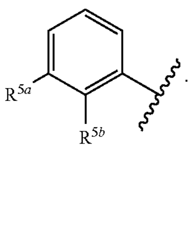

In some embodiments, $R^5$ is

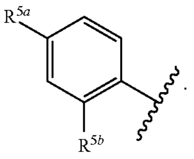

In some embodiments, $R^5$ is

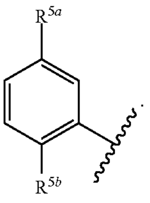

In some embodiments, $R^5$ is

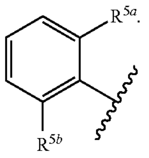

In some embodiments, $R^5$ is

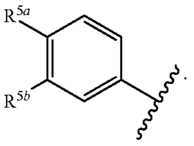

In some embodiments, $R^5$ is

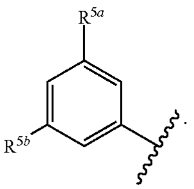

Each $R^{5a}$ and $R^{5b}$ is independently —F, —Cl, —Br, —$CH_3$, —$CH_2CH_3$, —$CH(CH_3)_2$, —$OCH_3$, —$CF_3$, —$OCF_3$, —$OCHF_2$, —$OCH_2F$, —$OCH_2CF_3$, or —O-cyclopropyl. In some embodiments, each $R^{5a}$ and $R^{5b}$ is independently —F or —$OCF_3$. In some embodiments, each $R^{5a}$ and $R^{5b}$ is independently —Cl or —$OCF_3$. In some embodiments, each $R^{5a}$ and $R^{5b}$ is independently —Br or —$OCF_3$.

In some embodiments, $R^5$ is

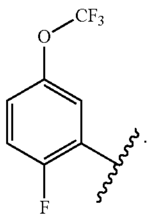 [SMILES: *c1cc(OC(F)(F)F)ccc1F]

In certain aspect, the disclosure provides a compound having a structure of formula (IV-A):

(IV-A)

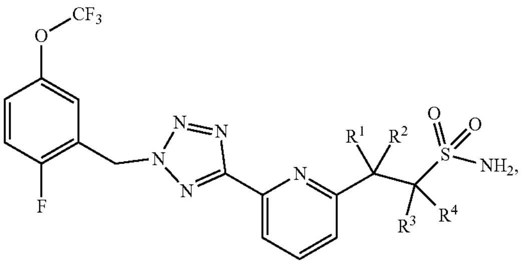

or a pharmaceutically acceptable salt thereof. $R^1$, $R^2$, $R^3$, and $R^4$ are as describe above.

In certain aspect, the disclosure provides a compound having a structure of formula (IV-B):

(IV-B)

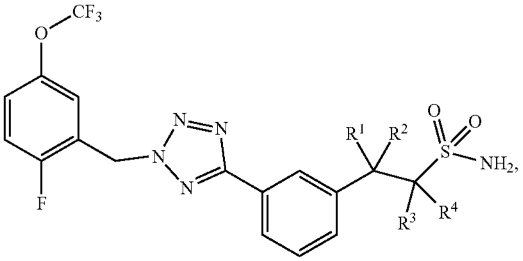

or a pharmaceutically acceptable salt thereof. $R^1$, $R^2$, $R^3$, and $R^4$ are as describe above.

In some embodiments, the compound is selected from the group consisting of:

2-(6-(2-(2-fluoro-5-(trifluoromethoxy)benzyl)-2H-tetrazol-5-yl)pyridin-2-yl)-2-hydroxypropane-1-sulfonamide;

2-hydroxy-2-(6-(2-((2,2,5-trifluorobenzo[d][1,3]dioxol-4-yl)methyl)-2H-tetrazol-5-yl)pyridin-2-yl)propane-1-sulfonamide;

2-(2-fluoro-5-(2-(2-fluoro-5-(trifluoromethoxy)benzyl)-2H-tetrazol-5-yl)phenyl)-2-hydroxypropane-1-sulfonamide;

2-(4-chloro-3-(2-(2-fluoro-5-(trifluoromethoxy)benzyl)-2H-tetrazol-5-yl)phenyl)-2-hydroxypropane-1-sulfonamide;

2-(4-fluoro-3-(2-(2-fluoro-5-(trifluoromethoxy)benzyl)-2H-tetrazol-5-yl)phenyl)-2-hydroxypropane-1-sulfonamide;

2-(2-fluoro-3-(2-(2-fluoro-5-(trifluoromethoxy)benzyl)-2H-tetrazol-5-yl)phenyl)-2-hydroxypropane-1-sulfonamide;

3-(6-(2-(2-fluoro-5-(trifluoromethoxy)benzyl)-2H-tetrazol-5-yl)pyridin-2-yl)-3-hydroxybutane-2-sulfonamide;

2-(6-(2-(2,5-difluorobenzyl)-2H-tetrazol-5-yl)pyridin-2-yl)-2-hydroxypropane-1-sulfonamide;

2-(6-(2-(2-fluoro-5-(trifluoromethyl)benzyl)-2H-tetrazol-5-yl)pyridin-2-yl)-2-hydroxypropane-1-sulfonamide;

2-(6-(2-(5-chloro-2-fluorobenzyl)-2H-tetrazol-5-yl)pyridin-2-yl)-2-hydroxypropane-1-sulfonamide;

2-(3-fluoro-5-(2-(2-fluoro-5-(trifluoromethoxy)benzyl)-2H-tetrazol-5-yl)phenyl)-2-hydroxypropane-1-sulfonamide;

2-(3-(2-(2-fluoro-5-(trifluoromethoxy)benzyl)-2H-tetrazol-5-yl)phenyl)-2-hydroxypropane-1-sulfonamide;

2-(5-chloro-6-(2-(2-fluoro-5-(trifluoromethoxy)benzyl)-2H-tetrazol-5-yl)pyridin-2-yl)-2-hydroxypropane-1-sulfonamide;

2-(6-(2-(2-fluoro-5-(2,2,2-trifluoroethoxy)benzyl)-2H-tetrazol-5-yl)pyridin-2-yl)-2-hydroxypropane-1-sulfonamide;

3-(6-(2-(2-fluoro-5-(trifluoromethoxy)benzyl)-2H-tetrazol-5-yl)pyridin-2-yl)-1-hydroxybutane-2-sulfonamide;

2-(6-(1-(2-fluoro-5-(trifluoromethoxy)benzyl)-1H-pyrazol-3-yl)pyridin-2-yl)-2-hydroxybutane-1-sulfonamide;

2-(6-(1-(2-fluoro-5-(trifluoromethoxy)benzyl)-1H-pyrazol-3-yl)pyridin-2-yl)-2-hydroxyethane-1-sulfonamide;

2-(6-(1-(2-fluoro-5-(trifluoromethoxy)benzyl)-1H-pyrazol-3-yl)pyridin-2-yl)-2-hydroxypropane-1-sulfonamide;

3,3,3-trifluoro-2-(6-(1-(2-fluoro-5-(trifluoromethoxy)benzyl)-1H-pyrazol-3-yl)pyridin-2-yl)-2-hydroxypropane-1-sulfonamide;

2-hydroxy-2-(6-(2-(3-(trifluoromethyl)benzyl)-2H-tetrazol-5-yl)pyridin-2-yl)propane-1-sulfonamide;

2-(3-chloro-6-(2-(2-fluoro-5-(trifluoromethoxy)benzyl)-2H-tetrazol-5-yl)pyridin-2-yl)-2-hydroxypropane-1-sulfonamide;

2-(3-fluoro-6-(2-(2-fluoro-5-(trifluoromethoxy)benzyl)-2H-tetrazol-5-yl)pyridin-2-yl)-2-hydroxypropane-1-sulfonamide;

2-(6-(2-(5-cyclopropoxy-2-fluorobenzyl)-2H-tetrazol-5-yl)pyridin-2-yl)-2-hydroxypropane-1-sulfonamide;

2-(6-(2-(2-fluoro-5-(trifluoromethoxy)benzyl)-2H-tetrazol-5-yl)pyridin-2-yl)-2-hydroxyethane-1-sulfonamide;

1-(6-(2-(2-fluoro-5-(trifluoromethoxy)benzyl)-2H-tetrazol-5-yl)pyridin-2-yl)-1-hydroxypropane-2-sulfonamide;

1-(6-(1-(2-fluoro-5-(trifluoromethoxy)benzyl)-1H-pyrazol-3-yl)pyridin-2-yl)-1-hydroxy-2-methylpropane-2-sulfonamide;

3-(6-(1-(2-fluoro-5-(trifluoromethoxy)benzyl)-1H-pyrazol-3-yl)pyridin-2-yl)-3-hydroxy-2-methylbutane-2-sulfonamide;

2-(6-(1-(2-fluoro-5-(trifluoromethoxy)benzyl)-1H-1,2,4-triazol-3-yl)pyridin-2-yl)-2-hydroxypropane-1-sulfonamide;

2-(6-(3-(2-fluoro-5-(trifluoromethoxy)benzyl)-1,2,4-oxadiazol-5-yl)pyridin-2-yl)-2-hydroxypropane-1-sulfonamide;

2-(6-(1-(2-fluoro-5-(trifluoromethoxy)benzyl)-1H-1,2,3-triazol-4-yl)pyridin-2-yl)-2-hydroxypropane-1-sulfonamide;

2-(6-(2-(2-fluoro-5-(trifluoromethoxy)benzyl)-2H-1,2,3-triazol-4-yl)pyridin-2-yl)-2-hydroxypropane-1-sulfonamide;

2-(6-(2-(2-chloro-6-fluoro-3-methylbenzyl)-2H-tetrazol-5-yl)pyridin-2-yl)-2-hydroxypropane-1-sulfonamide;

2-(6-(2-(2-bromo-5-fluorobenzyl)-2H-tetrazol-5-yl)pyridin-2-yl)-2-hydroxypropane-1-sulfonamide;

2-(6-(2-(4-bromo-2-fluorobenzyl)-2H-tetrazol-5-yl)pyridin-2-yl)-2-hydroxypropane-1-sulfonamide;

2-(6-(2-(3-bromo-2-fluorobenzyl)-2H-tetrazol-5-yl)pyridin-2-yl)-2-hydroxypropane-1-sulfonamide;
2-(6-(2-(2-bromo-6-fluorobenzyl)-2H-tetrazol-5-yl)pyridin-2-yl)-2-hydroxypropane-1-sulfonamide;
2-hydroxy-2-(6-(2-(2,3,5-trimethylbenzyl)-2H-tetrazol-5-yl)pyridin-2-yl)propane-1-sulfonamide;
2-(6-(2-(2,3-dimethylbenzyl)-2H-tetrazol-5-yl)pyridin-2-yl)-2-hydroxypropane-1-sulfonamide;
2-(6-(2-(2,3-dichlorobenzyl)-2H-tetrazol-5-yl)pyridin-2-yl)-2-hydroxypropane-1-sulfonamide;
2-(6-(2-(5-bromo-2-fluorobenzyl)-2H-tetrazol-5-yl)pyridin-2-yl)-2-hydroxypropane-1-sulfonamide;
2-hydroxy-2-(6-(2-(5-isopropyl-2-methylbenzyl)-2H-tetrazol-5-yl)pyridin-2-yl)propane-1-sulfonamide;
2-(6-(2-(3-chloro-2,6-difluorobenzyl)-2H-tetrazol-5-yl)pyridin-2-yl)-2-hydroxypropane-1-sulfonamide;
2-(6-(2-(2-chloro-5-(trifluoromethyl)benzyl)-2H-tetrazol-5-yl)pyridin-2-yl)-2-hydroxypropane-1-sulfonamide;
2-(6-(2-(2-fluoro-3-(trifluoromethoxy)benzyl)-2H-tetrazol-5-yl)pyridin-2-yl)-2-hydroxypropane-1-sulfonamide;
2-(6-(2-(2-fluoro-5-methoxybenzyl)-2H-tetrazol-5-yl)pyridin-2-yl)-2-hydroxypropane-1-sulfonamide;
2-(6-(2-(2-chloro-5-(trifluoromethoxy)benzyl)-2H-tetrazol-5-yl)pyridin-2-yl)-2-hydroxypropane-1-sulfonamide;
2-(6-(2-(2,5-dichlorobenzyl)-2H-tetrazol-5-yl)pyridin-2-yl)-2-hydroxypropane-1-sulfonamide;
2-(6-(2-(2-fluoro-6-(trifluoromethyl)benzyl)-2H-tetrazol-5-yl)pyridin-2-yl)-2-hydroxypropane-1-sulfonamide;
2-(6-(2-(4-chloro-3-(trifluoromethyl)benzyl)-2H-tetrazol-5-yl)pyridin-2-yl)-2-hydroxypropane-1-sulfonamide;
2-(6-(2-(5-chloro-2,4-difluorobenzyl)-2H-tetrazol-5-yl)pyridin-2-yl)-2-hydroxypropane-1-sulfonamide;
2-hydroxy-2-(6-(2-(3-(trifluoromethoxy)benzyl)-2H-tetrazol-5-yl)pyridin-2-yl)propane-1-sulfonamide;
2-(6-(2-(3,5-bis(trifluoromethyl)benzyl)-2H-tetrazol-5-yl)pyridin-2-yl)-2-hydroxypropane-1-sulfonamide;
2-(6-(2-(5-(difluoromethoxy)-2-fluorobenzyl)-2H-tetrazol-5-yl)pyridin-2-yl)-2-hydroxypropane-1-sulfonamide;
2-(6-(2-(2,6-dichlorobenzyl)-2H-tetrazol-5-yl)pyridin-2-yl)-2-hydroxypropane-1-sulfonamide;
2-(6-(2-(2-bromo-5-(trifluoromethoxy)benzyl)-2H-tetrazol-5-yl)pyridin-2-yl)-2-hydroxypropane-1-sulfonamide;
2-(6-(2-(2,3-dichloro-6-(trifluoromethyl)benzyl)-2H-tetrazol-5-yl)pyridin-2-yl)-2-hydroxypropane-1-sulfonamide;
2-(6-(2-(3-chloro-5-(trifluoromethoxy)benzyl)-2H-tetrazol-5-yl)pyridin-2-yl)-2-hydroxypropane-1-sulfonamide;
2-(6-(2-(5-chloro-2-(trifluoromethyl)benzyl)-2H-tetrazol-5-yl)pyridin-2-yl)-2-hydroxypropane-1-sulfonamide; and
2-hydroxy-2-(6-(2-(2,3,5-trichlorobenzyl)-2H-tetrazol-5-yl)pyridin-2-yl)propane-1-sulfonamide.

In some embodiments, the compound is selected from the group consisting of:

2-(6-(2-(2-fluoro-5-(trifluoromethoxy)benzyl)-2H-tetrazol-5-yl)pyridin-2-yl)-2-hydroxypropane-1-sulfonamide;
2-hydroxy-2-(6-(2-((2,2,5-trifluorobenzo[d][1,3]dioxol-4-yl)methyl)-2H-tetrazol-5-yl)pyridin-2-yl)propane-1-sulfonamide;
2-(2-fluoro-5-(2-(2-fluoro-5-(trifluoromethoxy)benzyl)-2H-tetrazol-5-yl)phenyl)-2-hydroxypropane-1-sulfonamide;
2-(4-chloro-3-(2-(2-fluoro-5-(trifluoromethoxy)benzyl)-2H-tetrazol-5-yl)phenyl)-2-hydroxypropane-1-sulfonamide;
2-(4-fluoro-3-(2-(2-fluoro-5-(trifluoromethoxy)benzyl)-2H-tetrazol-5-yl)phenyl)-2-hydroxypropane-1-sulfonamide;
2-(2-fluoro-3-(2-(2-fluoro-5-(trifluoromethoxy)benzyl)-2H-tetrazol-5-yl)phenyl)-2-hydroxypropane-1-sulfonamide;
3-(6-(2-(2-fluoro-5-(trifluoromethoxy)benzyl)-2H-tetrazol-5-yl)pyridin-2-yl)-3-hydroxybutane-2-sulfonamide;
2-(6-(2-(2,5-difluorobenzyl)-2H-tetrazol-5-yl)pyridin-2-yl)-2-hydroxypropane-1-sulfonamide;
2-(6-(2-(2-fluoro-5-(trifluoromethyl)benzyl)-2H-tetrazol-5-yl)pyridin-2-yl)-2-hydroxypropane-1-sulfonamide;
2-(6-(2-(5-chloro-2-fluorobenzyl)-2H-tetrazol-5-yl)pyridin-2-yl)-2-hydroxypropane-1-sulfonamide;
2-(3-fluoro-5-(2-(2-fluoro-5-(trifluoromethoxy)benzyl)-2H-tetrazol-5-yl)phenyl)-2-hydroxypropane-1-sulfonamide;
2-(3-(2-(2-fluoro-5-(trifluoromethoxy)benzyl)-2H-tetrazol-5-yl)phenyl)-2-hydroxypropane-1-sulfonamide;
2-(5-chloro-6-(2-(2-fluoro-5-(trifluoromethoxy)benzyl)-2H-tetrazol-5-yl)pyridin-2-yl)-2-hydroxypropane-1-sulfonamide;
2-(6-(2-(2-fluoro-5-(2,2,2-trifluoroethoxy)benzyl)-2H-tetrazol-5-yl)pyridin-2-yl)-2-hydroxypropane-1-sulfonamide;
3-(6-(2-(2-fluoro-5-(trifluoromethoxy)benzyl)-2H-tetrazol-5-yl)pyridin-2-yl)-1-hydroxybutane-2-sulfonamide;
2-(6-(1-(2-fluoro-5-(trifluoromethoxy)benzyl)-1H-pyrazol-3-yl)pyridin-2-yl)-2-hydroxybutane-1-sulfonamide;
2-(6-(1-(2-fluoro-5-(trifluoromethoxy)benzyl)-1H-pyrazol-3-yl)pyridin-2-yl)-2-hydroxyethane-1-sulfonamide;
2-(6-(1-(2-fluoro-5-(trifluoromethoxy)benzyl)-1H-pyrazol-3-yl)pyridin-2-yl)-2-hydroxypropane-1-sulfonamide;
3,3,3-trifluoro-2-(6-(1-(2-fluoro-5-(trifluoromethoxy)benzyl)-1H-pyrazol-3-yl)pyridin-2-yl)-2-hydroxypropane-1-sulfonamide;
2-hydroxy-2-(6-(2-(3-(trifluoromethyl)benzyl)-2H-tetrazol-5-yl)pyridin-2-yl)propane-1-sulfonamide;
2-(3-chloro-6-(2-(2-fluoro-5-(trifluoromethoxy)benzyl)-2H-tetrazol-5-yl)pyridin-2-yl)-2-hydroxypropane-1-sulfonamide;
2-(3-fluoro-6-(2-(2-fluoro-5-(trifluoromethoxy)benzyl)-2H-tetrazol-5-yl)pyridin-2-yl)-2-hydroxypropane-1-sulfonamide;
2-(6-(2-(5-cyclopropoxy-2-fluorobenzyl)-2H-tetrazol-5-yl)pyridin-2-yl)-2-hydroxypropane-1-sulfonamide;
2-(6-(2-(2-fluoro-5-(trifluoromethoxy)benzyl)-2H-tetrazol-5-yl)pyridin-2-yl)-2-hydroxyethane-1-sulfonamide;
1-(6-(2-(2-fluoro-5-(trifluoromethoxy)benzyl)-2H-tetrazol-5-yl)pyridin-2-yl)-1-hydroxypropane-2-sulfonamide;
1-(6-(1-(2-fluoro-5-(trifluoromethoxy)benzyl)-1H-pyrazol-3-yl)pyridin-2-yl)-1-hydroxy-2-methylpropane-2-sulfonamide;
3-(6-(1-(2-fluoro-5-(trifluoromethoxy)benzyl)-1H-pyrazol-3-yl)pyridin-2-yl)-3-hydroxy-2-methylbutane-2-sulfonamide;
2-(6-(1-(2-fluoro-5-(trifluoromethoxy)benzyl)-1H-1,2,4-triazol-3-yl)pyridin-2-yl)-2-hydroxypropane-1-sulfonamide;
2-(6-(3-(2-fluoro-5-(trifluoromethoxy)benzyl)-1,2,4-oxadiazol-5-yl)pyridin-2-yl)-2-hydroxypropane-1-sulfonamide;
2-(6-(1-(2-fluoro-5-(trifluoromethoxy)benzyl)-1H-1,2,3-triazol-4-yl)pyridin-2-yl)-2-hydroxypropane-1-sulfonamide;
2-(6-(2-(2-fluoro-5-(trifluoromethoxy)benzyl)-2H-1,2,3-triazol-4-yl)pyridin-2-yl)-2-hydroxypropane-1-sulfonamide;
(R)-2-(6-(2-(2-chloro-6-fluoro-3-methylbenzyl)-2H-tetrazol-5-yl)pyridin-2-yl)-2-hydroxypropane-1-sulfonamide;
(R)-2-(6-(2-(2-bromo-5-fluorobenzyl)-2H-tetrazol-5-yl)pyridin-2-yl)-2-hydroxypropane-1-sulfonamide;
(R)-2-(6-(2-(4-bromo-2-fluorobenzyl)-2H-tetrazol-5-yl)pyridin-2-yl)-2-hydroxypropane-1-sulfonamide;

(R)-2-(6-(2-(3-bromo-2-fluorobenzyl)-2H-tetrazol-5-yl)pyridin-2-yl)-2-hydroxypropane-1-sulfonamide;

(R)-2-(6-(2-(2-bromo-6-fluorobenzyl)-2H-tetrazol-5-yl)pyridin-2-yl)-2-hydroxypropane-1-sulfonamide;

(R)-2-hydroxy-2-(6-(2-(2,3,5-trimethylbenzyl)-2H-tetrazol-5-yl)pyridin-2-yl)propane-1-sulfonamide;

(R)-2-(6-(2-(2,3-dimethylbenzyl)-2H-tetrazol-5-yl)pyridin-2-yl)-2-hydroxypropane-1-sulfonamide;

(R)-2-(6-(2-(2,3-dichlorobenzyl)-2H-tetrazol-5-yl)pyridin-2-yl)-2-hydroxypropane-1-sulfonamide;

(R)-2-(6-(2-(5-bromo-2-fluorobenzyl)-2H-tetrazol-5-yl)pyridin-2-yl)-2-hydroxypropane-1-sulfonamide;

(R)-2-hydroxy-2-(6-(2-(5-isopropyl-2-methylbenzyl)-2H-tetrazol-5-yl)pyridin-2-yl)propane-1-sulfonamide;

(R)-2-(6-(2-(3-chloro-2,6-difluorobenzyl)-2H-tetrazol-5-yl)pyridin-2-yl)-2-hydroxypropane-1-sulfonamide;

(R)-2-(6-(2-(2-chloro-5-(trifluoromethyl)benzyl)-2H-tetrazol-5-yl)pyridin-2-yl)-2-hydroxypropane-1-sulfonamide;

(R)-2-(6-(2-(2-fluoro-3-(trifluoromethoxy)benzyl)-2H-tetrazol-5-yl)pyridin-2-yl)-2-hydroxypropane-1-sulfonamide;

(R)-2-(6-(2-(2-fluoro-5-methoxybenzyl)-2H-tetrazol-5-yl)pyridin-2-yl)-2-hydroxypropane-1-sulfonamide;

(R)-2-(6-(2-(2-chloro-5-(trifluoromethoxy)benzyl)-2H-tetrazol-5-yl)pyridin-2-yl)-2-hydroxypropane-1-sulfonamide;

(R)-2-(6-(2-(2,5-dichlorobenzyl)-2H-tetrazol-5-yl)pyridin-2-yl)-2-hydroxypropane-1-sulfonamide;

(R)-2-(6-(2-(2-fluoro-6-(trifluoromethyl)benzyl)-2H-tetrazol-5-yl)pyridin-2-yl)-2-hydroxypropane-1-sulfonamide;

(R)-2-(6-(2-(4-chloro-3-(trifluoromethyl)benzyl)-2H-tetrazol-5-yl)pyridin-2-yl)-2-hydroxypropane-1-sulfonamide;

(R)-2-(6-(2-(5-chloro-2,4-difluorobenzyl)-2H-tetrazol-5-yl)pyridin-2-yl)-2-hydroxypropane-1-sulfonamide;

(R)-2-hydroxy-2-(6-(2-(3-(trifluoromethoxy)benzyl)-2H-tetrazol-5-yl)pyridin-2-yl)propane-1-sulfonamide;

(R)-2-(6-(2-(3,5-bis(trifluoromethyl)benzyl)-2H-tetrazol-5-yl)pyridin-2-yl)-2-hydroxypropane-1-sulfonamide;

(R)-2-(6-(2-(5-(difluoromethoxy)-2-fluorobenzyl)-2H-tetrazol-5-yl)pyridin-2-yl)-2-hydroxypropane-1-sulfonamide;

(R)-2-(6-(2-(2,6-dichlorobenzyl)-2H-tetrazol-5-yl)pyridin-2-yl)-2-hydroxypropane-1-sulfonamide;

(R)-2-(6-(2-(2-bromo-5-(trifluoromethoxy)benzyl)-2H-tetrazol-5-yl)pyridin-2-yl)-2-hydroxypropane-1-sulfonamide;

(R)-2-(6-(2-(2,3-dichloro-6-(trifluoromethyl)benzyl)-2H-tetrazol-5-yl)pyridin-2-yl)-2-hydroxypropane-1-sulfonamide;

(R)-2-(6-(2-(3-chloro-5-(trifluoromethoxy)benzyl)-2H-tetrazol-5-yl)pyridin-2-yl)-2-hydroxypropane-1-sulfonamide;

(R)-2-(6-(2-(5-chloro-2-(trifluoromethyl)benzyl)-2H-tetrazol-5-yl)pyridin-2-yl)-2-hydroxypropane-1-sulfonamide; and (R)-2-hydroxy-2-(6-(2-(2,3,5-trichlorobenzyl)-2H-tetrazol-5-yl)pyridin-2-yl)propane-1-sulfonamide.

In a first embodiment (Embodiment 1), disclosed herein is a compound of formula (I'):

(I')

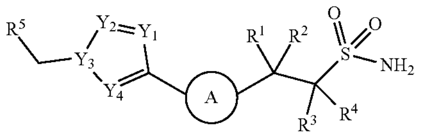

or a pharmaceutically acceptable salt thereof, wherein ring A is:

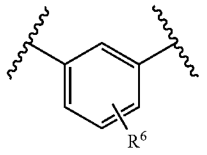

or

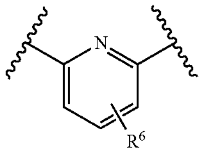

$R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

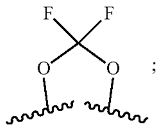 [SMILES: *OC(F)(F)O*]
;

$R^6$ is selected from H, F and Cl;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

Unless specified otherwise, the term "compounds of the present disclosure" or "compound of the present disclosure" refers to compounds of any of formulae (I), (II), (III), (IV) or (V), and exemplified compounds, or pharmaceutically acceptable salts thereof, as well as all stereoisomers (including diastereomers and enantiomers), rotamers, tautomers, hydrates, solvates, polymorphs, co-crystals, and isotopically labeled compounds (including deuterium substitutions), as well as inherently formed moieties.

Various (enumerated) embodiments are described herein. It will be recognized that features specified in each embodiment may be combined with other specified features to provide further embodiments.

Embodiment 2. A compound according to embodiment 1, or a pharmaceutically acceptable salt thereof, wherein ring A is:

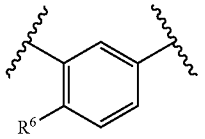

or

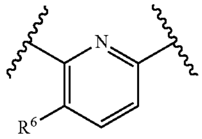
, wherein $R^6$ is selected from H, F and $C_1$.

Embodiment 3. A compound according to embodiment 1 or embodiment 2, or a pharmaceutically acceptable salt thereof, wherein $R^6$ is H.

Embodiment 4. A compound according to embodiment 3, said compound being of formula (II'):

(II')

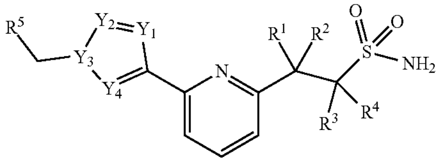

or a pharmaceutically acceptable salt thereof, wherein $R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

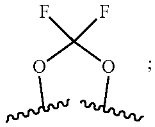 [SMILES: *OC(F)(F)O*]

;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

Embodiment 5. A compound according to any one of embodiments 1 to 4, or a pharmaceutically acceptable salt thereof, wherein each of $Y_1$, $Y_2$, $Y_3$ and $Y_4$ are N; or $Y_2$ is CH and each of $Y_1$, $Y_3$ and $Y_4$ are N; or each of $Y_1$ and $Y_2$ are CH and each of $Y_3$ and $Y_4$ are N.

Embodiment 6. A compound according to any one of embodiments 1 to 5, said compound being of formula (III):

(III')

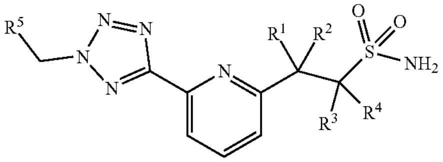

or a pharmaceutically acceptable salt thereof, wherein $R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

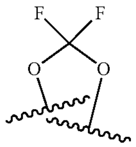

.

Embodiment 7. A compound according to any one of embodiments 1 to 6, or a pharmaceutically acceptable salt thereof, wherein $R^3$ is H and $R^4$ is H.

Embodiment 8. A compound according to any one of embodiments 1 to 7, or a pharmaceutically acceptable salt thereof, wherein $R^1$ is OH.

Embodiment 9. A compound according to any one of embodiments 1 to 8, or a pharmaceutically acceptable salt thereof, wherein $R^2$ is selected from H, —$CH_3$ and —$CH_2CH_3$.

Embodiment 10. A compound according to embodiment 9, or a pharmaceutically acceptable salt thereof, wherein $R^2$ is H or —$CH_3$.

Embodiment 11. A compound according to any one of embodiments 1 to 10, or a pharmaceutically acceptable salt thereof, wherein $R^1$ is OH and $R^2$ is $CH_3$.

Embodiment 12. A compound according to any one of embodiments 1 to 11, or a pharmaceutically acceptable salt thereof, wherein $R^5$ is phenyl substituted with at least two groups selected from F, Cl, —$CF_3$, —$OCF_3$ and —$OCH_2CF_3$.

Embodiment 13. A compound according to any one of embodiments 1 to 12, or a pharmaceutically acceptable salt thereof, wherein $R^5$ is:

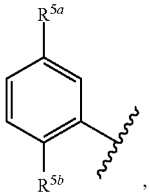

, wherein, $R^{5a}$ and $R^{5b}$ are independently selected from F, Cl, —$CF_3$, —$OCF_3$ and —$OCH_2CF_3$.

Embodiment 14. A compound according to any one of embodiments 1 to 12, or a pharmaceutically acceptable salt thereof, wherein $R^5$ is phenyl substituted with F and —$OCF_3$.

Embodiment 15. A compound according to any one of embodiments 1 to 14, or a pharmaceutically acceptable salt thereof, wherein $R^5$ is:

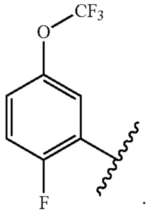 [SMILES: *c1cc(OC(F)(F)F)ccc1F]

.

Embodiment 16. A compound according to any one of embodiments 1 to 15, said compound being of formula (IV'):

(IV')

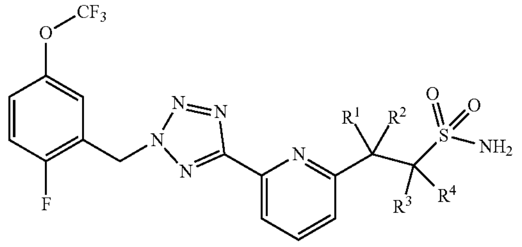

or a pharmaceutically acceptable salt thereof, wherein $R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$.

Embodiment 17. A compound of formula (I) according to embodiment 1, or a pharmaceutically acceptable salt thereof, wherein the compound is selected from the group consisting of:

2-(6-(2-(2-fluoro-5-(trifluoromethoxy)benzyl)-2H-tetrazol-5-yl)pyridin-2-yl)-2-hydroxypropane-1-sulfonamide;

2-hydroxy-2-(6-(2-((2,2,5-trifluorobenzo[d][1,3]dioxol-4-yl)methyl)-2H-tetrazol-5-yl)pyridin-2-yl)propane-1-sulfonamide;

2-(2-fluoro-5-(2-(2-fluoro-5-(trifluoromethoxy)benzyl)-2H-tetrazol-5-yl)phenyl)-2-hydroxypropane-1-sulfonamide;

2-(4-chloro-3-(2-(2-fluoro-5-(trifluoromethoxy)benzyl)-2H-tetrazol-5-yl)phenyl)-2-hydroxypropane-1-sulfonamide;

2-(4-fluoro-3-(2-(2-fluoro-5-(trifluoromethoxy)benzyl)-2H-tetrazol-5-yl)phenyl)-2-hydroxypropane-1-sulfonamide;

2-(2-fluoro-3-(2-(2-fluoro-5-(trifluoromethoxy)benzyl)-2H-tetrazol-5-yl)phenyl)-2-hydroxypropane-1-sulfonamide;

3-(6-(2-(2-fluoro-5-(trifluoromethoxy)benzyl)-2H-tetrazol-5-yl)pyridin-2-yl)-3-hydroxybutane-2-sulfonamide;

2-(6-(2-(2,5-difluorobenzyl)-2H-tetrazol-5-yl)pyridin-2-yl)-2-hydroxypropane-1-sulfonamide;

2-(6-(2-(2-fluoro-5-(trifluoromethyl)benzyl)-2H-tetrazol-5-yl)pyridin-2-yl)-2-hydroxypropane-1-sulfonamide;

2-(6-(2-(5-chloro-2-fluorobenzyl)-2H-tetrazol-5-yl)pyridin-2-yl)-2-hydroxypropane-1-sulfonamide;

2-(3-fluoro-5-(2-(2-fluoro-5-(trifluoromethoxy)benzyl)-2H-tetrazol-5-yl)phenyl)-2-hydroxypropane-1-sulfonamide;

2-(3-(2-(2-fluoro-5-(trifluoromethoxy)benzyl)-2H-tetrazol-5-yl)phenyl)-2-hydroxypropane-1-sulfonamide;

2-(5-chloro-6-(2-(2-fluoro-5-(trifluoromethoxy)benzyl)-2H-tetrazol-5-yl)pyridin-2-yl)-2-hydroxypropane-1-sulfonamide;

2-(6-(2-(2-fluoro-5-(2,2,2-trifluoroethoxy)benzyl)-2H-tetrazol-5-yl)pyridin-2-yl)-2-hydroxypropane-1-sulfonamide;

3-(6-(2-(2-fluoro-5-(trifluoromethoxy)benzyl)-2H-tetrazol-5-yl)pyridin-2-yl)-1-hydroxybutane-2-sulfonamide;

2-(6-(1-(2-fluoro-5-(trifluoromethoxy)benzyl)-1H-pyrazol-3-yl)pyridin-2-yl)-2-hydroxybutane-1-sulfonamide;

2-(6-(1-(2-fluoro-5-(trifluoromethoxy)benzyl)-1H-pyrazol-3-yl)pyridin-2-yl)-2-hydroxyethane-1-sulfonamide;

2-(6-(1-(2-fluoro-5-(trifluoromethoxy)benzyl)-1H-pyrazol-3-yl)pyridin-2-yl)-2-hydroxypropane-1-sulfonamide;

3,3,3-trifluoro-2-(6-(1-(2-fluoro-5-(trifluoromethoxy)benzyl)-1H-pyrazol-3-yl)pyridin-2-yl)-2-hydroxypropane-1-sulfonamide;

2-hydroxy-2-(6-(2-(3-(trifluoromethyl)benzyl)-2H-tetrazol-5-yl)pyridin-2-yl)propane-1-sulfonamide;

2-(3-chloro-6-(2-(2-fluoro-5-(trifluoromethoxy)benzyl)-2H-tetrazol-5-yl)pyridin-2-yl)-2-hydroxypropane-1-sulfonamide;

2-(3-fluoro-6-(2-(2-fluoro-5-(trifluoromethoxy)benzyl)-2H-tetrazol-5-yl)pyridin-2-yl)-2-hydroxypropane-1-sulfonamide;

2-(6-(2-(5-cyclopropoxy-2-fluorobenzyl)-2H-tetrazol-5-yl)pyridin-2-yl)-2-hydroxypropane-1-sulfonamide;

2-(6-(2-(2-fluoro-5-(trifluoromethoxy)benzyl)-2H-tetrazol-5-yl)pyridin-2-yl)-2-hydroxyethane-1-sulfonamide;

1-(6-(2-(2-fluoro-5-(trifluoromethoxy)benzyl)-2H-tetrazol-5-yl)pyridin-2-yl)-1-hydroxypropane-2-sulfonamide;

1-(6-(1-(2-fluoro-5-(trifluoromethoxy)benzyl)-1H-pyrazol-3-yl)pyridin-2-yl)-1-hydroxy-2-methylpropane-2-sulfonamide;

3-(6-(1-(2-fluoro-5-(trifluoromethoxy)benzyl)-1H-pyrazol-3-yl)pyridin-2-yl)-3-hydroxy-2-methylbutane-2-sulfonamide;

2-(6-(1-(2-fluoro-5-(trifluoromethoxy)benzyl)-1H-1,2,4-triazol-3-yl)pyridin-2-yl)-2-hydroxypropane-1-sulfonamide;

2-(6-(3-(2-fluoro-5-(trifluoromethoxy)benzyl)-1,2,4-oxadiazol-5-yl)pyridin-2-yl)-2-hydroxypropane-1-sulfonamide;

2-(6-(1-(2-fluoro-5-(trifluoromethoxy)benzyl)-1H-1,2,3-triazol-4-yl)pyridin-2-yl)-2-hydroxypropane-1-sulfonamide; and 2-(6-(2-(2-fluoro-5-(trifluoromethoxy)benzyl)-2H-1,2,3-triazol-4-yl)pyridin-2-yl)-2-hydroxypropane-1-sulfonamide.

Embodiment 18. A compound of formula (I) according to embodiment 1, or a pharmaceutically acceptable salt thereof, wherein the compound is selected from the group consisting of:

2-(6-(2-(2-fluoro-5-(trifluoromethoxy)benzyl)-2H-tetrazol-5-yl)pyridin-2-yl)-2-hydroxypropane-1-sulfonamide,

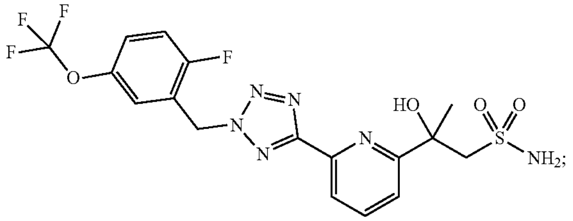 [SMILES: CC(O)(CS(N)(=O)=O)c1cccc(-c2nnn(Cc3cc(OC(F)(F)F)ccc3F)n2)n1]

2-(6-(2-(2-fluoro-5-(2,2,2-trifluoroethoxy)benzyl)-2H-tetrazol-5-yl)pyridin-2-yl)-2-hydroxypropane-1-sulfonamide,

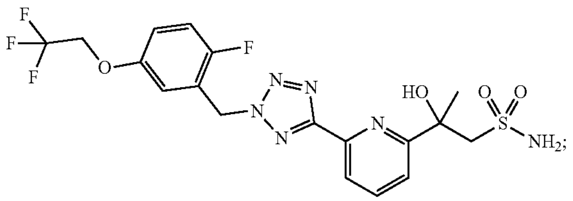 [SMILES: CC(O)(CS(N)(=O)=O)c1cccc(-c2nnn(Cc3cc(OCC(F)(F)F)ccc3F)n2)n1]

2-(5-chloro-6-(2-(2-fluoro-5-(trifluoromethoxy)benzyl)-2H-tetrazol-5-yl)pyridin-2-yl)-2-hydroxypropane-1-sulfonamide,

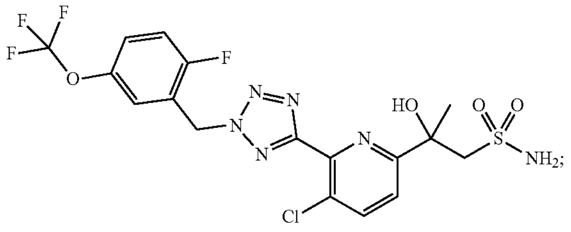 [SMILES: CC(O)(CS(N)(=O)=O)c1ccc(Cl)c(-c2nnn(Cc3cc(OC(F)(F)F)ccc3F)n2)n1]

2-(6-(1-(2-fluoro-5-(trifluoromethoxy)benzyl)-1H-pyrazol-3-yl)pyridin-2-yl)-2-hydroxypropane-1-sulfonamide,

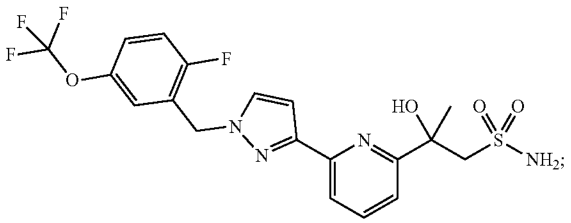 [SMILES: CC(O)(CS(N)(=O)=O)c1cccc(-c2ccn(Cc3cc(OC(F)(F)F)ccc3F)n2)n1]

and 2-(4-chloro-3-(2-(2-fluoro-5-(trifluoromethoxy)benzyl)-2H-tetrazol-5-yl)phenyl)-2-hydroxypropane-1-sulfonamide,

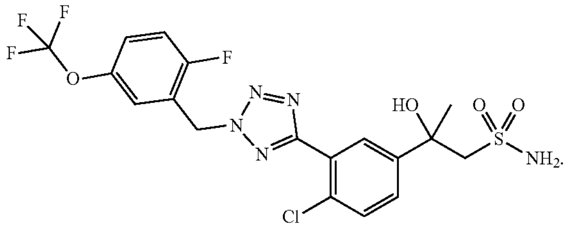

Embodiment 19. A compound of formula (I) according to embodiment 1, which is 2-(6-(2-(2-fluoro-5-(trifluoromethoxy)benzyl)-2H-tetrazol-5-yl)pyridin-2-yl)-2-hydroxypropane-1-sulfonamide,

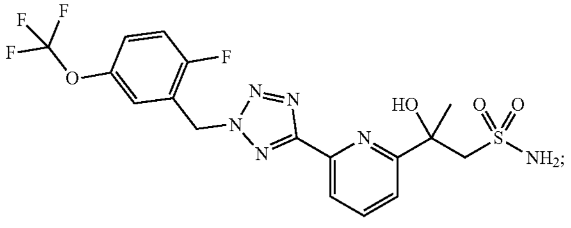 [SMILES: CC(O)(CS(N)(=O)=O)c1cccc(-c2nnn(Cc3cc(OC(F)(F)F)ccc3F)n2)n1]

or a pharmaceutically acceptable salt thereof.

Embodiment 20. A compound of formula (I) according to embodiment 1, or a pharmaceutically acceptable salt thereof, which is selected from the group consisting of (R)-2-(6-(2-(2-fluoro-5-(trifluoromethoxy)benzyl)-2H-tetrazol-5-yl)pyridin-2-yl)-2-hydroxypropane-1-sulfonamide,

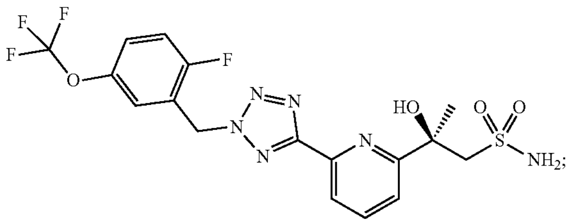 [SMILES: C[C@](O)(CS(N)(=O)=O)c1cccc(-c2nnn(Cc3cc(OC(F)(F)F)ccc3F)n2)n1]

and (S)-2-(6-(2-(2-fluoro-5-(trifluoromethoxy)benzyl)-2H-tetrazol-5-yl)pyridin-2-yl)-2-hydroxypropane-1-sulfonamide,

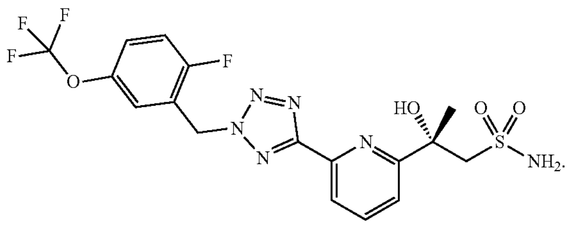 [SMILES: C[C@@](O)(CS(N)(=O)=O)c1cccc(-c2nnn(Cc3cc(OC(F)(F)F)ccc3F)n2)n1]

Embodiment 21. A compound of formula (I) according to embodiment 1, which is (R)-2-(6-(2-(2-fluoro-5-(trifluoromethoxy)benzyl)-2H-tetrazol-5-yl)pyridin-2-yl)-2-hydroxypropane-1-sulfonamide,

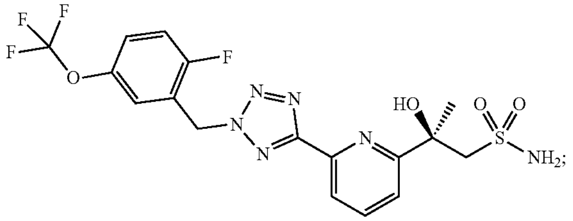 [SMILES: C[C@](O)(CS(N)(=O)=O)c1cccc(-c2nnn(Cc3cc(OC(F)(F)F)ccc3F)n2)n1]

or a pharmaceutically acceptable salt thereof.

Embodiment 22. A compound of formula (I) according to embodiment 1, which is 2-(6-(2-(2-fluoro-5-(2,2,2-trifluoroethoxy)benzyl)-2H-tetrazol-5-yl)pyridin-2-yl)-2-hydroxypropane-1-sulfonamide,

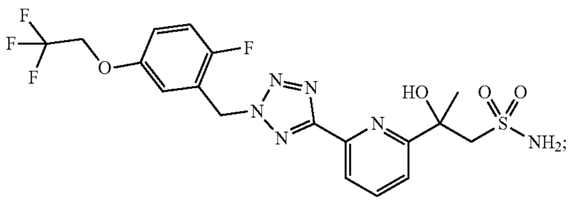 [SMILES: CC(O)(CS(N)(=O)=O)c1cccc(-c2nnn(Cc3cc(OCC(F)(F)F)ccc3F)n2)n1]

or a pharmaceutically acceptable salt thereof.

Embodiment 23. A compound of formula (I) according to embodiment 1, or a pharmaceutically acceptable salt thereof, which is selected from the group consisting of (R)-2-(6-(2-(2-fluoro-5-(2,2,2-trifluoroethoxy)benzyl)-2H-tetrazol-5-yl)pyridin-2-yl)-2-hydroxypropane-1-sulfonamide,

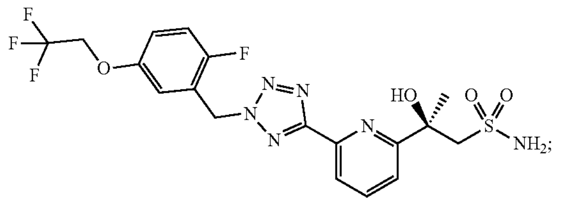 [SMILES: C[C@](O)(CS(N)(=O)=O)c1cccc(-c2nnn(Cc3cc(OCC(F)(F)F)ccc3F)n2)n1]

and (S)-2-(6-(2-(2-fluoro-5-(2,2,2-trifluoroethoxy)benzyl)-2H-tetrazol-5-yl)pyridin-2-yl)-2-hydroxypropane-1-sulfonamide,

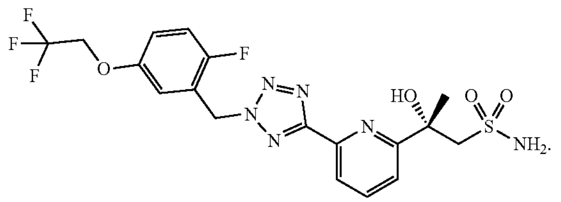 [SMILES: C[C@@](O)(CS(N)(=O)=O)c1cccc(-c2nnn(Cc3cc(OCC(F)(F)F)ccc3F)n2)n1]

Embodiment 24. A compound of formula (I) according to embodiment 1, which is (R)-2-(6-(2-(2-fluoro-5-(2,2,2-trifluoroethoxy)benzyl)-2H-tetrazol-5-yl)pyridin-2-yl)-2-hydroxypropane-1-sulfonamide,

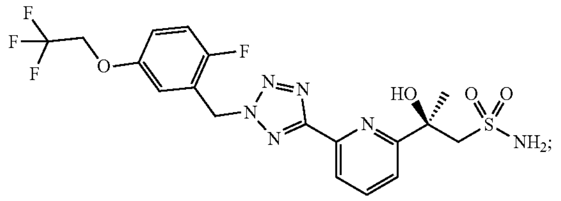 [SMILES: C[C@](O)(CS(N)(=O)=O)c1cccc(-c2nnn(Cc3cc(OCC(F)(F)F)ccc3F)n2)n1]

or a pharmaceutically acceptable salt thereof.

Embodiment 25. A compound of formula (I) according to embodiment 1, which is 2-(5-chloro-6-(2-(2-fluoro-5-(trifluoromethoxy)benzyl)-2H-tetrazol-5-yl)pyridin-2-yl)-2-hydroxypropane-1-sulfonamide,

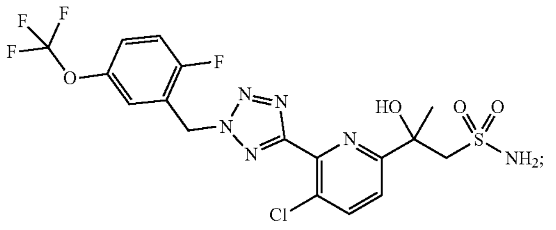 [SMILES: CC(O)(CS(N)(=O)=O)c1ccc(Cl)c(-c2nnn(Cc3cc(OC(F)(F)F)ccc3F)n2)n1]

or a pharmaceutically acceptable salt thereof.

Embodiment 26. A compound of formula (I) according to embodiment 1, or a pharmaceutically acceptable salt thereof, which is selected from the group consisting of:

(R)-2-(5-chloro-6-(2-(2-fluoro-5-(trifluoromethoxy)benzyl)-2H-tetrazol-5-yl)pyridin-2-yl)-2-hydroxypropane-1-sulfonamide,

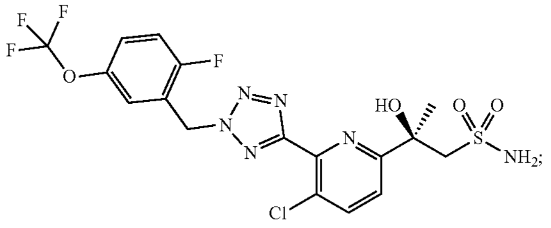 [SMILES: C[C@](O)(CS(N)(=O)=O)c1ccc(Cl)c(-c2nnn(Cc3cc(OC(F)(F)F)ccc3F)n2)n1]

and (S)-2-(5-chloro-6-(2-(2-fluoro-5-(trifluoromethoxy)benzyl)-2H-tetrazol-5-yl)pyridin-2-yl)-2-hydroxypropane-1-sulfonamide,

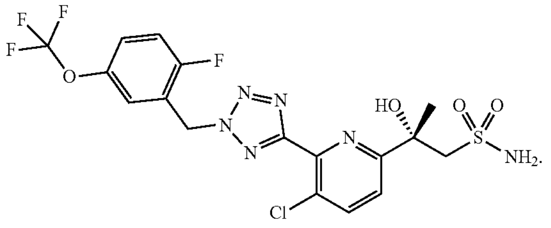 [SMILES: C[C@@](O)(CS(N)(=O)=O)c1ccc(Cl)c(-c2nnn(Cc3cc(OC(F)(F)F)ccc3F)n2)n1]

Embodiment 27. A compound of formula (I) according to embodiment 1, which is (R)-2-(5-chloro-6-(2-(2-fluoro-5-(trifluoromethoxy)benzyl)-2H-tetrazol-5-yl)pyridin-2-yl)-2-hydroxypropane-1-sulfonamide,

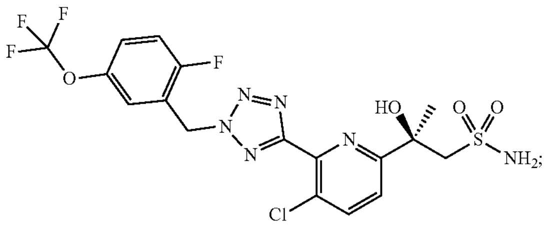 [SMILES: C[C@](O)(CS(N)(=O)=O)c1ccc(Cl)c(-c2nnn(Cc3cc(OC(F)(F)F)ccc3F)n2)n1]

or a pharmaceutically acceptable salt thereof.

Embodiment 28. A compound of formula (I) according to embodiment 1, which is 2-(6-(1-(2-fluoro-5-(trifluoromethoxy)benzyl)-1H-pyrazol-3-yl)pyridin-2-yl)-2-hydroxypropane-1-sulfonamide,

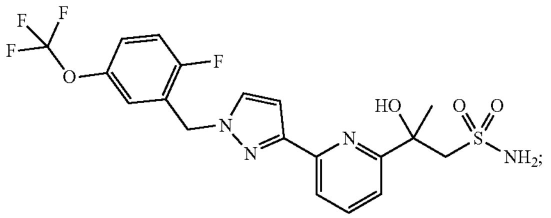 [SMILES: CC(O)(CS(N)(=O)=O)c1cccc(-c2ccn(Cc3cc(OC(F)(F)F)ccc3F)n2)n1]

or a pharmaceutically acceptable salt thereof.

Embodiment 29. A compound of formula (I) according to embodiment 1, or a pharmaceutically acceptable salt thereof, which is selected from the group consisting of:

(R)-2-(6-(1-(2-fluoro-5-(trifluoromethoxy)benzyl)-1H-pyrazol-3-yl)pyridin-2-yl)-2-hydroxypropane-1-sulfonamide:

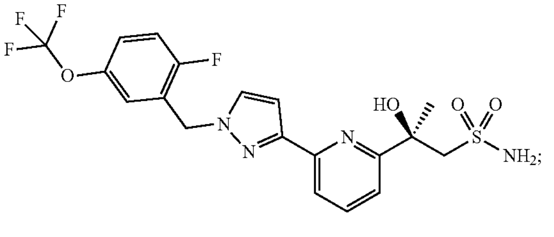 [SMILES: C[C@](O)(CS(N)(=O)=O)c1cccc(-c2ccn(Cc3cc(OC(F)(F)F)ccc3F)n2)n1]

and (S)-2-(6-(1-(2-fluoro-5-(trifluoromethoxy)benzyl)-1H-pyrazol-3-yl)pyridin-2-yl)-2-hydroxypropane-1-sulfonamide:

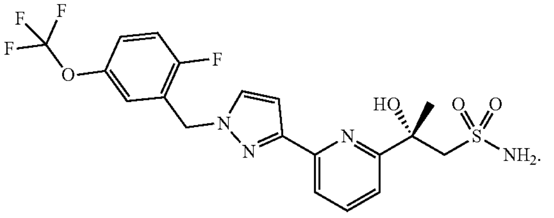 [SMILES: C[C@@](O)(CS(N)(=O)=O)c1cccc(-c2ccn(Cc3cc(OC(F)(F)F)ccc3F)n2)n1]

Embodiment 30. A compound of formula (I) according to embodiment 1, which is (R)-2-(6-(1-(2-fluoro-5-(trifluoromethoxy)benzyl)-1H-pyrazol-3-yl)pyridin-2-yl)-2-hydroxypropane-1-sulfonamide,

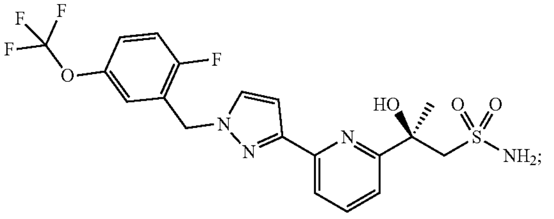 [SMILES: C[C@](O)(CS(N)(=O)=O)c1cccc(-c2ccn(Cc3cc(OC(F)(F)F)ccc3F)n2)n1]

or a pharmaceutically acceptable salt thereof.

Embodiment 31. A compound of formula (I) according to embodiment 1, which is 2-(4-chloro-3-(2-(2-fluoro-5-(trifluoromethoxy)benzyl)-2H-tetrazol-5-yl)phenyl)-2-hydroxypropane-1-sulfonamide,

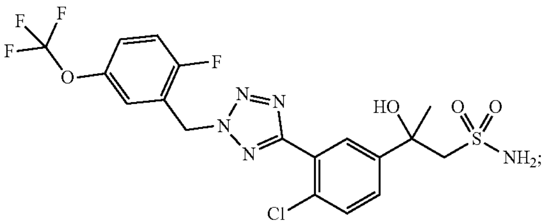

or a pharmaceutically acceptable salt thereof.

Embodiment 32. A compound of formula (I) according to embodiment 1, or a pharmaceutically acceptable salt thereof, which is selected from the group consisting of:

(R)-2-(4-chloro-3-(2-(2-fluoro-5-(trifluoromethoxy)benzyl)-2H-tetrazol-5-yl)phenyl)-2-hydroxypropane-1-sulfonamide:

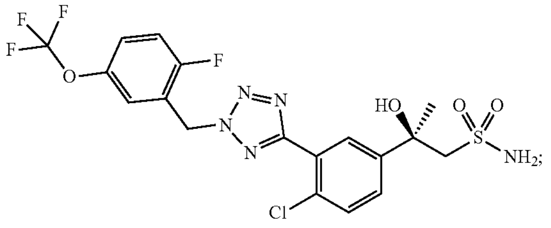 [SMILES: C[C@](O)(CS(N)(=O)=O)c1ccc(Cl)c(-c2nnn(Cc3cc(OC(F)(F)F)ccc3F)n2)c1]

and (S)-2-(4-chloro-3-(2-(2-fluoro-5-(trifluoromethoxy)benzyl)-2H-tetrazol-5-yl)phenyl)-2-hydroxypropane-1-sulfonamide:

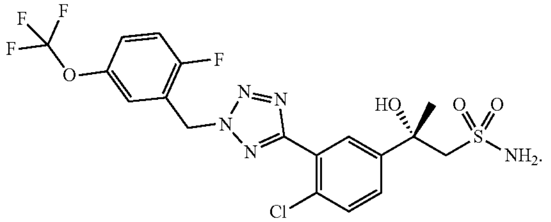 [SMILES: C[C@@](O)(CS(N)(=O)=O)c1ccc(Cl)c(-c2nnn(Cc3cc(OC(F)(F)F)ccc3F)n2)c1]

Embodiment 33. A compound of formula (I) according to embodiment 1, which is (R)-2-(4-chloro-3-(2-(2-fluoro-5-(trifluoromethoxy)benzyl)-2H-tetrazol-5-yl)phenyl)-2-hydroxypropane-1-sulfonamide,

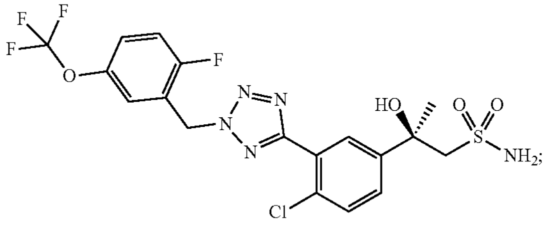 [SMILES: C[C@](O)(CS(N)(=O)=O)c1ccc(Cl)c(-c2nnn(Cc3cc(OC(F)(F)F)ccc3F)n2)c1]

or a pharmaceutically acceptable salt thereof.

Depending on the choice of the starting materials and procedures, the compounds can be present in the form of one of the possible stereoisomers or as mixtures thereof, for example as pure optical isomers, or as stereoisomeric mixtures, such as racemates and mixtures of diastereomers, depending on the number of asymmetric centers. The present disclosure is meant to include all such possible stereoisomers, including racemic mixtures, diastereomeric mixtures and optically pure forms. Optically active (R)- and (S)-stereoisomers may be prepared using chiral synthons or chiral reagents or resolved using conventional techniques. All tautomeric forms are also intended to be included.

In some embodiments, there is provided a compound of the Examples wherein the compound has one chiral carbon atom as an isolated stereoisomer wherein the stereoisomer is in the (R) configuration. In some embodiments, there is provided a compound of the Examples wherein the compound has one chiral carbon atom as an isolated stereoisomer wherein the stereoisomer is in the (S) configuration. In some embodiments, there is provided a compound of the Examples wherein the compound has two chiral carbon atoms as an isolated stereoisomer wherein the stereoisomer is in the (R,R) configuration. In some embodiments, there is provided a compound of the Examples wherein the compound has two chiral carbon atoms as an isolated stereoisomer wherein the stereoisomer is in the (R,S) configuration. In some embodiments, there is provided a compound of the Examples wherein the compound has two chiral carbon atoms as an isolated stereoisomer wherein the stereoisomer is in the (S,S) configuration. In some embodiments, there is provided a compound of the Examples wherein the compound has two chiral carbon atoms as an isolated stereoisomer wherein the stereoisomer is in the (S,R) configuration.

Terms not specifically defined herein should be given the meanings that would be given to them by one of skill in the art in light of the disclosure and the context. For purposes of interpreting this specification, the following definitions will apply unless specified otherwise and whenever appropriate, terms used in the singular will also include the plural and vice versa.

The terms "halo" and "halogen", as used herein, means halogen and includes chlorine (Cl), fluorine (F), bromine (Br), and iodine (I).

A "$C_{1-4}$-alkyl" group is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl n-butyl, sec-butyl, tert-butyl, pentyl hexyl, pentyl and octyl. A $C_1$-$C_4$ straight chained or branched alkyl group is also referred to as a "lower alkyl" group. An "alkylene" group is a divalent straight chained or branched non-aromatic hydrocarbon which is completely saturated. Typically, a divalent straight chained or branched alkylene group has from 1 to about 20 carbon atoms, preferably from 1 to about 10 unless otherwise defined Examples of divalent straight chained and branched alkylene groups include methylene, ethylene, n-propylene, iso-propylene, n-butylene, sec-butylene, tert-butylene, pentylene, hexylene, pentylene and octylene.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc.

The term "alkoxy", as used herein, refers to an alkyl group as defined herein, preferably a lower alkyl group, having an oxygen attached thereto, e.g., —O—$C_{1-4}$alkyl. Representative alkoxy groups include, but are not limited to, methoxy, ethoxy, propoxy, tert-butoxy and the like. Representative substituted alkoxy groups include, but are not limited to, —$OCF_3$ and the like.

A "cycloalkyl" group is a cyclic hydrocarbon which is completely saturated. "Cycloalkyl" includes monocyclic and bicyclic rings. Typically, a monocyclic cycloalkyl group has from 3 to 10 carbon atoms, more typically from 3 to 8 carbon atoms, preferably from 3 to 6 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heteroatom" as used herein means an atom of any element other than carbon or hydrogen. Preferred heteroatoms are nitrogen (N), oxygen (O), and sulfur (S).

The term "optionally substituted" means that a given chemical moiety (e.g., an alkyl group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen, wherein the substituents are as defined herein. "Optionally substituted" as used herein also refers to substituted or unsubstituted whose meaning is described herein.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the terms "salt" or "salts" refers to an acid addition salt of a compound of the present disclosure. "Salts" include in particular "pharmaceutical acceptable salts". The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid salts by virtue of the presence of amino groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present disclosure provides compounds of the present disclosure in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

In another aspect, the disclosure provides a compound of formula (V'):

(V')

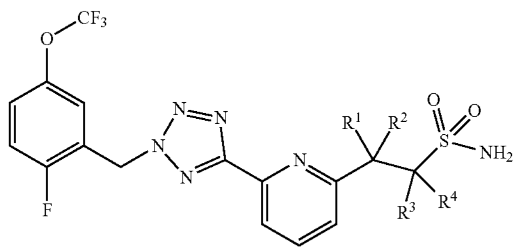

or a pharmaceutically acceptable salt thereof, wherein $R^1$ is selected from OH, OD, $CH_3$, $CHD_2$, $CH_2D$ and $CD_3$;

$R^2$ is selected from H, D, $CH_3$, $CHD_2$, $CH_2D$, $CD_3$, $CH_2CH_3$, $CHDCH_3$, $CD_2CH_3$, $CHDCHD_2$, $CHDCCH_2D$, $CHDCD_3$, $CD_2CHD_2$, $CD_2CCH_2D$, $CD_2CD_3$ and $CF_3$;

$R^3$ is selected from H, D, $CH_3$, $CHD_2$, $CH_2D$ and $CD_3$;

$R^4$ is selected from H, D, $CH_3$, $CHD_2$, $CH_2D$ and $CD_3$, $CH_2OH$, CHDOH, $CD_2OH$, $CH_2OD$, CHDOD and $CD_2OD$, wherein D is deuterium, and provided that there is at least one deuterium present in the compound.

In other embodiments, there are multiple deuterium atoms present in the compound of formula (V').

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present disclosure. The concentration of deuterium may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the disclosure include isotopes of hydrogen, carbon, nitrogen, fluorine, and chlorine, such as $^3H$, $^{11}C$, $^{13}C$, $^{14}C$ $^{15}N$, $^{18}F$ $^{36}Cl$, respectively. Accordingly, it should be understood that the disclosure includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of the present disclosure can generally be prepared by conventional techniques known to those skilled in the art or by processes analogous to those described in the accompanying Examples and Preparations using an appropriate isotopically-labeled reagent in place of the non-labeled reagent previously employed.

As used herein, the term "pharmaceutical composition" refers to a compound of the disclosure, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present disclosure refers to an amount of the compound of the present disclosure that will elicit the biological or medical response of a subject, for example, modulation, reduction, blockage or inhibition of an enzyme or a protein activity, or ameliorate symptoms, alleviate conditions, slow or delay disease progression, or prevent a disease, etc. In some embodiments, the term "a therapeutically effective amount" refers to the amount of the compound of the present disclosure that, when administered to a subject, is effective to (1) at least partially alleviate, prevent and/or ameliorate a condition, or a disorder or a disease (i) mediated by Nav1.5, or (ii) associated with Nav1.5 activity, or (iii) characterized by activity (normal or abnormal) of Nav1.5; or (2) modulated, reduce, block, or inhibit the activity of Nav1.5; or (3) reduce or inhibit the expression of Nav1.5. In another embodiment, the term "a therapeutically effective amount" refers to the amount of the compound of the present disclosure that, when administered to a cell, or a tissue, or a non-cellular biological material, or a medium, is effective to at least partially modulate, reduce, block, or inhibit the activity of Nav1.5; or at least partially reduce or inhibit the expression of Nav1.5.

As used herein, the term "subject" refers to primates (e.g., humans, male or female), dogs, rabbits, guinea pigs, pigs, rats, and mice. In certain embodiments, the subject is a primate. In yet other embodiments, the subject is a human.

As used herein, the term "sodium channel Nav1.5," "sodium channel protein type 5 subunit alpha," "SCN5A," or "Nav1.5" refers to a membrane protein as a part of tetrodotoxin-resistant voltage-gated sodium channel subunit. The sodium channel Nav1.5 is integrated in a membrane and primarily present or expressed in cardiac muscle cells (cardiomyocytes), and plays a crucial role for the upstroke of action potential and excitation of cardiomyocytes. The sodium channel Nav1.5 is encoded by SCN5A, for example, which may be encoded in human SCN5A gene (e.g., NCBI Reference Sequence: NC_000003.12; NCBI_Gene:6331; or UniProtKB: Q14524), variants or mutants thereof, but the examples of SCN5A gene are not limited thereto.

As used herein, the terms "modulate", "modulation", "modulating", "inhibit", "inhibition", "inhibiting", "block", "blocker", "blocking", refers to the change, reduction, or suppression of a given condition, symptom, or disorder, or disease, or a significant change or significant decrease in the baseline activity of a biological activity or process.

As used herein, "activity of Nav1.5" refers to the ability of the Nav1.5 channel to permit sodium current flow. Modulating, reducing, blocking, or inhibiting Nav1.5 activity thus modulates, reduces, blocks, or inhibits Nav1.5 dependent sodium current flow, typically in a reversable and dose-dependent manner.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, a subject is "in need of" a treatment if such subject would benefit biologically, medically or in quality of life from such treatment.

As used herein, the term "a," "an," "the" and similar terms used in the context of the present disclosure (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g., or "such as") provided herein is intended merely to better illuminate the disclosure and does not pose a limitation on the scope of the disclosure otherwise claimed.

Any asymmetric atom (e.g., carbon or the like) of the compound(s) of the present disclosure can be present in racemic or enantiomerically enriched, for example the (R)-, (S)- or (R,S)—configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Accordingly, as used herein a compound of the present disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present disclosure or racemic intermediates can also be resolved by chiral chromatography, e.g., high pressure liquid chromatography (HPLC) using a chiral adsorbent.

Solid Forms

The compounds of the present disclosure, or pharmaceutically acceptable salts thereof, may under appropriate conditions be isolated in one or more crystalline forms. The term "crystalline form" as used herein refers to anhydrous crystalline forms, hydrate crystalline forms, solvate crystalline forms or mixtures of crystalline forms.

The term "about" as used herein is understood as within a range of normal tolerance in the art, for example within 2 standard deviations of the mean. For example, "about" can be understood as within 15%, 10%, 9%, 8%, 7%, 6%, 5%, 4%, 3%, 2%, 1%, 0.5%, 0.1%, 0.05%, or 0.01% of the stated numbers, values, and/or expressions referring to quantities of ingredients, ratio, reaction conditions, and formulations, etc.

The term "hydrate" as used herein refers to a crystalline form containing one or more water molecules in a three-dimensional periodic arrangement. It can include non-stoichiometric hydrates or stoichiometric hydrates, such as hemihydrates, monohydrates, dihydrates and trihydrates.

The term "anhydrous" as used herein refers to a crystalline form free from water in a three-dimensional periodic arrangement.

The term "solvate" as used herein refers to a crystalline form containing one or more solvent molecules other than water in a three-dimensional periodic arrangement. The solvate may comprise either a stoichiometric or non-stoichiometric amount of the solvent molecules.

In some embodiments, the compounds of formula (I) or pharmaceutically acceptable salts thereof according to the present disclosure may inherently or by design form hydrates or solvates with pharmaceutically acceptable solvents.

In some embodiments, the compounds of the present disclosure that contain groups capable of acting as donors and/or acceptors for hydrogen bonds may be capable of forming co-crystalline forms with suitable co-crystal formers.

The terms "co-crystalline" and "co-crystal" are used herein interchangeably to mean a co-crystal comprising a compound of the present disclosure and a suitable co-crystal former. These co-crystals may be prepared from compounds of formula (I) or pharmaceutically acceptable salts thereof by known co-crystal forming procedures such as, e.g., grinding, heating, co-subliming, co-melting, or contacting in solution compounds of formula (I) or pharmaceutically acceptable salts thereof with a co-crystal former under crystallization conditions and isolating co-crystals thereby formed. Suitable co-crystal formers include, for instance, those described in WO 2004/078163.

In some embodiments, the present disclosure provides a co-crystal comprising a compound of the present disclosure, or a pharmaceutically acceptable salt thereof, and a co-crystal former.

In some embodiments, the present disclosure provides a co-crystal comprising a compound of the present disclosure, or a pharmaceutically acceptable salt thereof, and L-proline.

The molar ratio of the compound of the present disclosure, or a pharmaceutically acceptable salt thereof, to the co-crystal former in the co-crystals according to the present disclosure may be stoichiometric or non-stoichiometric. For example, suitable molar ratios of the compound of the present disclosure, or a pharmaceutically acceptable salt thereof, to the co-crystal former in the co-crystals according to the present disclosure are of from about 1:3 to about 3:1, or from about 1:2 to about 2:1, or from about 1.5:1 to about 1:1.5, or about 1:1.

In some embodiments, the present disclosure provides a co-crystal comprising a compound of the present disclosure and L-proline, wherein the molar ratio of the compound of the present disclosure to L-proline is of from about 1:3 to about 3:1, or from about 1:2 to about 2:1, or from about 1.5:1 to about 1:1.5, or about 1:1.

In some embodiments, a crystalline form of the compound of the present disclosure, or a pharmaceutically acceptable salt thereof, is provided in substantially pure form. As used herein, "substantially pure," when used in reference to a crystalline form, means a compound having a purity greater than 90% by weight, including greater than 90, 91, 92, 93, 94, 95, 96, 97, 98, and 99% by weight, and also including equal to about 100% by weight of a compound of the present disclosure, or a pharmaceutically acceptable salt thereof, based on the weight of the compound. The remaining material comprises other form(s) of the compound of the present disclosure, and/or reaction impurities and/or processing impurities arising from its preparation. For example, a crystalline form of a compound of the present disclosure, or a pharmaceutically acceptable salt thereof, may be deemed substantially pure in that it has a purity greater than 90% by weight, as measured by means that are at this time known and generally accepted in the art, where the remaining less than 10% by weight of material comprises other form(s) of the compound of the present disclosure and/or reaction impurities and/or processing impurities.

A particular crystalline form of the compound of the present disclosure, or a pharmaceutically acceptable salt thereof, may be referred to as "crystalline form X", "crystal form X", "co-crystal form", "polymorph form X", "modification X", or "HX" where 'X' is the letter which is assigned to that particular crystalline form. The names used herein to characterize a specific crystalline form, e.g. "A-1" etc., should not be considered limiting with respect to any other substance possessing similar or identical physical and chemical characteristics, but rather it should be understood that these designations are mere identifiers that should be interpreted according to the characterization information also presented herein.

In some embodiments, the present disclosure relates to a crystalline form of a compound of the present disclosure, or a pharmaceutically acceptable salt thereof, wherein the crystalline form is selected from the various modifications detailed herein, for example, Modifications A-1, A-2, and A-3 disclosed herein.

Each modification is characterized by its X-ray powder diffraction pattern with peaks as essentially depicted in the Figures. Thus, there is provided a crystalline form selected from the various modifications detailed herein, characterized in that said crystalline form has an X-ray powder diffraction pattern substantially in accordance with that shown in the corresponding Figure.

In further embodiments, the present disclosure provides any of the crystalline forms of the compound of the present disclosure, or a pharmaceutically acceptable salt thereof, as described in the Examples, in the form of a specific modification, characterized in that said crystalline form has at least one of the following characteristics:

(a) an X-ray powder diffraction pattern substantially in accordance with that shown in the Figure associated with that particular Modification; and/or
(b) a melting point, as set out for each Modification in the Examples section; and/or
(c) a differential scanning calorimetry thermogram, as set out for each Modification in the Examples section.

In one embodiment of the present disclosure, there is provided a co-crystal form comprising (R)-2-(6-(2-(2-fluoro-5-(trifluoromethoxy)benzyl)-2H-tetrazol-5-yl)pyridin-2-yl)-2-hydroxypropane-1-sulfonamide and L-proline, hereinafter referred to as Modification A-1, wherein the molar ratio of (R)-2-(6-(2-(2-fluoro-5-(trifluoromethoxy)benzyl)-2H-tetrazol-5-yl)pyridin-2-yl)-2-hydroxypropane-1-sulfonamide to L-proline is about 1:1, characterized in that said co-crystal form has an X-ray powder diffraction pattern substantially in accordance with that shown in FIG. 1, or comprises four or more peaks at 2θ angles (±0.2 degree), when measured using a CuKa radiation with a wavelength of 1.5418 Å at a temperature of about 22° C., selected from the 2θ angles as set forth in Table 1A:

TABLE 1A

| No. | Angle 2θ | d value Å | Relative Intensity % |
|---|---|---|---|
| 1 | 6.8 | 13.0 | 11.9 |
| 2 | 8.0 | 11.0 | 42.6 |
| 3 | 10.2 | 8.6 | 16.9 |
| 4 | 10.6 | 8.4 | 30.5 |
| 5 | 11.3 | 7.8 | 100.0 |
| 6 | 12.1 | 7.3 | 14.6 |
| 7 | 15.4 | 5.7 | 59.8 |
| 8 | 16.1 | 5.5 | 13.2 |
| 9 | 17.2 | 5.2 | 95.9 |
| 10 | 18.0 | 4.9 | 49.1 |
| 11 | 18.7 | 4.7 | 28.9 |
| 12 | 19.1 | 4.6 | 65.1 |
| 13 | 20.2 | 4.4 | 87.3 |
| 14 | 21.4 | 4.1 | 13.9 |
| 15 | 23.9 | 3.7 | 13.3 |
| 16 | 26.0 | 3.4 | 15.0 |

Preferably, the co-crystal form of Modification A-1 has an X-ray powder diffraction pattern substantially in accordance with that shown in FIG. 1, or comprises four or more peaks at 2θ angles (±0.2 degree), when measured using a CuKa radiation with a wavelength of 1.5418 Å at a temperature of about 22° C., selected from the 2θ angles as set forth in Table 1B:

TABLE 1B

| No. | Angle 2θ | d value Å | Relative Intensity % |
|---|---|---|---|
| 5 | 11.3 | 7.8 | 100.0 |
| 7 | 15.4 | 5.7 | 59.8 |
| 9 | 17.2 | 5.2 | 95.9 |
| 12 | 19.1 | 4.6 | 65.1 |
| 13 | 20.2 | 4.4 | 87.3 |

The co-crystal form of Modification A-1 is usually provided as an anhydrous co-crystal form.

In another embodiment of the present disclosure, there is provided a co-crystal form comprising (R)-2-(6-(2-(2-fluoro-5-(trifluoromethoxy)benzyl)-2H-tetrazol-5-yl)pyridin-2-yl)-2-hydroxypropane-1-sulfonamide and L-proline, hereinafter referred to as Modification A-2, wherein the molar ratio of (R)-2-(6-(2-(2-fluoro-5-(trifluoromethoxy)benzyl)-2H-tetrazol-5-yl)pyridin-2-yl)-2-hydroxypropane-1-sulfonamide to L-proline is about 1:2.9, characterized in that said co-crystal form has an X-ray powder diffraction pattern substantially in accordance with that shown in FIG. 4, or comprises four or more peaks at 2θ angles (±0.2 degree), when measured using a CuKa radiation with a wavelength of 1.5418 Å at a temperature of about 22° C., selected from the 2θ angles as set forth in the Table 1C:

TABLE 1C

| No. | Angle 2θ | d value Å | Relative Intensity % |
|---|---|---|---|
| 1 | 5.5 | 16.0 | 21.7 |
| 2 | 8.7 | 10.2 | 38.0 |
| 3 | 9.4 | 9.4 | 12.5 |
| 4 | 11.1 | 8.0 | 32.1 |
| 5 | 12.7 | 7.0 | 9.0 |
| 6 | 15.3 | 5.8 | 19.2 |
| 7 | 16.6 | 5.3 | 95.8 |
| 8 | 17.2 | 5.1 | 53.2 |
| 9 | 18.8 | 4.7 | 100.0 |
| 10 | 19.2 | 4.6 | 60.9 |
| 11 | 20.1 | 4.4 | 31.6 |
| 12 | 21.7 | 4.1 | 39.3 |
| 13 | 22.2 | 4.0 | 59.7 |
| 14 | 25.3 | 3.5 | 10.8 |
| 15 | 26.2 | 3.4 | 22.7 |
| 16 | 28.7 | 3.1 | 11.4 |
| 17 | 30.8 | 2.9 | 17.5 |

Figure 4:
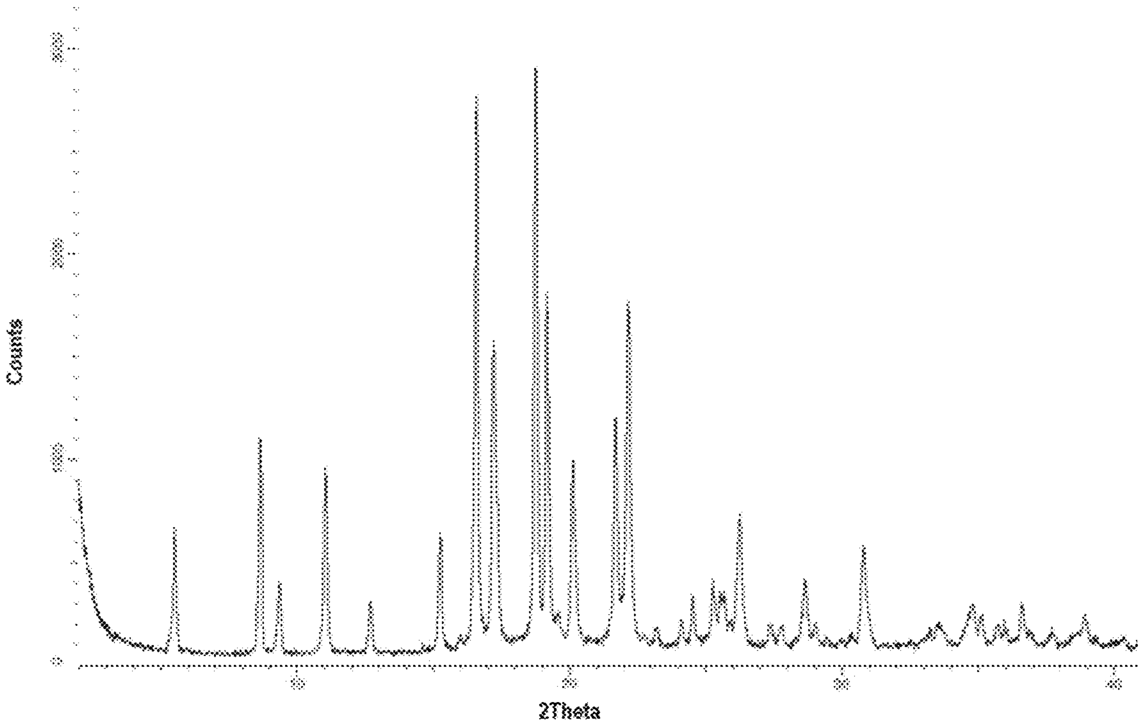
FIG. 4 shows the X-ray powder diffraction pattern of Modification A-2.

Preferably, the co-crystal form of Modification A-2 has an X-ray powder diffraction pattern substantially in accordance with that shown in FIG. 4, or comprises four or more peaks at 2θ angles (±0.2 degree), when measured using a CuKa radiation with a wavelength of 1.5418 Å at a temperature of about 22° C., selected from the 2θ angles as set forth in the Table 1D:

TABLE 1D

| No. | Angle 2θ | d value Å | Relative Intensity % |
|---|---|---|---|
| 7 | 16.6 | 5.3 | 95.8 |
| 8 | 17.2 | 5.1 | 53.2 |
| 9 | 18.8 | 4.7 | 100.0 |
| 10 | 19.2 | 4.6 | 60.9 |
| 13 | 22.2 | 4.0 | 59.7 |

The co-crystal form of Modification A-2 is usually provided as a monohydrate co-crystal form.

In another embodiment of the present disclosure, there is provided a crystalline form of hydrochloride salt of (R)-2-(6-(2-(2-fluoro-5-(trifluoromethoxy)benzyl)-2H-tetrazol-5-yl)pyridin-2-yl)-2-hydroxypropane-1-sulfonamide, hereinafter referred to as Modification A-3, characterized in that said crystalline form has an X-ray powder diffraction pattern substantially in accordance with that shown in FIG. 7, or comprises four or more peaks at 2θ angles (±0.2 degree), when measured using a CuKa radiation with a wavelength of 1.5418 Å at a temperature of about 22° C., selected from the 2θ angles as set forth in Table 1E:

TABLE 1E

| No. | Angle 2θ | d value Å | Relative Intensity % |
|---|---|---|---|
| 1 | 7.5 | 11.7 | 21.0 |
| 2 | 11.2 | 7.9 | 9.0 |
| 3 | 14.3 | 6.2 | 100.0 |
| 4 | 15.5 | 5.7 | 5.9 |
| 5 | 16.6 | 5.3 | 2.4 |
| 6 | 17.9 | 5.0 | 3.5 |
| 7 | 18.5 | 4.8 | 32.6 |
| 8 | 19.1 | 4.6 | 27.0 |
| 9 | 20.0 | 4.4 | 39.0 |
| 10 | 20.4 | 4.4 | 3.1 |
| 11 | 21.4 | 4.1 | 4.5 |
| 12 | 22.5 | 4.0 | 3.0 |
| 13 | 22.8 | 3.9 | 3.5 |
| 14 | 23.9 | 3.7 | 32.2 |
| 15 | 28.8 | 3.1 | 13.9 |

Figure 7:
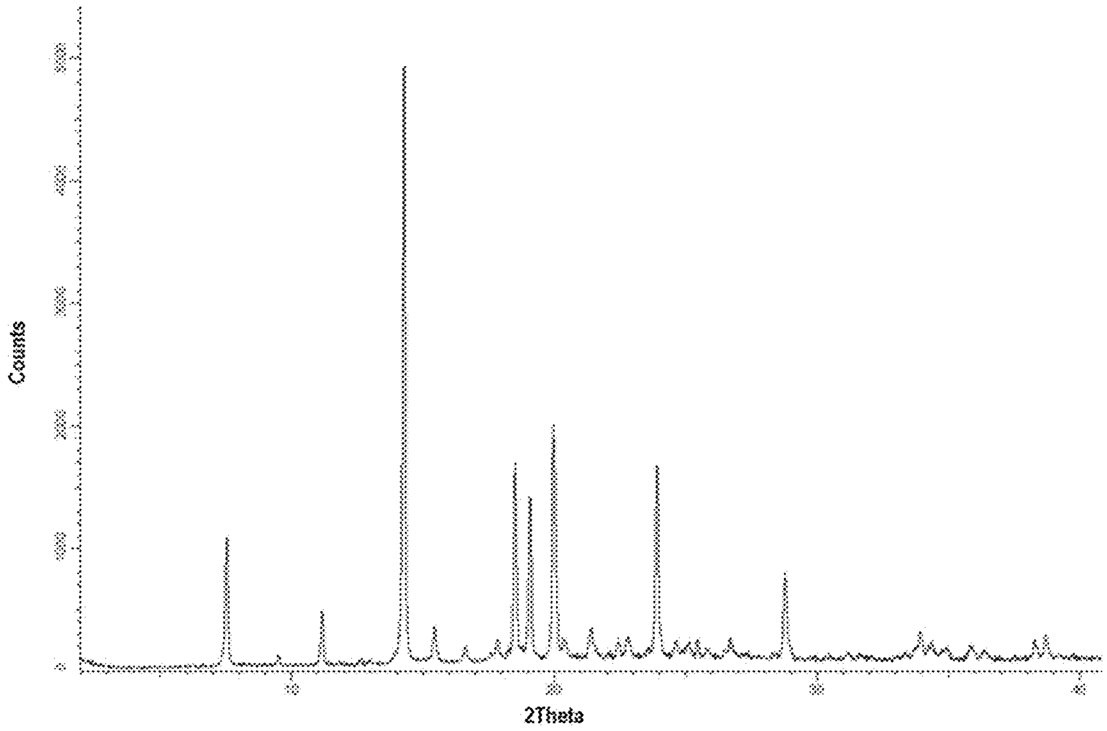
FIG. 7 shows the X-ray powder diffraction pattern of Modification A-3.

Preferably, the crystalline form of Modification A-3 has an X-ray powder diffraction pattern substantially in accordance with that shown in FIG. 7, or comprises four or more peaks at 2θ angles (±0.2 degree), when measured using a CuKa radiation with a wavelength of 1.5418 Å at a temperature of about 22° C., selected from the 2θ angles as set forth in Table 1F:

TABLE 1F

| No. | Angle 2θ | d value Å | Relative Intensity % |
|---|---|---|---|
| 3 | 14.3 | 6.2 | 100.0 |
| 7 | 18.5 | 4.8 | 32.6 |
| 8 | 19.1 | 4.6 | 27.0 |
| 9 | 20.0 | 4.4 | 39.0 |
| 14 | 23.9 | 3.7 | 32.2 |

The crystalline form of Modification A-3 is usually provided as a solvate crystalline form.

SYNTHESIS

Compounds of the disclosure may be prepared according to the following schemes, wherein A is N or CH; $R^1$, $R^2$, $R^3$, $R^4$, $R^5$ and $R^6$ are as defined herein supra. $P_1$ and $P_2$ are nitrogen protecting groups, such as 4-methoxybenzyl, or potentially other alkoxybenzyl groups (for example 4-$C_{1-6}$alkoxybenzyl); benzyl; carbamate groups such as tert-butyl carbamate, benzyl carbamate, methyl or ethyl carbamate etc.; diphenyl methyl; triphenyl methyl; or Fmoc (fluorenylmethyloxycarbonyl).

Scheme 1

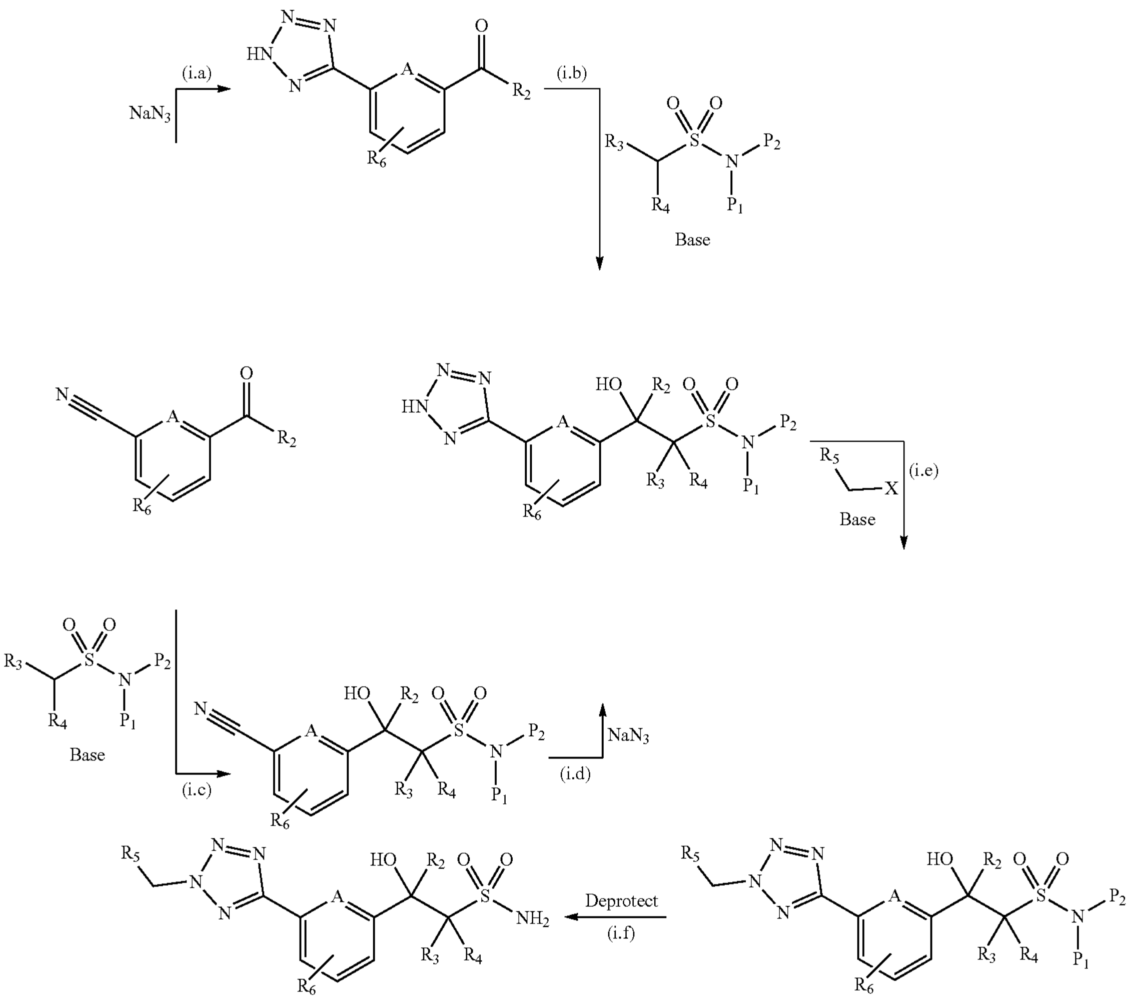

Step (i.a) and (i.d): tetrazole formation is achieved using sodium azide in the presence of triethyl amine-hydrochloride and triethyl amine. As an alternative, trimethylsilyl-azide can be used as the azide source with $Et_3N$—HF.

Step (i.b) and (i.c): carbonyl addition using a sulfonamide anion, typically generated with an alkyl lithium base such as n-BuLi in THF. Alternatively, other strong bases such as s-BuLi, t-BuLi, lithium diisopropylamide, hexamethyldisilazide or other ether solvents can be used.

Step (i.e): alkylation using a benzylic halide (preferably bromide or chloride) is typically carried out in the presence of carbonate base in THF solvent with sodium iodide additive. Alternatively, other benzylic electrophiles, bases and solvents can be used.

Step (i.f): protecting group deprotection under acidic conditions is typically carried out with trifluoroacetic acid in dichloromethane solvent. Alternatively, other acids can be used.

Scheme 2

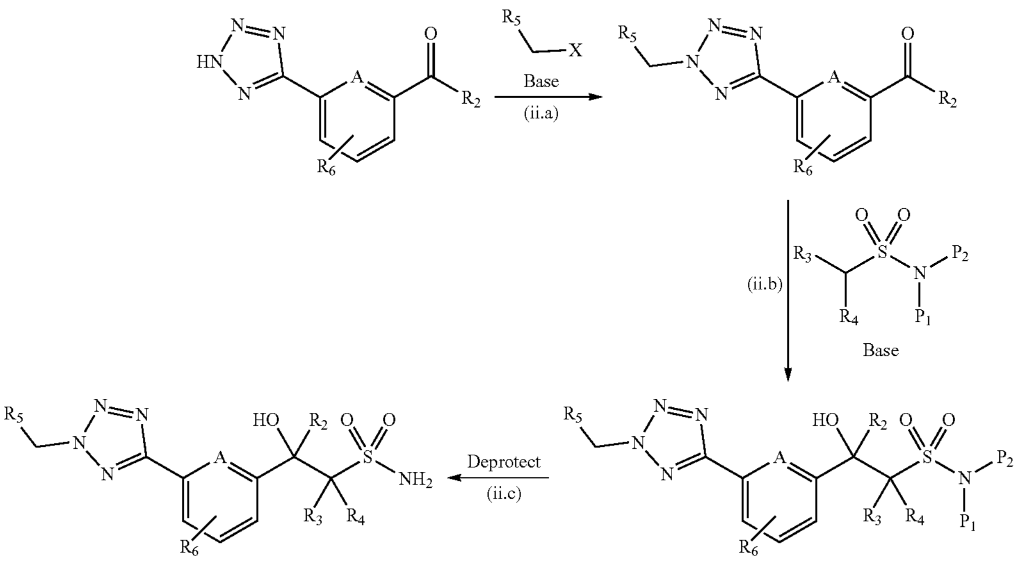

Step (ii.a): Same as Step (i.e).
Step (ii.b): Same as Step (i.b).
Step (ii.c): Same as Step (i.f).

Scheme 3

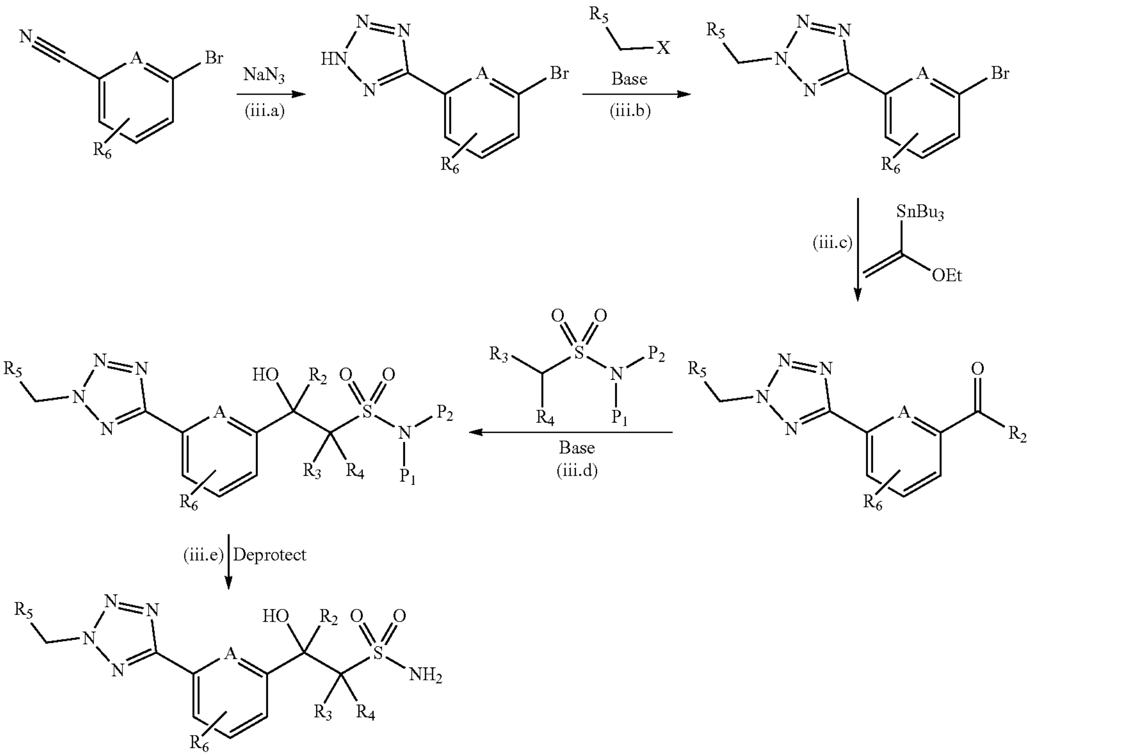

Step (iii.a): Same as Step (i.a).
Step (iii.b): Same as Step (i.e).
Step (iii.c): Stannane cross-coupling using palladium catalysis is typically performed using $Pd(PPh_3)_4$ in toluene at 110° C. followed by treatment with 2N hydrochloric acid in tetrahydrofuran. Alternatively, other palladium catalysts can be used.
Step (iii.d): Same as Step (i.b).
Step (iii.e): Same as Step (i.f).

Scheme 3a

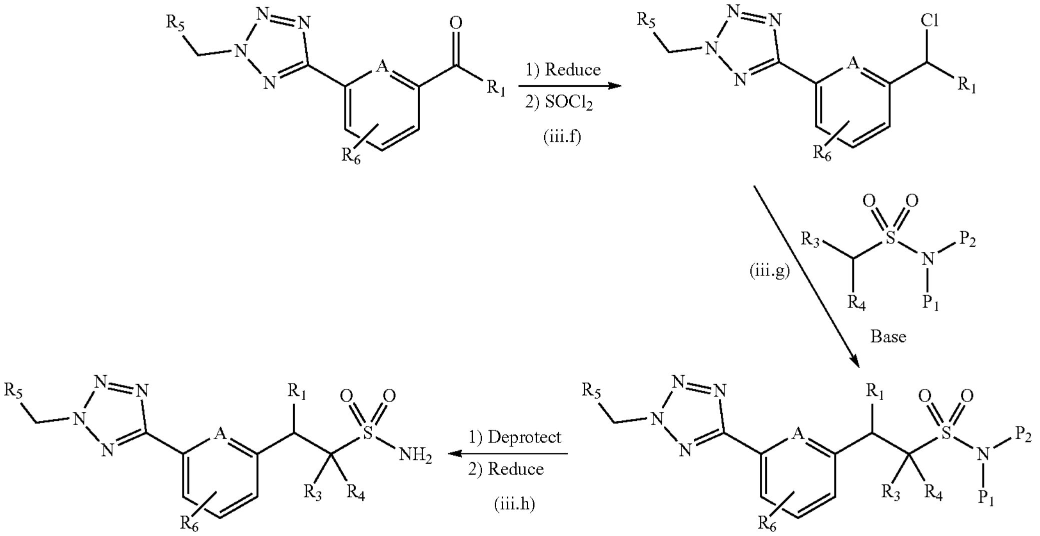

Step (iii.f): 1) ketone reduction is typically performed using sodium borohydride in THF-methanol followed by 2) conversion to chloride using thionyl chloride in dichloromethane. Alternatively, other hydride reagents or other chlorinating reagents (example: oxalyl chloride or phosphorus oxychloride) can be used.

Step (iii.g): $SN_2$ displacement using a sulfamoyl acetate is typically performed using a carbonate base in dimethylformamide solvent with potassium iodide as an additive. Alternatively, other bases and solvents can be used.

Step (iii.h): protecting group deprotection is typically performed using acidic conditions (example: trifluoroacetic acid) followed by ester reduction using a hydride reagent such as lithium borohydride in THF. Alternatively, other hydride reagents or other acid reagents can be used.

Scheme 4

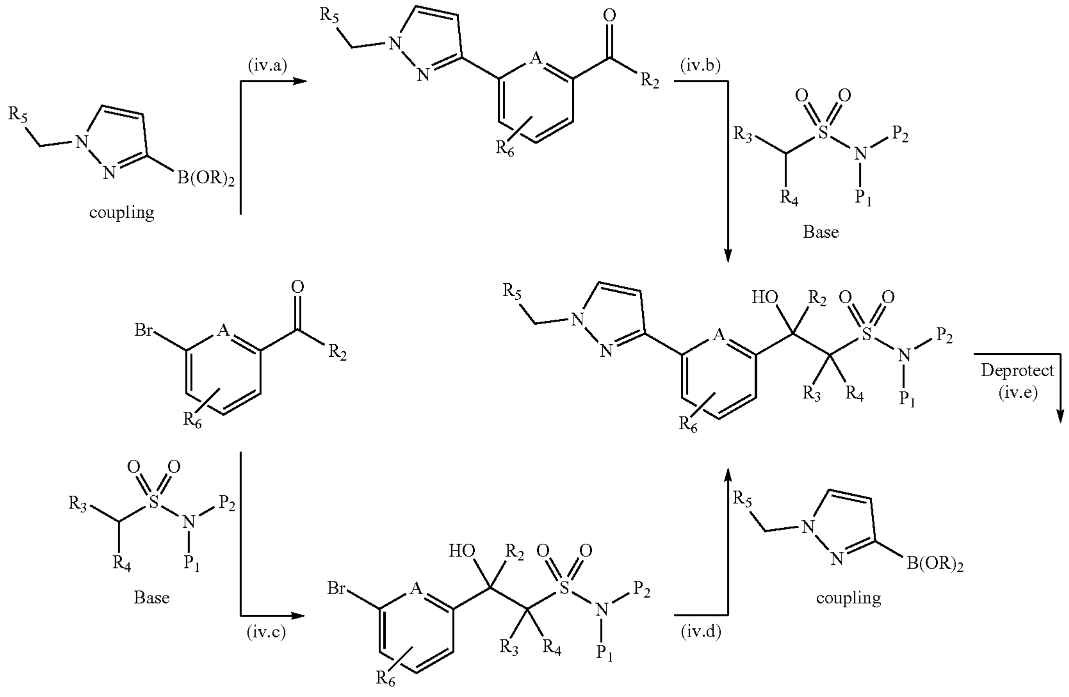

-continued

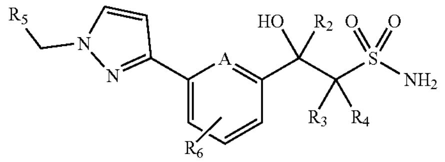

Step (iv.a): boronic ester cross-coupling using palladium catalysis is typically performed using Xphos-Pd-G2 with potassium carbonate base in 1,4-dioxane-water solvent system at 105° C. Alternatively, other palladium catalysts, bases or solvents can be used.
Step (iv.b): Same as Step (i.b).
Step (iv.c): Same as Step (i.b).
Step (iv.d): boronic ester cross-coupling using palladium catalysis is typically performed using Pd(amphos)$Cl_2$ with cesium flouride in 1,4-dioxane-water solvent system at 90° C. Alternatively, other palladium catalysts, bases or solvents can be used.
Step (iv.e): Same as Step (i.f).

Scheme 5

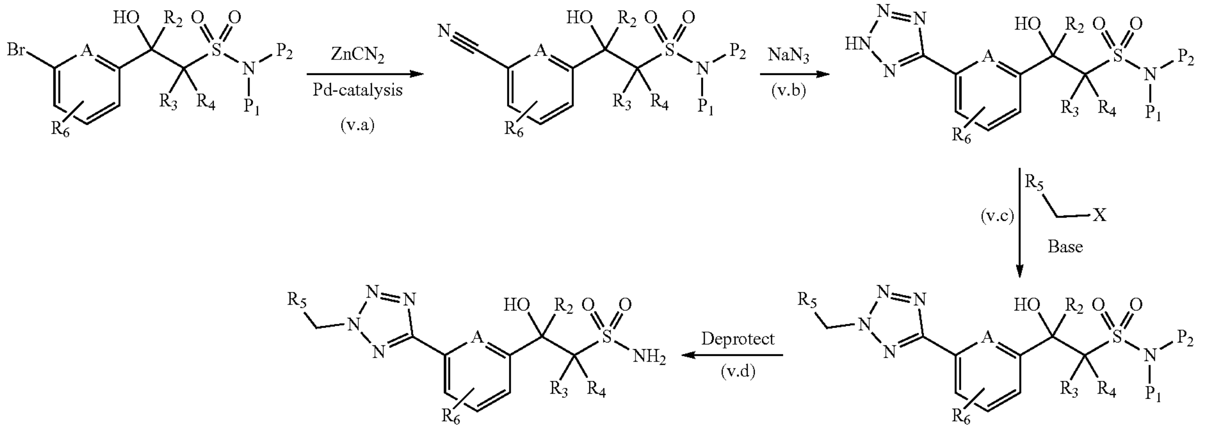

Step (v.a): cyanation of an aryl bromide using palladium catalysis is typically performed using $Zn(CN)_2$ with $Pd(Phh_3)_4$ in dimethylformamide at 110° C. Alternatively, other palladium catalysts can be used.
Step (v.b): Same as Step (i.a).
Step (v.c): Same as Step (v.e).
Step (v.d): Same as Step (i.f).

Scheme 6

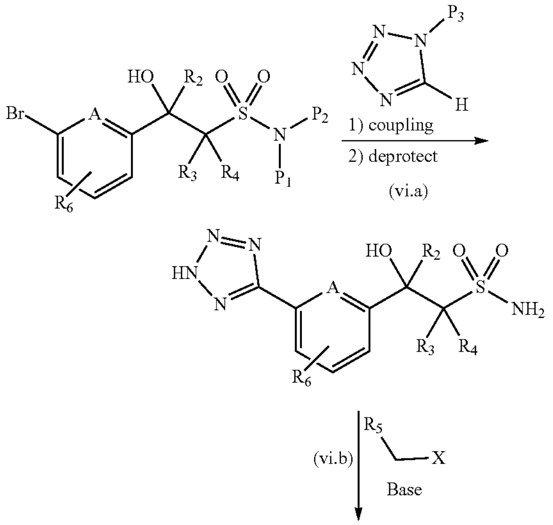

-continued

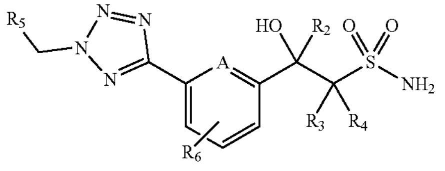

Step (vi.a): CH-tetrazole coupling using palladium catalysis is typically performed using $Pd(Oac)_2$ with DavePhos and Iodo[4,5-bis(diphenylphosphino)-9,9-dimethylxanthene]copper(I), using cesium carbonate as base in acetonitrile as 60° C. Deprotection is typically performed with trifluoroacetic acid in dichloromethane. Alternatively, deprotection could be performed with other acidic reagents.
Step (vi.b): Same as Step (i.e).

Scheme 7

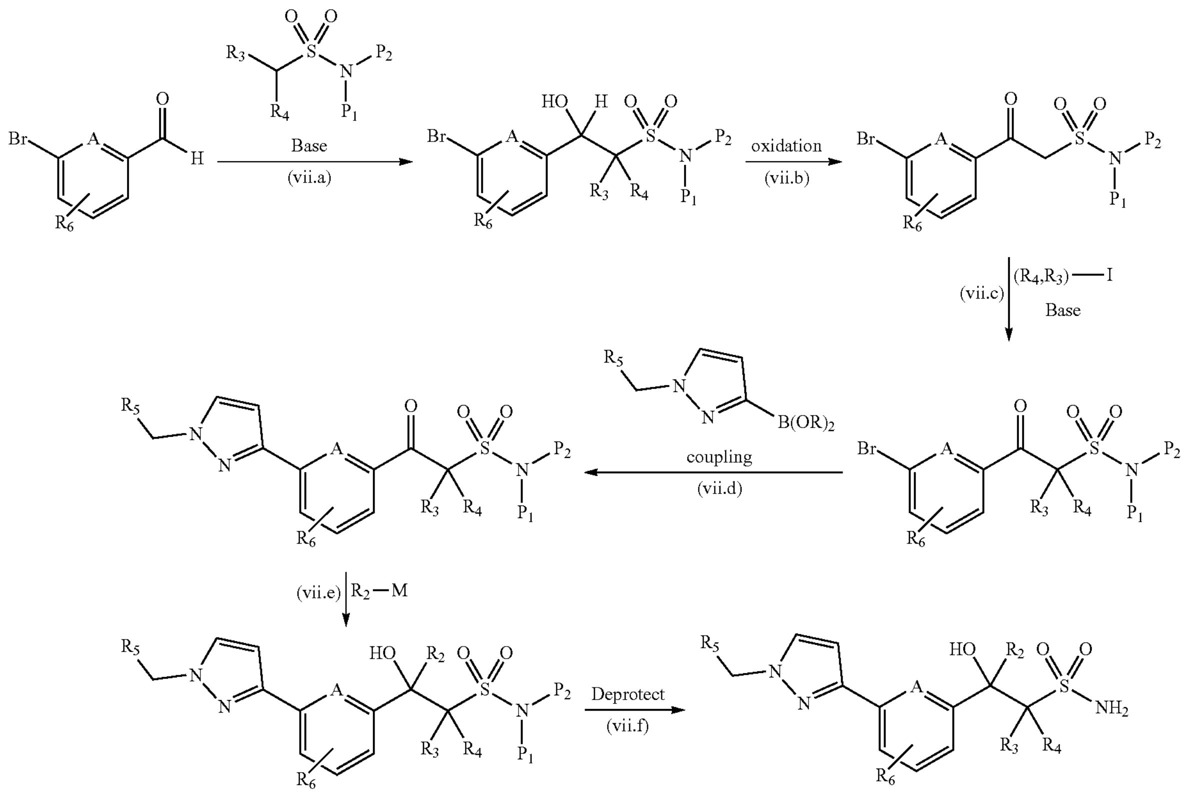

Step (vii.a): Same as Step (i.b).
Step (vii.b): alcohol oxidation is typically performed using an oxidizing agent such as Dess-Martin periodinane. Alternatively, other oxidation agents can be used.
Step (vii.c): CH-alkylation is performed using methyl iodide in the presence of potassium carbonate in dimethylformamide solvent. Alternatively, other alkylating agents, bases or solvents can be used.
Step (vii.d): Same as Step (iv.a).
Step (vii.e): ketone reduction is typically performed with sodium borohydride in methanol. Ketone addition is typically performed with methyl magnesium bromide in ether solvent. Alternatively other hydride reagents or methyl nucleophiles (example: methyl lithium or methyl cuprate) can be used.
Step (vii.f): Same as Step (i.f).

Scheme 8

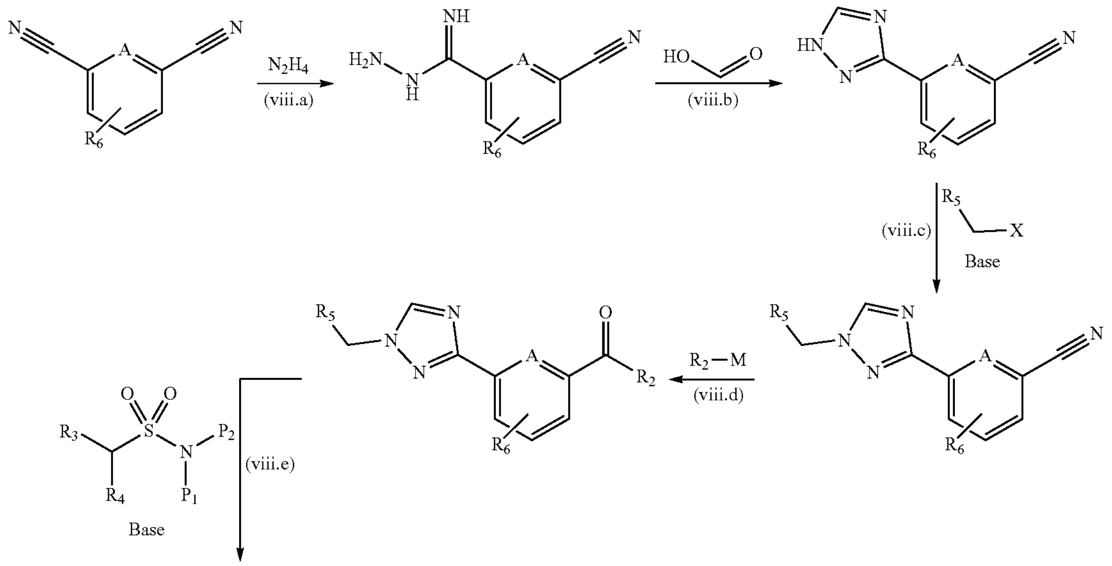

-continued

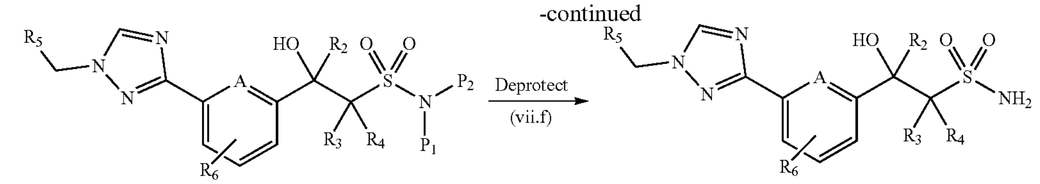

Step (viii.a): addition to nitrile using hydrazine is typically performed using hydrazine-hydrate in ethanol.
Step (viii.b): triazole formation is typically performed using formic acid at 110° C. Alternatively, a trialkyl orthoformate or N,N-dimethylformamide dimethyl acetal could be used.
Step (viii.c): Same as Step (i.e).
Step (viii.d): nitrile addition is typically performed using methyl magnesium bromide in THF at 70° C. Alternatively, methyl lithium or methyl cuprate could be used.
Step (viii.e): Same as Step (i.b).
Step (viii.f): Same as Step (i.f).

Scheme 9

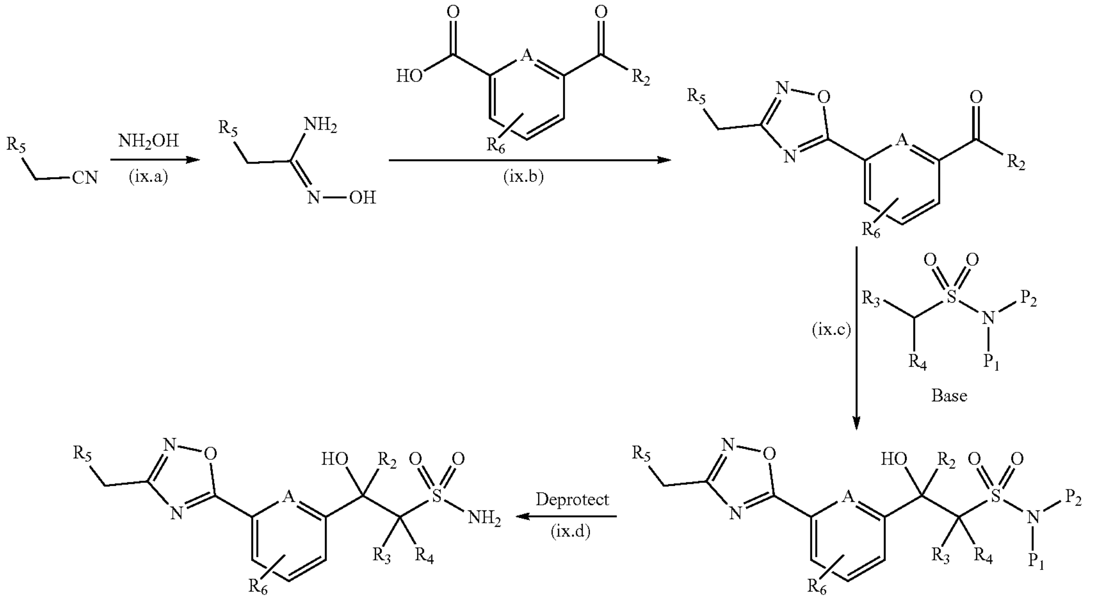

Step (ix.a): nitrile addition is typically performed using hydroxylamine in ethanol.
Step (ix.b): oxadiazole formation is typically performed using propylphosphonic acid anhydride in ethyl acetate. Alternatively, other dehydrating/coupling agents can be used.
Step (ix.c): Same as Step (i.b).
Step (ix.d): Same as Step (i.f).

Scheme 10

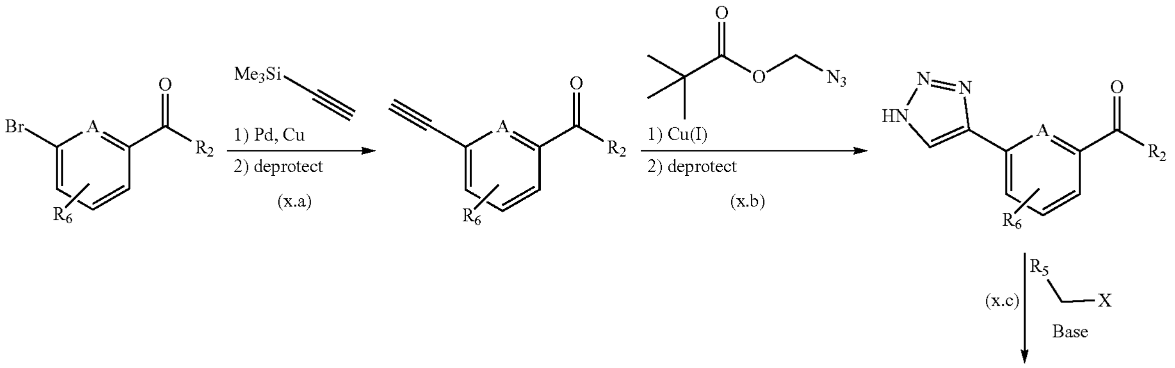

-continued

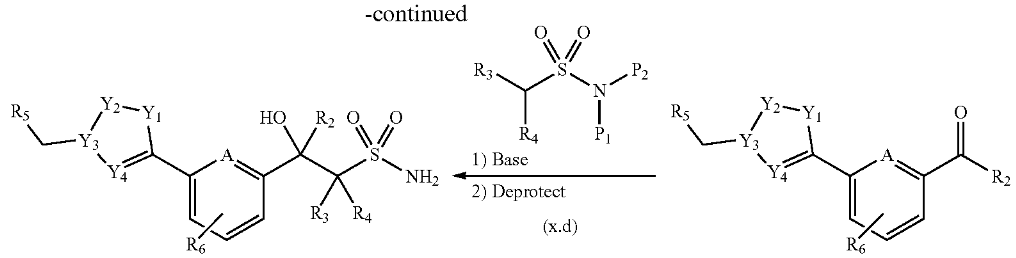

Step (x.a): alkyne cross-coupling is typically performed using a catalysts system of $Pd(PPh_3)_2Cl_2$ and copper (I) iodide with triethylamine base in dimethylformamide solvent. Trimethylsilyl deprotection is typically performed using potassium carbonate in methanol.

Alternatively, other palladium catalysts or copper (I) reagents or solvents can be used.

Step (x.b): triazole formation is typically performed using azidomethyl pivalate with copper (II) sulfate-pentahydrate and sodium ascorbate in t-butanol-water solvent. Deprotection is typically performed using hydroxide base in methanol.

Step (x.c): Same as Step (i.e).

Step (x.d): Same as Step (i.b) and Step (i.f).

The disclosure further includes any variant of the present processes, in which an intermediate obtainable at any stage thereof is used as starting material and the remaining steps are carried out, or in which the starting materials are formed in situ under the reaction conditions, or in which the reaction components are used in the form of their salts or optically pure material. Compounds of the present disclosure and intermediates can also be converted into each other according to methods generally known to those skilled in the art.

In another aspect, the present disclosure provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g., by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Methods of Use

The compounds of the present disclosure in free form or in pharmaceutically acceptable salt form, exhibit valuable pharmacological properties, for example, Nav1.5 modulating properties, as indicated in the in vitro tests as provided herein, and are therefore indicated for therapy related to modulation of Nav1.5, or for use as research chemicals, e.g., as tool compounds.

Compounds of the present disclosure may be useful in the treatment or prevention of a disease, disorder, or condition selected from long QT syndrome (LQTS) (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia. Suitably, compounds of the present disclosure may be useful in the treatment or prevention of atrial fibrillation.

Thus, as a further aspect, the present disclosure provides the use of a compound of the present disclosure (in particular according to any one of embodiments 1 to 33, in particular any one of embodiments 17 to 33, more particularly any one of embodiments 20, 23, 26, 29, and 33), or a pharmaceutically acceptable salt thereof, in therapy. In an embodiment, the therapy is treatment of a disease, disorder, or condition by modulating, reducing, blocking, or inhibiting Nav1.5 activity. In another embodiment, the disease, disorder, or condition is selected from long QT syndrome (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia, suitably atrial fibrillation. In a further embodiment there is provided use of a compound, or a pharmaceutically acceptable salt thereof, according to any one of previous embodiments 1 to 33 (in particular any one of embodiments 17 to 33, more particularly, any one of embodiments 20, 23, 26, 29, and 33), for the treatment or prevention of atrial fibrillation.

Thus, as a further aspect, the present disclosure provides a compound of the present disclosure (in particular according to any one of embodiments 1 to 33, in particular any one of embodiments 17 to 33, more particularly any one of embodiments 20, 23, 26, 29, and 33), or a pharmaceutically acceptable salt thereof, for use in therapy. In an embodiment, the therapy is treatment or prevention of a disease, disorder, or condition by modulating, reducing, blocking, or inhibiting Nav1.5 activity. In another embodiment, the therapy is treatment or prevention of a disease, disorder, or condition selected from long QT syndrome (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia, suitably atrial fibrillation. Thus, as a further embodiment there is provided a compound, or a pharmaceutically acceptable salt thereof, according to any one of previous embodiments 1 to 33 (in particular any one of embodiments 17 to 33, more particularly any one of embodiments 20, 23, 26, 29, and 33), for use in the treatment or prevention of long QT syndrome (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia. In a further embodiment there is provided a compound, or a pharmaceutically acceptable salt thereof, according to any one of previous embodiments 1 to 33 (in particular any one of embodiments 17 to 33, more particularly any one of embodiments 20, 23, 26, 29, and 33), for use in the treatment or prevention of atrial fibrillation.

In another aspect, the disclosure provides a method of treating or preventing a disease, disorder, or condition by modulating, reducing, blocking, or inhibiting Nav1.5 activity comprising administration of a therapeutically acceptable amount of a compound of the present disclosure (in particular according to any one of embodiments 1 to 33, in particular any one of embodiments 17 to 33, more particularly any one of embodiments 20, 23, 26, 29, and 33), or a pharmaceutically acceptable salt thereof. In an embodiment, the disease, disorder, or condition is selected from long QT syndrome (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia, suitably atrial fibrillation. In a further embodiment there is provided a method of treating or preventing atrial fibrillation comprising administration of a therapeutically acceptable amount of a compound, or a pharmaceutically acceptable salt thereof, according to any one of previous embodiments 1 to 33 (in particular any one of embodiments 17 to 33, more particularly any one of embodiments 20, 23, 26, 29, and 33).

Thus, as a further aspect, the present disclosure provides the use of a compound of the present disclosure (in particular according to any one of embodiments 1 to 33, in particular any one of embodiments 17 to 33, more particularly any one of embodiments 20, 23, 26, 29, and 33), or a pharmaceutically acceptable salt thereof, for the manufacture of a medicament. In an embodiment, the medicament is for treatment or prevention of a disease, disorder, or condition by modulating, reducing, blocking, or inhibiting Nav1.5 activity. In another embodiment, the disease, disorder, or condition is selected from long QT syndrome (in particular, LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15), atrial fibrillation, ventricular fibrillation, ventricular tachycardia, LQT-associated ventricular arrhythmias, hypertrophic cardiomyopathy, angina, heart failure, peripheral pain, and myotonia, suitably atrial fibrillation. In a further embodiment there is provided use of a compound, or a pharmaceutically acceptable salt thereof, according to any one of previous embodiments 1 to 33 (in particular any one of embodiments 17 to 33, more particularly, any one of embodiments 20, 23, 26, 29, and 33), for the manufacture of a medicament for the treatment or prevention of atrial fibrillation.

The pharmaceutical composition or combination of the present disclosure may, for example, be in unit dosage of about 1-1000 mg of active ingredient(s) for a subject of about 50-70 kg.

Combinations

The compound of the present disclosure may be administered either simultaneously with, or before or after, one or more other therapeutic agent. A compound of the present disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present disclosure.

In some embodiments, the disclosure provides a product comprising a compound of the present disclosure and at least one other therapeutic agent as a combined preparation for simultaneous, separate, or sequential use in therapy. In some embodiments, the therapy is the treatment of a disease or condition mediated by Nav1.5. Products provided as a combined preparation include a composition comprising the compound of the present disclosure and the other therapeutic agent(s) together in the same pharmaceutical composition, or the compound of the present disclosure and the other therapeutic agent(s) in separate form, e.g., in the form of a kit.

In some embodiments, the disclosure provides a pharmaceutical composition comprising a compound of the present disclosure and at least one other therapeutic agent. Optionally, the pharmaceutical composition may comprise a pharmaceutically acceptable carrier, as described above.

In some embodiments, this disclosure provides a kit comprising two or more separate pharmaceutical compositions, at least one of which contains a compound of the present disclosure. In some embodiments, the kit comprises means for separately retaining said compositions, such as a container, divided bottle, or divided foil packet. An example of such a kit is a blister pack, as typically used for the packaging of tablets, capsules and the like.

The kit of this disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of this disclosure, the compound of the present disclosure and the other therapeutic agent(s) may be manufactured and/or formulated by the same or different manufacturers. Moreover, the compound of the present disclosure and the other therapeutic agent(s) may be brought together into a combination therapy: (i) prior to release of the combination product to physicians (e.g., in the case of a kit comprising the compound of the present disclosure and the other therapeutic agent(s)); (ii) by the physician themselves (or under the guidance of the physician) shortly before administration; (iii) in the patient themselves, e.g., during sequential administration of the compound of the present disclosure and the other therapeutic agent(s).

Accordingly, the disclosure provides the use of a compound of the present disclosure for treating a disease or condition mediated by Nav1.5, wherein the medicament is prepared for administration with another therapeutic agent. The disclosure also provides the use of another therapeutic agent for treating a disease or condition mediated by Nav1.5, wherein the medicament is administered with a compound of the present disclosure.

The disclosure also provides a compound of the present disclosure for use in a method of treating a disease or condition mediated by Nav1.5, wherein the compound of the present disclosure is prepared for administration with another therapeutic agent. The disclosure also provides another therapeutic agent for use in a method of treating a disease or condition mediated by Nav1.5, wherein the other therapeutic agent is prepared for administration with a compound of the present disclosure. The disclosure also provides a compound of the present disclosure for use in a method of treating a disease or condition mediated by Nav1.5, wherein the compound of the present disclosure is administered with another therapeutic agent. The disclosure also provides another therapeutic agent for use in a method of treating a disease or condition mediated by Nav1.5, wherein the other therapeutic agent is administered with a compound of the present disclosure.

The disclosure also provides the use of a compound of the present disclosure for treating a disease or condition mediated by Nav1.5, wherein the patient has previously (e.g., within 24 hours) been treated with another therapeutic agent. The disclosure also provides the use of another therapeutic agent for treating a disease or condition mediated by Nav1.5, wherein the patient has previously (e.g., within 24 hours) been treated with a compound of the present disclosure.

In some embodiments, the other therapeutic agent is selected from a class III antiarrhythmic agent. In an embodiment the class III antiarrhythmic agent is selected from dofetilide, sotalol, amiodarone, dronedarone and nikefalant.

Combination of a compound of the present disclosure with a class III antiarrhythmic agent selected from dofetilide and sotalol may mitigate excessive QTc prolongation and potentially confer additional efficacy.

Combination of a compound of the present disclosure with a class III antiarrhythmic agent selected from amiodarone and dronedarone may, as an adjunct therapy, further improve anti-VT/VF efficacy/outcome.

In one embodiment of the disclosure, there is provided a product comprising a compound, or pharmaceutically acceptable salt thereof, according to any one of previous embodiments 1 to 33 (in particular any one of embodiments 17 to 33, more particularly, any one of embodiments 20, 23, 26, 29, and 33 and dofetilide, sotalol, amiodarone or dronedarone as a combined preparation for simultaneous, separate, or sequential use in therapy.

In one embodiment of the disclosure, there is provided a pharmaceutical composition comprising a compound, or pharmaceutically acceptable salt thereof, according to any one of previous embodiments 1 to 33 (in particular any one of embodiments 17 to 33, more particularly, any one of embodiments 20, 23, 26, 29, and 33, together with dofetilide, sotalol, amiodarone or dronedarone, and a pharmaceutically acceptable carrier.

EMBODIMENTS

Embodiment P1: A compound of formula (I''):

(I'')

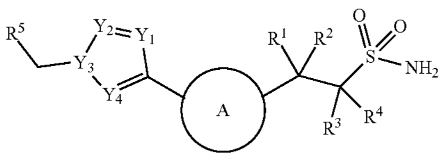

or a pharmaceutically acceptable salt thereof, wherein ring A is:

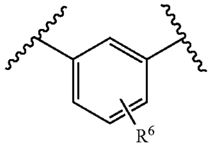

or

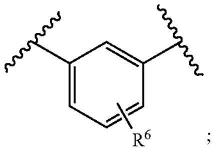

;

$R^1$ is selected from —OH and $C_{1-4}$-alkyl;

$R^2$ is selected from H and $C_{1-4}$-alkyl optionally substituted with one or more halogen atoms;

$R^3$ is selected from H and $C_{1-4}$-alkyl;

$R^4$ is selected from H and $C_{1-4}$-alkyl optionally substituted with —OH;

$R^5$ is phenyl substituted with (i) at least one group selected from halogen, $C_{1-4}$-alkyl, —O—$C_{1-4}$-alkyl, and O—$C_{3-5}$-cycloalkyl, wherein the $C_{1-4}$-alkyl is optionally substituted with one or more halogen atoms, or (ii) two adjacent groups bonded together to form a 4- to 7-membered heterocyclyl containing two or more heteroatoms selected from O, S and N, wherein the 4- to 7-membered heterocyclyl is optionally substituted with one or more halogen atoms;

$R^6$ is H or a halogen atom;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

Embodiment P2: A compound according to Embodiment P1, wherein $R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

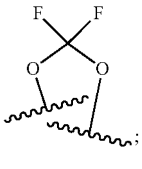 [SMILES: *OC(F)(F)O*]

;

and $R^6$ is selected from H, F and $C_1$.

Embodiment P3: A compound according to Embodiment P1 or Embodiment P2, or a pharmaceutically acceptable salt thereof, wherein $R^6$ is H.

Embodiment P4: A compound according to any one of Embodiments P1 to P3, said compound being of formula (II")):

(II″)

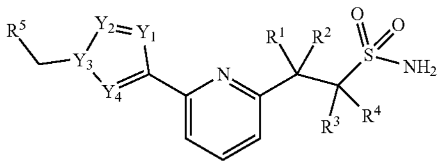

or a pharmaceutically acceptable salt thereof.

Embodiment P5: A compound according to any one of Embodiments P1 to P4, or a pharmaceutically acceptable salt thereof, wherein each of $Y_1$, $Y_2$, $Y_3$ and $Y_4$ are N; or $Y_2$ is CH and each of $Y_1$, $Y_3$ and $Y_4$ are N; or each of $Y_1$ and $Y_2$ are CH and each of $Y_3$ and $Y_4$ are N.

Embodiment P6: A compound according to any one of Embodiments P1 to P5, said compound being of formula (III")):

(III″)

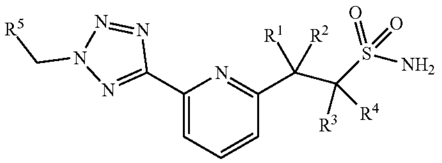

or a pharmaceutically acceptable salt thereof.

Embodiment P7: A compound according to any one of Embodiments P1 to P6, or a pharmaceutically acceptable salt thereof, wherein $R^3$ is H and $R^4$ is H.

Embodiment P8: A compound according to any one of Embodiments P1 to P7, or a pharmaceutically acceptable salt thereof, wherein $R^1$ is —OH.

Embodiment P9: A compound according to any one of Embodiments P1 to P8, or a pharmaceutically acceptable salt thereof, wherein $R^2$ is selected from H, —$CH_3$ and —$CH_2CH_3$.

Embodiment P10: A compound according to any one of Embodiments P1 to P9, or a pharmaceutically acceptable salt thereof, wherein $R^1$ is —OH and $R^2$ is —$CH_3$.

Embodiment P11: A compound according to any one of Embodiments P1 to P10, or a pharmaceutically acceptable salt thereof, wherein $R^5$ is phenyl substituted with at least two groups selected from F, Cl, —$CF_3$, —$OCF_3$ and —$OCH_2CF_3$.

Embodiment P12: A compound according to any one of Embodiments P1 to P11, or a pharmaceutically acceptable salt thereof, wherein $R^5$ is:

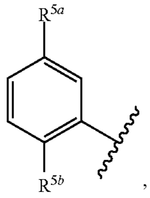, wherein, $R^{5a}$ and $R^{5b}$ are independently selected from F, Cl, —$CF_3$, —$OCF_3$ and —$OCH_2CF_3$.

Embodiment P13: A compound according to any one of Embodiments P1 to P12, or a pharmaceutically acceptable salt thereof, wherein $R^5$ is:

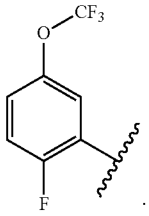 [SMILES: *c1cc(OC(F)(F)F)ccc1F].

Embodiment P14: A compound according to any one of Embodiments P1 to P13, said compound being of formula (IV")):

(IV″)

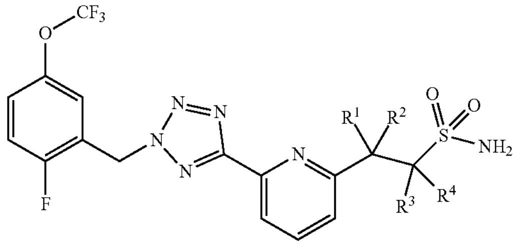

or a pharmaceutically acceptable salt thereof.

Embodiment P15: A compound of formula (I) according to Embodiment P1, or a pharmaceutically acceptable salt thereof, wherein the compound is selected from the group consisting of:

2-(6-(2-(2-fluoro-5-(trifluoromethoxy)benzyl)-2H-tetrazol-5-yl)pyridin-2-yl)-2-hydroxypropane-1-sulfonamide;

2-hydroxy-2-(6-(2-((2,2,5-trifluorobenzo[d][1,3]dioxol-4-yl)methyl)-2H-tetrazol-5-yl)pyridin-2-yl)propane-1-sulfonamide;

2-(2-fluoro-5-(2-(2-fluoro-5-(trifluoromethoxy)benzyl)-2H-tetrazol-5-yl)phenyl)-2-hydroxypropane-1-sulfonamide;

2-(4-chloro-3-(2-(2-fluoro-5-(trifluoromethoxy)benzyl)-2H-tetrazol-5-yl)phenyl)-2-hydroxypropane-1-sulfonamide;

2-(4-fluoro-3-(2-(2-fluoro-5-(trifluoromethoxy)benzyl)-2H-tetrazol-5-yl)phenyl)-2-hydroxypropane-1-sulfonamide;

2-(2-fluoro-3-(2-(2-fluoro-5-(trifluoromethoxy)benzyl)-2H-tetrazol-5-yl)phenyl)-2-hydroxypropane-1-sulfonamide;

3-(6-(2-(2-fluoro-5-(trifluoromethoxy)benzyl)-2H-tetrazol-5-yl)pyridin-2-yl)-3-hydroxybutane-2-sulfonamide;

2-(6-(2-(2,5-difluorobenzyl)-2H-tetrazol-5-yl)pyridin-2-yl)-2-hydroxypropane-1-sulfonamide;

2-(6-(2-(2-fluoro-5-(trifluoromethyl)benzyl)-2H-tetrazol-5-yl)pyridin-2-yl)-2-hydroxypropane-1-sulfonamide;

2-(6-(2-(5-chloro-2-fluorobenzyl)-2H-tetrazol-5-yl)pyridin-2-yl)-2-hydroxypropane-1-sulfonamide;

2-(3-fluoro-5-(2-(2-fluoro-5-(trifluoromethoxy)benzyl)-2H-tetrazol-5-yl)phenyl)-2-hydroxypropane-1-sulfonamide;

2-(3-(2-(2-fluoro-5-(trifluoromethoxy)benzyl)-2H-tetrazol-5-yl)phenyl)-2-hydroxypropane-1-sulfonamide;

2-(5-chloro-6-(2-(2-fluoro-5-(trifluoromethoxy)benzyl)-2H-tetrazol-5-yl)pyridin-2-yl)-2-hydroxypropane-1-sulfonamide;

2-(6-(2-(2-fluoro-5-(2,2,2-trifluoroethoxy)benzyl)-2H-tetrazol-5-yl)pyridin-2-yl)-2-hydroxypropane-1-sulfonamide;

3-(6-(2-(2-fluoro-5-(trifluoromethoxy)benzyl)-2H-tetrazol-5-yl)pyridin-2-yl)-1-hydroxybutane-2-sulfonamide;

2-(6-(1-(2-fluoro-5-(trifluoromethoxy)benzyl)-1H-pyrazol-3-yl)pyridin-2-yl)-2-hydroxybutane-1-sulfonamide;

2-(6-(1-(2-fluoro-5-(trifluoromethoxy)benzyl)-1H-pyrazol-3-yl)pyridin-2-yl)-2-hydroxyethane-1-sulfonamide;

2-(6-(1-(2-fluoro-5-(trifluoromethoxy)benzyl)-1H-pyrazol-3-yl)pyridin-2-yl)-2-hydroxypropane-1-sulfonamide;

3,3,3-trifluoro-2-(6-(1-(2-fluoro-5-(trifluoromethoxy)benzyl)-1H-pyrazol-3-yl)pyridin-2-yl)-2-hydroxypropane-1-sulfonamide;

2-hydroxy-2-(6-(2-(3-(trifluoromethyl)benzyl)-2H-tetrazol-5-yl)pyridin-2-yl)propane-1-sulfonamide;

2-(3-chloro-6-(2-(2-fluoro-5-(trifluoromethoxy)benzyl)-2H-tetrazol-5-yl)pyridin-2-yl)-2-hydroxypropane-1-sulfonamide;

2-(3-fluoro-6-(2-(2-fluoro-5-(trifluoromethoxy)benzyl)-2H-tetrazol-5-yl)pyridin-2-yl)-2-hydroxypropane-1-sulfonamide;

2-(6-(2-(5-cyclopropoxy-2-fluorobenzyl)-2H-tetrazol-5-yl)pyridin-2-yl)-2-hydroxypropane-1-sulfonamide;

2-(6-(2-(2-fluoro-5-(trifluoromethoxy)benzyl)-2H-tetrazol-5-yl)pyridin-2-yl)-2-hydroxyethane-1-sulfonamide;

1-(6-(2-(2-fluoro-5-(trifluoromethoxy)benzyl)-2H-tetrazol-5-yl)pyridin-2-yl)-1-hydroxypropane-2-sulfonamide;

1-(6-(1-(2-fluoro-5-(trifluoromethoxy)benzyl)-1H-pyrazol-3-yl)pyridin-2-yl)-1-hydroxy-2-methylpropane-2-sulfonamide;

3-(6-(1-(2-fluoro-5-(trifluoromethoxy)benzyl)-1H-pyrazol-3-yl)pyridin-2-yl)-3-hydroxy-2-methylbutane-2-sulfonamide;

2-(6-(1-(2-fluoro-5-(trifluoromethoxy)benzyl)-1H-1,2,4-triazol-3-yl)pyridin-2-yl)-2-hydroxypropane-1-sulfonamide;

2-(6-(3-(2-fluoro-5-(trifluoromethoxy)benzyl)-1,2,4-oxadiazol-5-yl)pyridin-2-yl)-2-hydroxypropane-1-sulfonamide;

2-(6-(1-(2-fluoro-5-(trifluoromethoxy)benzyl)-1H-1,2,3-triazol-4-yl)pyridin-2-yl)-2-hydroxypropane-1-sulfonamide; and 2-(6-(2-(2-fluoro-5-(trifluoromethoxy)benzyl)-2H-1,2,3-triazol-4-yl)pyridin-2-yl)-2-hydroxypropane-1-sulfonamide.

Embodiment P16: A compound of formula (I) according to Embodiment P1, or a pharmaceutically acceptable salt thereof, which is 2-(6-(2-(2-fluoro-5-(trifluoromethoxy)benzyl)-2H-tetrazol-5-yl)pyridin-2-yl)-2-hydroxypropane-1-sulfonamide,

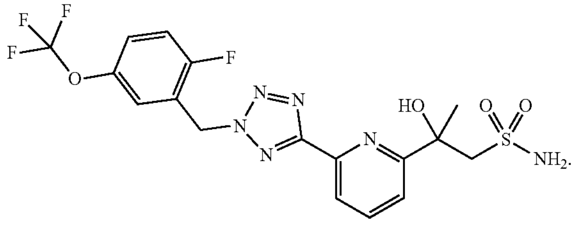

Embodiment P17: A compound of formula (I) according to Embodiment P1, or a pharmaceutically acceptable salt thereof, which is selected from the group consisting of:

(R)-2-(6-(2-(2-fluoro-5-(trifluoromethoxy)benzyl)-2H-tetrazol-5-yl)pyridin-2-yl)-2-hydroxypropane-1-sulfonamide,

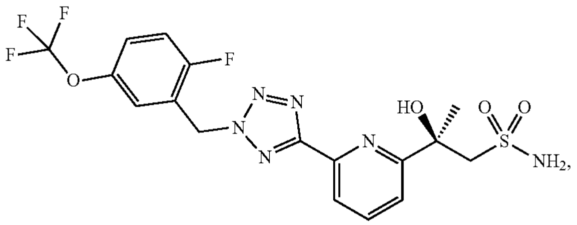 [SMILES: C[C@](O)(CS(N)(=O)=O)c1cccc(-c2nnn(Cc3cc(OC(F)(F)F)ccc3F)n2)n1]

and (S)-2-(6-(2-(2-fluoro-5-(trifluoromethoxy)benzyl)-2H-tetrazol-5-yl)pyridin-2-yl)-2-hydroxypropane-1-sulfonamide,

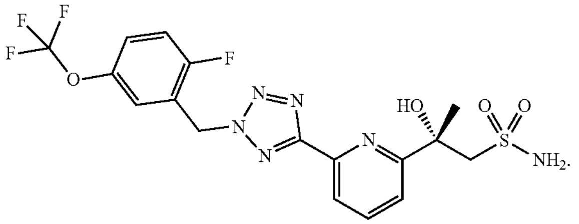 [SMILES: C[C@@](O)(CS(N)(=O)=O)c1cccc(-c2nnn(Cc3cc(OC(F)(F)F)ccc3F)n2)n1]

Embodiment P18: A compound of formula (I) according to Embodiment 1, or a pharmaceutically acceptable salt thereof, which is (R)-2-(6-(2-(2-fluoro-5-(trifluoromethoxy)benzyl)-2H-tetrazol-5-yl)pyridin-2-yl)-2-hydroxypropane-1-sulfonamide,

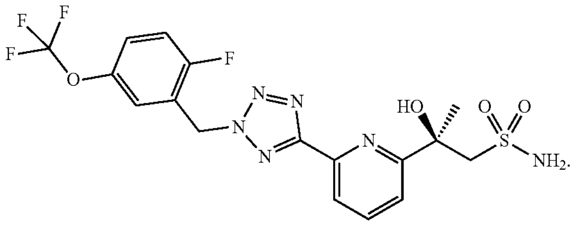 [SMILES: C[C@](O)(CS(N)(=O)=O)c1cccc(-c2nnn(Cc3cc(OC(F)(F)F)ccc3F)n2)n1]

Embodiment P19: A crystalline form of the compound of Embodiment P18, said crystalline form being a co-crystal form named Modification A-1 comprising (R)-2-(6-(2-(2-fluoro-5-(trifluoromethoxy)benzyl)-2H-tetrazol-5-yl)pyridin-2-yl)-2-hydroxypropane-1-sulfonamide and L-proline, wherein the molar ratio of (R)-2-(6-(2-(2-fluoro-5-(trifluoromethoxy)benzyl)-2H-tetrazol-5-yl)pyridin-2-yl)-2-hydroxypropane-1-sulfonamide to L-proline is about 1:1, characterized in that said co-crystal form has an X-ray powder diffraction pattern comprising four or more peaks at 2θ angles (±0.2 degree) selected from 6.8°, 8.0°, 10.2°, 10.6°, 11.3°, 12.1°, 15.4°, 16.1°, 17.2°, 18.0°, 18.7°, 19.1°, 20.2°, 21.4°, 23.9° and 26.0°, when measured using a CuKa radiation with a wavelength of 1.5418 Å at a temperature of about 22° C.

Embodiment P20: A crystalline form of the compound of Embodiment P18, said crystalline form being a co-crystal form named Modification A-2 comprising (R)-2-(6-(2-(2-fluoro-5-(trifluoromethoxy)benzyl)-2H-tetrazol-5-yl)pyridin-2-yl)-2-hydroxypropane-1-sulfonamide and L-proline, wherein the molar ratio of (R)-2-(6-(2-(2-fluoro-5-(trifluoromethoxy)benzyl)-2H-tetrazol-5-yl)pyridin-2-yl)-2-hydroxypropane-1-sulfonamide to L-proline is about 1:2.9, characterized in that said co-crystal form has an X-ray powder diffraction pattern comprising four or more peaks at 2θ angles (±0.2 degree) selected from 55°, 8.7°, 9.4° 11.1°, 12.7°, 15.3°, 16.6°, 17.2°, 18.8°, 19.2°, 20.1°, 21.7°, 22.2°, 25.3°, 26.2°, 28.7° and 30.8°, when measured using a CuKa radiation with a wavelength of 1.5418 Å at a temperature of about 22° C.

Embodiment P21: A crystalline form of the compound of Embodiment P18, said crystalline form being a hydrochloride salt of (R)-2-(6-(2-(2-fluoro-5-(trifluoromethoxy)benzyl)-2H-tetrazol-5-yl)pyridin-2-yl)-2-hydroxypropane-1-sulfonamide named Modification A-3, characterized in that said crystalline form has an X-ray powder diffraction pattern comprising four or more peaks at 2θ angles (+0.2 degree) selected from 7.5°, 11.2°, 14.3°, 15.5°, 16.6°, 17.9°, 18.5°, 19.1°, 20.0°, 20.4°, 21.4°, 22.5°, 22.8°, 23.9° and 28.8°, when measured using a CuKa radiation with a wavelength of 1.5418 Å at a temperature of about 22° C.

Embodiment P22: A pharmaceutical composition comprising a compound according to any one of Embodiments P1 to P21, or a pharmaceutically acceptable salt thereof, and one or more pharmaceutically acceptable carriers.

Embodiment P23: A combination comprising of a compound according to any one of Embodiments P1 to P21, or a pharmaceutically acceptable salt thereof, and one or more therapeutically active agents.

Embodiment P24: A method of modulating Nav1.5 activity in a subject, wherein the method comprises administering to the subject a therapeutically effective amount of the compound according to any one of Embodiments P1 to P21, or a pharmaceutically acceptable salt thereof.

Embodiment P25: A method of treating a disease, disorder, or condition selected from a long QT syndrome LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15, atrial fibrillation, ventricular fibrillation, ventricular tachycardia, LQT-associated ventricular arrhythmias, hypertrophic cardiomyopathy, angina, heart failure, peripheral pain, and myotonia, wherein the method comprises administering to the subject a therapeutically effective amount of the compound according to any one of Embodiments P1 to P21, or a pharmaceutically acceptable salt thereof.

Embodiment P26: A compound according to any one of Embodiments P1 to P21, or a pharmaceutically acceptable salt thereof, for use as a medicament.

Embodiment P27: A compound according to any one of Embodiments P1 to P21, or a pharmaceutically acceptable salt thereof, for use in the treatment of a disease, disorder, or condition selected from a long QT syndrome LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15, atrial fibrillation, ventricular fibrillation, ventricular tachycardia, LQT-associated ventricular arrhythmias, hypertrophic cardiomyopathy, angina, heart failure, peripheral pain, and myotonia.

Embodiment P28: Use of a compound according to any one of Embodiments P1 to P21, or a pharmaceutically acceptable salt thereof, in the manufacture of a medicament for the treatment of a disease, disorder, or condition selected from a long QT syndrome LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15, atrial fibrillation, ventricular fibrillation, ventricular tachycardia, LQT-associated ventricular arrhythmias, hypertrophic cardiomyopathy, angina, heart failure, peripheral pain, and myotonia.

EXAMPLES

Preparation of Compounds

Compounds of the present disclosure can be prepared as described in any of Schemes 1 to 10 or in the following Examples.

The disclosure is further illustrated by the following examples and synthetic methods, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

All starting materials, building blocks, reagents, acids, bases, dehydrating agents, solvents, and catalysts utilized to synthesize the compounds of the present disclosure are either commercially available or can be produced by organic synthesis methods known to one of ordinary skill in the art. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) Protective Groups in Organic Synthesis, 5th edition, John Wiley & Sons). These groups are removed at a convenient stage of the compound synthesis using methods that are readily apparent to those skilled in the art for protecting group removal. Unless otherwise noted, reagents and solvents were used as received from commercial suppliers.

The chemical names were generated using ChemDraw Professional v19.1.2.36 from PerkinElmer.

Temperatures are given in degrees Celsius. As used herein, unless specified otherwise, the term "room temperature" means a temperature of from 15° C. to 30° C., such as from 20° C. to 30° C., such as from 20° C. to 25° C. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

ABBREVIATIONS calc.: calculated
$CO_2$: carbon dioxide
d: day
DBDMH: 1,3-dibromo-5,5-dimethylhydantoin
DCM: dichloromethane
DEA: diethylamine
DIPEA: diisopropylethylamine
Dppf: 1,1'-ferrocenediyl-bis(diphenylphosphine)
e.e.: enantiomeric excess
eq: equivalents
EtOAc: ethyl acetate
EtOH: ethanol g: gram
h: hour
HCOOH: formic acid
HPLC: high-performance liquid chromatography
HRMS: high resolution mass spectrometry
Hz: hertz
IPA: isopropanol
$K_2CO_3$: potassium carbonate
L: liter
LCMS: liquid chromatography-mass spectrometry
$LiBH_4$: lithium borohydride
M: molar
MeMgBr: methyl magnesium bromide
MeOH: methanol
mg: milligram
MHz: megahertz
min.: minute
mL: milliliter
mm: millimeter
mM: millimolar
mmol: millimoles
mol: mole
N: Normal
$NaBH_4$: sodium borohydride
$Na_2SO_4$: sodium sulphate
$Na_2S_2O_3$: sodium thiosulfate
NaCl: sodium chloride
$NaHCO_3$: sodium bicarbonate
$Na_2CO_3$: sodium carbonate
$NH_4Cl$: ammonium chloride
$NH_4OH$: ammonium hydroxide
nm: nanometers
NMP: N-methyl-2-pyrrolidone
NMR: Nuclear Magnetic Resonance
$Pd(PPh_3)_4$: tetrakis(triphenylphosphine)palladium(0)
$Pd_2(dba)_3$: tris(dibenzylideneacetone)dipalladium(0)
PDA: Photodiode Array
Prep: preparative
rpm: revolutions per minute
Rt: retention time
SFC: supercritical fluid chromatography
TFA: trifluoroacetic acid
THF: tetrahydrofuran
T3P: propanephosphonic acid anhydride
UPLC: Ultra Performance Liquid Chromatography
UV: ultra violet

General Methods

Solvents and chemicals used were reagent grade. Chemical shifts (6) are reported in parts per million (ppm) relative to residual undeuterated solvent as internal reference: DMSO-$d_6$ 2.50 ppm, $CDCl_3$ 7.26 ppm, $CD_3OD$ 3.31 ppm. Coupling constants (J) are reported in hertz (Hz). Column chromatography was performed by an ISCO CombiFlash or a Biotage SP1 apparatus using disposable normal phase silica gel columns. Microwave reactions were conducted using a Biotage initiator. The purity of all target compounds was >95% as determined by analytical HPLC and $^1H$ NMR.

The conditions for determining the mass and the retention times were as follows: LCMS Method 1: The retention times in minutes (Rt) were obtained on a Waters AcQuity UPLC with a Waters Qda mass spectrometer using an AcQuity UPLC BEH C18 1.7 μm 2.1×30 mm column at an oven temperature of 50° C. A gradient of water (+0.1% formic acid)/acetonitrile (0.1% formic acid) 98/2 to 2/98 was applied over 1.5 min., then held for 0.3 min. (1 mL/min.). Electrospray mass spectra (+) and (−) with UV detection 210-400 nm (Waters AcQuity UPLC PDA).

LCMS Method 2: The retention times in minutes (Rt) were obtained on a Waters AcQuity UPLC with a Waters Qda mass spectrometer using an AcQuity UPLC BEH C18 1.7 μm 2.1×30 mm column at an oven temperature of 50° C. A gradient of water (5 mM ammonium hydroxide)/acetonitrile (5 mM ammonium hydroxide) 98/2 to 2/98 was applied over 1.5 min., then held for 0.3 min. (1 mL/min.). Electrospray mass spectra (+) and (−) with UV detection 210-400 nm (Waters AcQuity UPLC PDA).

LCMS Method 3: The retention times in minutes (Rt) were obtained on a Waters AcQuity UPLC with a Waters Qda mass spectrometer using an AcQuity UPLC BEH C18 1.7 μm 2.1×50 mm column at an oven temperature of 50° C. A gradient of water (5 mM ammonium hydroxide)/acetonitrile (5 mM ammonium hydroxide) 98/2 to 2/98 was applied over 4.4 min., then held for 0.75 min. (1 mL/min.). Electrospray mass spectra (+) and (−) with UV detection 210-400 nm (Waters AcQuity UPLC PDA).

LCMS Method 4: Instrument: Shimadzu LC-MS-2020 with Single Quad. Column: Kinetex 2.6 μm, C18 100 A, 30×3 mm; Gradient: A—0.1% formic acid in water, B—acetonitrile; Time (min.)/% B: 0.1/20, 0.25/20, 0.75/95, 1.75/95, 2/20, 2.5/20; Flow rate: 1.0 mL/min.; Ion Source: DUIS-ESI & APCI; Nebulizing Gas Flow:1.5 L/min.; DL Temperature: 250° C.; Heat Block Temperature: 400° C.; UV detection array 200-400 nm; Mass detection 100-1000 (electrospray ionization); Column temperature: 40° C.

LCMS Method 5: Instrument: SCI EX API 3200 Column: Kinetex EVO C18 2.6 μm, 50×4.6 mm; Gradient: A—0.1% formic acid in water, B—0.1% $HCO_2H$ in $CH_3CN$; Time (min.)/% B: 0/30, 0.2/30, 0.7/95, 2.0/95, 2.5/30, 3.5/30; Flow rate: 1.0 mL/min.; Ion Source: Turbo Spray; Flow: 1.5 L/min.; DL Temperature: 450° C.; UV detection array 200-400 nm; Mass detection 100-1000 (electrospray ionization); Column temperature: 30° C.

LCMS Method 6: Instrument: Shimadzu Nexera LC-MS-2020 with Single Quad. Column: Synergi 2.5μ (20×4.0 mm), MAX-RP 100 A Mercury; Gradient: A—0.1% formic acid in water, B—acetonitrile; Time (min.)/% B: 0.1/5, 0.5/5, 1.0/95, 1.5/95, 2.0/5, 3.0/5; Flow rate: 2.0 mL/min.; UV detection array 200-400 nm; Mass detection 100-1000 (electrospray ionization); Column temperature: 40° C.

LCMS Method 7: Instrument: Shimadzu LCMS-2020 with Single Quad. Column: Synergi 2.5μ MAX-RP 100 A Mercury; Gradient: A—0.1% formic acid in water, B—acetonitrile; Time (min.)/% B: 0.1/5, 0.5/5, 1.0/95, 1.5/95, 2.0/5, 3.0/5; Flow: 2.0 mL/min.; Ion Source: DUIS-ESI & APCI; Nebulizing Gas Flow:1.5 L/min.; DL Temperature: 250° C.; Heat Block Temperature:400° C.; UV detection array 200-400 nm; Mass detection 100-1000 (electrospray ionization); Column temperature: 40° C.

LCMS Method 8: The retention times in minutes (Rt) were obtained on a Waters AcQuity UPLC with a Waters Qda mass spectrometer using an AcQuity UPLC BEH C18 1.7 μm 2.1×50 mm column at an oven temperature of 50° C. A gradient of water (+0.1% formic acid)/acetonitrile (0.1% formic acid) 98/2 to 2/98 was applied over 4.4 min., then held for 0.75 min. (1 mL/min.). Electrospray mass spectra (+) and (−) with UV detection 210-400 nm (Waters AcQuity UPLC PDA).

LCMS Method 9: The retention times in minutes (Rt) were obtained on a Waters AcQuity UPLC with a Waters Qda mass spectrometer using with an AcQuity UPLC BEH C18 1.7 μm 2.1×30 mm column at an oven temperature of 50° C. A gradient of water (5 mM ammonium hydroxide)/ acetonitrile (5 mM ammonium hydroxide) 99/1 to 70/30 was applied over 1.2 min. and then from 70/30 to 2/98 over 0.95 min. (1 mL/min.). Electrospray mass spectra (+) and (−) with UV detection 210-400 nm (Waters AcQuity UPLC PDA).

HRMS Method 10: High-resolution mass spectra were obtained on a Waters Acquity UPLC with Waters Xevo G2 Otof Mass spectrometer using an AcQuity UPLC CSH C18 1.7 μm 2.1×50 mm column at an oven temperature of 50° C. A gradient of water (+0.05% ftrifluoroacetic acid)/acetonitrile (0.05% trifluoroacetic acid) 98/2 to 2/98 was applied over 1.7 min., then held for 0.25 min. (1 mL/min.). UV detection 210-400 nm (Waters AcQuity UPLC PDA).

SYNTHESIS OF INTERMEDIATES

Intermediate 1: 4-(bromomethyl)-2,2,5-trifluorobenzo[d][1,3]dioxole

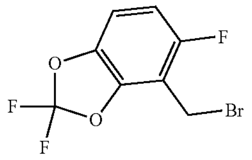 [SMILES: Fc1ccc2c(c1CBr)OC(F)(F)O2]

Step 1: 4-fluorobenzene-1,2-diol

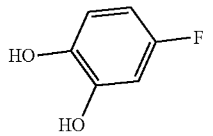

To a solution of 4-fluoro-1,2-dimethoxybenzene (150 g, 0.96 mol, 1.00 eq) in DCM (3 L) cooled to −78° C. was added borane tribromide (664 g, 2.7 mol, 2.76 eq). The reaction mixture was allowed to stir at room temperature for 12 h and then quenched by addition of methanol (1.14 L). Stirring was continued at room temperature for 1 h, at which point the reaction was diluted with water and extracted with ethyl acetate.

The combined organic phase was washed with a saturated aqueous NaCl solution, dried over $Na_2SO_4$, and concentrated under reduced pressure to afford the title compound as a grey solid (113 g, 92% crude yield), which was used directly in the next step without further purification.

Step 2: 5-fluorobenzo[d][1,3]dioxole-2-thione

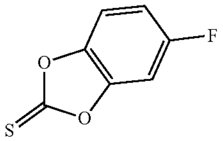 [SMILES: Fc1ccc2oc(=S)oc2c1]

To a solution of 4-fluorobenzene-1,2-diol (113 g, 0.88 mol, 1.0 eq) in DCM (4.2 L) was added DMAP (216 g, 2.0 eq), $CSCl_2$ (183 g, 1.6 mol, 1.8 eq) at 0° C. The mixture was stirred at room temperature for 1 h, after which time HPLC showed the reaction was completed. The reaction was quenched by addition of water (4 L) and extracted by DCM (2×2 L). The combined organic phase was dried over $Na_2SO_4$, filtered and concentrated under reduced pressure to afford a crude residue. The crude material was purified by silica gel column chromatography (30:1 petroleum ether: ethyl acetate) to afford the title product as a yellow solid (107 g, 71% crude yield).

Step 3: 5-bromo-2,2,6-trifluorobenzo[d][1,3]dioxole

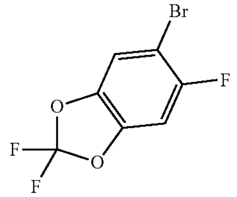 [SMILES: Fc1cc2c(cc1Br)OC(F)(F)O2]

To a solution of 5-fluorobenzo[d][1,3]dioxole-2-thione (104 g, 0.61 mol, 1.0 eq) in DCM (3 L) cooled to −78° C. was added dropwise 70% Py·HF (732 g, 5.2 mol, 8.5 eq) followed by DBDMH (524 g, 1.8 mol, 3.0 eq). The resulting mixture was warmed to 0° C. to stir for 1 h. The reaction was quenched by addition of 5M aqueous NaOH solution (50 V) and $Na_2S_2O_3$ (48.3 g, 0.31 mol, 0.5 eq). The mixture was filtered and the filtrate was extracted with DCM (10 L). The combined organic phase was dried over $Na_2SO_4$, filtered and concentrated under reduced pressure to afford the title compound as a crude brown oil (107 g, 69% crude yield), which was used directly in the next step without further purification.

Step 4: 2,2,5-trifluorobenzo[d][1,3]dioxole-4-carbaldehyde

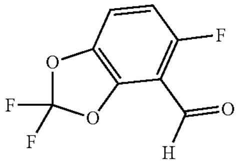 [SMILES: O=Cc1c(F)ccc2c1OC(F)(F)O2]

To a solution of 5-bromo-2,2,6-trifluorobenzo[d][1,3]dioxole (50 g, 0.19 mol, 1.0 eq) in THF (500 mL) cooled to −78° C. was added n-BuLi (91 mL, 0.23 mol, 1.2 eq). The resulting reaction mixture was stirred at −78° C. for 1 h until HPLC showed the reaction was completed. To the resulting cold mixture was added DMF (28.8 g, 0.38 mol, 2.0 eq) and stirring was continued until HPLC showed the reaction was completed. The reaction was quenched by addition of 2N aqueous HCl solution (600 mL) and the resulting mixture was extracted with ethyl acetate (2×500 mL). The combined the organic phase was dried over $Na_2SO_4$, filtered and concentrated to afford the title compound as a crude brown oil (37.6 g, 94% crude yield), which was used directly in the next step without further purification.

$^1H$ NMR (400 MHz, $CDCl_3$) δ 10.29 (s, 1H), 7.25 (dd, J=8.9, 4.0 Hz, 1H), 6.94 (dd, J=10.6, 9.0 Hz, 1H).

Step 5: (2,2,5-trifluorobenzo[d][1,3]dioxol-4-yl) methanol

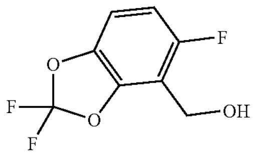 [SMILES: OCc1c(F)ccc2c1OC(F)(F)O2]

To a solution of 2,2,5-trifluorobenzo[d][1,3]dioxole-4-carbaldehyde (37.6 g, 0.18 mol, 1.0 eq) in methanol (376 mL) cooled to 0° C. was added $NaBH_4$ (3.4 g, 0.09 mol, 0.5 eq). The mixture was stirred at 0° C. for 40 min. until HPLC showed the reaction was completed. The reaction was quenched by careful addition of water (200 mL) and the resulting mixture was extracted with DCM (2×200 mL). The combined organic phase was dried over $Na_2SO_4$, filtered and concentrated to afford a crude residue. The crude material was purified by silica gel column chromatography (50:1 to 30:1 petroleum ether:ethyl acetate) to afford the title compound as a yellow oil (11.4 g, 30% crude yield).

Step 6: 4-(bromomethyl)-2,2,5-trifluorobenzo[d][1,3]dioxole

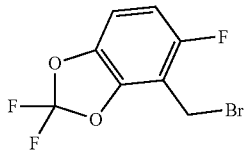 [SMILES: Fc1ccc2c(c1CBr)OC(F)(F)O2]

To a solution of (2,2,5-trifluorobenzo[d][1,3]dioxol-4-yl) methanol (11.4 g, 55.3 mmol, 1.0 eq) in DCM (285 mL, 25 V) cooled to 0° C. was added $PBr_3$ (15 g, 55 mmol, 1.0 eq). The mixture was stirred for 2 h at room temperature until HPLC showed the reaction was completed. The resulting reaction mixture was quenched by addition of water (200 mL) and the mixture was extracted with DCM (2×200 mL). The combined organic phase was dried over $Na_2SO_4$, filtered and concentrated to afford a crude residue which was purified by silica gel column chromatography (eluting with heptane) to afford the title compound as a colorless oil (8.4 g, 48% yield, HPLC purity 97.90%, Rt: 4.796 min.).

$^1$H NMR (400 MHz, $CDCl_3$) δ 6.97 (dd, J=8.8, 4.1 Hz, 1H), 6.82 (dd, J=9.9, 9.0 Hz, 1H), 4.48 (s, 2H).

Chemical purity was determined by HPLC according to the following conditions:

Instrument: Agilent 1260 HPLC

Column: Agilent Poroshell 120 C18 4.6×50 mm, 2.7 mm

Mobile phase: water (0.1% trifluoroacetic acid)/acetonitrile (0.1% trifluoroacetic acid);

gradient 95/5 to 5/95 over 5 min. and hold at 5/95 for 2 min.

Flow rate: 1.2 mL/min.

Detection: UV @210 nm

Intermediate 2: 3-acetyl-4-fluorobenzonitrile

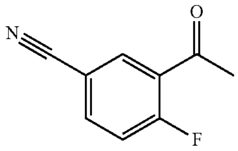

Purchased from commercial source (CAS: 267875-54-7).

Intermediate 3: 5-acetyl-2-chlorobenzonitrile

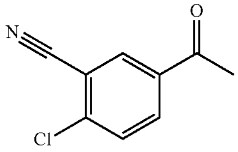

Prepared from 5-bromo-2-chlorobenzonitrile by analogy to Example 27-28, Step 3. Product was isolated as yellow solid (3.0 g, 91% yield). $^1$H NMR (400 MHz, $CD_3OD$) δ 8.39 (s, 1H), 8.22 (dd, J=8.4, 2.0 Hz, 1H), 7.78 (d, J=8.8 Hz, 1H), 2.62 (s, 3H).

Intermediate 4: 5-acetyl-2-fluorobenzonitrile

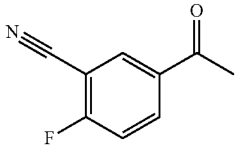

Purchased from commercial source (CAS: 288309-07-9).

Intermediate 5: 3-acetyl-2-fluorobenzonitrile

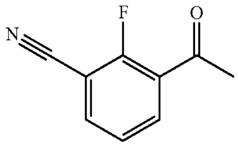

Prepared from 3-bromo-2-fluorobenzonitrile by analogy to Example 27-28, Step 3. Product was isolated as yellow solid (1.8 g, 44% yield). $^1$H NMR (300 MHz, $CDCl_3$) δ 8.16-8.11 (m, 1H), 7.84-7.80 (m, 1H), 7.38 (t, J=7.6 Hz, 1H), 2.69 (d, J=5.2 Hz, 3H).

Intermediate 6: 3-acetyl-5-fluorobenzonitrile

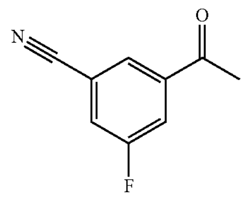

Prepared from 3-bromo-5-fluorobenzonitrile (10.0 g, 52.3 mmol) by analogy to Example 27-28, Step 3. Product was isolated as yellow solid (3.9 g, 46% yield). $^1$H NMR (300 MHz, $CDCl_3$) δ 8.02 (s, 1H), 7.88 (d, J=8.7 Hz, 1H), 7.56 (d, J=7.2 Hz, 1H), 2.63 (s, 3H).

Intermediate 7: 2-(chloromethyl)-1-fluoro-4-(2,2,2-trifluoroethoxy)benzene

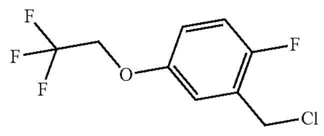 [SMILES: Fc1ccc(OCC(F)(F)F)cc1CCl]

Step 1: 2-fluoro-5-(2,2,2-trifluoroethoxy)benzaldehyde

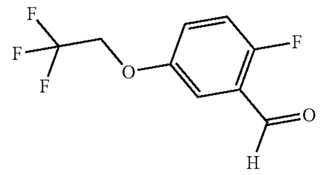 [SMILES: O=Cc1cc(OCC(F)(F)F)ccc1F]

To a solution of 2-fluoro-5-hydroxybenzaldehyde (3.8 g, 27.1 mmol) and potassium carbonate (7.5 g, 54.2 mmol) in 40 mL of DMF was added 2,2,2-trifluoroethyl trifluoromethanesulfonate (12.59 g, 54.2 mmol) at room temperature. The resulted reaction mixture was stirred for 2.5 hours at room temperature and monitored by LCMS. The reaction mixture was quenched with cold water, extracted with diethyl ether twice. The combined organic layer was dried over sodium sulfate, filtered and concentrated under reduced pressure. The crude product was purified with silica gel column chromatography (0%-100% ethyl acetate in heptane) to provide the title compound (4.2 g, 70% yield).

ESI-MS m/z: 223.2 [M+H]$^+$ (Rt: 0.98 min., LCMS Method 1). $^1$H NMR (400 MHz, DMSO-$d_6$) δ 10.20 (s, 1H), 7.50-7.37 (m, 3H), 4.87 (q, J=8.8 Hz, 2H).

Step 2: (2-fluoro-5-(2,2,2-trifluoroethoxy)phenyl)methanol

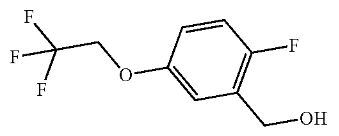 [SMILES: OCc1cc(OCC(F)(F)F)ccc1F]

To a stirred solution of 2-fluoro-5-(2,2,2-trifluoroethoxy)benzaldehyde (4.2 g, 18.91 mmol) in 15 mL of MeOH and 30 mL of THF, $NaBH_4$ (1.07 g, 28.4 mmol) was added at 0° C. Then the reaction mixture was stirred at room temperature for two hours and it was monitored by LCMS. The reaction mixture was quenched with water and extracted with EtOAc two times. The combined organic layer was washed with brine, dried over $Na_2SO_4$, filtered and concentrated under reduced pressure. The crude product was purified with silica gel column chromatography (0%-100% ethyl acetate in heptane) to provide the title compound (3.82 g, 90% yield).

$^1$H NMR (400 MHz, DMSO-$d_6$) δ 7.16-7.07 (m, 2H), 6.96 (dt, J=9.0, 3.7 Hz, 1H), 5.30 (t, J=5.6 Hz, 1H), 4.73 (q, J=8.9 Hz, 2H), 4.51 (d, J=5.8 Hz, 2H).

Step 3: 2-(chloromethyl)-1-fluoro-4-(2,2,2-trifluoroethoxy)benzene

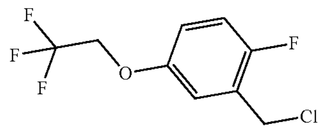 [SMILES: Fc1ccc(OCC(F)(F)F)cc1CCl]

To a solution of (2-fluoro-5-(2,2,2-trifluoroethoxy)phenyl)methanol (3.6 g, 16.06 mmol) in 12 mL of DCM, thionyl chloride (46.9 mL, 642 mmol) was added at room temperature. The resulting brown color solution was stirred at 70° C. for 48 h. Then the reaction mixture was poured onto ice-cold water carefully and extracted with DCM three times. The combined organic layer was washed with brine, dried over $Na_2SO_4$, filtered and concentrated under reduced pressure to give the title compound (3.9 g, 100% yield). It was used without further purification.

$^1$H NMR (400 MHz, DMSO-$d_6$) δ 7.32-7.07 (m, 3H), 4.82-4.68 (m, 4H).

Intermediate 8: 2-(chloromethyl)-4-cyclopropoxy-1-fluorobenzene

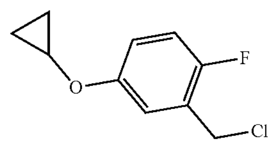 [SMILES: Fc1ccc(OC2CC2)cc1CCl]

Step 1: 4-fluoro-3-(hydroxymethyl) phenol

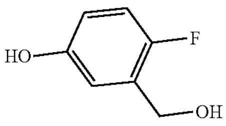

To a stirred solution of 2-fluoro-5-hydroxybenzaldehyde (5.0 g, 36 mmol) in THF/MeOH (40 mL/20 mL) was added sodium borohydride (2.0 g, 54 mmol) portion wise at 0° C. The reaction mixture was allowed to stir at room temperature for 1 h and then diluted with water (100 mL) and extracted with EtOAc (3×50 mL). The combined organic phase was washed with saturated aqueous NaCl solution (100 mL), dried over anhydrous $Na_2SO_4$, filtered and concentrated under reduced pressure to provide the title compound as a colorless oil (6.5 g, crude).

$^1$H NMR (400 MHz, $CDCl_3$) δ 6.91-6.85 (m, 2H), 6.71-6.67 (m, 1H), 6.14 (brs, 1H), 4.69 (s, 2H).

Step 2: (5-cyclopropoxy-2-fluorophenyl)methanol

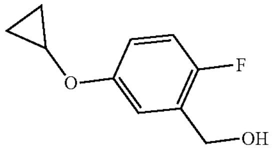 [SMILES: OCc1cc(OC2CC2)ccc1F]

To a stirred solution of 4-fluoro-3-(hydroxymethyl)phenol (6.5 g, 46 mmol) in NMP (60 mL) was added bromo cyclopropane (27.7 g, 229 mmol) followed by potassium iodide (7.6 g, 46 mmol) and cesium carbonate (22.4 g, 68.6 mmol) at room temperature and the reaction mixture was heated at 150° C. for 16 h. The reaction mixture was cooled to room temperature, diluted with water (100 mL) and extracted with diethyl ether (2×100 mL). The combined organic phase was washed with saturated aqueous NaCl solution (100 mL), dried over $Na_2SO_4$, filtered and concentrated under reduced pressure to afford a crude material. The crude material was purified by silica gel column chromatography (20-30% ethyl acetate in hexane) to afford the title compound (3.0 g, 36% yield).

$^1$H NMR (300 MHz, $CDCl_3$) δ 7.11-7.08 (m, 1H), 6.99-6.89 (m, 2H), 4.73 (d, J=5.7 Hz, 2H), 3.74-3.68 (m, 1H), 1.84 (t, J=6.3 Hz, 1H), 0.77-0.75 (m, 4H).

Step 3: 2-(chloromethyl)-4-cyclopropoxy-1-fluorobenzene

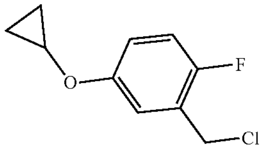 [SMILES: Fc1ccc(OC2CC2)cc1CCl]

Thionyl chloride (30 mL) was added to (5-cyclopropoxy-2-fluorophenyl) methanol (3.0 g, 17 mmol) followed by DMF (1.5 mL) at 0° C. The reaction mixture was stirred at room temperature for 5 h before being poured into ice-water (100 mL) and extracted with DCM (3×50 mL). The combined organic phase was washed with water (3×50 mL) followed by saturated $NaHCO_3$ aqueous solution (2×50 mL) and with saturated aqueous NaCl solution (1×50 mL), dried over anhydrous $Na_2SO_4$, filtered and concentrated under reduced pressure to afford the title compound as a brown oil (3.8 g, crude).

$^1$H NMR (400 MHz, $CDCl_3$) δ 7.08-7.06 (m, 1H), 7.01-6.95 (m, 2H), 4.60 (s, 2H), 3.72-3.69 (m, 1H), 0.79-0.75 (m, 4H).

Synthesis of Compounds of Formula (I)

Synthesis of Examples 1 and 2

Example 1: (R)-2-(6-(2-(2-fluoro-5-(trifluoromethoxy) benzyl)-2H-tetrazol-5-yl)pyridin-2-yl)-2-hydroxypropane-1-sulfonamide and Example 2: (S)-2-(6-(2-(2-fluoro-5-(trifluoromethoxy)benzyl)-2H-tetrazol-5-yl)pyridin-2-yl)-2-hydroxypropane-1-sulfonamide Prepared according to Scheme 1.

Example 1

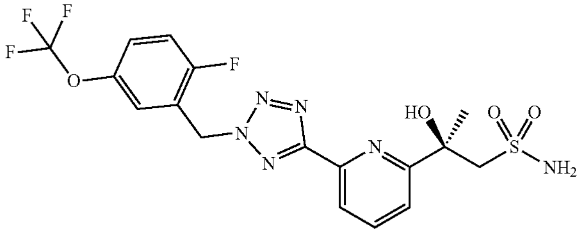

Example 2

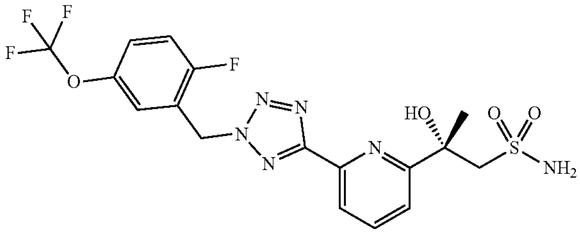

Step 1: N,N-bis(4-methoxybenzyl)methanesulfonamide

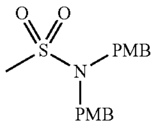

To a solution of bis(4-methoxybenzyl)amine (7.51 g, 29.2 mmol) and triethylamine (3.84 g, 38.0 mmol) in DCM (50 mL) was added methanesulfonyl chloride (4.01 g, 35.0 mmol) dropwise at 0° C. The reaction mixture was then stirred at room temperature for 2 h. Water was added to quench the reaction mixture followed by extraction with DCM (3×). The DCM layers were combined, dried over anhydrous $Na_2SO_4$, filtered, and concentrated under reduced pressure. The residue was purified with silica gel column chromatography (10-20% ethyl acetate in heptane) to afford the title compound as a white solid (6.98 g, 68% yield).

$^{1}H$ NMR (400 MHz, DMSO-$d_6$) δ 7.26-7.12 (m, 4H), 6.97-6.82 (m, 4H), 4.19 (s, 4H), 3.75 (s, 6H), 2.89 (s, 3H).

Step 2: 1-(6-(2H-tetrazol-5-yl)pyridin-2-yl)ethan-1-one

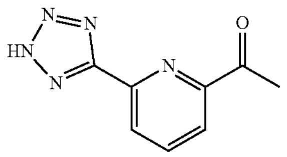

This reaction was carried out in 12 small reaction batches as described below:

To a mixture of 6-acetylpicolinonitrile (1 g, 6.84 mmol), triethylamine hydrochloride (1.413 g, 10.26 mmol), triethylamine (0.238 mL, 1.711 mmol) and 1,4-dioxane (5 mL) in a vial (30 mL) was added sodium azide (0.623 g, 9.58 mmol). The vial was tightly capped and the mixture was stirred vigorously at 90° C. for 15 h.

Each reaction was then diluted with 3:1 EtOAc/EtOH (10-15 mL), manually shaken, added to a stirred sodium bicarbonate (11.5 g, 137 mmol) slurry in EtOAc/EtOH (100 mL, v/v 3:1), and rinsed in with another 10-15 mL of EtOAc/EtOH. The combined suspension was stirred for 30 min., filtered through celite bed, rinsed with additional EtOAc/EtOH. The filtrate was concentrated under reduced pressure to dryness, and the resulting oil was triturated with heptane to remove residual triethylamine. To the oil residue was added acetone (100 mL) and the resulting suspension was filtered through celite bed and the filter cake was rinsed with acetone. To a stirred solution of the resulting dark amber filtrate cooled in an ice-water bath was added an HCl solution (2.5 M in EtOH, 41.1 mL, 103 mmol) dropwise, resulting in a brown mustard-colored suspension. To this was added heptane (50 mL) and the mixture was cooled in an ice-water bath for 30 min. The solids were removed by vacuum filtration and washed with an acetone/heptane mixture until the filtrate was colorless. The amber filtrate was concentrated under reduced pressure and the resulting oil was taken up in acetone and water. The resulting suspension was let stand for 30 minutes and the solids were collected by vacuum filtration and washed with deionized water. The orange-yellow filter cake was dried under vacuum at room temperature to afford the title compound (13.8 g, 89% yield).

ESI-MS m/z: $[M-H]^-$ 188.0 (Rt: 0.91 min., LCMS Method 1).

$^{1}H$ NMR (400 MHz, DMSO-$d_6$): δ 8.44 (dd, J=7.8, 1.1 Hz, 1H), 8.26 (t, J=7.8 Hz, 1H), 8.11 (dd, J=7.8, 1.1 Hz, 1H), 2.79 (s, 3H).

Step 3: 2-(6-(2H-tetrazol-5-yl)pyridin-2-yl)-2-hydroxy-N,N-bis(4-methoxybenzyl)propane-1-sulfonamide

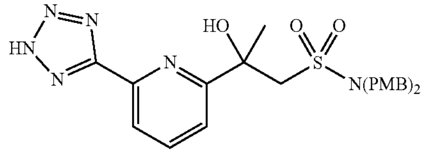

To a solution of N,N-bis(4-methoxybenzyl)methanesulfonamide (19.9 g, 59.3 mmol) in THF (350 mL) cooled in dry ice/acetone bath was added n-BuLi (1.6 M in hexanes, 37.1 mL, 59.3 mmol). The mixture was stirred at −78° C. for 35 min. Then 1-(6-(2H-tetrazol-5-yl)pyridin-2-yl)ethan-1-one (5.0 g, 26.4 mmol) was added to the mixture in one batch. The cloudy mixture was stirred while letting the temperature slowly rise to room temperature overnight. The reaction mixture became clear after overnight stirring. To the reaction mixture was added 40 mL of aqueous saturated $NH_4Cl$ solution followed by removal of the THF under reduced pressure. To the residue was added DCM (40 mL) followed by quenching with 1 N aqueous HCl (12 mL, 12 mmol). The pH of the aqueous layer was then adjusted with saturated aqueous $NaHCO_3$ solution to pH ~6. Another 15 mL of aqueous saturated NaCl solution was added. The mixture was extracted with EtOAc (3×) and then with DCM once. All organics were combined and concentrated followed by purifying with silica gel column chromatography (0-5% MeOH/DCM) to afford sticky white solid as the title compound (10.96 g, 73% yield).

ESI-MS m/z: $[M+H]^+$ 525.1 (Rt: 1.02 min., LCMS Method 1).

$^{1}H$ NMR (400 MHz, DMSO-$d_6$) δ 8.11-8.04 (m, 2H), 7.90-7.84 (m, 1H), 7.21-7.13 (m, 0.5H, tautomer), 7.09-7.00 (m, 4H), 6.92-6.83 (m, 0.5H, tetrazole tautomer), 6.80-6.74 (m, 4H), 5.98 (s, 1H), 4.14 (s, 4H), 3.96 (d, J=14.2 Hz, 1H), 3.82-3.71 (m, 1H), 3.69 (s, 6H), 1.63 (s, 3H).

HRMS: M+H, found 525.1915, calc. 525.1920 (HRMS Method 10).

Step 4: 2-(6-(2-(2-fluoro-5-(trifluoromethoxy)benzyl)-2H-tetrazol-5-yl)pyridin-2-yl)-2-hydroxy-N,N-bis(4-methoxybenzyl)propane-1-sulfonamide

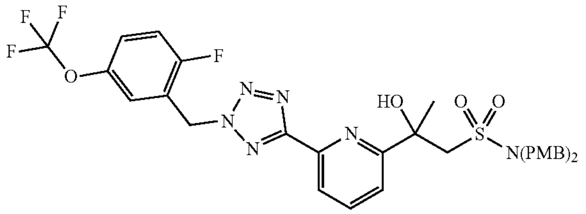

To a stirred mixture of 2-((6-(2H-tetrazol-5-yl)pyridin-2-yl)-2-hydroxy-N,N-bis(4-methoxybenzyl)propane-1-sulfonamide (9.85 g, 18.8 mmol), sodium iodide (14.1 g, 94 mmol), potassium carbonate (7.78 g, 56.3 mmol) in THF (400 mL) under $N_2$ protection was added a solution of 2-(bromomethyl)-1-fluoro-4-(trifluoromethoxy)benzene (5.95 g, 21.8 mmol) in THF (50 mL) at room temperature. The mixture was then stirred at 60° C. under $N_2$ protection for 12 h. The mixture was filtered through a celite bed and the filter cake was rinsed with DCM. The combined filtrate was concentrated under reduced pressure and then the residue was purified with silica gel column chromatography (10-30% ethyl acetate in heptane) to afford two batches of sticky solid: first batch (the first major product eluted from the column as pure title compound, 8.21 g) and second batch: mixture of the desired title compound and N1-alkylated regioisomeric byproduct (second product eluted from the column), 3.09 g total (LCMS result indicates around 20% of N1-alkylated byproduct in second batch). Total yield 79%. Both batches were used in the next step.

ESI-MS m/z: $[M+H]^+$ 717.3 (Rt: 1.28 min., LCMS Method 1).

$^1$H NMR (400 MHz, DMSO-$d_6$) δ 8.06-7.94 (m, 2H), 7.84 (dd, J=7.5, 1.5 Hz, 1H), 7.62 (dd, J=5.9, 3.0 Hz, 1H), 7.54-7.46 (m, 1H), 7.41 (t, J=9.2 Hz, 1H), 7.10-7.00 (m, 4H), 6.85-6.73 (m, 4H), 6.11 (s, 2H), 5.92 (s, 1H), 4.12 (s, 4H), 3.85 (d, J=14.1 Hz, 1H), 3.69 (m, 7H), 1.58 (s, 3H).

Step 5: 2-(6-(2-(2-fluoro-5-(trifluoromethoxy)benzyl)-2H-tetrazol-5-yl)pyridin-2-yl)-2-hydroxypropane-1-sulfonamide

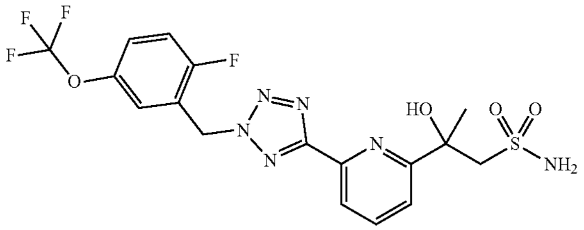 [SMILES: CC(O)(CS(N)(=O)=O)c1cccc(-c2nnn(Cc3cc(OC(F)(F)F)ccc3F)n2)n1]

To a solution of 2-(6-(2-(2-fluoro-5-(trifluoromethoxy)benzyl)-2H-tetrazol-5-yl)pyridin-2-yl)-2-hydroxy-N,N-bis(4-methoxybenzyl)propane-1-sulfonamide (11.2 g, 15.7 mmol) in DCM (60 mL) was added TFA (75.7 mL, 112 g, 982 mmol) and the mixture was stirred at room temperature for 12 h. All volatiles (including DCM and TFA) were removed under reduced pressure and to the residue was added excess triethylamine (30 mL). Volatiles were removed under reduced pressure again. The residue was purified with silica gel column chromatography (0-5% MeOH in DCM) to afford the crude product. Further purification with silica gel column chromatography (30-60% ethyl acetate in heptane) afforded the title compound as a racemate (Rac-1+2) (6.66 g, 89% yield).

ESI-MS m/z: $[M+H]^+$ 477.0 (Rt: 0.96 min., LCMS Method 1).

$^1$H NMR (400 MHz, DMSO-$d_6$) δ 8.05-7.96 (m, 2H), 7.84 (dd, J=6.9, 2.0 Hz, 1H), 7.70 (dd, J=6.1, 3.1 Hz, 1H), 7.55 (dt, J=7.4, 3.6 Hz, 1H), 7.47 (t, J=9.1 Hz, 1H), 6.68 (s, 2H), 6.16 (s, 2H), 5.83 (s, 1H), 3.67 (d, J=3.1 Hz, 2H), 1.62 (s, 3H).

Chiral separation of the racemate of the title compound (Rac-1+2) (13.4 g) provided Example 2 as the first eluting peak (5.52 g, 41% yield, e.e. >99%) and Example 1 as the second eluting peak (5.97 g, 44% yield, e.e. >99%).

Chiral Prep HPLC:

Instrument: Thar 80 system

Column: Chiralcel OD-H (30×250 mm, 5 μm)

Mobile phase: IPA with 10 mM ammonia in MeOH/$CO_2$ (30/70)

Flow rate: 80 g/min.

Detection: UV @272 nm

Example 2

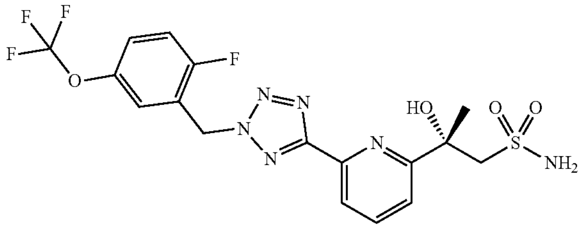

Peak 1 (Example 2): ESI-MS m/z: $[M+H]^+$ 477.3 (Rt: 0.95 min., LCMS Method 1). $^1$H NMR (400 MHz, DMSO-$d_6$) δ 8.-6-7.95 (m, 2H), 7.84 (dd, J=7.0, 2.2 Hz, 1H), 7-2-7.66 (m, 1H), 7-9-7.51 (m, 1H), 7.47 (t, J=9.1 Hz, 1H), 6.67 (s, 2H), 6.16 (s, 2H), 5.83 (s, 1H), 3.-4-3.61 (m, 2H), 1.62 (s, 3H).

e.e. >99% (chiral analysis conditions as below).

Example 1

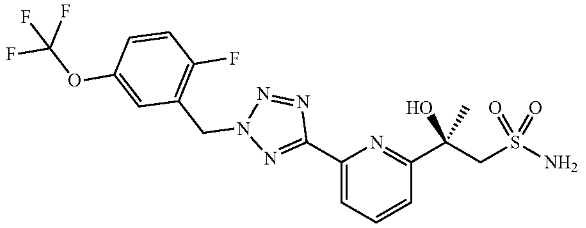

Peak 2 (Example 1): ESI-MS m/z: $[M+H]^+$ 477.0 (Rt: 0.96 min., LCMS Method 2). $^1$H NMR (400 MHz, DMSO-$d_6$) δ 8.03-7.95 (m, 2H), 7.83 (dd, J=6.9, 2.1 Hz, 1H), 7.69 (dd, J=6.4, 2.9 Hz, 1H), 7.54 (dddd, J=9.1, 4.2, 3.1, 0.9 Hz, 1H), 7.46 (t, J=9.1 Hz, 1H), 6.67 (s, 2H), 6.15 (s, 2H), 5.81 (s, 1H), 3.67 (d, J=3.0 Hz, 2H), 1.62 (s, 3H). e.e. >99% (chiral analysis conditions as below).

Enantiomeric excess was determined using the following conditions:

Instrument: Waters $UPC^2$ system

Column: Chiralcel OD-3 (3×100 mm, 3 μm)

Mobile phase: IPA with 0.1% ammonium hydroxide (modifier)/$CO_2$; Gradient: 5% modifier for 0.2 minutes, increase to 55% modifier over 3.0 minutes, and hold at 55% modifier for 0.4 minutes Flow rate: 2.5 mL/min.

Detection: PDA detector (210-400 nm)

Crystalline Forms of Example 1

The absolute stereochemistry of the compound of Example 1 was determined by X-ray analysis to be the (R)-configuration. The absolute stereochemistry of the compound of Example 2 is assumed to be (S)-configuration by analogy.

Crystalline forms of the compound of Example 1 have been isolated as shown in Modifications A-1, A-2 and A-3 as set forth below. The crystalline forms of the compound of Example 1 have been characterized by X-Ray Powder Diffraction (XRPD), Differential Scanning Calorimetry (DSC), Thermogravimetric Analysis (TGA) and NMR using the analytical methods as shown in Table 2 below.

The XRPD profiles for the respective crystalline forms are shown in FIGS. 1, 4 and 7. Lists of characteristic XRPD peaks are given herein in the tables below and described in FIGS. 1, 4 and 7. The peaks listed herein are given as 2-Theta (2θ) angles ±0.2 degree. As will be appreciated by the skilled person, the relative intensities of the various peaks within the tables given below may vary due to a number of factors such as for example orientation effects of crystals in the X-ray beam or the purity of the material being analyzed or the degree of crystallinity of the sample. The peak positions may also shift for variations in sample height but the peak positions will remain substantially as defined in given tables. The skilled person will also appreciate that measurements using a different wavelength will result in different shifts according to the Bragg equation—nλ=2d sin θ. Such alternative XRPD patterns generated by use of alternative wavelengths are nevertheless representations of the same material.

TABLE 2

| Analytical methods | |
|---|---|
| Analytical method | Details |
| **TGA method** | |
| Instrument | TA Discovery |
| Temperature range | Room temperature to 300° C. |
| Scan rate | 10 K/min |
| Nitrogen flow | 20 mL/min |
| Sample mass | Approximately 2-10 mg |
| **DSC method** | |
| Instrument | TA Discovery |
| Temperature range | 0° C. to 250° C. or 300° C. |
| Scan rate | 10 K/min |
| Nitrogen flow | 50 mL/min |
| Sample mass | Approximately 2 mg |
| **XRPD method 1 & 2** | |
| Instrument | Bruker D8 Advance |
| Detector | LynxEye (1D mode), open angle: 2.948° |
| Radiation | CuKa (wavelength = 0.15418 nm) |
| Monochromator | Ni-filter |
| X-ray generator power | 40 kV, 40 mA |
| Step size | 0.0164° or 0.0410° (2-Theta) |
| Time per step | 0.15 s |
| Scan range | 2°-40° 2-Theta (2θ) |
| Scan time | 356.4 s |
| Slits | Primary fixed illuminated sample size: 10 mm, secondary: open angle: 2.2°, axial soller: 2.5° |
| **NMR** | |
| Instrument | Bruker ASCEND 400 MHz |
| Probe | 5 mm PABBO BB-1H/D Z-GRD Z108618/0226 |
| Temperature | 295.7 K |
| Relaxation delay | 1 second |

Modification A-1: Co-crystal of (R)-2-(6-(2-(2-fluoro-5-(trifluoromethoxy)benzyl)-2H-tetrazol-5-yl)pyridin-2-yl)-2-hydroxypropane-1-sulfonamide with L-proline The compound of Example 1 (1.01 g) and L-proline (0.25 g) were dissolved in 11 mL of EtOH/water (98/2, v/v) at room temperature and then filtered to form a clear solution. Heptane (25 mL) was added to the resulting solution within 80 minutes. 1-3 mg of seeds were added to the solution during addition of heptane. The mixture was stirred overnight at 25° C. starting from 300 rpm and further increased to 600 rpm for one hour. The suspension so obtained was filtered by centrifuge at 4000 rpm to yield a crystalline solid (0.71 g) after drying at 40° C. for four hours.

The solid residue was analyzed by XRPD, DSC, TGA and NMR.

The co-crystal form of Modification A-1 is provided as an anhydrous crystalline form. It is not hygroscopic and shows a reversible water uptake of about 0.10% at 90% relative humidity. Its physicochemical properties are represented in Table 3.

Figure 2:
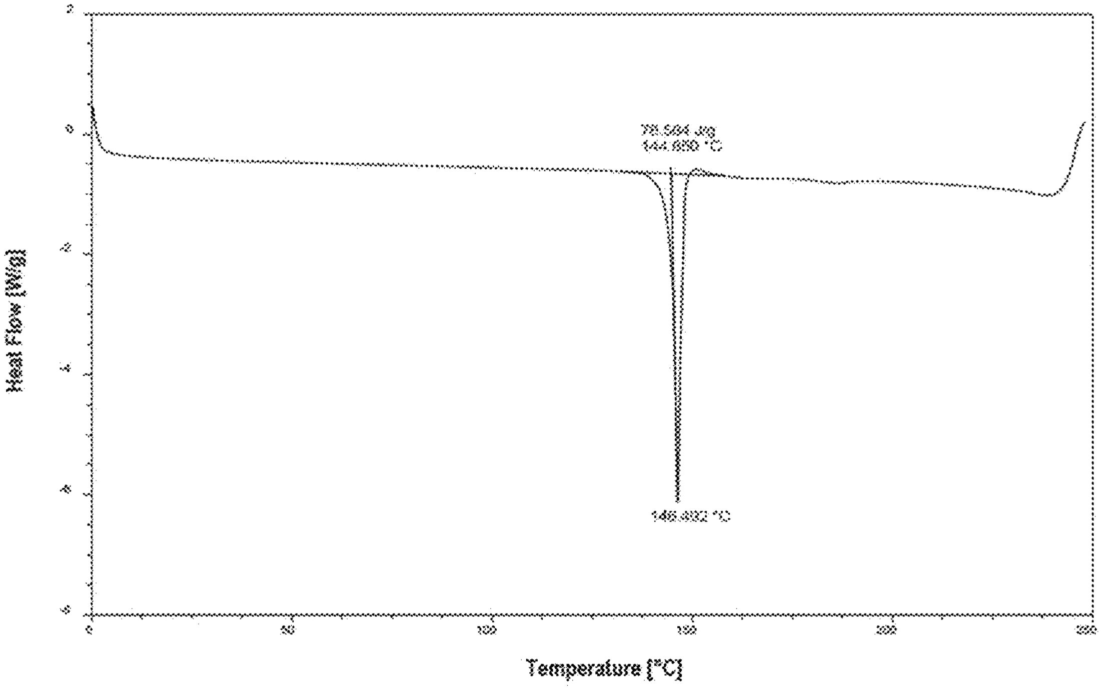
FIG. 2 shows the Differential Scanning Calorimetry thermogram of Modification A-1.
Figure 3:
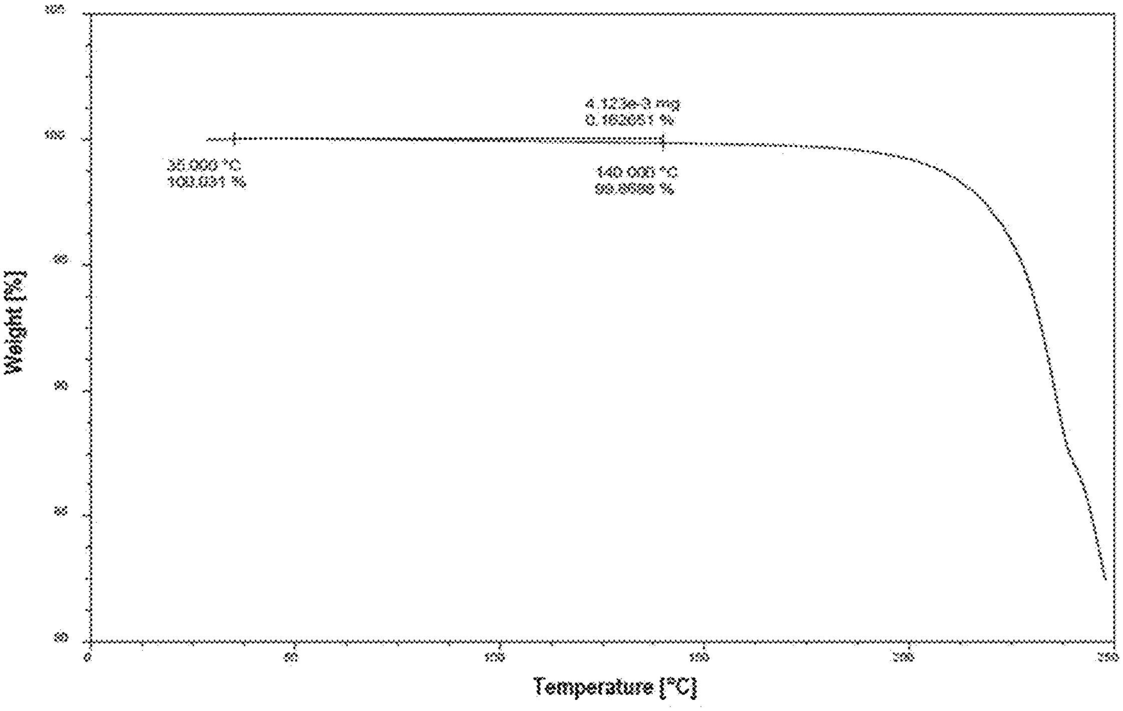
FIG. 3 shows the Thermogravimetric Analysis of Modification A-1.

The XRPD pattern of the co-crystal of Modification A-1 is shown in FIG. 1. The DSC thermogram of the co-crystal of Modification A-1 is shown in FIG. 2. The TGA of the co-crystal of Modification A-1 is shown in FIG. 3. DSC data showing the melting transitions of the co-crystal of Modification A-1 and the total water loss (Loss on Drying—LOD) as measured by TGA are represented in Table 3.

TABLE 3

| Physicochemical properties of Modifications A-1, A-2 and A-3 | | | |
|---|---|---|---|
| Parameter | Modification A-1 | Modification A-2 | Modification A-3 |
| Purity (HPLC) | 99.49% | 99.73% | 99.45% |
| Molar ratio (NMR) | 1:1.02 (L-proline) | 1:2.90 (L-proline) | 1:1.03 (Cl) |
| $T_{onset}$ melting point (DSC) | 144.9° C./ 78.6 J/g | 112.6° C./ 53.8 J/g | 78.7° C./ 163.4 J/g |
| LOD (TGA) | 0.2% at 140° C. | 1.3% at 100° C. | 14.6% at 160° C. |

The XRPD peaks of the co-crystal form of Modification A-1 at 2θ angles (±0.2 degree), when measured using a CuKa radiation with a wavelength of 1.5418 Å at a temperature of about 22° C., are as set forth in Table 4A:

TABLE 4A

| No. | Angle 2θ | d value Å | Relative Intensity % |
|---|---|---|---|
| 1 | 6.8 | 13.0 | 11.9 |
| 2 | 8.0 | 11.0 | 42.6 |
| 3 | 10.2 | 8.6 | 16.9 |
| 4 | 10.6 | 8.4 | 30.5 |
| 5 | 11.3 | 7.8 | 100.0 |
| 6 | 12.1 | 7.3 | 14.6 |
| 7 | 15.4 | 5.7 | 59.8 |
| 8 | 16.1 | 5.5 | 13.2 |
| 9 | 17.2 | 5.2 | 95.9 |
| 10 | 18.0 | 4.9 | 49.1 |
| 11 | 18.7 | 4.7 | 28.9 |
| 12 | 19.1 | 4.6 | 65.1 |
| 13 | 20.2 | 4.4 | 87.3 |
| 14 | 21.4 | 4.1 | 13.9 |
| 15 | 23.9 | 3.7 | 13.3 |
| 16 | 26.0 | 3.4 | 15.0 |

Modification A-2: Co-crystal of (R)-2-(6-(2-(2-fluoro-5-(trifluoromethoxy)benzyl)-2H-tetrazol-5-yl)pyridin-2-yl)-2-hydroxypropane-1-sulfonamide with L-proline The compound of Example 1 (1.00 g) was dissolved in 6 mL of acetonitrile (water content around 0.8%) and then heated to 50° C. L-proline (0.24 g) was suspended in 4 mL of acetonitrile and then heated to 50° C. The solution of the compound of Example 1 was added into the L-proline suspension and stirred for 3.5 hours at 50° C. and then cooled to room temperature over 2 days. The suspension so obtained was filtered by centrifuge at 4000 rpm to yield a crystalline solid (0.47 g) after drying at 50° C. for 24 hours.

The solid reside was analyzed by XRPD, DSC, TGA and NMR.

The co-crystal form of Modification A-2 is provided as a monohydrate crystalline form. It is hygroscopic and shows gel formation at 70% relative humidity and above. Its physicochemical properties are represented in Table 3.

Figure 5:
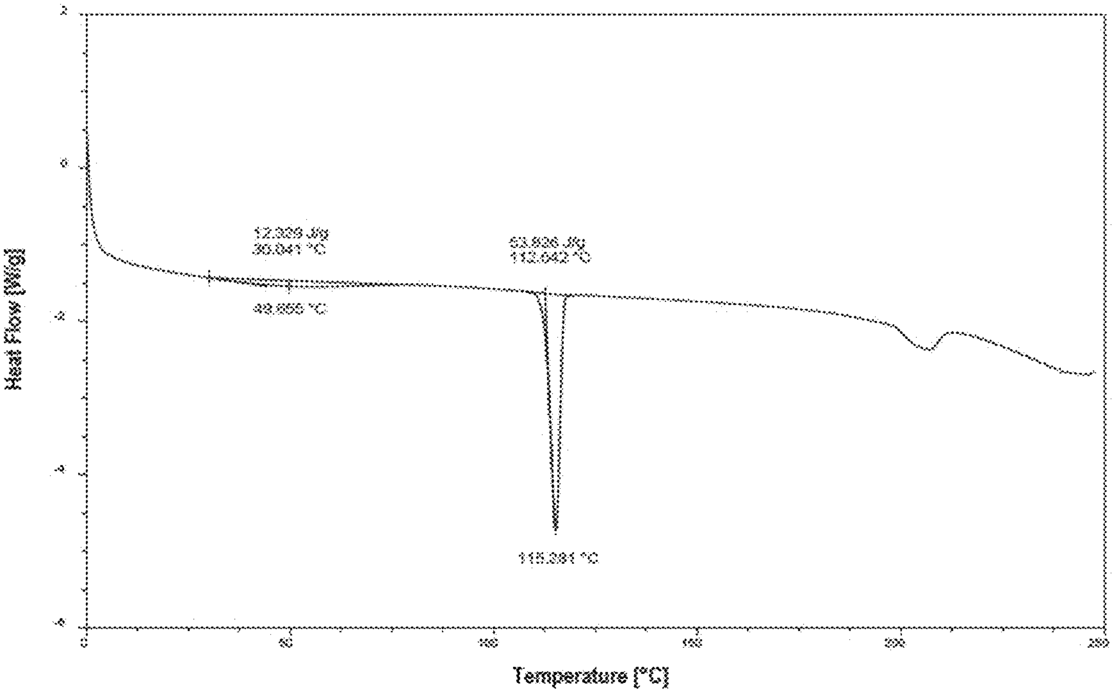
FIG. 5 shows the Differential Scanning Calorimetry thermogram of Modification A-2.
Figure 6:
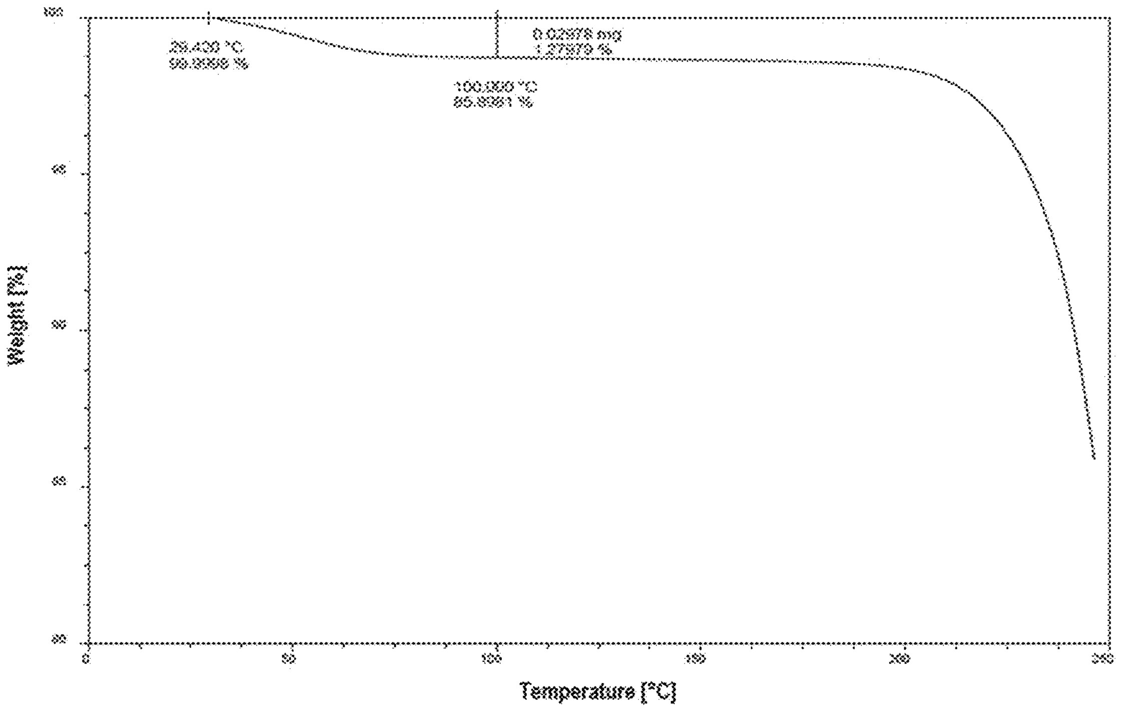
FIG. 6 shows the Thermogravimetric Analysis of Modification A-2.

The XRPD pattern of the co-crystal of Modification A-2 is shown in FIG. 4. The DSC thermogram of the co-crystal of Modification A-2 is shown in FIG. 5. The TGA of the co-crystal of Modification A-2 is shown in FIG. 6. DSC data showing the melting transitions of the co-crystal of Modification A-2 and the total water loss (Loss on Drying—LOD) as measured by TGA are represented in Table 3.

The XRPD peaks of the co-crystal of Modification A-2 at 2θ angles (±0.2 degree), when measured using a CuKa radiation with a wavelength of 1.5418 Å at a temperature of about 22° C., are as set forth in Table 4B:

TABLE 4B

| No. | Angle 2θ | d value Å | Relative Intensity % |
|---|---|---|---|
| 1 | 5.5 | 16.0 | 21.7 |
| 2 | 8.7 | 10.2 | 38.0 |
| 3 | 9.4 | 9.4 | 12.5 |
| 4 | 11.1 | 8.0 | 32.1 |
| 5 | 12.7 | 7.0 | 9.0 |
| 6 | 15.3 | 5.8 | 19.2 |
| 7 | 16.6 | 5.3 | 95.8 |
| 8 | 17.2 | 5.1 | 53.2 |
| 9 | 18.8 | 4.7 | 100.0 |
| 10 | 19.2 | 4.6 | 60.9 |
| 11 | 20.1 | 4.4 | 31.6 |
| 12 | 21.7 | 4.1 | 39.3 |
| 13 | 22.2 | 4.0 | 59.7 |
| 14 | 25.3 | 3.5 | 10.8 |
| 15 | 26.2 | 3.4 | 22.7 |
| 16 | 28.7 | 3.1 | 11.4 |
| 17 | 30.8 | 2.9 | 17.5 |

Modification A-3: Crystalline form of hydrochloride salt of (R)-2-(6-(2-(2-fluoro-5-(trifluoromethoxy)benzyl)-2H-tetrazol-5-yl)pyridin-2-yl)-2-hydroxypropane-1-sulfonamide The compound of Example 1 (25.00 g) was dissolved in 270 mL of 4-methyl-2-pentanone (MIBK) at room temperature in an EasyMax vessel at 300 rpm and the solution so obtained was heated to 50° C. To this was added a solution of 12M hydrochloric acid (4.60 mL) in MIBK (130 mL) by dropwise addition over 5.5 hours at 50° C. using an injection pump. To the resulting suspension was added 9 mg of seed crystals. The resulting mixture was stirred for 7 hours at 50° C. followed by 8 hours at 20° C. The resulting solid was collected by vacuum filtration, washed with MIBK and dried at ambient temperature (about 25° C. with 45% relative humidity) for 1 day to yield a crystalline solid (24.31 g).

The solid reside was analyzed by XRPD, DSC, TGA and NMR.

The crystalline form of Modification A-3 is provided as a MIBK solvate crystalline form. It is hygroscopic and shows gel formation at 70% relative humidity and above. Its physicochemical properties are represented in Table 3.

Figure 8:
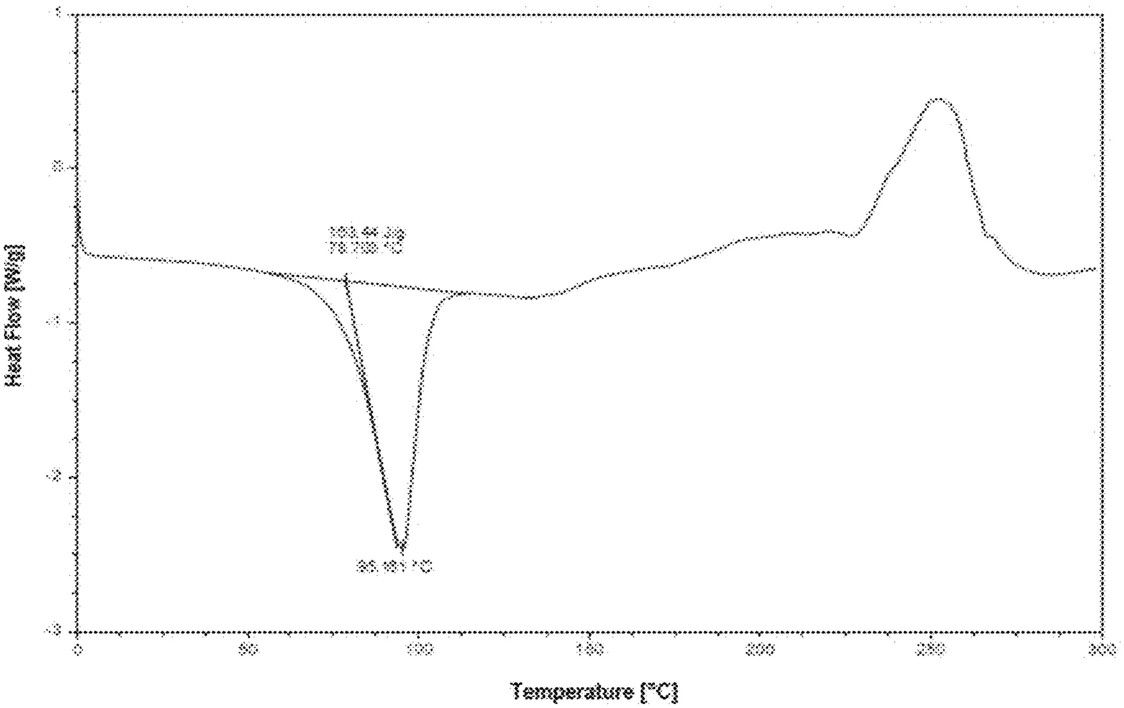
FIG. 8 shows the Differential Scanning Calorimetry thermogram of Modification A-3.
Figure 9:
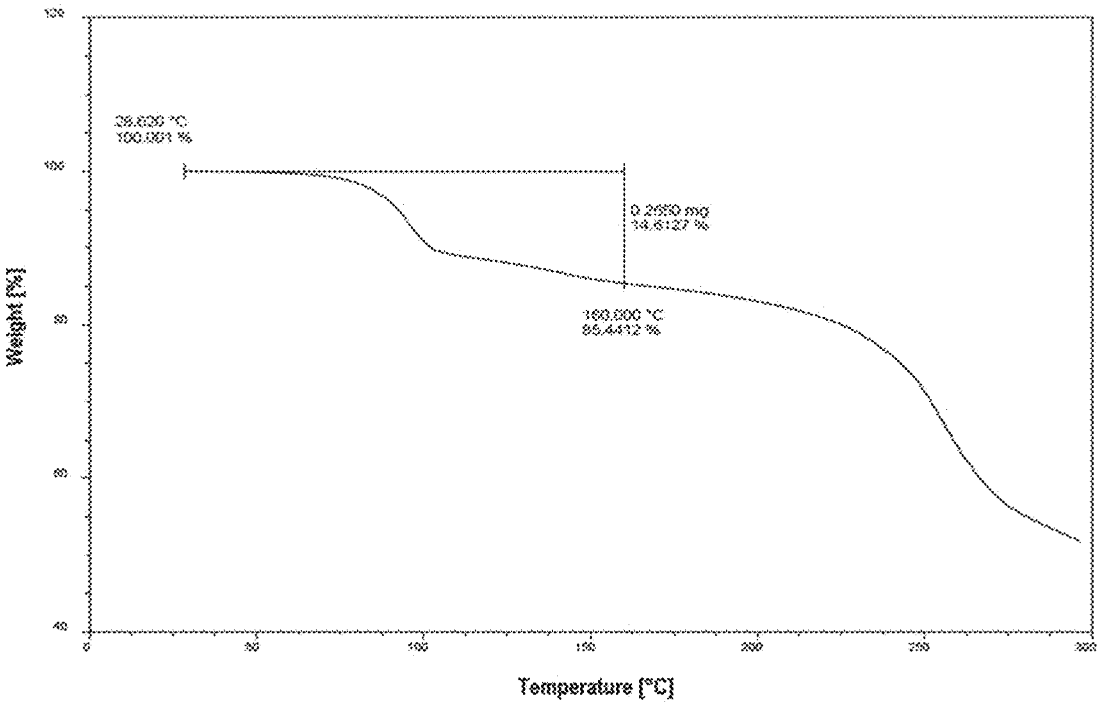
FIG. 9 shows the Thermogravimetric Analysis of Modification A-3.

The XRPD pattern of the crystalline form of Modification A-3 is shown in FIG. 7. The DSC thermogram of the crystalline form of Modification A-3 is shown in FIG. 8. The TGA of the crystalline form of Modification A-3 is shown in FIG. 9. DSC data showing the melting transitions of the crystalline form of Modification A-3 and the total water loss (Loss on Drying—LOD) as measured by TGA are represented in Table 3.

The XRPD peaks of the crystalline form of Modification A-3 at 2θ angles (±0.2 degree), when measured using a CuKa radiation with a wavelength of 1.5418 Å at a temperature of about 22° C., are as set forth in Table 4C:

TABLE 4C

| No. | Angle 2θ | d value Å | Relative Intensity % |
|---|---|---|---|
| 1 | 7.5 | 11.7 | 21.0 |
| 2 | 11.2 | 7.9 | 9.0 |
| 3 | 14.3 | 6.2 | 100.0 |
| 4 | 15.5 | 5.7 | 5.9 |
| 5 | 16.6 | 5.3 | 2.4 |
| 6 | 17.9 | 5.0 | 3.5 |
| 7 | 18.5 | 4.8 | 32.6 |
| 8 | 19.1 | 4.6 | 27.0 |
| 9 | 20.0 | 4.4 | 39.0 |
| 10 | 20.4 | 4.4 | 3.1 |
| 11 | 21.4 | 4.1 | 4.5 |
| 12 | 22.5 | 4.0 | 3.0 |
| 13 | 22.8 | 3.9 | 3.5 |
| 14 | 23.9 | 3.7 | 32.2 |
| 15 | 28.8 | 3.1 | 13.9 |

Synthesis of Examples 3 to 62

Example 3: (R or S)-2-hydroxy-2-(6-(2-((2,2,5-trifluorobenzo[d][1,3]dioxol-4-yl)methyl)-2H-tetrazol-5-yl)pyridin-2-yl)propane-1-sulfonamide and Example 4: (R or S)-2-hydroxy-2-(6-(2-((2,2,5-trifluorobenzo[d][1,3]dioxol-4-yl)methyl)-2H-tetrazol-5-yl)pyridin-2-yl)propane-1-sulfonamide Prepared by analogy to Examples 1 and 2 according to Scheme 1 by replacing 2-(bromomethyl)-1-fluoro-4-(trifluoromethoxy)benzene with Intermediate 1 to afford the racemate of the title compound (Rac-3+4) (180 mg).

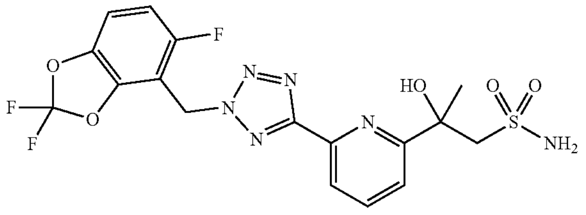 [SMILES: CC(O)(CS(N)(=O)=O)c1cccc(-c2nnn(Cc3c(F)ccc4c3OC(F)(F)O4)n2)n1]

Chiral separation of the racemate (180 mg) provided Example 3 as the first eluting peak (87 mg, 48% yield, chiral HPLC: e.e. 97.54%, Rt: 2.12 min.) and Example 4 as the second eluting peak (90 mg, 50% yield, chiral HPLC: e.e. 96.22%, Rt: 2.36 min.) as white solids.

Chiral Prep HPLC:

Instrument: Waters Preparative SFC80

Column: Chiralpak IG (21×250 mm, 5 μm) @35° C.

Mobile phase: methanol/$CO_2$ (25/75)

Flow rate: 80 g/min.

Detection: UV @230 nm

Peak 1 (Example 3): ESI-MS m/z: 473.2 $[M+H]^+$ (Rt: 1.94 min., LCMS Method 3); $^1$H NMR (400 MHz, DMSO-$d_6$) δ 8.05-7.94 (m, 2H), 7.84 (dd, J=7.3, 1.9 Hz, 1H), 7.56 (dd, J=8.9, 4.2 Hz, 1H), 7.23 (dd, J=10.7, 8.9 Hz, 1H), 6.67 (s, 2H), 6.20 (s, 2H), 5.83 (s, 1H), 3.67 (d, J=2.9 Hz, 2H), 1.62 (s, 3H). e.e. 97.54%, Rt: 2.12 min. (chiral analysis conditions as below).

Peak 2 (Example 4): ESI-MS m/z: 473.1 $[M+H]^+$ (Rt: 1.95 min., LCMS Method 3); $^1$H NMR (400 MHz, DMSO-$d_6$) δ 8.05-7.94 (m, 2H), 7.84 (dd, J=7.3, 1.9 Hz, 1H), 7.56 (dd, J=9.0, 4.1 Hz, 1H), 7.23 (dd, J=10.5, 9.0 Hz, 1H), 6.67 (s, 2H), 6.20 (s, 2H), 5.83 (s, 1H), 3.67 (d, J=2.9 Hz, 2H), 1.62 (s, 3H). e.e. 96.22%, Rt: 2.36 min. (chiral analysis conditions as below).

Enantiomeric excess was determined using the following conditions:

Instrument: Waters UPC$^2$ system

Column: Chiralpak IG-3 (3 μm, 3×100 mm) @40° C.

Mobile phase: Methanol with 0.1% ammonium hydroxide (modifier)/$CO_2$; Gradient: 5% modifier for 0.2 minutes, increase to 55% modifier over 3.0 minutes, and hold at 55% modifier for 0.4 minutes Flow rate: 2.5 mL/min.

Detection: PDA detector (210-400 nm)

Example 5: (R or S)-2-(2-fluoro-5-(2-(2-fluoro-5-(trifluoromethoxy)benzyl)-2H-tetrazol-5-yl)phenyl)-2-hydroxypropane-1-sulfonamide and Example 6: (R or S)-2-(2-fluoro-5-(2-(2-fluoro-5-(trifluoromethoxy)benzyl)-2H-tetrazol-5-yl)phenyl)-2-hydroxypropane-1-sulfonamide Prepared by analogy to Examples 1 and 2 according to Scheme 1 starting from Intermediate 2 to afford the racemate of the title compound (1.0 g).

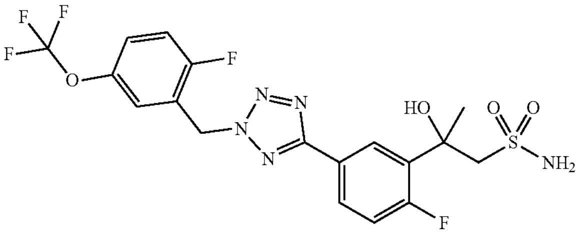 [SMILES: CC(O)(CS(N)(=O)=O)c1cc(-c2nnn(Cc3cc(OC(F)(F)F)ccc3F)n2)ccc1F]

Chiral separation of the racemate (1.0 g) provided Example 6 as the first eluting peak (223 mg, 23% yield. Chiral HPLC purity: 98.5%, Rt: 4.875 min.) and Example 5 as the second eluting peak (143 mg, 14% yield. Chiral HPLC purity: 99.5%, Rt: 7.450 min.) as white solids.

Chiral Prep HPLC:

Instrument: Agilent 1260 Infinity

Column: CHIRAL PAK-IG (250 mm×20 mm), 5 μm

Mobile phase: 15% DCM in hexane (A); 0.1% ammonia in EtOH: MeOH (50:50, B); Isocratic: 75(A):25(B)

Flow rate: 15 m/min.

Detection: UV 210 nm

Peak 1 (Example 6): MS (ESI+): m/z 494.15 (M+H), Rt: 0.830 min. [LCMS Method 4]; $^1$H NMR (400 MHz, $CD_3OD$) δ 8.47 (dd, J=8.0, 2.4 Hz, 1H), 8.07-8.02 (m, 1H), 7.49-7.46 (m, 1H), 7.42-7.37 (m, 1H), 7.31 (t, J=8.8 Hz, 1H), 7.20 (dd, J=11.6, 8.4 Hz, 1H), 6.00 (d, J=5.2 Hz, 2H), 3.80 (d, J=14.8 Hz, 1H), 3.69 (d, J=14.8 Hz, 1H), 1.73 (d, J=0.8 Hz, 3H).

Peak 2 (Example 5): MS (ESI+): m/z 494.15 (M+H), Rt: 0.828 min. [LCMS Method 4]; $^1$H NMR (400 MHz, $CD_3OD$) δ 8.47 (dd, J=8.0, 2.4 Hz, 1H), 8.07-8.02 (m, 1H), 7.49-7.46 (m, 1H), 7.42-7.37 (m, 1H), 7.31 (t, J=9.2 Hz, 1H), 7.20 (dd, J=12.0, 8.8 Hz, 1H), 6.00 (s, 2H), 3.81 (d, J=14.4 Hz, 1H), 3.69 (d, J=14.8 Hz, 1H), 1.73 (d, J=0.8 Hz, 3H).

Chiral HPLC retention times were obtained using the following conditions:

Instrument: Agilent 1260 Infinity II

Column: CHIRAL PAK-IG (150 mm×4.6 mm), 5 μm

Mobile phase: n-hexane (A); 0.1% NH4OH in EtOH: MeOH (50:50, B); Isocratic: 70(A):
30(B)

Flow rate: 1.0 mL/min.

Detection: UV @210 nm

Example 7: (R or S)-2-(4-chloro-3-(2-(2-fluoro-5-(trifluoromethoxy)benzyl)-2H-tetrazol-5-yl)phenyl)-2-hydroxypropane-1-sulfonamide and Example 8: (R or S)-2-(4-chloro-3-(2-(2-fluoro-5-(trifluoromethoxy)benzyl)-2H-tetrazol-5-yl)phenyl)-2-hydroxypropane-1-sulfonamide Prepared by analogy to examples 1 and 2 according to Scheme 1 starting from intermediate 3 to afford the racemate of the title compound (120 mg).

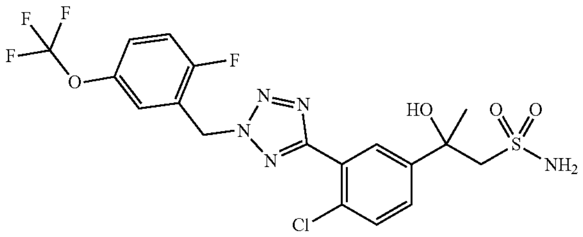 [SMILES: CC(O)(CS(N)(=O)=O)c1ccc(Cl)c(-c2nnn(Cc3cc(OC(F)(F)F)ccc3F)n2)c1]

Chiral separation of the racemate (120 mg) provided Example 7 as the first eluting peak (23 mg, 19% yield, chiral HPLC purity: 97.99%, Rt: 5.173 min.) and Example 8 as the second eluting peak (27 mg, 23% yield, chiral HPLC purity: 97.60%, 7.332 min.) as white solids.

Chiral Prep HPLC:

Instrument: Agilent 1260 Infinity

Column: CHIRALPAK IG, (250 mm×20 mm), 5.0 μm

Mobile phase: n-hexane (A); EtOH: MeOH (1:1, B); Isocratic: 50(A):50(B)

Flow rate: 15 m/min.

Detection: UV @210 nm

Peak 1 (Example 7): MS (ESI+): m/z 510.2 (M+H), Rt: 1.657 min. [LCMS Method 5]; $^1$H NMR (400 MHz, $CD_3OD$) δ 8.05 (d, J=2.4 Hz, 1H), 7.65 (dd, J=8.4, 2.4 Hz, 1H), 7.55 (d, J=8.4 Hz, 1H), 7.49-7.46 (m, 1H), 7.43-7.37 (m, 1H), 7.32 (d, J=8.8 Hz, 1H), 6.05 (s, 2H), 3.63 (s, 2H), 1.75 (s, 3H).

Peak 2 (Example 8): MS (ESI+): m/z 510.2 (M+H), Rt: 1.67 min. [LCMS Method 5]; $^1$H NMR (400 MHz, $CD_3OD$) δ 8.05 (d, J=2.4 Hz, 1H), 7.64 (dd, J=8.4, 2.4 Hz, 1H), 7.54 (d, J=8.4 Hz, 1H), 7.49-7.46 (m, 1H), 7.43-7.37 (m, 1H), 7.32 (d, J=9.2 Hz, 1H), 6.05 (s, 2H), 3.61 (s, 2H), 1.74 (s, 3H).

Chiral HPLC retention times were obtained using the following conditions:

Instrument: Agilent 1260 Infinity II

Column: CHIRALPAK-IG, (150 mm×4.6 mm), 5.0 μm

Mobile phase: n-hexane (A); 0.1% DEA in EtOH: MeOH (70:30, B); Isocratic: 50(A): 50(B)

Flow rate: 1.0 mL/min.

Detection: UV @210 nm

Example 9: (R or S)-2-(4-fluoro-3-(2-(2-fluoro-5-(trifluoromethoxy)benzyl)-2H-tetrazol-5-yl)phenyl)-2-hydroxypropane-1-sulfonamide and Example 10: (R or S)-2-(4-fluoro-3-(2-(2-fluoro-5-(trifluoromethoxy)benzyl)-2H-tetrazol-5-yl)phenyl)-2-hydroxypropane-1-sulfonamide

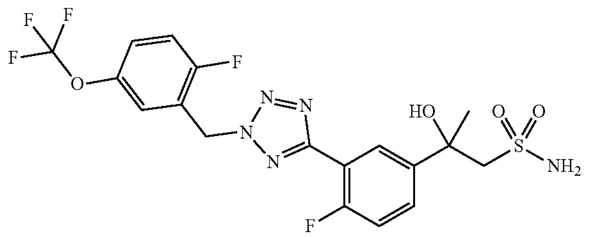 [SMILES: CC(O)(CS(N)(=O)=O)c1ccc(F)c(-c2nnn(Cc3cc(OC(F)(F)F)ccc3F)n2)c1]

Step 1: 2-(3-cyano-4-fluorophenyl)-2-hydroxy-N,N-bis(4-methoxybenzyl)propane-1-sulfonamide

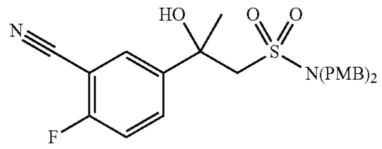

Prepared according to the procedure followed in Step 3 of examples 1 and 2 starting from Intermediate 4 (0.60 g, 3.677 mmol) to afford the title product as yellow gummy compound. Yield: 2.0 g (Crude). MS (ESI+): m/z 499.25 (M+H), Rt: 1.599 min. [LCMS Method 6].

Step 2: 2-(4-fluoro-3-(2H-tetrazol-5-yl)phenyl)-2-hydroxy-N,N-bis(4-methoxybenzyl)propane-1-sulfonamide

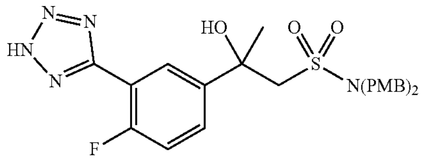

Prepared according to the procedure followed in Step 2 from examples 1 and 2 to afford the title compound as brown gummy material. Yield: 2.0 g (92% yield). MS (ESI+): m/z 542.3 (M+H), Rt: 0.404 min. [LCMS Method 5].

Step 3: 2-(4-fluoro-3-(2-(2-fluoro-5-(trifluoromethoxy)benzyl)-2H-tetrazol-5-yl)phenyl)-2-hydroxy-N,N-bis(4-methoxybenzyl)propane-1-sulfonamide

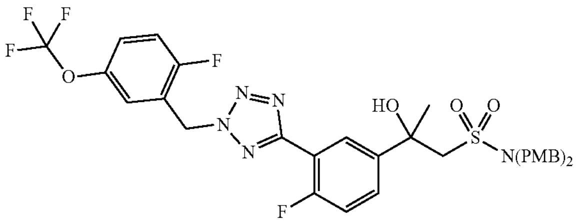

Prepared according to procedure followed in Step 4 from examples 1 and 2 to afford the title compound as yellow sticky material. Yield: 1.6 g (51% yield). MS (ESI+): m/z 734.25 (M+H), Rt: 0.973 min. [LCMS Method 4].

Step 4: 2-(4-fluoro-3-(2-(2-fluoro-5-(trifluoromethoxy)benzyl)-2H-tetrazol-5-yl)phenyl)-2-hydroxypropane-1-sulfonamide

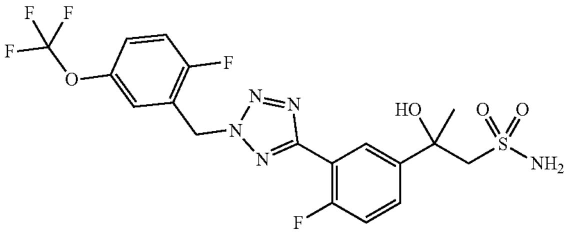 [SMILES: CC(O)(CS(N)(=O)=O)c1ccc(F)c(-c2nnn(Cc3cc(OC(F)(F)F)ccc3F)n2)c1]

Prepared according to procedure followed in Step 5 from examples 1 and 2 to afford the racemate of the title compound (400 mg).

Chiral separation of the racemate (400 mg) provided Example 10 as the first eluting peak (132 mg, 33% yield, chiral HPLC purity: 98.9%, Rt: 5.414 min.) and Example 9 as the second eluting peak (145 mg, 36% yield, chiral HPLC purity: 99.1%, Rt: 8.939 min.) as white solids.

Chiral Prep HPLC:

Instrument: Agilent 1260 Infinity

Column: CHIRAL PAK IG (20.0 mm×250 mm), 5 μm

Mobile phase: n-hexane (A); EtOH: MeOH (1:1, B); Isocratic: 60(A): 40(B)

Flow rate: 15 m/min.

Detection: UV @210 nm

Peak 1 (Example 10): MS (ESI+): m/z 494.4 (M+H), Rt: 0.383 min. [LCMS Method 5]; $^1$H NMR (400 MHz, $CD_3OD$) δ 8.22 (dd, J=6.8, 2.4 Hz, 1H), 7.70-7.64 (m, 1H), 7.50-7.46 (m, 1H), 7.41-7.36 (m, 1H), 7.34-7.21 (m, 2H), 6.03 (s, 2H), 3.58 (s, 2H), 1.74 (s, 3H).

Peak 2 (Example 9): MS (ESI+): m/z 494.2 (M+H), Rt: 0.375 min. [LCMS Method 5]; $^1$H NMR (400 MHz, $CD_3OD$) δ 8.22 (dd, J=6.8, 2.8 Hz, 1H), 7.70-7.64 (m, 1H), 7.50-7.46 (m, 1H), 7.41-7.36 (m, 1H), 7.34-7.21 (m, 2H), 6.03 (s, 2H), 3.57 (s, 2H), 1.74 (s, 3H).

Chiral HPLC retention times were obtained using the following conditions:

Instrument: Agilent 1260 Infinity II

Column: CHIRAL PAK-IG (150 mm×4.6 mm), 5 μm

Mobile phase: n-hexane (A); 0.1% HCOOH EtOH: MeOH (80:20, B); Isocratic: 70(A): 30(B)

Flow rate: 1.0 mL/min.

Detection: UV @210 nm

Example 11: (R or S)-2-(2-fluoro-3-(2-(2-fluoro-5-(trifluoromethoxy)benzyl)-2H-tetrazol-5-yl)phenyl)-2-hydroxypropane-1-sulfonamide and Example 12: (R or S)-2-(2-fluoro-3-(2-(2-fluoro-5-(trifluoromethoxy)benzyl)-2H-tetrazol-5-yl)phenyl)-2-hydroxypropane-1-sulfonamide Prepared by analogy to Examples 9 and 10 according to Scheme 1 starting from Intermediate 5 to afford the racemate of the title compound (830 mg).

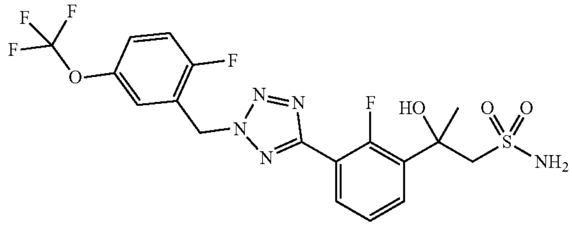 [SMILES: CC(O)(CS(N)(=O)=O)c1cccc(-c2nnn(Cc3cc(OC(F)(F)F)ccc3F)n2)c1F]

Chiral separation of the racemate (830 mg) provided Example 12 as the first eluting peak (290 mg, 35% yield, chiral HPLC purity: 99.1%, Rt: 5.521 min.) and Example 11 as the second eluting peak (266 mg, 32% yield, chiral HPLC purity: 98.8%, Rt: 6.888 min.) as white solids.

Chiral Prep HPLC:

Instrument: Agilent 1260 Infinity

Column: CHIRALPAK IH (250 mm×20 mm), 5 μm

Mobile phase: n-hexane (A); EtOH: MeOH (1:1, B); Isocratic: 75(A): 25(B)

Flow rate: 15 m/min.

Detection: UV @210 nm

Peak 1 (Example 12): MS (ESI+): m/z 494.0 (M+H), Rt: 1.501 min. [LCMS Method 6]; $^{1}H$ NMR (400 MHz, $CD_3OD$) δ 8.01-7.96 (m, 1H), 7.92-7.85 (m, 1H), 7.52-7.49 (m, 1H), 7.44-7.39 (m, 1H), 7.37-7.31 (m, 2H), 6.05 (s, 2H), 3.87 (d, J=14.4 Hz, 1H), 3.72 (d, J=14.4 Hz, 1H), 1.76 (d, J=0.8 Hz, 3H).

Peak 2 (Example 11): MS (ESI+): m/z 494.05 (M+H), Rt: 1.500 min. [LCMS Method 6]; $^{1}H$ NMR (400 MHz, $CD_3OD$) δ 8.01-7.96 (m, 1H), 7.92-7.85 (m, 1H), 7.52-7.49 (m, 1H), 7.44-7.39 (m, 1H), 7.37-7.31 (m, 2H), 6.05 (s, 2H), 3.87 (d, J=14.4 Hz, 1H), 3.72 (d, J=14.4 Hz, 1H), 1.76 (s, 3H).

Chiral HPLC retention times were obtained using the following conditions:

Instrument: Agilent 1260 Infinity II

Column: CHIRALPAK-IH (150 mm×4.6 mm), 5 μm

Mobile phase: n-hexane (A); EtOH: MeOH (1:1, B); Isocratic: 70(A):30(B)

Flow rate: 1.0 mL/min.

Detection: UV @210 nm

Example 13: (2R or 2S, 3R or 3S)-3-(6-(2-(2-fluoro-5-(trifluoromethoxy)benzyl)-2H-tetrazol-5-yl)pyridin-2-yl)-3-hydroxybutane-2-sulfonamide and Example 14: (2R or 2S,3R or 3S)-3-(6-(2-(2-fluoro-5-(trifluoromethoxy)benzyl)-2H-tetrazol-5-yl)pyridin-2-yl)-3-hydroxybutane-2-sulfonamide and Example 15: (2R or 2S,3R or 3S)-3-(6-(2-(2-fluoro-5-(trifluoromethoxy)benzyl)-2H-tetrazol-5-yl)pyridin-2-yl)-3-hydroxybutane-2-sulfonamide and Example 16: (2R or 2S, 3R or 3S)-3-(6-(2-(2-fluoro-5-(trifluoromethoxy)benzyl)-2H-tetrazol-5-yl)pyridin-2-yl)-3-hydroxybutane-2-sulfonamide Prepared according to Scheme 2.

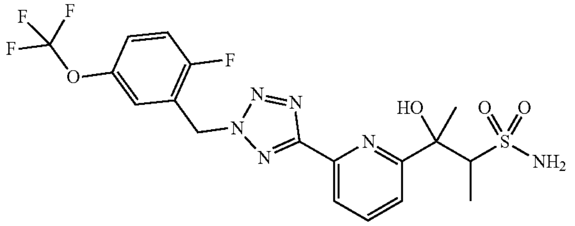 [SMILES: CC(C(C)(O)c1cccc(-c2nnn(Cc3cc(OC(F)(F)F)ccc3F)n2)n1)S(N)(=O)=O]

Step 1: 1-(6-(2-(2-fluoro-5-(trifluoromethoxy)benzyl)-2H-tetrazol-5-yl)pyridin-2-yl)ethan-1-one

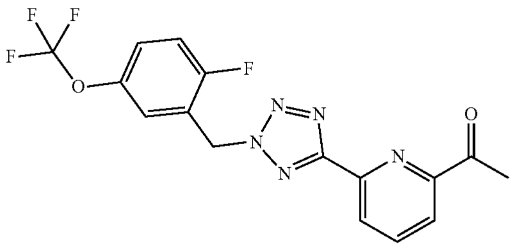 [SMILES: CC(=O)c1cccc(-c2nnn(Cc3cc(OC(F)(F)F)ccc3F)n2)n1]

To a stirred mixture of 1-(6-(2H-tetrazol-5-yl)pyridin-2-yl)ethan-1-one (8.4 g, 44.4 mmol), $K_2CO_3$ (18.41 g, 133 mmol) and NaI (33.3 g, 222 mmol) in THF (200 mL) was added a solution of 2-(bromomethyl)-1-fluoro-4-(trifluoromethoxy)benzene (13.34 g, 48.9 mmol) in THF (50 mL). The mixture was stirred under $N_2$ protection at 65° C. for 15 h. The resulting reaction mixture was filtered through a celite bed and the filter cake was rinsed with EtOAc. The combined filtrate was concentrated under reduced pressure to dryness. The residue was purified with silica gel column chromatography (0-25-35% ethyl acetate in heptane) to afford the title compound (the first major peak eluted out as the desired regioisomer: 10.0 g, 54% yield. $^{1}H$ NMR (400 MHz, DMSO-$d_6$): δ 8.36 (dd, J=7.8, 1.1 Hz, 1H), 8.21 (t, J=7.8 Hz, 1H), 8.09 (dd, J=7.8, 1.1 Hz, 1H), 7.76-7.67 (m, 1H), 7.55 (dddd, J=9.1, 4.2, 3.2, 0.9 Hz, 1H), 7.47 (t, J=9.2 Hz, 1H), 6.18 (s, 2H), 2.69 (s, 3H).

Step 2: N,N-bis(4-methoxybenzyl)ethanesulfonamide

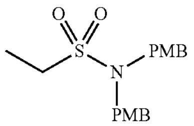

To a stirred solution of bis(4-methoxybenzyl)amine (6.68 g, 26.0 mmol), triethylamine (7.24 mL, 5.25 g, 51.9 mmol) in DCM (150 mL) was added ethanesulfonyl chloride (4.00 g, 31.2 mmol) and the mixture was stirred at room temperature for 12 h. Volatiles were removed under reduced pressure and the resulting residue was purified with silica gel column chromatography (0-20% ethyl acetate in heptane) to afford the title compound (8.2 g, 90% yield). $^1$H NMR (400 MHz, DMSO-$d_6$) δ 7.28-7.09 (m, 4H), 6.97-6.80 (m, 4H), 4.20 (s, 4H), 3.74 (s, 6H), 3.05 (q, J=7.3 Hz, 2H), 1.18 (t, J=7.3 Hz, 3H).

Step 3: 3-(6-(2-(2-fluoro-5-(trifluoromethoxy)benzyl)-2H-tetrazol-5-yl)pyridin-2-yl)-3-hydroxy-N,N-bis(4-methoxybenzyl)butane-2-sulfonamide

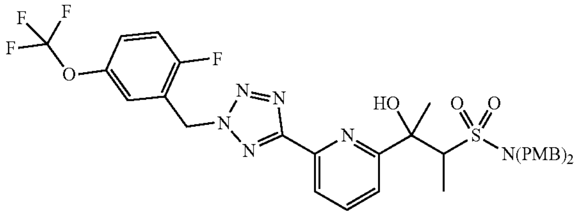

To a stirred solution of N,N-bis(4-methoxybenzyl)ethanesulfonamide (1.83 g, 5.23 mmol) in THF (50 mL) cooled in dry ice/acetone bath was added BuLi (1.6 M in hexanes, 3.27 mL, 5.23 mmol) dropwise. The mixture was stirred at −78° C. for 20 min., then at room temperature for 30 min. The mixture was cooled to −78° C. again and to the mixture was added 1-(6-(2-(2-fluoro-5-(trifluoromethoxy)benzyl)-2H-tetrazol-5-yl)pyridin-2-yl)ethan-1-one (950 mg, 2.49 mmol). The mixture was then stirred at −78° C. for 1 h, at room temperature for 12 h, then at 50° C. for 40 min. The reaction mixture was quenched with saturated aqueous $NH_4Cl$ solution. Volatiles were removed under reduced pressure and the residue was purified with silica gel column chromatography (10-25% ethyl acetate in heptane) to afford two major fractions (two enantiomer pairs):

For enantiomer pair I (first eluting peak): 573 mg, 32% yield.

ESI-MS m/z: 731.3 [M+H]$^+$ (Rt: 1.33 min., LCMS Method 2).

For enantiomer pair II (second eluting peak): 370 mg, 20% yield.

ESI-MS m/z: 731.1 [M+H]$^+$ (Rt: 1.33 min., LCMS Method 2).

Step 4a: enantiomer pair I of 3-(6-(2-(2-fluoro-5-(trifluoromethoxy)benzyl)-2H-tetrazol-5-yl)pyridin-2-yl)-3-hydroxybutane-2-sulfonamide

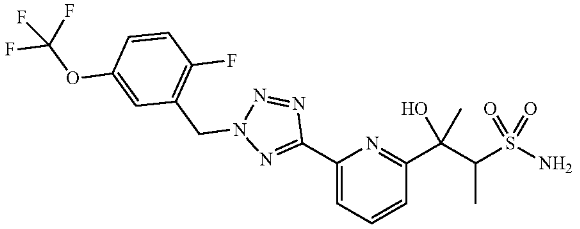 [SMILES: CC(C(C)(O)c1cccc(-c2nnn(Cc3cc(OC(F)(F)F)ccc3F)n2)n1)S(N)(=O)=O]

To a solution of 3-(6-(2-(2-fluoro-5-(trifluoromethoxy)benzyl)-2H-tetrazol-5-yl)pyridin-2-yl)-3-hydroxy-N,N-bis(4-methoxybenzyl)butane-2-sulfonamide (enantiomer pair I, 568 mg, 0.777 mmol) in DCM (4 mL) was added TFA (6.0 mL) and the mixture was stirred at room temperature for 12 h. Volatiles were removed under reduced pressure and to the residue was added 6 mL of triethylamine. Then volatiles were removed under reduced pressure again. The residue was purified with silica gel column chromatography (20-60% ethyl acetate in heptane) to afford the enantiomer pair I of the title compound (263 mg, 69% yield).

ESI-MS m/z: 491.4 [M+H]$^+$ (Rt: 0.97 min., LCMS Method 2).

Chiral separation of the racemate (260 mg) provided Example 15 as the first eluting peak (92 mg, 34% yield, e.e. >99%) and Example 13 as the second eluting peak (98 mg, 36% yield, e.e. >99%).

Chiral Prep HPLC:

Instrument: Thar 80 system
Column: Chiralpak IG (21×250 mm, 5 μm)
Mobile phase: methanol/$CO_2$ (25/75)
Flow rate: 80 g/min.
Detection: UV @230 nm Peak 1 (Example 15): ESI-MS m/z: 491.1 [M+H]$^+$ (Rt: 0.97 min., LCMS Method 2); $^1$H NMR (400 MHz, DMSO-$d_6$) δ 8.07-7.95 (m, 2H), 7.80 (dd, J=7.3, 1.7 Hz, 1H), 7.68 (dd, J=6.3, 3.0 Hz, 1H), 7.58-7.51 (m, 1H), 7.47 (t, J=9.1 Hz, 1H), 6.75 (s, 2H), 6.15 (s, 2H), 5.43 (s, 1H), 3.74 (q, J=7.0 Hz, 1H), 1.74 (s, 3H), 1.07 (d, J=7.0 Hz, 3H); HRMS: M+H, found 491.1122, calc. 491.1125 (HRMS Method 10).

Peak 2 (Example 13): ESI-MS m/z: 491.1 [M+H]$^+$ (Rt: 1.00 min., LCMS Method 2); $^1$H NMR (400 MHz, DMSO-$d_6$) δ 8.08-7.94 (m, 2H), 7.80 (dd, J=7.3, 1.7 Hz, 1H), 7.68 (dd, J=6.2, 3.0 Hz, 1H), 7.54 (dt, J=7.8, 3.3 Hz, 1H), 7.47 (t, J=9.1 Hz, 1H), 6.75 (s, 2H), 6.15 (s, 2H), 5.43 (s, 1H), 3.74 (q, J=6.9 Hz, 1H), 1.74 (s, 3H), 1.07 (d, J=7.0 Hz, 3H); HRMS: M+H, found 491.1134, calc. 491.1125 (HRMS Method 10).

Enantiomeric excess was determined using the following conditions:

Instrument: Waters UPC$^2$ system
Column: Chiralpak IG-3 (3 μm, 3×100 mm)
Mobile phase: MeOH:IPA(1:1) with 0.1% ammonium hydroxide (modifier)/$CO_2$
Gradient: 5% modifier for 0.2 minutes, increase to 55% modifier over 3.0 minutes, and hold at 55% modifier for 0.4 minutes
Flow rate: 2.5 mL/min.
Detection: PDA detector (210-400 nm)

Step 4b: enantiomer pair II of 3-(6-(2-(2-fluoro-5-(trifluoromethoxy)benzyl)-2H-tetrazol-5-yl)pyridin-2-yl)-3-hydroxybutane-2-sulfonamide

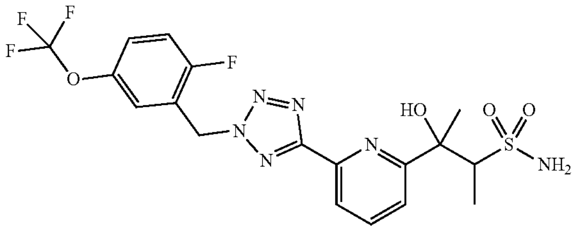 [SMILES: CC(C(C)(O)c1cccc(-c2nnn(Cc3cc(OC(F)(F)F)ccc3F)n2)n1)S(N)(=O)=O]

The enantiomer pair II obtained in Step 3 was subjected to the same procedure as Step 4a to afford the enantiomer pair II of the title compound in 810% yield.

ESI-MS m/z: 491.1 $[M+H]^+$ (Rt: 0.99 min., LCMS Method 2).

Chiral separation of the racemate (195 mg) provided Example 16 as the first eluting peak (73 mg, 36% yield, e.e. >99%) and Example 14 as the second eluting peak (78 mg, 38% yield, e.e. >99%).

Chiral Prep HPLC:

Instrument: Thar 80 system

Column: Chiralpak IG (21×250 mm, 5 μm)

Mobile phase: methanol/$CO_2$ (25/75)

Flow rate: 80 g/min.

Detection: UV @230 nm

Peak 1 (Example 16): ESI-MS m/z: $[M+H]^+$ 491.1 (Rt: 0.99 min., LCMS Method 2); $^1$H NMR (400 MHz, DMSO-$d_6$) δ 8.00-7.90 (m, 2H), 7.81 (dd, J=6.2, 2.8 Hz, 1H), 7.69 (dd, J=6.1, 3.0 Hz, 1H), 7.54 (dddd, J=8.2, 4.2, 3.1, 1.0 Hz, 1H), 7.46 (t, J=9.1 Hz, 1H), 6.42 (s, 2H), 6.15 (s, 2H), 5.83 (d, J=3.1 Hz, 1H), 3.85 (q, J=7.0 Hz, 1H), 1.49 (s, 3H), 1.42 (d, J=7.1 Hz, 3H); HRMS: M+H, found 491.1120, calc. 491.1125 (HRMS Method 10).

Peak 2 (Example 14): ESI-MS m/z: $[M+H]^+$ 491.3 (Rt: 0.94 min., LCMS Method 2); LCMS, 5 min. UPLC-MS, $^1$H NMR (400 MHz, DMSO-$d_6$) δ 8.01-7.91 (m, 2H), 7.81 (dd, J=6.2, 2.8 Hz, 1H), 7.69 (dd, J=6.1, 3.0 Hz, 1H), 7.54 (dt, J=7.6, 3.7 Hz, 1H), 7.46 (t, J=9.1 Hz, 1H), 6.42 (s, 2H), 6.15 (s, 2H), 5.82 (s, 1H), 3.85 (q, J=7.1 Hz, 1H), 1.49 (s, 3H), 1.42 (d, J=7.1 Hz, 3H); HRMS: M+H, found 491.1118, calc. 491.1125 (HRMS Method 10).

Enantiomeric excess was determined using the following conditions:

Instrument: Waters UPC$^2$ system

Column: Chiralpak IG-3 (3 μm, 3×100 mm)

Mobile phase: MeOH:IPA (1:1) with 0.1% ammonium hydroxide (modifier)/$CO_2$

Gradient: 5% modifier for 0.2 minutes, increase to 55% modifier over 3.0 minutes, and hold at 55% modifier for 0.4 minutes Flow rate: 2.5 mL/min.

Detection: PDA detector (210-400 nm)

Example 17: (R or S)-2-(6-(2-(2,5-difluorobenzyl)-2H-tetrazol-5-yl)pyridin-2-yl)-2-hydroxypropane-1-sulfonamide and Example 18: (R or S)-2-(6-(2-(2,5-difluorobenzyl)-2H-tetrazol-5-yl)pyridin-2-yl)-2-hydroxypropane-1-sulfonamide Prepared by analogy to Examples 13-16 according to Scheme 2 by replacing 2-(bromomethyl)-1-fluoro-4-(trifluoromethoxy)benzene with 2-(bromomethyl)-1,4-difluorobenzene to afford the racemate of the title compound (230 mg).

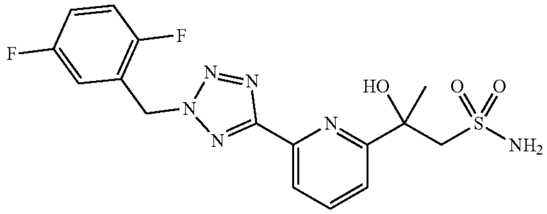 [SMILES: CC(O)(CS(N)(=O)=O)c1cccc(-c2nnn(Cc3cc(F)ccc3F)n2)n1]

Chiral separation of the racemate (230 mg) provided Example 17 as the first eluting peak (60 mg, 26% yield, chiral HPLC purity: 99.8%, Rt: 10.179 min.) and Example 18 as the second eluting peak (60 mg, 26% yield, chiral HPLC purity: 99.5%, Rt: 14.759 min.) as white solids.

Chiral Prep HPLC:

Instrument: Agilent 1260 Infinity

Column: CHIRAL PAK IH (21.0 mm×250 mm), 5 μm

Mobile phase: n-HEXANE (A); EtOH:MeOH (1:1, B); Isocratic: 60(A):40(B)

Flow rate: 15 mL/min.

Detection: UV@210 nm

Peak 1 (Example 17): MS (ESI+): m/z 410.85 (M+H), Rt: 1.420 min. [LCMS Method 6]; $^1$H NMR (400 MHz, $CD_3OD$) δ 8.04 (d, J=7.6 Hz, 1H), 7.95 (t, J=7.6 Hz, 1H), 7.84 (d, J=7.6 Hz, 1H), 7.31-7.25 (m, 1H), 7.24-7.19 (m, 2H), 6.03 (s, 2H), 4.05 (d, J=14.4 Hz, 1H), 3.78 (d, J=14.8 Hz, 1H), 1.70 (s, 3H).

Peak 2 (Example 18): MS (ESI+): m/z 410.85 (M+H), Rt: 1.420 min. [LCMS Method 6]; $^1$H NMR (400 MHz, $CD_3OD$) δ 8.04 (d, J=8.0 Hz, 1H), 7.95 (t, J=7.6 Hz, 1H), 7.83 (d, J=7.6 Hz, 1H), 7.31-7.25 (m, 1H), 7.24-7.19 (m, 2H), 6.03 (s, 2H), 4.05 (d, J=14.4 Hz, 1H), 3.78 (d, J=14.8 Hz, 1H), 1.70 (s, 3H).

Chiral HPLC retention times were obtained using the following conditions:

Instrument: Agilent 1260 Infinity II

Column: CHIRAL PAK IH (150×4.6 mm), 5 μm

Mobile phase: n-HEXANE (A); EtOH (B); Isocratic: 70(A):30(B)

Flow rate: 1.0 mL/min.

Detection: UV@210 nm

Example 19: (R or S)-2-(6-(2-(2-fluoro-5-(trifluoromethyl)benzyl)-2H-tetrazol-5-yl)pyridin-2-yl)-2-hydroxypropane-1-sulfonamide and Example 20: (R or S)-2-(6-(2-(2-fluoro-5-(trifluoromethyl)benzyl)-2H-tetrazol-5-yl)pyridin-2-yl)-2-hydroxypropane-1-sulfonamide Prepared by analogy to Examples 13-16 according to Scheme 2 by replacing 2-(bromomethyl)-1-fluoro-4-(trifluoromethoxy)benzene with 2-(bromomethyl)-1-fluoro-4-(trifluoromethyl)benzene to afford the racemate of the title compound (200 mg).

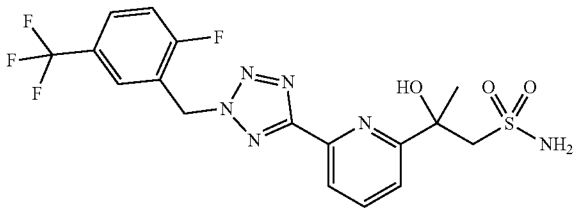 [SMILES: CC(O)(CS(N)(=O)=O)c1cccc(-c2nnn(Cc3cc(C(F)(F)F)ccc3F)n2)n1]

Chiral separation of the racemate (200 mg) provided Example 20 as the first eluting peak (47 mg, 24% yield, chiral HPLC purity: 99.0%, Rt: 6.392 min.) and Example 19 as the second eluting peak (59 mg, 30% yield, chiral HPLC purity: 99.3%, Rt: 8.395 min.) as white solids.

Chiral Prep HPLC:
- Instrument: Agilent 1260 Infinity
- Column: CHIRALPAK IH, 250 mm×21 mm, 5 μm
- Mobile phase: n-HEXANE (A); EtOH:MeOH (1:1, B); Isocratic: 70(A):30(B)
- Flow rate: 15 m/min.
- Detection: UV @210 nm Peak 1 (Example 20): MS (ESI+): m/z 461.1 (M+H), Rt: 1.142 min. [LCMS Method 7]; $^1$H NMR (400 MHz, $CD_3OD$) δ 8.02 (d, J=7.2 Hz, 1H), 7.95 (t, J=8.0 Hz, 2H), 7.84 (d, J=8.0 Hz, 2H), 7.42 (t, J=9.2 Hz, 1H), 6.12 (s, 2H), 4.00 (d, J=14.4 Hz, 1H), 3.74 (d, J=14.4 Hz, 1H), 1.70 (s, 3H).

Peak 2 (Example 19): MS (ESI+): m/z 461.1 (M+H), Rt: 1.149 min. [LCMS Method 7]; $^1$H NMR (400 MHz, $CD_3OD$) δ 8.03 (d, J=7.6 Hz, 1H), 7.97-7.90 (m, 2H), 7.83 (d, J=7.2 Hz, 2H), 7.42 (t, J=9.2 Hz, 1H), 6.12 (s, 2H), 4.05 (d, J=14.4 Hz, 1H), 3.78 (d, J=14.4 Hz, 1H), 1.70 (s, 3H).

Chiral HPLC retention times were obtained using the following conditions:
- Instrument: Agilent 1260 Infinity II
- Column: CHIRALPAK-IH, 150 mm×4.6 mm, 5 μm
- Mobile phase: A: n-hexane, B: 0.1% HCOOH in EtOH: MeOH (80:20); Isocratic: 70(A):30(B)
- Flow rate: 1.0 mL/min.
- Detection: UV @210 nm

Example 21: (R or S)-2-(6-(2-(5-chloro-2-fluorobenzyl)-2H-tetrazol-5-yl)pyridin-2-yl)-2-hydroxypropane-1-sulfonamide and Example 22: (R or S)-2-(6-(2-(5-chloro-2-fluorobenzyl)-2H-tetrazol-5-yl)pyridin-2-yl)-2-hydroxypropane-1-sulfonamide Prepared by analogy to Examples 13-16 according to Scheme 2 by replacing 2-(bromomethyl)-1-fluoro-4-(trifluoromethoxy)benzene with 2-(bromomethyl)-4-chloro-1-fluorobenzene to afford the racemate of the title compound (120 mg).

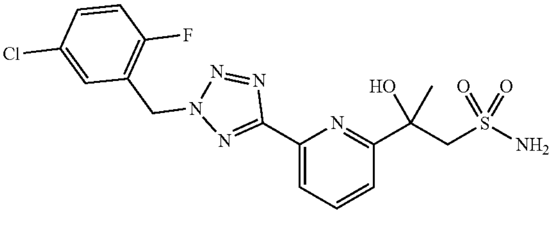 [SMILES: CC(O)(CS(N)(=O)=O)c1cccc(-c2nnn(Cc3cc(Cl)ccc3F)n2)n1]

Chiral separation of the racemate (120 mg) provided Example 22 as the first eluting peak (41 mg, 34% yield, chiral HPLC purity: 99.4%, Rt: 8.688 min.) and Example 21 as the second eluting peak (28 mg, 23% yield, chiral HPLC purity: 99.5%, Rt: 11.791 min.) as white solids.

Chiral Prep HPLC:
- Instrument: Agilent 1260 Infinity
- Column: CHIRAL PAK IH (21.0 mm×250 mm), 5 μm
- Mobile phase: n-HEXANE (A); EtOH: MeOH (1:1, B); Isocratic: 50(A):50(B)
- Flow rate: 15 mL/min.
- Detection: UV @210 nm Peak 1 (Example 22): MS (ESI+): m/z 427.1 (M+H), Rt: 1.133 min. [LCMS Method 7]; $^1$H NMR (400 MHz, $CD_3OD$) δ 8.04 (d, J=8.0 Hz, 1H), 7.95 (t, J=7.6 Hz, 1H), 7.84 (d, J=7.6 Hz, 1H), 7.56-7.54 (m, 1H), 7.48-7.43 (m, 1H), 7.22 (t, J=8.8 Hz, 1H), 6.02 (s, 2H), 4.04 (d, J=14.0 Hz, 1H), 3.77 (d, J=14.4 Hz, 1H), 1.70 (s, 3H).

Peak 2 (Example 21): MS (ESI+): m/z 427.1 (M+H), Rt: 1.134 min. [LCMS Method 7]; $^1$H NMR (400 MHz, $CD_3OD$) δ 8.04 (d, J=8.0 Hz, 1H), 7.95 (t, J=7.6 Hz, 1H), 7.84 (d, J=8.0 Hz, 1H), 7.56-7.54 (m, 1H), 7.48-7.44 (m, 1H), 7.22 (t, J=9.2 Hz, 1H), 6.02 (s, 2H), 4.04 (d, J=14.4 Hz, 1H), 3.77 (d, J=14.4 Hz, 1H), 1.70 (s, 3H).

Chiral HPLC retention times were obtained using the following conditions:
- Instrument: Agilent 1260 Infinity II
- Column: CHIRAL PAK-IH (150×4.6 mm×5 μm)
- Mobile phase: A:n-HEXANE, B: 0.1% HCOOH in ethanol:methanol (80:20); Isocratic: 70(A):30(B)
- Flow rate: 1.0 mL/min.
- Detection: UV @210 nm

Example 23: (R or S)-2-(3-fluoro-5-(2-(2-fluoro-5-(trifluoromethoxy)benzyl)-2H-tetrazol-5-yl)phenyl)-2-hydroxypropane-1-sulfonamide and Example 24: (R or S)-2-(3-fluoro-5-(2-(2-fluoro-5-(trifluoromethoxy)benzyl)-2H-tetrazol-5-yl)phenyl)-2-hydroxypropane-1-sulfonamide Prepared by analogy to Examples 13-16 according to Scheme 2 starting from Intermediate 6 to afford the racemate of the title compound (460 mg).

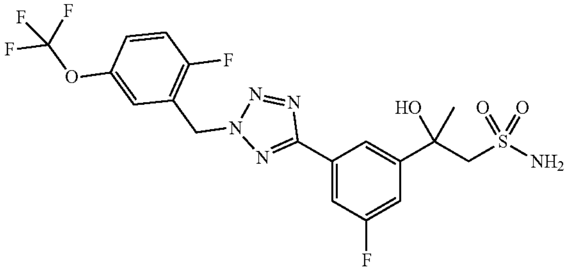 [SMILES: CC(O)(CS(N)(=O)=O)c1cc(F)cc(-c2nnn(Cc3cc(OC(F)(F)F)ccc3F)n2)c1]

Chiral separation of the racemate (460 mg) provided Example 24 as the first eluting peak (60 mg, 17% yield; chiral HPLC purity: 99.0%, Rt: 6.589 min.) and Example 23 as the second eluting peak (70 mg, 21%; chiral HPLC purity: 98.6%, Rt: 10.072 min.) as white solids.

Chiral Prep HPLC:
- Instrument: Agilent 1260 Infinity
- Column: CHIRAL PAK-IG (250 mm×20 mm), 5 μm
- Mobile phase: n-hexane (A); ethanol:methanol (80:20, B); Isocratic: 70(A):30(B)

Flow rate: 15 mL/min.

Detection: UV @210 nm

Peak 1 (Example 24): MS (ESI+): m/z 494.1 (M+H), Rt: 1.195 min. [LCMS Method 7]; $^1$H NMR (400 MHz, $CD_3OD$) δ 8.09 (t, J=1.6 Hz, 1H), 7.71-7.66 (m, 1H), 7.51-7.38 (m, 3H), 7.32 (t, J=9.2 Hz, 1H), 6.02 (s, 2H), 3.63 (s, 2H), 1.75 (s, 3H).

Peak 2 (Example 23): MS (ESI+): m/z 494.1 (M+H), Rt: 1.198 min. [LCMS Method 7]; $^1$H NMR (400 MHz, $CD_3OD$) δ 8.09 (t, J=1.6 Hz, 1H), 7.71-7.65 (m, 1H), 7.51-7.38 (m, 3H), 7.32 (t, J=9.2 Hz, 1H), 6.02 (s, 2H), 3.64 (s, 2H), 1.76 (s, 3H).

Chiral HPLC retention times were obtained using the following conditions:

Instrument: Agilent 1260 Infinity II

Column: CHIRAL PAK-IG (150 mm×4.6 mm), 5 μm

Mobile phase: n-hexane (A); 0.1% HCOOH in EtOH: MeOH (80:20, B); Isocratic: 80(A):20(B)

Flow rate: 1.0 mL/min.

Detection: UV @210 nm

Example 25: (R or S)-2-(3-(2-(2-fluoro-5-(trifluoromethoxy)benzyl)-2H-tetrazol-5-yl)phenyl)-2-hydroxypropane-1-sulfonamide and Example 26: (R or S)-2-(3-(2-(2-fluoro-5-(trifluoromethoxy)benzyl)-2H-tetrazol-5-yl)phenyl)-2-hydroxypropane-1-sulfonamide Prepared by analogy to Examples 13-16 according to Scheme 2 starting from 3-acetylbenzonitrile to afford the racemate of the title compound (Rac-25+26) (120 mg).

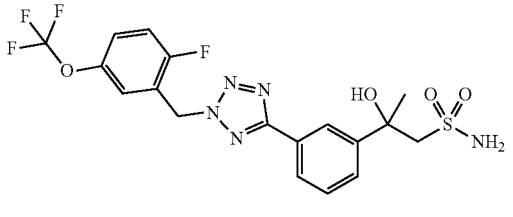 [SMILES: CC(O)(CS(N)(=O)=O)c1cccc(-c2nnn(Cc3cc(OC(F)(F)F)ccc3F)n2)c1]

Chiral separation of the racemate (120 mg) provided Example 26 as the first eluting peak (30 mg, 25% yield; chiral HPLC purity: 97.8%, Rt: 4.575 min.) and Example 25 as the second eluting peak (30 mg, 25% yield; chiral HPLC purity: 99.5%, Rt: 5.772 min.) as white solids.

Chiral Prep HPLC:

Instrument: Agilent 1260 Infinity

Column: CHIRAL PAK IG (20.0 mm×250 mm), 5 μm

Mobile phase: n-Hexane (A); EtOH: MeOH (1:1, B); Isocratic: 50(A):50(B)

Flow rate: 15 mL/min.

Detection: UV @210 nm

Peak 1 (Example 26): MS (ESI+): m/z 476.15 (M+H), Rt: 0.813 min. [LCMS Method 4]; $^1$H NMR (400 MHz, $CD_3OD$) δ 8.29 (t, J=1.6 Hz, 1H), 7.99-7.97 (m, 1H), 7.66-7.64 (m, 1H), 7.52-7.46 (m, 2H), 7.42-7.37 (m, 1H), 7.32 (t, J=9.2 Hz, 1H), 6.01 (s, 2H), 3.60 (d, J=1.6 Hz, 2H), 1.77 (s, 3H).

Peak 2 (Example 25): MS (ESI+): m/z 476.15 (M+H), Rt: 0.806 min. [LCMS Method 4]; $^1$H NMR (400 MHz, $CD_3OD$) δ 8.29 (t, J=1.6 Hz, 1H), 7.98 (d, J=7.6 Hz, 1H), 7.66-7.64 (m, 1H), 7.52-7.46 (m, 2H), 7.42-7.37 (m, 1H), 7.32 (t, J=8.8 Hz, 1H), 6.01 (s, 2H), 3.57 (s, 2H), 1.77 (s, 3H).

Chiral HPLC retention times were obtained using the following conditions:

Instrument: Agilent 1260 Infinity II

Column: CHIRAL PAK-IG (150×4.6 mm), 5 μm

Mobile phase: A: n-HEXANE, B: 0.1% DEA in Ethanol: Methanol (70:30); Isocratic: 50:50

Flow rate: 1.0 mL/min.

Detection: UV@254 nm

Example 27: (R or S)-2-(5-chloro-6-(2-(2-fluoro-5-(trifluoromethoxy)benzyl)-2H-tetrazol-5-yl)pyridin-2-yl)-2-hydroxypropane-1-sulfonamide and Example 28: (R or S)-2-(5-chloro-6-(2-(2-fluoro-5-(trifluoromethoxy)benzyl)-2H-tetrazol-5-yl)pyridin-2-yl)-2-hydroxypropane-1-sulfonamide Prepared according to Scheme 3.

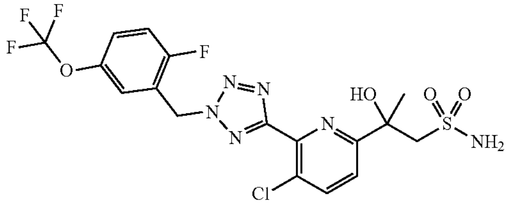 [SMILES: CC(O)(CS(N)(=O)=O)c1ccc(Cl)c(-c2nnn(Cc3cc(OC(F)(F)F)ccc3F)n2)n1]

Step 1: 6-bromo-3-chloro-2-(2H-tetrazol-5-yl)pyridine

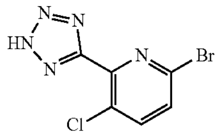 [SMILES: Clc1ccc(Br)nc1-c1nn[nH]n1]

To a stirred solution of 6-bromo-3-chloropicolinonitrile (3.4 g, 15.63 mmol) in t-BuOH:water (v/v 2:1, 45 mL) was added sodium azide (1.52 g, 23.5 mmol) followed by zinc bromide (5.28 g, 23.5 mmol) at room temperature. The reaction mixture was heated at 90° C. for 3 h. The reaction mixture was cooled to room temperature, diluted with water (10 mL), acidified with 1 M aqueous HCl solution (10.0 mL) and extracted with EtOAc (3×50 mL). The combined organic layers were washed with a saturated aqueous NaCl solution (100.0 mL) and dried over anhydrous $Na_2SO_4$ and concentrated under reduced pressure to afford 6-bromo-3-chloro-2-(2H-tetrazol-5-yl)pyridine as brown solid (4.9 g, crude).

MS (ESI+): m/z 261.9 (M+H), Rt: 1.350 min. [LCMS Method 6].

Step 2: 6-bromo-3-chloro-2-(2-(2-fluoro-5-(trifluoromethoxy)benzyl)-2H-tetrazol-5-yl)pyridine

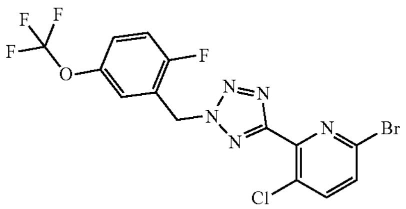 [SMILES: Fc1ccc(OC(F)(F)F)cc1Cn1nnc(-c2nc(Br)ccc2Cl)n1]

To a stirred solution of 6-bromo-3-chloro-2-(2H-tetrazol-5-yl)pyridine (9.60 g, 36.9 mmol) in acetone (200 mL), was added sodium carbonate (13.6 g, 129 mmol) followed by sodium iodide (6.0 g, 41 mmol) and 2-(chloromethyl)-3-fluoro-6-(trifluoromethoxy)pyridine (10.9 g, 47.9 mmol) at room temperature. The reaction mass was heated at 50° C. for 16 h. The reaction mixture was cooled to room temperature, diluted with water (200 mL) and extracted with EtOAc (3×100 mL). The combined organic layers were washed with a saturated aqueous NaCl solution (100 mL), dried over anhydrous $Na_2SO_4$ and concentrated under reduced pressure to furnish crude. The crude was purified with silica gel column chromatography (30-50% EtOAc in hexanes) to afford the title compound as a pale-yellow sticky compound (3.9 g, 23% yield).

MS (ESI+): m/z 453.95 (M+H), Rt: 1.648 min. [LCMS Method 6]; $^1$H NMR (400 MHz, $CDCl_3$) δ 7.72 (d, J=8.4 Hz, 1H), 7.55 (d, J=8.4 Hz, 1H), 7.29-7.20 (m, 2H), 7.19-7.14 (m, 1H), 5.98 (s, 2H).

Step 3: 1-(5-chloro-6-(2-(2-fluoro-5-(trifluoromethoxy)benzyl)-2H-tetrazol-5-yl)pyridin-2-yl)ethan-1-one

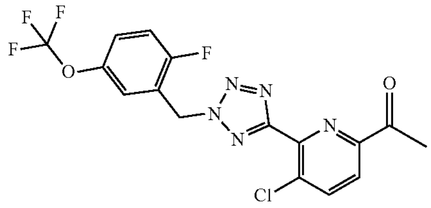 [SMILES: CC(=O)c1ccc(Cl)c(-c2nnn(Cc3cc(OC(F)(F)F)ccc3F)n2)n1]

To a stirred solution of 6-bromo-3-chloro-2-(2-(2-fluoro-5-(trifluoromethoxy)benzyl)-2H-tetrazol-5-yl)pyridine (3.90 g, 8.62 mmol) in Toluene (40 mL) was added tributyl (1-ethoxyvinyl)stannane (3.70 g, 10.3 mmol) and the reaction mixture was purged with $N_2$ for 10 min. Then tetrakis (triphenylphosphine)palladium(0) ($Pd(PPh_3)_4$, 1.05 g, 0.916 mmol) was added and the reaction mass was heated at 110° C. for 16 h. The reaction mixture was cooled to room temperature and filtered through celite pad and rinsed with EtOAc (100 mL). The combined filtrate was concentrated under reduced pressure to afford crude 3-chloro-6-(1-ethoxyvinyl)-2-(2-(2-fluoro-5-(trifluoromethoxy) benzyl)-2H-tetrazol-5-yl)pyridine as yellow sticky residue (8.7 g). The crude was re-dissolved in THF (50 mL) and to the resulting solution cooled in an ice-water bath was added a solution of 2N aqueous HCl (50 mL). The reaction mixture was let stir at room temperature for 16 h. To the reaction was added an aqueous solution of 2N NaOH (25 mL) and stirring was continued for 10 minutes. Then saturated aqueous $NaHCO_3$ solution (100 mL) was added. The mixture was stirred for 5 minutes and then extracted with EtOAc (2×100 mL). The combined EtOAc layers were dried over anhydrous $Na_2SO_4$ and concentrated under reduced pressure to furnish crude. The obtained crude was dissolved in EtOAc (25 mL) and 2N KF (aq., 100 mL) was added, and the solution was stirred at room temperature for 16 h. The resulted mixture was filtered through celite bed, rinsed with EtOAc (2×70 mL). The organic layers were combined, dried over anhydrous $Na_2SO_4$ and concentrated under reduced pressure to furnish crude. The crude was purified with silica gel column chromatography (20-30% EtOAc in hexanes) to afford the title compound as an off white solid (2.5 g, 70% yield).

MS (ESI+): m/z 416.05 (M+H), Rt: 1.604 min. [LCMS Method 6]; $^1$H NMR (400 MHz, $CD_3OD$) δ 8.20 (d, J=8.8 Hz, 1H), 8.11 (d, J=8.4 Hz, 1H), 7.53-7.51 (m, 1H), 7.42-7.40 (m, 1H), 7.34 (t, J=9.2 Hz, 1H), 6.12 (s, 2H), 2.69 (s, 3H).

Step 4: 2-(5-chloro-6-(2-(2-fluoro-5-(trifluoromethoxy)benzyl)-2H-tetrazol-5-yl)pyridin-2-yl)-2-hydroxy-N,N-bis(4-methoxybenzyl)propane-1-sulfonamide

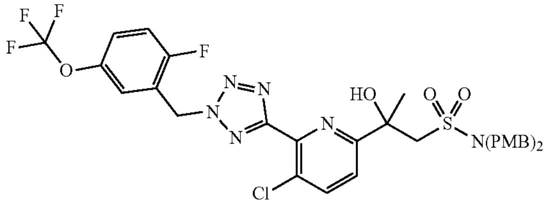

To a stirred solution of N,N-bis(4-methoxybenzyl)methanesulfonamide (484 mg, 1.44 mmol) in THF (4 mL) cooled with dry ice/acetone bath under $N_2$ protection was added n-BuLi solution (1.6 M in hexanes, 0.90 mL, 1.4 mmol) and the mixture was stirred at −78° C. for 30 min. Then to the mixture was added a solution of 1-(5-chloro-6-(2-(2-fluoro-5-(trifluoromethoxy)benzyl)-2H-tetrazol-5-yl)pyridin-2-yl) ethan-1-one (300 mg, 0.72 mmol) in THF (6 mL). The mixture was stirred at −78° C. for 2 h before being allowed to stir and warm to room temperature for 1 h. The reaction mixture was quenched with water (0.5 mL), and then concentrated under reduced pressure. The resulting residue was purified with silica gel column chromatography (10-30% ethyl acetate in heptane) to afford the title compound (125 mg, 23% yield).

ESI-MS m/z: 751.3 $[M+H]^+$ (Rt: 1.32 min., LCMS Method 2).

Step 5: 2-(5-chloro-6-(2-(2-fluoro-5-(trifluoromethoxy)benzyl)-2H-tetrazol-5-yl)pyridin-2-yl)-2-hydroxypropane-1-sulfonamide

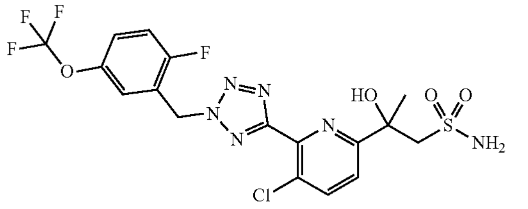 [SMILES: CC(O)(CS(N)(=O)=O)c1ccc(Cl)c(-c2nnn(Cc3cc(OC(F)(F)F)ccc3F)n2)n1]

To a solution of 2-(5-chloro-6-(2-(2-fluoro-5-(trifluoromethoxy)benzyl)-2H-tetrazol-5-yl)pyridin-2-yl)-2-hydroxy-N,N-bis(4-methoxybenzyl)propane-1-sulfonamide (125 mg, 0.166 mmol) in DCM (1 mL) was added TFA (2.6 mL) and the mixture was stirred at room temperature for 12 h. Volatiles were removed under reduced pressure and to the resulting residue was added excess triethylamine. Volatiles were removed under reduced pressure again. The resulting residue was purified with silica gel column chromatography (20-50% ethyl acetate in heptane) to afford the racemic title compound (65 mg, 73% yield).

ESI-MS m/z: 511.2 $[M+H]^+$ (Rt: 0.98 min., LCMS Method 2).

$^1$H NMR (400 MHz, DMSO-$d_6$) δ 8.15 (d, J=8.8 Hz, 1H), 7.87 (d, J=8.7 Hz, 1H), 7.68 (dd, J=6.0, 3.0 Hz, 1H), 7.56 (dt, J=7.6, 3.7 Hz, 1H), 7.48 (t, J=9.1 Hz, 1H), 6.66 (s, 2H), 6.19 (s, 2H), 5.94 (s, 1H), 3.73-3.51 (m, 2H), 1.58 (s, 3H).

HRMS: M+H, found 511.0581, calc. 511.0578 (HRMS Method 10).

Chiral separation of the racemate (150 mg) provided Example 27 as the first eluted peak (45 mg, 30% yield, e.e. >99%) and Example 28 as the second eluting peak (47 mg, 31% yield, e.e. >99%).

Chiral Prep HPLC:

Instrument: Waters SFC MS100 system

Column: Chiralcel OJ-H (21×250 mm, 5 μm)

Mobile phase: 15-35% IPA with 10 mM ammonia in $MeOH/CO_2$

Flow rate: 80 g/min.

Detection: UV @273 nm

Peak 1 (Example 27): ESI-MS m/z: 511.0 $[M+H]^+$ (Rt: 0.99 min., LCMS Method 2); $^1$H NMR (400 MHz, DMSO-$d_6$) δ 8.20 (d, J=8.4 Hz, 1H), 7.92 (d, J=8.7 Hz, 1H), 7.73 (dd, J=5.9, 3.0 Hz, 1H), 7.61 (dt, J=7.5, 3.7 Hz, 1H), 7.54 (t, J=9.1 Hz, 1H), 6.66 (s, 2H), 6.24 (s, 2H), 3.75-3.55 (m, 2H), 1.63 (s, 3H); HRMS: M+H, found 511.0577, calc 511.0578 (HRMS Method 10); e.e. >99%.

Peak 2 (Example 28): ESI-MS m/z: 510.9 $[M+H]^+$ (Rt: 1.01 min., LCMS Method 2); $^1$H NMR (400 MHz, DMSO-$d_6$) δ 8.15 (d, J=8.7 Hz, 1H), 7.87 (d, J=8.7 Hz, 1H), 7.68 (dd, J=6.0, 3.0 Hz, 1H), 7.56 (dt, J=7.5, 3.8 Hz, 1H), 7.48 (t, J=9.1 Hz, 1H), 6.66 (s, 2H), 6.19 (s, 2H), 5.94 (s, 1H), 3.69-3.49 (m, 2H), 1.58 (s, 3H); HRMS: M+H, found 511.0587, calc. 511.0578 (HRMS Method 10); e.e. >99%.

Enantiomeric excess was determined using the following conditions:

Instrument: Waters UPC$^2$ system

Column: Chiralcel OJ-3 (3 μm, 3×100 mm)

Mobile phase: IPA with 0.1% ammonium hydroxide (modifier)/$CO_2$; Gradient: 5% modifier for 0.2 minutes, increase to 55% modifier over 3.0 minutes, and hold at 55% modifier for 0.4 minutes Flow rate: 2.5 mL/min.

Detection: PDA detector (210-400 nm)

Examples 29: (R or S)-2-(6-(2-(2-fluoro-5-(2,2,2-trifluoroethoxy)benzyl)-2H-tetrazol-5-yl)pyridin-2-yl)-2-hydroxypropane-1-sulfonamide and Example 30: (R or S)-2-(6-(2-(2-fluoro-5-(2,2,2-trifluoroethoxy)benzyl)-2H-tetrazol-5-yl)pyridin-2-yl)-2-hydroxypropane-1-sulfonamide Prepared by analogy to Examples 27 and 28 according to Scheme 3 starting from 6-bromo-picolinonitrile and by replacing 2-(bromomethyl)-1-fluoro-4-(trifluoromethoxy)benzene with Intermediate 7 to afford the racemate of the title compound (Rac-29+30) (140 mg).

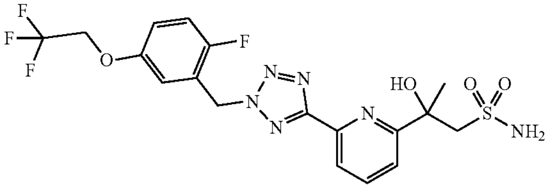 [SMILES: CC(O)(CS(N)(=O)=O)c1cccc(-c2nnn(Cc3cc(OCC(F)(F)F)ccc3F)n2)n1]

Chiral separation of the racemate (140 mg) provided Example 29 as the first eluted peak (50 mg, 36% yield, chiral HPLC: e.e. >99%, Rt: 1.93 min.) and Example 30 as the second eluting peak (45 mg, 32% yield, chiral HPLC: e.e. 96.64%, Rt: 2.18 min.) as white solids.

Chiral Prep HPLC:

Instrument: Waters SFC MS100

Column: Chiralpak ID (21×250 mm, 5 μm) @35° C.

Mobile phase: 20-40% methanol/$CO_2$

Flow rate: 80 g/min.

Detection: UV @275 nm

Peak 1 (Example 29): ESI-MS m/z: 491.1 $[M+H]^+$ (Rt: 2.05 min., LCMS Method 3); $^1$H NMR (400 MHz, DMSO-$d_6$) δ 8.04-7.95 (m, 2H), 7.83 (dd, J=6.5, 2.6 Hz, 1H), 7.34-7.23 (m, 2H), 7.17 (dt, J=9.2, 3.8 Hz, 1H), 6.67 (s, 2H), 6.05 (s, 2H), 5.81 (s, 1H), 4.77 (q, J=8.8 Hz, 2H), 3.73-3.60 (m, 2H), 1.61 (s, 3H).

Peak 2 (Example 30): ESI-MS m/z: 491.6 $[M+H]^+$ (Rt: 2.01 min., LCMS Method 3); $^1$H NMR (400 MHz, DMSO-$d_6$) δ 8.05-7.95 (m, 2H), 7.83 (dd, J=6.5, 2.6 Hz, 1H), 7.34-7.23 (m, 2H), 7.18 (t, J=3.7 Hz, 1H), 6.68 (s, 2H), 6.06 (s, 2H), 5.82 (s, 1H), 4.77 (q, J=8.9 Hz, 2H), 3.73-3.61 (m, 2H), 1.62 (s, 3H).

Enantiomeric excess was determined using the following conditions:

Instrument: Waters UPC$^2$ system

Column: Chiralpak ID-3(3 μm, 3×100 mm) @40° C.

Mobile phase: Methanol with 0.1% ammonium hydroxide (modifier)/$CO_2$; Gradient: 5% modifier for 0.15 minutes, increase to 55% modifier over 1.5 minutes, and hold at 55% modifier for 0.65 minutes Flow rate: 2.5 mL/min.
Detection: PDA detector (210-400 nm)

Example 31: (2R or 2S, 3R or 3S)-3-(6-(2-(2-fluoro-5-(trifluoromethoxy)benzyl)-2H-tetrazol-5-yl)pyridin-2-yl)-1-hydroxybutane-2-sulfonamide and Example 32: (2R or 2S,3R or 3S)-3-(6-(2-(2-fluoro-5-(trifluoromethoxy)benzyl)-2H-tetrazol-5-yl)pyridin-2-yl)-1-hydroxybutane-2-sulfonamide and Example 33: (2R or 2S,3R or 3S)-3-(6-(2-(2-fluoro-5-(trifluoromethoxy)benzyl)-2H-tetrazol-5-yl)pyridin-2-yl)-1-hydroxybutane-2-sulfonamide and Example 34: (2R or 2S, 3R or 3S)-3-(6-(2-(2-fluoro-5-(trifluoromethoxy)benzyl)-2H-tetrazol-5-yl)pyridin-2-yl)-1-hydroxybutane-2-sulfonamide Prepared according to Scheme 3a.

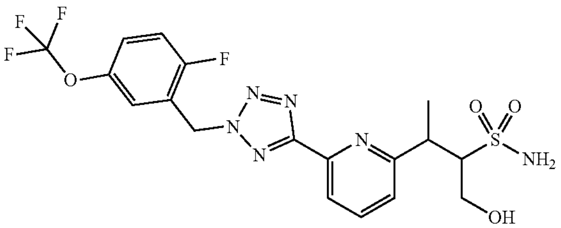 [SMILES: CC(c1cccc(-c2nnn(Cc3cc(OC(F)(F)F)ccc3F)n2)n1)C(CO)S(N)(=O)=O]

Step 1: ethyl 2-(N,N-bis(4-methoxybenzyl)sulfamoyl)acetate

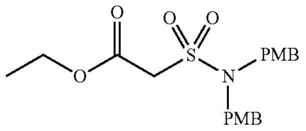

Compound was synthesized according to procedure followed in example 1 and 2, Step 1, starting from ethyl 2-(chlorosulfonyl)acetate (6.60 g, 25.7 mmol) to afford the title product (3.6 g, 41% yield).

MS (ESI+): m/z 406.05 (M−H); Rt: 0.883 min. [LCMS Method 4]; $^1$H NMR (400 MHz, $CDCl_3$) δ 7.22 (dd, J=6.4, 2.0 Hz, 4H), 6.85 (dd, J=6.8, 2.0 Hz, 4H), 4.33 (s, 4H), 4.22 (q, J=7.2 Hz, 2H), 3.80 (m, 8H), 1.29 (t, J=7.2 Hz, 3H).

Step 2: Synthesis of 1-(6-(2H-tetrazol-5-yl)pyridin-2-yl)ethan-1-one

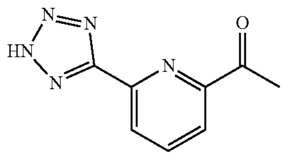

Compound was synthesized according to procedure followed in example 1 and 2, Step 2, starting from 6-acetylpicolinonitrile (8.0 g, 5.47 mmol) and the product was isolated as white solid. Yield: 8.5 g (crude).

MS (ESI+): m/z 190.05 (M+H), Rt: 0.318 min. [LCMS Method 4]; $^1$H NMR (300 MHz, DMSO-$d_6$) δ 8.44 (d, J=7.8 Hz, 1H), 8.26 (t, J=7.8 Hz, 1H), 8.11 (d, J=7.5 Hz, 1H), 2.78 (s, 3H).

Step 3: Synthesis of 1-(6-(2-(2-fluoro-5-(trifluoromethoxy)benzyl)-2H-tetrazol-5-yl)pyridin-2-yl)ethan-1-one

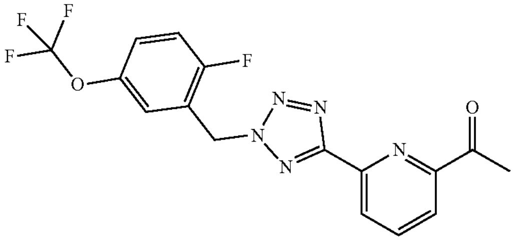 [SMILES: CC(=O)c1cccc(-c2nnn(Cc3cc(OC(F)(F)F)ccc3F)n2)n1]

Compound was synthesized according to procedure followed in example 13-16, Step 1, by replacing 2-(bromomethyl)-1-fluoro-4-(trifluoromethoxy)benzene with 2-(chloromethyl)-1-fluoro-4-(trifluoromethoxy)benzene and the product was isolated as yellow sticky compound. Yield: 8.2 g (48%).

MS (ESI+): m/z 382.0 (M+H), Rt: 1.573 min. [LCMS Method 6]; $^1$H NMR (400 MHz, $CDCl_3$) δ 8.37 (d, J=8.0 Hz, 1H), 8.14 (d, J=8.0 Hz, 1H), 8.00 (t, J=7.6 Hz, 1H), 7.29-7.24 (m, 2H), 7.22-7.19 (m, 1H), 5.96 (s, 2H), 2.84 (s, 3H).

Step 4: Synthesis of 1-(6-(2-(2-fluoro-5-(trifluoromethoxy) benzyl)-2H-tetrazol-5-yl)pyridin-2-yl)ethan-1-ol

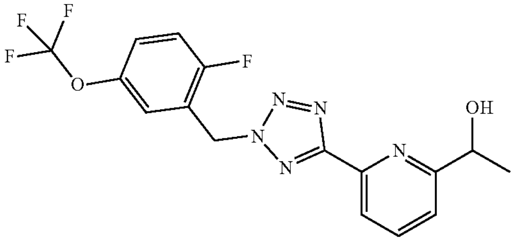 [SMILES: CC(O)c1cccc(-c2nnn(Cc3cc(OC(F)(F)F)ccc3F)n2)n1]

To a stirred solution of 1-(6-(2-(2-fluoro-5-(trifluoromethoxy) benzyl)-2H-tetrazol-5-yl)pyridin-2-yl)ethan-1-one (4.00 g, 10.5 mmol) in a mixture of THF/MeOH (v/v 2:1, 150 mL) was added sodium borohydride (595 mg, 15.7 mmol) portion wise at 0° C. and the reaction mixture was stirred at room temperature for 1 h. The reaction mixture was then concentrated under reduced pressure, diluted with water (100 mL) and extracted with ethyl acetate (3×50 mL). The combined organic layer was washed with a solution of saturated aqueous NaCl (100 mL), dried over anhydrous $Na_2SO_4$ and concentrated under reduced pressure to afford the title compound as yellow sticky solid (3.8 g, crude).

MS (ESI+): m/z 384.0 (M+H), Rt: 1.502 min. [LCMS Method 6]; $^1$H NMR (300 MHz, $CDCl_3$) δ 8.12 (d, J=7.5 Hz, 1H), 7.87 (t, J=7.8 Hz, 1H), 7.45 (d, J=7.5 Hz, 1H), 7.25-7.15 (m, 3H), 5.94 (s, 2H), 5.04-5.01 (m, 1H), 3.95 (d, J=5.1 Hz, 1H), 1.57 (d, J=6.6 Hz, 3H).

Step 5: Synthesis of 2-(1-chloroethyl)-6-(2-(2-fluoro-5-(trifluoromethoxy) benzyl)-2H-tetrazol-5-yl)pyridine

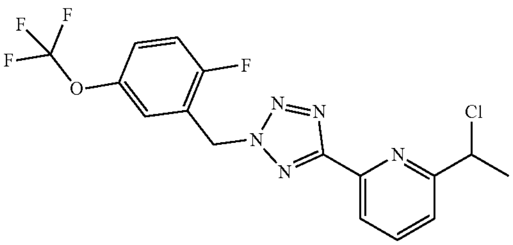 [SMILES: CC(Cl)c1cccc(-c2nnn(Cc3cc(OC(F)(F)F)ccc3F)n2)n1]

To a stirred solution of 1-(6-(2-(2-fluoro-5-(trifluoromethoxy)benzyl)-2H-tetrazol-5-yl)pyridin-2-yl)ethan-1-ol (3.80 g, 9.91 mmol) in DCM (10 mL) was added thionyl chloride (40 mL). The reaction mixture was stirred at 75° C. for 2 h before being concentrated under reduced pressure. The resulting residue was partitioned between a saturated aqueous solution of $NaHCO_3$ (100 mL) and DCM (50 mL). The aqueous phase was extracted with DCM (2×50 mL) and the combined organic phase was washed with a saturated aqueous NaCl solution (50 mL), dried over anhydrous $Na_2SO_4$ and concentrated under reduced pressure to furnish crude. The crude was purified with silica gel column chromatography (20-30% EtOAc in hexane) to afford the title compound as an off white solid (3.3 g, 83% yield).

MS (ESI+): m/z 402.15, Rt: 0.924 min. [LCMS Method 4]; $^1H$ NMR (300 MHz, $CDCl_3$) δ 8.16 (d, J=7.8 Hz, 1H), 7.91 (t, J=7.8 Hz, 1H), 7.72 (d, J=7.8 Hz, 1H), 7.24-7.14 (m, 3H), 5.94 (s, 2H), 5.32 (q, J=6.9 Hz, 1H), 1.91 (d, J=6.9 Hz, 3H).

Step 6: Synthesis of ethyl 2-(N,N-bis(4-methoxybenzyl)sulfamoyl)-3-(6-(2-(2-fluoro-5-(trifluoromethoxy)benzyl)-2H-tetrazol-5-yl)pyridin-2-yl) butanoate

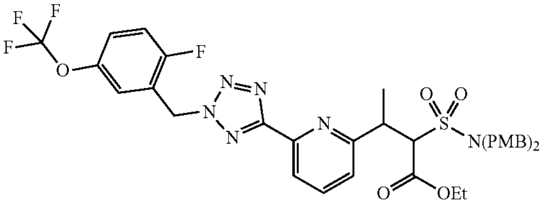

To a stirred solution of ethyl 2-(N,N-bis(4-methoxybenzyl)sulfamoyl)acetate (2.00 g, 4.9 mmol) in DMF (40 mL) was added cesium carbonate (3.20 g, 9.8 mmol) followed by potassium iodide (1.20 g, 7.4 mmol) and 2-(1-chloroethyl)-6-(2-(2-fluoro-5-(trifluoromethoxy) benzyl)-2H-tetrazol-5-yl)pyridine (2.50 g, 6.4 mmol) at room temperature. The reaction mixture was stirred at 80° C. for 2.5 h. The reaction mixture was then diluted with water (50 mL) and extracted with EtOAc (3×50 mL). The combined organic layer was washed with a saturated aqueous NaCl solution (100 mL), dried over anhydrous $Na_2SO_4$ and concentrated under reduced pressure to furnish crude. The crude was purified with silica gel column chromatography (10-20% EtOAc in hexane) to obtain the title compound as yellow sticky solid (1.7 g, 45% yield).

MS (ESI+): m/z 773.20 (M+H), Rt: 1.064 min. [LCMS Method 7].

Step 7: Synthesis of ethyl 3-(6-(2-(2-fluoro-5-(trifluoromethoxy) benzyl)-2H-tetrazol-5-yl) pyridin-2-yl)-2-sulfamoylbutanoate

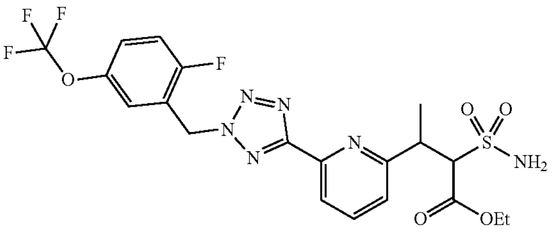 [SMILES: CCOC(=O)C(C(C)c1cccc(-c2nnn(Cc3cc(OC(F)(F)F)ccc3F)n2)n1)S(N)(=O)=O]

To a stirred solution of ethyl 2-(N, N-bis(4-methoxybenzyl)sulfamoyl)-3-(6-(2-(2-fluoro-5-(trifluoromethoxy) benzyl)-2H-tetrazol-5-yl)pyridin-2-yl)butanoate (1.40 g, 1.81 mmol) in DCM (15 mL) was added TFA (30 mL) at room temperature and the reaction mixture was stirred for 16 h. The reaction mixture concentrated under reduced pressure and basified with saturated $NaHCO_3$ aqueous solution (40 mL) and extracted with DCM (3×30 mL). The combined organic layer was washed with saturated aqueous NaCl solution (50 mL), dried over anhydrous $Na_2SO_4$ and concentrated under reduced pressure to furnish crude. The crude was purified with silica gel column chromatography (10-20% EtOAc in Hexane) to obtain the title compound as yellow sticky solid (580 mg, 60% yield).

MS (ESI+): m/z 533.10 (M+H), Rt: 0.916 min. [LCMS Method 7].

Step 8: Synthesis of 3-(6-(2-(2-fluoro-5-(trifluoromethoxy) benzyl)-2H-tetrazol-5-yl)pyridin-2-yl)-1-hydroxybutane-2-sulfonamide

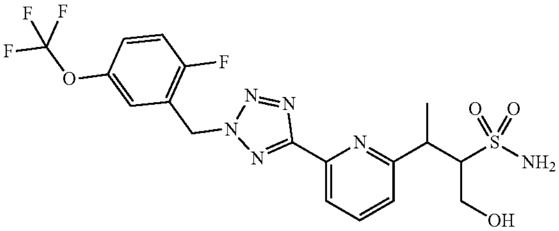 [SMILES: CC(c1cccc(-c2nnn(Cc3cc(OC(F)(F)F)ccc3F)n2)n1)C(CO)S(N)(=O)=O]

To a stirred solution of ethyl 3-(6-(2-(2-fluoro-5-(trifluoromethoxy)benzyl)-2H-tetrazol-5-yl)pyridin-2-yl)-2-sulfamoylbutanoate (790 mg, 1.48 mmol) in THF (5.0 mL) cooled in an ice-water bath was added $LiBH_4$ (4.4 mL, 8.8 mmol, 2.0 M in THF) dropwise at 0° C. and the reaction mixture was stirred at 0° C. for 1 h and then at room temperature for 4 h. The reaction was quenched with water (10 mL) and extracted with EtOAc (3×30 mL). The combined organic layer was washed with a saturated aqueous NaCl solution (20 mL), dried over anhydrous $Na_2SO_4$ and concentrated under reduced pressure to furnish crude. The crude was purified with silica gel column chromatography (5-10% MeOH in DCM) followed by prep-HPLC under the following conditions:

Instrument: Agilent 1260 Infinity II

Column: KINETEX (20.0 mm×150 mm), 5 μm

Mobile phase: 0.1% HCOOH in water (A) and acetonitrile (B); Gradient (Time (min.), % B): (0, 20), (2, 30), (8, 50)

Flow rate: 18 mL/min.

Detection: UV @210 nm

Title compound was isolated as a mixture of racemic pairs of diastereomers as colorless sticky solid. (0.4 g, 55% yield). MS (ESI+): m/z 491.10 (M+H), Rt: 0.845 min. [LCMS Method 7].

Purification of the racemic mixture (0.4 g) using chiral preparative HPLC afforded four diastereomeric products as off-white solids (Peak-1: 40 mg, 10% yield; Peak-2&3 mixture: 130 mg (mixture) and Peak-4: 43 mg, 110% yield).

Instrument: Agilent 1260 Infinity

Column: CHIRAL PAK IG (20.0 mm×250 mm), 5 μm

Mobile phase: n-hexane (A); EtOH: MeOH (1:1, B); Isocratic: 60(A):40(B)

Flow rate: 15 mL/min.

Detection: UV @210 nm

The Peak 2&3 (0.13 g) mixture was repurified by chiral preparative HPLC to provide the other two diastereomers of the title compound as off-white solids (Peak-2: 42 mg, 11% yield and Peak-3: 42 mg, 110% yield).

Chiral Prep HPLC Conditions:

Instrument: Agilent 1260 Infinity

Column: CHIRAL PAK IJ (21.2 mm×250 mm) 5 μm

Mobile phase: n-hexane (A); EtOH: MeOH (1:1, B); Isocratic: 60(A):40(B)

Flow rate: 15 mL/min.

Detection: UV @210 nm

Peak 1 (Example 31): MS (ESI+): m/z 491.05 (M+H), Rt: 0.845 min. [LCMS Method 7]; $^1$H NMR (400 MHz, $CD_3OD$) δ 8.04 (d, J=8.0 Hz, 1H), 7.92 (t, J=8.0 Hz, 1H), 7.53-7.50 (m, 2H), 7.42-7.39 (m, 1H), 7.33 (t, J=9.2 Hz, 1H), 6.06 (s, 2H), 3.97-3.93 (m, 1H), 3.88-3.71 (m, 3H), 1.61 (d, J=7.2 Hz, 3H).

Chiral HPLC purity: 98.8%, Rt: 6.476 min.

Peak 4 (Example 32): MS (ESI+): m/z 491.05 (M+H), Rt: 0.837 min. [LCMS Method 7]; $^1$H NMR (400 MHz, $CD_3OD$) δ 8.04 (d, J=7.6 Hz, 1H), 7.92 (t, J=7.6 Hz, 1H), 7.53-7.50 (m, 2H), 7.43-7.39 (m, 1H), 7.33 (t, J=9.2 Hz, 1H), 6.06 (s, 2H), 3.97-3.71 (m, 4H), 1.61 (d, J=7.2 Hz, 3H).

Chiral HPLC purity: 98.6%, Rt: 12.020 min.

Chiral HPLC retention times for Peak 1 and Peak 4 were obtained using the following conditions:

Instrument: Agilent 1260 Infinity II

Column: CHIRAL PAK-IG (150×4.6 mm), 5 μm

Mobile phase: n-hexane (A); EtOH: MeOH (1:1, B); Isocratic: 70(A):30(B)

Flow rate: 1.0 mL/min.

Detection: UV @210 nm

Peak 2 (Example 33): MS (ESI+): m/z 491.30 (M+H), Rt: 0.793 min. [LCMS Method 4]; $^1$H NMR (400 MHz, $CD_3OD$) δ 8.04 (d, J=8.0 Hz, 1H), 7.94 (t, J=8.0 Hz, 1H), 7.54 (d, J=8.0 Hz, 1H), 7.52-7.49 (m, 1H), 7.42-7.39 (m, 1H), 7.31 (t, J=8.8 Hz, 1H), 6.06 (s, 2H), 4.17-4.15 (m, 2H), 3.92-3.89 (m, 1H), 3.84-3.82 (m, 1H), 1.51 (d, J=7.2 Hz, 3H).

Chiral HPLC purity: 98.87%, Rt: 6.463 min.

Peak 3 (Example 34): MS (ESI+): m/z 491.30 (M+H), Rt: 0.794 min. [LCMS Method 4]; $^1$H NMR (400 MHz, $CD_3OD$) δ 8.03 (d, J=7.6 Hz, 1H), 7.93 (t, J=8.0 Hz, 1H), 7.53 (d, J=8.0 Hz, 1H), 7.52-7.50 (m, 1H), 7.43-7.39 (m, 1H), 7.33 (t, J=9.2 Hz, 1H), 6.06 (s, 2H), 4.17-4.15 (m, 2H), 3.92-3.89 (m, 1H), 3.84-3.82 (m, 1H), 1.51 (d, J=6.8 Hz, 3H).

Chiral HPLC purity: 97.07%, Rt: 11.288 min.

Chiral HPLC retention times for Peak 2 and Peak 3 were obtained using the following conditions:

Instrument: Agilent 1260 Infinity II

Column: CHIRAL PAK-IJ (150×4.6 mm), 5 μm

Mobile phase: n-hexane (A), B: 0.1% $NH_4OH$ in EtOH: MeOH (50:50, B); Isocratic: 70(A):30(B)

Flow rate: 1.0 mL/min.

Detection: UV @210 nm

Example 35: 2-(6-(1-(2-fluoro-5-(trifluoromethoxy)benzyl)-1H-pyrazol-3-yl)pyridin-2-yl)-2-hydroxybutane-1-sulfonamide Prepared according to Scheme 4.

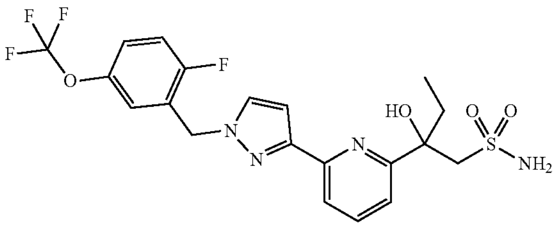 [SMILES: CCC(O)(CS(N)(=O)=O)c1cccc(-c2ccn(Cc3cc(OC(F)(F)F)ccc3F)n2)n1]

Step 1: 1-(2-fluoro-5-(trifluoromethoxy)benzyl)-3-(4,4,5,5-tetramethyl-1,3,2-dioxaborolan-2-yl)-1H-pyrazole

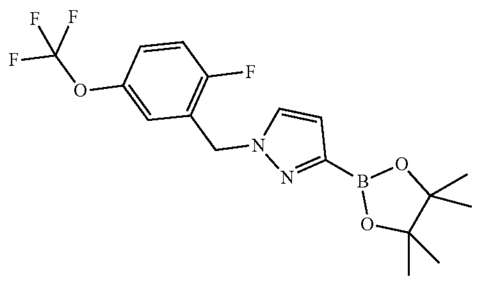 [SMILES: CC1(C)OB(c2ccn(Cc3cc(OC(F)(F)F)ccc3F)n2)OC1(C)C]

A mixture of 3-(4,4,5,5-tetramethyl-1,3,2-dioxaborolan-2-yl)-1H-pyrazole (500 mg, 2.58 mmol), 2-(bromomethyl)-1-fluoro-4-(trifluoromethoxy)benzene (739 mg, 2.71 mmol) and potassium carbonate (534 mg, 3.87 mmol) in acetonitrile (25 mL) was stirred at 80° C. for 12 h. The solid was filtered out and volatiles in filtrate were removed under reduced pressure to afford the crude title compound. It was used directly in next step without further purification. ESI-MS m/z: 305.0 (Rt: 0.73 min., the corresponding boronic acid MW was shown on LCMS, LCMS Method 2).

Step 2: 1-(6-(1-(2-fluoro-5-(trifluoromethoxy)benzyl)-1H-pyrazol-3-yl)pyridin-2-yl)propan-1-one

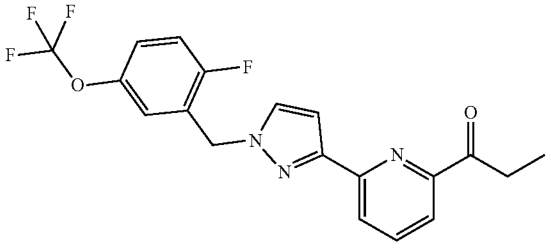 [SMILES: CCC(=O)c1cccc(-c2ccn(Cc3cc(OC(F)(F)F)ccc3F)n2)n1]

A mixture of 1-(6-bromopyridin-2-yl)propan-1-one (150 mg, 0.701 mmol), 1-(2-fluoro-5-(trifluoromethoxy)benzyl)-3-(4,4,5,5-tetramethyl-1,3,2-dioxaborolan-2-yl)-1H-pyrazole (325 mg, 0.841 mmol), chloro(2-dicyclohexylphosphino-2',4',6'-triisopropyl-1,1'-biphenyl)[2-(2'-amino-1,1'-biphenyl)]palladium(II) (Xphos-Pd-G2, 55 mg, 0.070 mmol) and potassium carbonate (291 mg, 2.10 mmol) in 1,4-dioxane/water (4 mL/0.5 mL) was heated with microwave at 105° C. for 15 min. The reaction mixture was purified directly with silica gel column chromatography (10-20% ethyl acetate in heptane) to afford crude title compound (252 mg, 91% yield).

ESI-MS m/z: 394.2 $[M+H]^+$ (Rt: 1.25 min., LCMS Method 2).

Step 3: 2-(6-(1-(2-fluoro-5-(trifluoromethoxy)benzyl)-1H-pyrazol-3-yl)pyridin-2-yl)-2-hydroxy-N,N-bis(4-methoxybenzyl)butane-1-sulfonamide

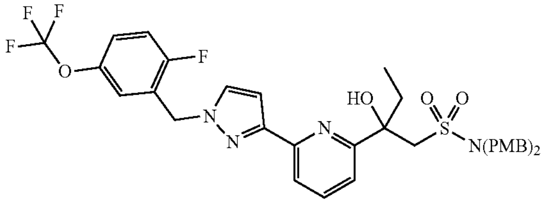

To a solution of N,N-bis(4-methoxybenzyl)methanesulfonamide (277 mg, 0.826 mmol) in THF (6 mL) cooled in dry ice/acetone bath was added n-BuLi (1.6 M in hexanes, 0.516 mL, 0.826 mmol) and the mixture was stirred at −78° C. for 1 h. To the resulting reaction mixture was added a solution of 1-(6-(1-(2-fluoro-5-(trifluoromethoxy)benzyl)-1H-pyrazol-3-yl)pyridin-2-yl)propan-1-one (250 mg, 0.636 mmol) in THF (2 mL). The mixture was stirred at room temperature for 12 h. Water was added to quench the reaction. The resulted mixture was concentrated under reduced pressure and the residue was purified with silica gel column chromatography (10-20% ethyl acetate in heptane) to afford the title compound (230 mg, 50% yield).

ESI-MS m/z: 729.1 $[M+H]^+$ (Rt: 1.36 min., LCMS Method 2).

Step 4: 2-(6-(1-(2-fluoro-5-(trifluoromethoxy)benzyl)-1H-pyrazol-3-yl)pyridin-2-yl)-2-hydroxybutane-1-sulfonamide

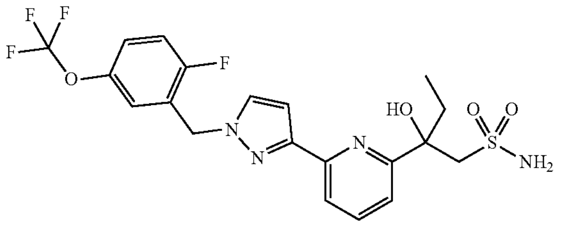 [SMILES: CCC(O)(CS(N)(=O)=O)c1cccc(-c2ccn(Cc3cc(OC(F)(F)F)ccc3F)n2)n1]

To a solution of 2-(6-(1-(2-fluoro-5-(trifluoromethoxy)benzyl)-1H-pyrazol-3-yl)pyridin-2-yl)-2-hydroxy-N,N-bis(4-methoxybenzyl)butane-1-sulfonamide (230 mg, 0.32 mmol) in DCM (1 mL) was added TFA (2 mL) and the mixture was stirred at room temperature for 12 h. Volatiles were removed under reduced pressure and to the residue was added excess triethylamine. Volatiles were removed under reduced pressure again, and the residue was purified with silica gel column chromatography (20-40% ethyl acetate in heptane) to afford the crude product which was then subjected to preparative HPLC purification to afford the title compound as a racemate (81 mg, 51% yield).

Conditions for Preparative HPLC:

Instrument: Waters AutoPurification System (equipped with 2545/515 pumps and 2998 detector)

Column: Waters Xbridge BEH C18, 5 μm, 30×50 mm

Mobile Phase: water (375 mM ammonium hydroxide)/acetonitrile (375 mM ammonium hydroxide) with a gradient of 65/35 held for 1 min., ramp to 40/60 over 3.2 min., then ramp to 5/95 over 0.5 min. followed by hold at 5/95 for 1.3 min.

Flow rate: 75 mL/min.

Detection: UV 210-400 nm

ESI-MS m/z: 488.9 $[M+H]^+$ (Rt: 1.04 min., LCMS Method 2).

$^1H$ NMR (400 MHz, DMSO-$d_6$) δ 7.95 (d, J=2.4 Hz, 1H), 7.79 (t, J=7.8 Hz, 1H), 7.70 (d, J=7.7 Hz, 1H), 7.53 (d, J=7.6 Hz, 1H), 7.48-7.37 (m, 2H), 7.31 (dd, J=6.3, 2.4 Hz, 1H), 6.91 (d, J=2.1 Hz, 1H), 6.61 (s, 2H), 5.52 (d, J=3.5 Hz, 3H), 3.76 (d, J=14.2 Hz, 1H), 3.66 (d, J=14.2 Hz, 1H), 1.98 (q, J=7.3 Hz, 2H), 0.61 (t, J=7.3 Hz, 3H).

HRMS: M+H, found 489.1220, calc. 489.1220 (HRMS Method 10).

Example 36: 2-(6-(1-(2-fluoro-5-(trifluoromethoxy)benzyl)-1H-pyrazol-3-yl)pyridin-2-yl)-2-hydroxyethane-1-sulfonamide Prepared according to Scheme 4.

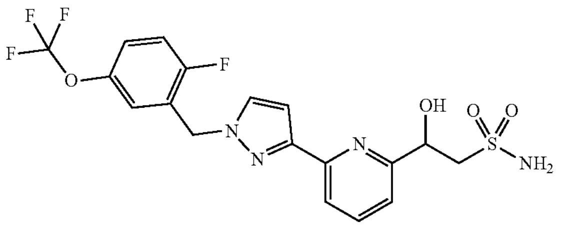 [SMILES: NS(=O)(=O)CC(O)c1cccc(-c2ccn(Cc3cc(OC(F)(F)F)ccc3F)n2)n1]

Step 1: 2-(6-bromopyridin-2-yl)-2-hydroxy-N,N-bis(4-methoxybenzyl)ethane-1-sulfonamide

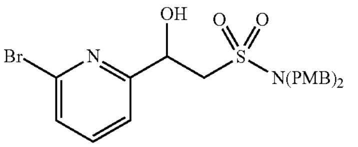

To a stirred solution of N,N-bis(4-methoxybenzyl)methanesulfonamide (905 mg, 2.70 mmol) in THF (22 mL) cooled to −78° C. was added n-BuLi (1.6 M in hexanes, 1.86 mL, 2.97 mmol). After stirring at −78° C. for 10 min, a solution of 6-bromopicolinaldehyde (552 mg, 2.97 mmol) in THF (8 mL) was added dropwise. The mixture was then stirred at −78° C. for 30 min., then at room temperature for 12 h. The reaction mixture was quenched with water, concentrated under reduced pressure and the crude residue was purified with silica gel column chromatography (10-30% ethyl acetate in heptane) to afford the title compound (1.17 g, 83% yield).

ESI-MS m/z: 523.4 $[M+H]^+$ (Rt: 1.15 min., LCMS Method 2).

Step 2: 2-(6-(1-(2-fluoro-5-(trifluoromethoxy)benzyl)-1H-pyrazol-3-yl)pyridin-2-yl)-2-hydroxy-N,N-bis(4-methoxybenzyl)ethane-1-sulfonamide

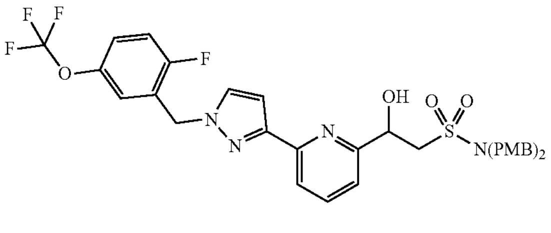

A mixture of 2-(6-bromopyridin-2-yl)-2-hydroxy-N,N-bis(4-methoxybenzyl)ethane-1-sulfonamide (85 mg, 0.163 mmol), 1-(2-fluoro-5-(trifluoromethoxy)benzyl)-3-(4,4,5,5-tetramethyl-1,3,2-dioxaborolan-2-yl)-1H-pyrazole (76 mg, 0.196 mmol), chloro[(4,5-bis(diphenylphosphino)-9,9-dimethylxanthene)-2-(2'-amino-1,1'-biphenyl)]palladium(II) (XantPhosPd-G2, 14.5 mg, 0.016 mmol) and potassium carbonate (68 mg, 0.489 mmol) in 1,4-dioxane/water (2 mL/0.6 mL) was heated at 100° C. with microwave for 15 min. The reaction mixture was purified directly with silica gel column chromatography (20-50% ethyl acetate in heptane) to afford the title compound (85 mg, 74% yield).

ESI-MS m/z: 701.1 $[M+H]^+$ (Rt: 1.31 min., LCMS Method 2).

Step 3: 2-(6-(1-(2-fluoro-5-(trifluoromethoxy)benzyl)-1H-pyrazol-3-yl)pyridin-2-yl)-2-hydroxyethane-1-sulfonamide

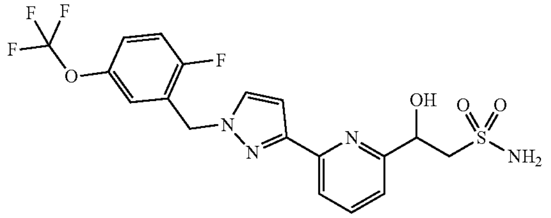 [SMILES: NS(=O)(=O)CC(O)c1cccc(-c2ccn(Cc3cc(OC(F)(F)F)ccc3F)n2)n1]

To a solution of 2-(6-(1-(2-fluoro-5-(trifluoromethoxy)benzyl)-1H-pyrazol-3-yl)pyridin-2-yl)-2-hydroxy-N,N-bis(4-methoxybenzyl)ethane-1-sulfonamide (85 mg, 0.12 mmol) in DCM (1 mL) was added TFA (2 mL) and the mixture was stirred at room temperature for 12 h. Volatiles were removed under reduced pressure. Then excess triethylamine was added to the residue and volatiles were removed under reduced pressure again. The residue was purified with preparative HPLC to afford the racemic title compound as a white solid (14 mg, 24% yield).

Conditions for Preparative HPLC:

Instrument: Waters AutoPurification System (equipped with 2545/515 pumps and 2998 detector)

Column: Waters Xbridge BEH C18, 5 μm, 30×50 mm

Mobile Phase: water (375 mM ammonium hydroxide)/acetonitrile (375 mM ammonium hydroxide) with a gradient of 75/25 held for 1 min., ramp to 50/50 over 3.2 min., then ramp to 5/95 over 0.5 min. followed by hold at 5/95 for 1.3 min.

Flow rate: 75 mL/min.

Detection: UV 210-400 nm

ESI-MS m/z: 461.3 $[M+H]^+$ (Rt: 0.92 min., LCMS Method 2).

$^1$H NMR (400 MHz, DMSO-$d_6$) δ 7.97 (d, J=2.4 Hz, 1H), 7.84 (t, J=7.8 Hz, 1H), 7.76 (d, J=7.8 Hz, 1H), 7.53-7.37 (m, 3H), 7.29-7.20 (m, 1H), 6.90 (d, J=2.4 Hz, 1H), 6.78 (s, 2H), 5.89 (s, 1H), 5.53 (s, 2H), 5.12 (dd, J=8.9, 3.0 Hz, 1H), 3.70 (dd, J=14.1, 3.1 Hz, 1H), 3.31 (dd, J=14.2, 9.2 Hz, 1H).

HRMS: M+H, found 461.0905, calc. 461.0907 (HRMS Method 10).

Example 37: (R or S)-2-(6-(1-(2-fluoro-5-(trifluoromethoxy)benzyl)-1H-pyrazol-3-yl)pyridin-2-yl)-2-hydroxypropane-1-sulfonamide and Example 38: (R or S)-2-(6-(1-(2-fluoro-5-(trifluoromethoxy)benzyl)-1H-pyrazol-3-yl)pyridin-2-yl)-2-hydroxypropane-1-sulfonamide Prepared by analogy to Example 36 according to Scheme 4 starting from 1-(6-bromopyridin-2-yl)ethan-1-one to afford the racemate of the title compound (Rac-37+38) (106 mg).

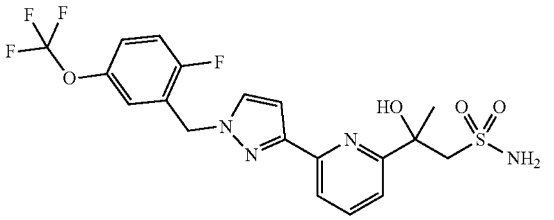

Chiral separation of the racemate (106 mg) provided Example 37 as the first eluting peak (39 mg, 37% yield, chiral HPLC: e.e. >99%, Rt: 1.93 min.) and Example 38 as the second eluting peak (38 mg, 36% yield, chiral HPLC: e.e. 96.64%, Rt: 2.18 min.) as white solids.

Chiral Prep HPLC:

Instrument: Waters SFC MS100

Column: Chiralcel OD-H (21×250 mm, 5 μm)

Mobile phase: 25-45% methanol/$CO_2$

Flow rate: 80 g/min.

Detection: UV @250 nm

Peak 1 (Example 37): ESI-MS m/z: 475.1 $[M+H]^+$ (Rt: 2.16 min., LCMS Method 8); $^1$H NMR (400 MHz, DMSO-$d_6$) δ 7.95 (d, J=2.4 Hz, 1H), 7.80 (t, J=7.8 Hz, 1H), 7.70 (d, J=7.8 Hz, 1H), 7.56 (d, J=7.7 Hz, 1H), 7.44-7.40 (m, 2H), 7.31-7.24 (m, 1H), 6.91 (d, J=2.4 Hz, 1H), 6.62 (s, 2H), 5.71 (s, 1H), 5.52 (s, 2H), 3.70 (d, J=14.2 Hz, 1H), 3.61 (d, J=14.2 Hz, 1H), 1.61 (s, 3H).

Peak 2 (Example 38): ESI-MS m/z: 475.1 $[M+H]^+$ (Rt: 2.16 min., LCMS Method 8). $^1$H NMR (400 MHz, DMSO-$d_6$) δ 7.96 (d, J=2.4 Hz, 1H), 7.81 (t, J=7.8 Hz, 1H), 7.71 (d, J=7.8 Hz, 1H), 7.57 (d, J=7.8 Hz, 1H), 7.45-7.41 (m, 2H), 7.31-7.25 (m, 1H), 6.91 (d, J=2.1 Hz, 1H), 6.63 (s, 2H), 5.71 (s, 1H), 5.52 (s, 2H), 3.70 (d, J=14.2 Hz, 1H), 3.62 (d, J=14.2 Hz, 1H), 1.62 (s, 3H).

Enantiomeric excess was determined using the following conditions:

Instrument: Waters UPC$^2$ system

Column: Chiralpak OD-3(3 μm, 3×100 mm) @40° C.

Mobile phase: Methanol with 0.1% ammonium hydroxide (modifier)/$CO_2$; Gradient: 5% modifier for 0.15 minutes, increase to 55% modifier over 1.5 minutes, and hold at 55% modifier for 0.65 minutes Flow rate: 2.5 mL/min.

Detection: PDA detector (210-400 nm)

Example 39: 3,3,3-trifluoro-2-(6-(1-(2-fluoro-5-(trifluoromethoxy)benzyl)-1H-pyrazol-3-yl)pyridin-2-yl)-2-hydroxypropane-1-sulfonamide Prepared by analogy to Example 36 according to Scheme 4 starting from 1-(6-bromopyridin-2-yl)-2,2,2-trifluoroethan-1-one to afford the racemate of the title compound.

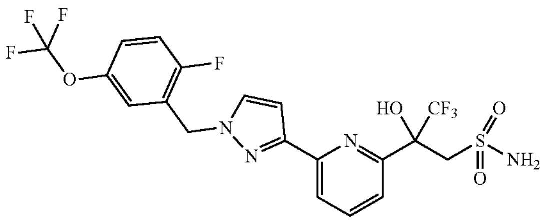 [SMILES: NS(=O)(=O)CC(O)(c1cccc(-c2ccn(Cc3cc(OC(F)(F)F)ccc3F)n2)n1)C(F)(F)F]

ESI-MS m/z: 529.7 $[M+H]^+$ (Rt: 2.43 min., LCMS Method 3).

$^1$H NMR (400 MHz, DMSO-$d_6$) δ 7.97 (d, J=2.4 Hz, 1H), 7.92 (t, J=7.7 Hz, 1H), 7.86 (d, J=7.7 Hz, 1H), 7.73 (d, J=7.7 Hz, 1H), 7.45-7.40 (m, 2H), 7.34-7.30 (m, 1H), 7.12 (s, 1H), 6.99 (d, J=2.1 Hz, 1H), 6.82 (s, 2H), 5.53 (s, 2H), 4.38 (d, J=14.2 Hz, 1H), 3.76 (d, J=14.1 Hz, 1H).

Example 40: (R or S)-2-hydroxy-2-(6-(2-(3-(trifluoromethyl)benzyl)-2H-tetrazol-5-yl)pyridin-2-yl)propane-1-sulfonamide and Example 41: (R or S)-2-hydroxy-2-(6-(2-(3-(trifluoromethyl)benzyl)-2H-tetrazol-5-yl)pyridin-2-yl)propane-1-sulfonamide Prepared according to Scheme 5.

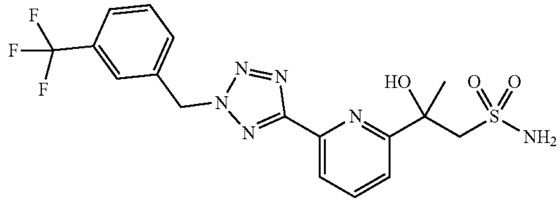 [SMILES: CC(O)(CS(N)(=O)=O)c1cccc(-c2nnn(Cc3cccc(C(F)(F)F)c3)n2)n1]

Step 1: 2-(6-bromopyridin-2-yl)-2-hydroxy-N,N-bis(4-methoxybenzyl)propane-1-sulfonamide

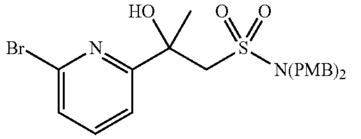

To a stirred solution of N,N-bis(4-methoxybenzyl)methanesulfonamide (1.6 g, 5.0 mmol) in THF (15 mL) was added n-BuLi (1.6 M in hexanes, 3.1 mL, 5.0 mmol) dropwise at −78° C. (reaction mixture color turned to pale yellow) and the reaction mixture was stirred at −78° C. for 2 h. Then 1-(6-bromopyridin-2-yl)ethan-1-one (0.50 g, 2.5 mmol) dissolved in THF (5.0 mL) was added dropwise at −78° C. (reaction mixture color turned to orange and then to yellow) and the reaction mixture was stirred at −78° C. for 1 h and then at room temperature for 16 h. The reaction mixture was quenched with a saturated $NH_4Cl$ solution (50 mL) and extracted with ethyl acetate (3×50 mL). The combined organic layer was washed with a saturated aqueous NaCl solution (1×100 mL) and dried over anhydrous $Na_2SO_4$ and concentrated under reduced pressure to furnish the crude product as an off-white solid (2.2 g), which was carried on to the next step without further purification.

MS (ESI+): m/z 536.9 (M+H), Rt: 1.626 min. [LCMS Method 6].

Step 2: 2-(6-cyanopyridin-2-yl)-2-hydroxy-N,N-bis(4-methoxybenzyl)propane-1-sulfonamide

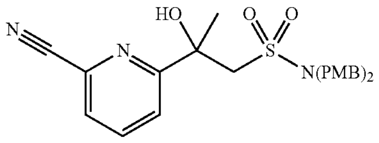

To a stirred solution of 2-(6-bromopyridin-2-yl)-2-hydroxy-N,N-bis(4-methoxybenzyl)propane-1-sulfonamide (2.20 g, 4.1 mmol) in DMF (20 mL) was added zinc cyanide (579 mg, 4.9 mmol) at room temperature and resulted solution was purged with argon gas for 10 minutes. Then $Pd(PPh_3)_4$ (569 mg, 0.49 mmol) was added and again the reaction mixture was purged with argon gas for 10 minutes before being set to stir at 110° C. for 2.5 h. The reaction mixture was cooled to room temperature, diluted with water (100 mL) and extracted with EtOAc (3×50 mL). The combined organic layer was washed with a saturated aqueous NaCl solution (2×50 mL) and dried over anhydrous $Na_2SO_4$ and concentrated under reduced pressure to furnish crude. The crude product was purified with silica gel column chromatography (30-50% EtOAc in hexane) to afford 2-(6-cyanopyridin-2-yl)-2-hydroxy-N,N-bis(4-methoxybenzyl)propane-1-sulfonamide as yellow sticky solid (1.5 g, 76% yield).

MS (ESI+): m/z 482.05 (M+H), Rt: 1.570 min. [LCMS Method 6].

Step 3: 2-(6-(2H-tetrazol-5-yl)pyridin-2-yl)-2-hydroxy-N,N-bis(4-methoxybenzyl)propane-1-sulfonamide

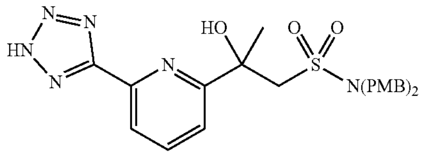

To a stirred solution of 2-(6-cyanopyridin-2-yl)-2-hydroxy-N,N-bis(4-methoxybenzyl)propane-1-sulfonamide (1.80 g, 3.7 mmol) in a mixture of solvent t-BuOH:$H_2O$ (2:1) (21 mL) was added $NaN_3$ (364 mg, 5.6 mmol) followed by zinc bromide (1.2 g, 5.6 mmol) at room temperature. The reaction mass was heated at 90° C. for 2 h. The reaction mixture was cooled to room temperature, diluted with water (10 mL), acidified with 1N HCl (10 mL) and extracted with ethyl acetate (3×50 mL). The combined organic layer was washed with a saturated aqueous NaCl solution (1×50.0 mL) and dried over anhydrous $Na_2SO_4$ and concentrated under reduced pressure to get 2-(6-(2H-tetrazol-5-yl)pyridin-2-yl)-2-hydroxy-N,N-bis(4-methoxybenzyl)propane-1-sulfonamide as yellow solid (2.1 g, crude).

MS (ESI+): m/z 525.2 (M+H), Rt: 0.823 min. [LCMS Method 4].

Step 4: 2-hydroxy-N,N-bis(4-methoxybenzyl)-2-(6-(2-(3-(trifluoromethyl)benzyl)-2H-tetrazol-5-yl)pyridin-2-yl)propane-1-sulfonamide

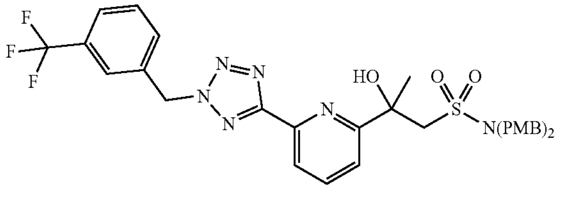

To a stirred solution of 2-(6-(2H-tetrazol-5-yl)pyridin-2-yl)-2-hydroxy-N,N-bis(4-methoxybenzyl)propane-1-sulfonamide (1.0 g, 1.9 mmol) in acetone (10 mL), was added sodium carbonate (0.71 g, 6.7 mmol) followed by sodium iodide (0.31 g, 2.1 mmol) and 1-(bromomethyl)-3-(trifluoromethyl)benzene (0.46 g, 1.9 mmol) at room temperature. The reaction mass was heated at 50° C. for 16 h. The reaction mixture was cooled to room temperature, diluted with water (10 mL) and extracted with EtOAc (3×50 mL). The combined organic layer was washed with saturated aqueous NaCl solution (1×100 mL) and dried over anhydrous $Na_2SO_4$ and concentrated under reduced pressure to furnish crude. The crude product was purified with silica gel column chromatography (30-50% EtOAc in hexane, desired product was first regioisomer to elute out) to afford the title compound as white sticky solid (0.76 g, 59%).

MS (ESI+): m/z 683.2 (M+H), Rt: 1.293 min. [LCMS Method 7]; $^1H$ NMR (300 MHz, $CDCl_3$) δ 8.09 (d, J=7.8 Hz, 1H), 7.89 (t, J=7.8 Hz, 1H), 7.80 (d, J=8.1 Hz, 1H), 7.72-7.70 (m, 1H), 7.60 (t, J=8.4 Hz, 2H), 7.46 (t, J=7.5 Hz, 1H), 7.13 (d, J=8.4 Hz, 4H), 6.82 (d, J=8.7 Hz, 4H), 5.89 (s, 2H), 4.15 (s, 4H), 3.76 (s, 6H), 3.74 (d, J=14.2 Hz, 1H), 3.58 (d, J=13.8 Hz, 1H), 1.74 (s, 3H).

Step 5: 2-hydroxy-2-(6-(2-(3-(trifluoromethyl)benzyl)-2H-tetrazol-5-yl)pyridin-2-yl)propane-1-sulfonamide

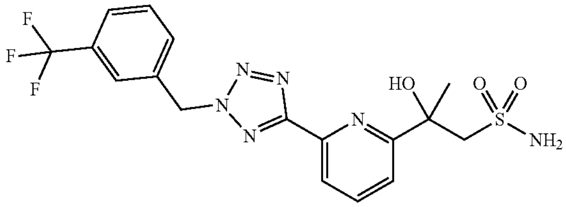 [SMILES: CC(O)(CS(N)(=O)=O)c1cccc(-c2nnn(Cc3cccc(C(F)(F)F)c3)n2)n1]

To a stirred solution of 2-hydroxy-N,N-bis(4-methoxybenzyl)-2-(6-(2-(3-(trifluoromethyl)benzyl)-2H-tetrazol-5-yl)pyridin-2-yl)propane-1-sulfonamide (768 mg, 1.1 mmol) in DCM (8 mL) was added TFA (15 mL) at room temperature and the reaction mixture was stirred for 16 h. The reaction mass was concentrated under reduced pressure and partitioned between a saturated aqueous $NaHCO_3$ solution (15 mL) and EtOAc (10 mL). The organic layer was separated, and aqueous layer was extracted with EtOAc (20 mL). The combined organic layer was washed with a saturated aqueous NaCl solution (1×20 mL) and dried over anhydrous $Na_2SO_4$ and concentrated under reduced pressure to furnish crude. The crude was purified with silica gel column chromatography (2-5% MeOH in DCM) followed by Prep-HPLC:

Instrument: Agilent 1260 Infinity II

Column: X SELECT (19.0 mm×250 mm), 5 μm

Mobile phase: 0.1% HCOOH in water and acetonitrile; Gradient (Time (min.), % B): (0, 30), (2, 40), (8, 60)

Flow rate: 18 mL/min.

Detection: UV @210 nm

The racemic title compound was afforded as a white sticky solid (239 mg, 48% yield).

MS (ESI+): m/z 442.9 (M+H), Rt: 1.462 min. [Method 6].

Chiral separation of the racemate (239 mg) provided Example 41 as the first eluting peak (95 mg, 40% yield, chiral HPLC purity: 99.6%, Rt: 6.981 min.) and Example 40 as the second eluting peak (63 mg, 26% yield, chiral HPLC purity: 99.1%, Rt: 9.819 min.) as white solids.

Chiral Prep HPLC:

Instrument: Agilent 1260 Infinity

Column: CHIRAL PAK IH (250 mm×20 mm), 5 μm

Mobile phase: n-hexane (A); EtOH: MeOH (1:1, B); Isocratic: 70(A): 30(B)

Flow rate: 15 mL/min.

Detection: UV @210 nm

Peak 1 (Example 41): MS (ESI+): m/z 443.1 (M+H), Rt: 1.149 min. [LCMS Method 7]; $^1$H NMR (400 MHz, $CD_3OD$) δ 8.04 (d, J=7.6 Hz, 1H), 7.94 (t, J=8.0 Hz, 1H), 7.85-7.80 (m, 2H), 7.73-7.68 (m, 2H), 7.64-7.59 (m, 1H), 6.07 (s, 2H), 4.04 (d, J=14.4 Hz, 1H), 3.77 (d, J=14.4 Hz, 1H), 1.69 (s, 3H).

Peak 2 (Example 40): MS (ESI+): m/z 443.1 (M+H), Rt: 1.149 min. [LCMS Method 7]; $^1$H NMR (400 MHz, $CD_3OD$) δ 8.07 (d, J=8.0 Hz, 1H), 7.97 (t, J=7.6 Hz, 1H), 7.88-7.83 (m, 2H), 7.76-7.71 (m, 2H), 7.67-7.61 (m, 1H), 6.10 (s, 2H), 4.06 (d, J=14.4 Hz, 1H), 3.80 (d, J=14.4 Hz, 1H), 1.72 (s, 3H).

Chiral HPLC retention times were obtained using the following conditions:

Instrument: Agilent 1260 Infinity II

Column: CHIRAL PAK IH (150 mm×4.6 mm), 5 μm

Mobile phase: n-hexane (A); 0.1% HCOOH in ethanol: MeOH (80:20, B); Isocratic: 70(A): 30(B)

Flow rate: 1.0 mL/min.

Detection: UV @210 nm

Example 42: (R or S)-2-(3-chloro-6-(2-(2-fluoro-5-(trifluoromethoxy)benzyl)-2H-tetrazol-5-yl)pyridin-2-yl)-2-hydroxypropane-1-sulfonamide and Example 43: (R or S)-2-(3-chloro-6-(2-(2-fluoro-5-(trifluoromethoxy)benzyl)-2H-tetrazol-5-yl)pyridin-2-yl)-2-hydroxypropane-1-sulfonamide Prepared by analogy to Examples 40 and 41 according to Scheme 5 starting from 1-(6-bromo-3-chloropyridin-2-yl) ethan-1-one and by replacing 1-(bromomethyl)-3-(trifluoromethyl)benzene with 2-(bromomethyl)-1-fluoro-4-(trifluoromethoxy)benzene to afford the racemate of the title compound (400 mg).

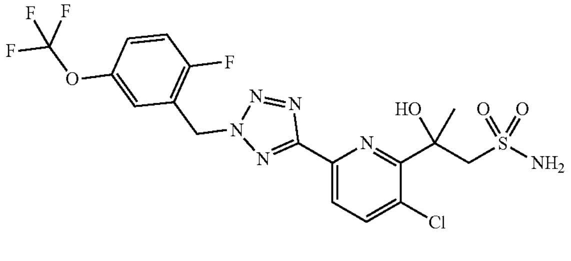 [SMILES: CC(O)(CS(N)(=O)=O)c1nc(-c2nnn(Cc3cc(OC(F)(F)F)ccc3F)n2)ccc1Cl]

Chiral separation of the racemate (400 mg) provided Example 43 as the first eluting peak (104 mg, 26% yield, chiral HPLC purity: 98.9%, Rt: 4.592 min.) and Example 42 as the second eluting peak (113 mg, 28% yield, chiral HPLC purity: 98.5%, Rt: 5.524 min.) as white solids.

Chiral Prep HPLC:

Instrument: Agilent 1260 Infinity

Column: LUX CELLULOSE-4, 250 mm×21.2 mm, 5 μm

Mobile phase: n-hexane (A); IPA: MeOH, 1:1 (B); Isocratic: 60 (A): 40(B)

Flow rate: 15 mL/min.

Detection: UV @210 nm

Peak 1 (Example 43): MS (ESI+): m/z 511.05 (M+H), Rt: 1.198 min. [LCMS Method 7]; $^1$H NMR (400 MHz, $CD_3OD$) δ 8.10 (d, J=8.4 Hz, 1H), 8.03 (d, J=8.0 Hz, 1H), 7.52-7.49 (m, 1H), 7.41-7.36 (m, 1H), 7.30 (t, J=9.2 Hz, 1H), 6.06 (s, 2H), 4.32 (d, J=14.8 Hz, 1H), 3.80 (d, J=14.8 Hz, 1H), 1.76 (s, 3H).

Peak 2 (Example 42): MS (ESI+): m/z 511.05 (M+H), Rt: 1.189 min. [LCMS Method 7]; $^1$H NMR (400 MHz, $CD_3OD$) δ 8.10 (d, J=8.4 Hz, 1H), 8.03 (d, J=8.0 Hz, 1H), 7.52-7.49 (m, 1H), 7.41-7.36 (m, 1H), 7.30 (t, J=9.2 Hz, 1H), 6.06 (s, 2H), 4.32 (d, J=14.8 Hz, 1H), 3.80 (d, J=15.2 Hz, 1H), 1.76 (s, 3H).

Chiral HPLC retention times were obtained using the following conditions:

Instrument: Agilent 1260 Infinity II

Column: LUX CELLULOSE-4 (150×4.6 mm), 5 μm

Mobile phase: n-hexane (A); 0.1% HCOOH in EtOH: MeOH (80:20, B); Isocratic: 50 (A): 50 (B)

Flow rate: 1.0 mL/min.

Detection: UV @210 nm

Example 44: (R or S)-2-(3-fluoro-6-(2-(2-fluoro-5-(trifluoromethoxy)benzyl)-2H-tetrazol-5-yl)pyridin-2-yl)-2-hydroxypropane-1-sulfonamide and Example 45: (R or S)-2-(3-fluoro-6-(2-(2-fluoro-5-(trifluoromethoxy)benzyl)-2H-tetrazol-5-yl)pyridin-2-yl)-2-hydroxypropane-1-sulfonamide Prepared by analogy to Examples 40 and 41 according to Scheme 5 starting from 1-(6-bromo-3-fluoropyridin-2-yl) ethan-1-one and by replacing 1-(bromomethyl)-3-(trifluoromethyl)benzene with 2-(bromomethyl)-1-fluoro-4-(trifluoromethoxy)benzene to afford the racemate of the title compound (64 mg).

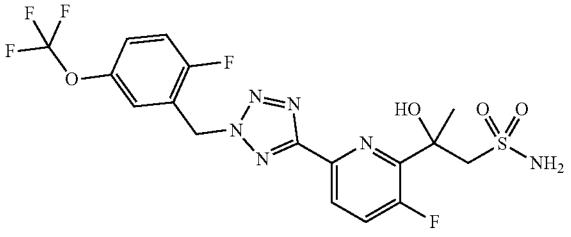 [SMILES: CC(O)(CS(N)(=O)=O)c1nc(-c2nnn(Cc3cc(OC(F)(F)F)ccc3F)n2)ccc1F]

Chiral separation of the racemate (64 mg) provided Example 45 as the first eluting peak (17 mg, 27% yield, chiral HPLC purity: 98.9%, Rt: 6.197 min.) and Example 44 as the second eluting peak (18 mg, 28% yield, chiral HPLC purity: 99.1%, Rt: 8.200 min.) as white solids.

Chiral Prep HPLC:

Instrument: Agilent 1260 Infinity

Column: LUX CELLULOSE-4 (21.2 mm×250 mm), 5 μm

Mobile phase: n-hexane (A); 0.1% HCOOH in EtOH: MeOH (1:1, B); Isocratic: 60(A):40(B)

Flow rate: 15 mL/min.

Detection: UV @210 nm

Peak 1 (Example 45): MS (ESI+): m/z 495.15 (M+H), Rt: 1.495 min. [LCMS Method 6]; $^1$H NMR (400 MHz, $CD_3OD$) δ 8.19 (dd, J=8.4, 3.2 Hz, 1H), 7.76 (dd, J=10.8, 8.8 Hz, 1H), 7.54-7.51 (m, 1H), 7.44-7.39 (m, 1H), 7.33 (t, J=9.2 Hz, 1H), 6.08 (s, 2H), 3.96 (d, J=14.8 Hz, 1H), 3.78 (d, J=14.8 Hz, 1H), 1.69 (s, 3H).

Peak 2 (Example 44): MS (ESI+): m/z 495.15 (M+H), Rt: 1.491 min. [LCMS Method 6]; $^1$H NMR (400 MHz, $CD_3OD$) δ 8.19 (dd, J=8.4, 3.2 Hz, 1H), 7.77 (dd, J=10.8, 8.8 Hz, 1H), 7.54-7.51 (m, 1H), 7.44-7.39 (m, 1H), 7.33 (t, J=9.2 Hz, 1H), 6.08 (s, 2H), 3.96 (d, J=14.8 Hz, 1H), 3.78 (d, J=14.4 Hz, 1H), 1.69 (d, J=1.2 Hz, 3H).

Chiral HPLC retention times were obtained using the following conditions:

Instrument: Agilent 1260 Infinity II
Column: LUX CELLULOSE-4 (150 mm×4.6 mm), 5 μm
Mobile phase: n-hexane (A); 0.1% HCOOH in EtOH: MeOH (8:2, B); Isocratic: 70(A):30(B)
Flow rate: 1.0 mL/min.
Detection: UV @210 nm Example 46: (R or S)-2-(6-(2-(5-cyclopropoxy-2-fluorobenzyl)-2H-tetrazol-5-yl)pyridin-2-yl)-2-hydroxypropane-1-sulfonamide and Example 47: (R or S)-2-(6-(2-(5-cyclopropoxy-2-fluorobenzyl)-2H-tetrazol-5-yl)pyridin-2-yl)-2-hydroxypropane-1-sulfonamide Prepared by analogy to Examples 40 and 41 according to Scheme 5 by replacing 1-(bromomethyl)-3-(trifluoromethyl)benzene with Intermediate 8 to afford the racemate of the title compound (340 mg).

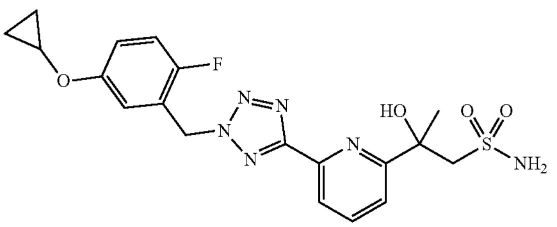 [SMILES: CC(O)(CS(N)(=O)=O)c1cccc(-c2nnn(Cc3cc(OC4CC4)ccc3F)n2)n1]

Chiral separation of the racemate (340 mg) provided Example 46 as the first eluting peak (125 mg, 37% yield, chiral HPLC purity: 99.6%, Rt: 8.821 min.) and Example 47 as the second eluting peak (125 mg, 37% yield, chiral HPLC purity: 99.5%, Rt: 10.685 min.) as white solids.

Chiral Prep HPLC:
Instrument: Agilent 1260 Infinity
Column: CHIRAL PAK IH (20.0 mm×250 mm), 5 μm
Mobile phase: n-hexane (A); EtOH: MeOH (1:1, B); Isocratic: 70(A):30(B)
Flow rate: 15 mL/min.
Detection: UV @210 nm Peak 1 (Example 46): MS (ESI+): m/z 448.95 (M+H), Rt: 1.484 min. [LCMS Method 6]; $^1$H NMR (400 MHz, $CD_3OD$) δ 8.04 (dd, J=7.6, 1.2 Hz, 1H), 7.95 (t, J=8.0 Hz, 1H), 7.83 (dd, J=8.0, 1.2 Hz, 1H), 7.14-7.08 (m, 3H), 5.99 (s, 2H), 4.04 (d, J=14.4 Hz, 1H), 3.77 (d, J=14.4 Hz, 1H), 3.76-3.75 (m, 1H), 1.70 (s, 3H), 0.78-0.75 (m, 2H), 0.67-0.66 (m, 2H).

Peak 2 (Example 47): MS (ESI+): m/z 449.1 (M+H), Rt: 1.477 min. [LCMS Method 6]; $^1$H NMR (400 MHz, $CD_3OD$) δ 8.04 (dd, J=7.6, 0.8 Hz, 1H), 7.95 (t, J=7.6 Hz, 1H), 7.83 (dd, J=8.0, 1.2 Hz, 1H), 7.14-7.08 (m, 3H), 5.99 (s, 2H), 4.04 (d, J=14.4 Hz, 1H), 3.77 (d, J=14.4 Hz, 1H), 3.76-3.74 (m, 1H), 1.70 (s, 3H), 0.78-0.75 (m, 2H), 0.67-0.66 (m, 2H).

Chiral HPLC retention times were obtained using the following conditions:

Instrument: Agilent 1260 Infinity II
Column: CHIRAL PAK-IH (150 mm×4.6 mm), 5 μm
Mobile phase: n-hexane (A); 0.1% TFA in EtOH: MeOH (80:20, B); Isocratic: 70(A):30(B)
Flow rate: 1.0 mL/min.
Detection: UV @210 nm Example 48: 2-(6-(2-(2-fluoro-5-(trifluoromethoxy)benzyl)-2H-tetrazol-5-yl)pyridin-2-yl)-2-hydroxyethane-1-sulfonamide Prepared according to Scheme 6.

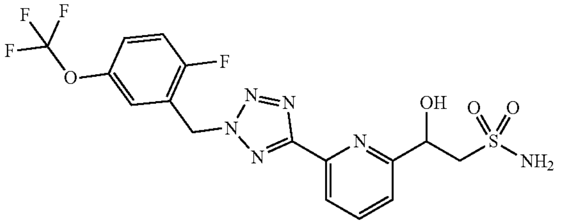 [SMILES: NS(=O)(=O)CC(O)c1cccc(-c2nnn(Cc3cc(OC(F)(F)F)ccc3F)n2)n1]

Step 1. 2-(6-bromopyridin-2-yl)-2-hydroxy-N,N-bis(4-methoxybenzyl)ethane-1-sulfonamide

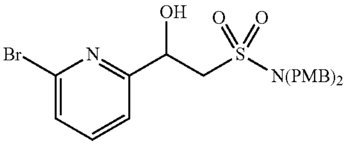

To a stirred solution of N,N-bis(4-methoxybenzyl)methanesulfonamide (905 mg, 2.7 mmol) in THF (22 mL) was added n-BuLi (1.6 M in hexanes, 1.86 mL, 2.97 mmol) at −78° C. After stirring at −78° C. for 10 min, a solution of 6-bromopicolinaldehyde (552 mg, 2.97 mmol) in THF (8 mL) was added dropwise. The mixture was then stirred at −78° C. for 30 min. before being allowed to stir and warm to room temperature for 12 h. The reaction mixture was quenched with water, concentrated under reduced pressure and the crude residue was purified with silica gel column chromatography (10-30% ethyl acetate in heptane) to afford the title compound (1.17 g, 83% yield).

ESI-MS m/z: 523.4 $[M+H]^+$ (Rt: 1.15 min., LCMS Method 2).

Step 2: 2-hydroxy-N,N-bis(4-methoxybenzyl)-2-(6-(1-(4-methoxybenzyl)-1H-tetrazol-5-yl)pyridin-2-yl)ethane-1-sulfonamide

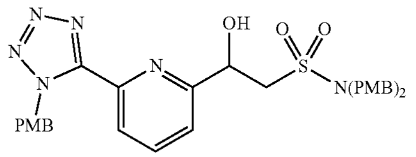

A mixture of 1-(4-methoxybenzyl)-1H-tetrazole (133 mg, 0.70 mmol), 2-(6-bromopyridin-2-yl)-2-hydroxy-N,N-bis (4-methoxybenzyl)ethane-1-sulfonamide (332 mg, 0.64 mmol), palladium(II) acetate (11.4 mg, 0.051 mmol), 2-dicyclohexylphosphino-2'-(N,N-dimethylamino)biphenyl (DavePhos, 40.1 mg, 0.10 mmol), Iodo[4, 5-bis(diphenylphosphino)-9,9-dimethylxanthene]copper(I) (157 mg, 0.20 mmol) and cesium carbonate (519 mg, 1.6 mmol) in acetonitrile (20 mL) was purged with $N_2$ gas twice. Then the mixture was stirred at 60° C. under $N_2$ protection for 23 h. The reaction mixture was filtered and the filter cake was rinsed with DCM/MeOH mixture and then with EtOAc. The combined filtrate was concentrated under reduced pressure and the resulting residue was purified with silica gel column chromatography (10-60% ethyl acetate in heptane) to afford the title compound (185 mg, 46% yield).

ESI-MS m/z: 631.2 $[M+H]^+$ (Rt: 1.13 min., LCMS Method 2).

Step 3: 2-(6-(1H-tetrazol-5-yl)pyridin-2-yl)-2-hydroxyethane-1-sulfonamide

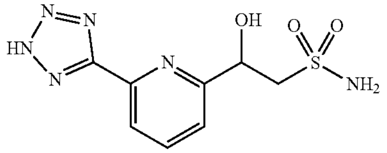 [SMILES: NS(=O)(=O)CC(O)c1cccc(-c2nn[nH]n2)n1]

To a solution of 2-hydroxy-N,N-bis(4-methoxybenzyl)-2-(6-(1-(4-methoxybenzyl)-1H-tetrazol-5-yl)pyridin-2-yl)ethane-1-sulfonamide (180 mg, 0.29 mmol) in DCM (7 mL) was added TFA (10 mL) and the mixture was stirred at 50° C. for 5 days. Volatiles were removed under reduced pressure and to the residue was added excess triethylamine. Then all volatiles were removed under reduced pressure again. The residue was purified with silica gel column chromatography (0-10% MeOH in DCM) to afford the title compound as a sticky solid (50 mg, 65% yield).

ESI-MS m/z: 271.0 $[M+H]^+$ (Rt: 0.19 min., LCMS Method 9).

Step 4: 2-(6-(2-(2-fluoro-5-(trifluoromethoxy)benzyl)-2H-tetrazol-5-yl)pyridin-2-yl)-2-hydroxyethane-1-sulfonamide

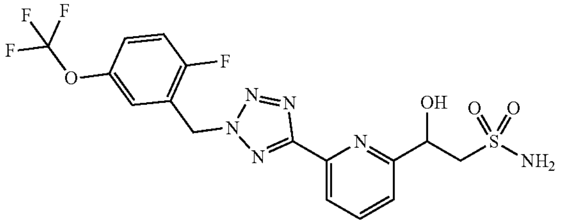 [SMILES: NS(=O)(=O)CC(O)c1cccc(-c2nnn(Cc3cc(OC(F)(F)F)ccc3F)n2)n1]

To a mixture of 2-(6-(1H-tetrazol-5-yl)pyridin-2-yl)-2-hydroxyethane-1-sulfonamide (50 mg, 0.19 mmol), sodium iodide (28 mg, 0.19 mmol) and potassium carbonate (33 mg, 0.24 mmol) in 2-butone (8 mL) was added 2-(bromomethyl)-1-fluoro-4-(trifluoromethoxy)benzene (51 mg, 0.19 mmol). The mixture was stirred at 65° C. under $N_2$ protection for 12 h. The reaction mixture was filtered, concentrated, and then purified with silica gel column chromatography (20-60% ethyl acetate in heptane) to afford two major products (regioisomers). The racemic title compound was isolated as the first eluting peak (25 mg, yield 28%).

ESI-MS m/z: 463.0 $[M+H]^+$ (Rt: 0.92 min., LCMS Method 2); $^1H$ NMR (400 MHz, DMSO-$d_6$) δ 8.05 (d, J=5.0 Hz, 2H), 7.79-7.66 (m, 2H), 7.55 (dt, J=7.8, 3.8 Hz, 1H), 7.47 (t, J=9.2 Hz, 1H), 6.81 (s, 2H), 6.16 (s, 2H), 6.03 (s, 1H), 5.18 (dd, J=8.8, 3.3 Hz, 1H), 3.65 (dd, J=14.1, 3.2 Hz, 1H), 3.33 (m, 1H); HRMS: M+H, found 463.0810, calc. 463.0812 (HRMS Method 10).

Example 49: (JR or 1S,2R or 2S)-1-(6-(2-(2-fluoro-5-(trifluoromethoxy)benzyl)-2H-tetrazol-5-yl)pyridin-2-yl)-1-hydroxypropane-2-sulfonamide and Example 50: (JR or 1S,2R or 2S)-1-(6-(2-(2-fluoro-5-(trifluoromethoxy)benzyl)-2H-tetrazol-5-yl)pyridin-2-yl)-1-hydroxypropane-2-sulfonamide and Example 51: (JR or 1S,2R or 2S)-1-(6-(2-(2-fluoro-5-(trifluoromethoxy)benzyl)-2H-tetrazol-5-yl)pyridin-2-yl)-1-hydroxypropane-2-sulfonamide and Example 52: (JR or 1S,2R or 2S)-1-(6-(2-(2-fluoro-5-(trifluoromethoxy)benzyl)-2H-tetrazol-5-yl)pyridin-2-yl)-1-hydroxypropane-2-sulfonamide Prepared according to Scheme 6.

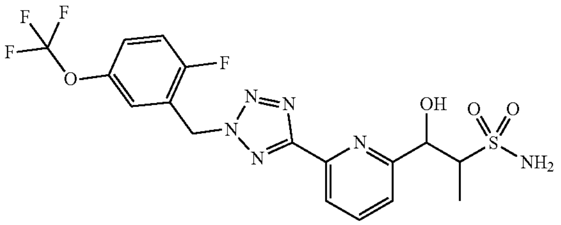 [SMILES: CC(C(O)c1cccc(-c2nnn(Cc3cc(OC(F)(F)F)ccc3F)n2)n1)S(N)(=O)=O]

Step 1: two enantiomer pairs of 1-(6-bromopyridin-2-yl)-1-hydroxy-N,N-bis(4-methoxybenzyl)propane-2-sulfonamide

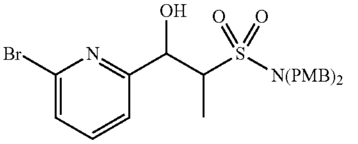

To a stirred solution of N,N-bis(4-methoxybenzyl)ethanesulfonamide (1.03 g, 2.94 mmol) in 2-methyl-THF (30 mL) cooled in dry ice/acetone bath was added n-BuLi (1.6 M in hexanes, 2.2 mL, 3.5 mmol) and the mixture was stirred at −78° C. for 10 min., then at room temperature for 30 min. The reaction mixture was cooled in dry ice/acetone bath again and a solution of 6-bromopicolinaldehyde (685 mg, 3.7 mmol) in 2-methyl-THF (5 mL) was added. The mixture was stirred at −78° C. for 1 h. After the temperature was raised to room temperature, to the reaction mixture was added a saturated aqueous $NH_4Cl$ solution followed by extraction with EtOAc (3×). All EtOAc layers were combined, dried over anhydrous $Na_2SO_4$, filtered, concentrated under reduced pressure and the residue was purified with silica gel column chromatography (10-20% ethyl acetate in heptane) to afford two products fractions (two enantiomer pairs):

Enantiomer pair A: the first peak eluted from the silica gel column, 472 mg, 30% yield. It was used directly in Step 2a without further purification.

Enantiomer pair B: the second product peak eluted from the silica gel column: 433 mg, 28% yield. It was used directly in Step 2b without further purification.

Step 2a: Enantiomer pair A of 1-hydroxy-N,N-bis(4-methoxybenzyl)-1-(6-(1-(4-methoxybenzyl)-1H-tetrazol-5-yl)pyridin-2-yl)propane-2-sulfonamide

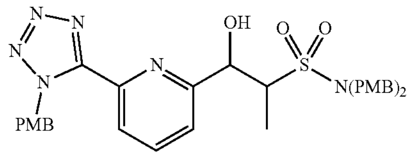

A mixture of 1-(6-bromopyridin-2-yl)-1-hydroxy-N,N-bis(4-methoxybenzyl)propane-2-sulfonamide (enantiomers pair A from last step, 472 mg, 0.88 mmol), 1-(4-methoxybenzyl)-1H-tetrazole (201 mg, 1.1 mmol), palladium(II) acetate (16 mg, 0.071 mmol), 2-dicyclohexylphosphino-2'-(N,N-dimethylamino)biphenyl (DavePhos, 56 mg, 0.14 mmol), Iodo[4, 5-bis(diphenylphosphino)-9,9-dimethylxanthene]copper(I) (217 mg, 0.28 mmol) and cesium carbonate (718 mg, 2.2 mmol) in acetonitrile (20 mL) were purge with $N_2$ gas two times. The mixture was stirred at 60° C. under $N_2$ gas protection for 23 h. The reaction mixture was filtered and the filter cake was rinsed with DCM/MeOH and then with EtOAc. The combined filtrate was concentrated under reduced pressure and the residue was purified with silica gel column chromatography (10-60% ethyl acetate in heptane) to afford crude enantiomer pair A of the title compound (212 mg, 37% yield).

ESI-MS m/z: $[M+H]^+$ 645.2 (Rt: 1.17 min., LCMS Method 2).

Step 3a: Enantiomer pair A of 1-hydroxy-1-(6-(1-(4-methoxybenzyl)-1H-tetrazol-5-yl)pyridin-2-yl)propane-2-sulfonamide

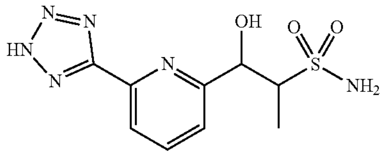 [SMILES: CC(C(O)c1cccc(-c2nn[nH]n2)n1)S(N)(=O)=O]

To a solution of 1-hydroxy-N,N-bis(4-methoxybenzyl)-1-(6-(1-(4-methoxybenzyl)-1H-tetrazol-5-yl)pyridin-2-yl)propane-2-sulfonamide (enantiomers pair A from Step 2a, 210 mg, 0.326 mmol) in DCM (2 mL) was added TFA (8 mL) and the mixture was stirred at room temperature for 12 h, then at 60° C. for 24 h. Volatiles were removed under reduced pressure and to the residue was added excess triethylamine. Volatiles were removed under reduced pressure again. The residue was purified with silica gel column chromatography (5-10% MeOH in DCM) to afford the crude enantiomer pair A of the title compound as a sticky oil which was used directly in the next step. ESI-MS m/z: $[M+H]^+$ 285.0 (Rt: 0.50 min., Method 1).

Step 4a: Enantiomer pair A of 1-(6-(2-(2-fluoro-5-(trifluoromethoxy)benzyl)-2H-tetrazol-5-yl)pyridin-2-yl)-1-hydroxypropane-2-sulfonamide

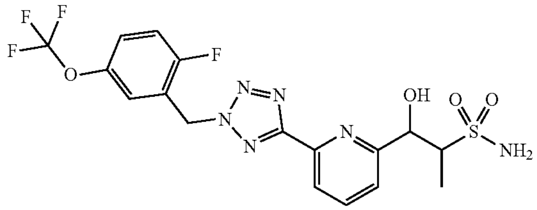 [SMILES: CC(C(O)c1cccc(-c2nnn(Cc3cc(OC(F)(F)F)ccc3F)n2)n1)S(N)(=O)=O]

To a mixture of crude 1-(6-(1H-tetrazol-5-yl)pyridin-2-yl)-1-hydroxypropane-2-sulfonamide (enantiomer pair A from Step 3a), sodium iodide (54 mg, 0.36 mmol) and potassium carbonate (68 mg, 0.49 mmol) in 2-butanone (10 mL) was added 2-(bromomethyl)-1-fluoro-4-(trifluoromethoxy)benzene (107 mg, 0.39 mmol) and the mixture was stirred at 60° C. for 12 h. The reaction mixture was filtered and the filtrate was concentrated under reduced pressure. The resulting residue was purified with silica gel column chromatography (10-40% ethyl acetate in heptane) three times to afford the title compound (the desired regioisomer eluted as the first major product peak, 32 mg, 21% total yield over steps 3a and 4a). ESI-MS m/z: $[M+H]^+$ 476.9 (Rt: 0.94 min., LCMS Method 2).

Chiral separation of the product from Step 4a provided Example 51 as the first eluting peak (11 mg, 33% yield) and Example 52 as the second eluting peak (11 mg, 33% yield).

Chiral Prep HPLC:

Instrument: Waters SFC MS100 system

Column: Chiralpak IE (21×250 mm, 5 μm)

Mobile phase: 25-45% methanol/$CO_2$

Flow rate: 80 g/min.

Detection: UV @274 nm

Peak 1 (Example 51): ESI-MS m/z: $[M+H]^+$ 477.3 (Rt: 0.92 min., LCMS Method 2); $^1$H NMR (400 MHz, DMSO-$d_6$) δ 8.10-7.99 (m, 2H), 7.70 (ddd, J=13.4, 6.5, 2.4 Hz, 2H), 7.55 (dt, J=7.6, 3.7 Hz, 1H), 7.47 (t, J=9.2 Hz, 1H), 6.71 (s, 2H), 6.15 (d, J=1.9 Hz, 2H), 5.86 (d, J=5.4 Hz, 1H), 5.39 (dd, J=5.5, 2.1 Hz, 1H), 3.65-3.52 (m, 1H), 1.07 (d, J=7.1 Hz, 3H); HRMS: M+H, found 477.0972, calc. 477.0968 (HRMS Method 10); e.e. >99%.

Peak 2 (Example 52): ESI-MS m/z: $[M+H]^+$ 476.9 (Rt: 0.95 min., LCMS Method 2); $^1$H NMR (400 MHz, DMSO-$d_6$) δ 8.10-7.99 (m, 2H), 7.70 (ddd, J=13.4, 6.6, 2.4 Hz, 2H), 7.55 (dt, J=7.7, 3.8 Hz, 1H), 7.47 (t, J=9.1 Hz, 1H), 6.71 (s, 2H), 6.15 (d, J=1.9 Hz, 2H), 5.86 (s, 1H), 5.39 (d, J=2.1 Hz, 1H), 3.58 (qd, J=6.9, 2.0 Hz, 1H), 1.07 (d, J=7.0 Hz, 3H); HRMS: M+H, found 477.0959, calc. 477.0968 (HRMS Method 10); e.e. =98.7%.

Enantiomeric excess was determined using the following conditions:

Instrument: Waters UPC$^2$ system

Column: Chiralpak IE-3 (3 μm, 3×100 mm)

Mobile phase: MeOH (modifier)/$CO_2$.; Gradient: 5% modifier for 0.2 minutes, increase to 55% modifier over 3.0 minutes, and hold at 55% modifier for 0.4 minutes Flow rate: 2.5 mL/min.
Detection: PDA detector (210-400 nm)

Step 2b: 1-hydroxy-N,N-bis(4-methoxybenzyl)-1-(6-(1-(4-methoxybenzyl)-1H-tetrazol-5-yl)pyridin-2-yl)propane-2-sulfonamide

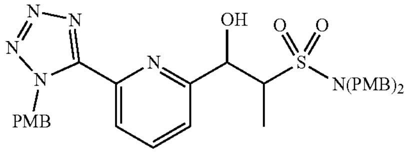

The same procedure in Step 2a was applied to the enantiomer pair B obtained in step 1 and provided enantiomer pair B of the title compound. Yield 42%.

ESI-MS m/z: $[M+H]^+$ 645.2 (Rt: 1.16 min., LCMS Method 2).

Step 3b: 1-(6-(1H-tetrazol-5-yl)pyridin-2-yl)-1-hydroxypropane-2-sulfonamide

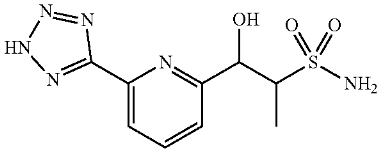 [SMILES: CC(C(O)c1cccc(-c2nn[nH]n2)n1)S(N)(=O)=O]

The enantiomer pair B obtained in Step 2b was subjected to the same procedure in step 3a to provide enantiomer pair B of the title compound. Crude product was used directly in the next step without further purification.

ESI-MS m/z: $[M+H]^+$ 285.0 (Rt: 0.26 min., LCMS Method 9).

Step 4b: 1-(6-(2-(2-fluoro-5-(trifluoromethoxy)benzyl)-2H-tetrazol-5-yl)pyridin-2-yl)-1-hydroxypropane-2-sulfonamide

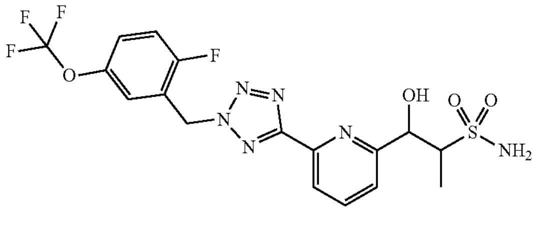 [SMILES: CC(C(O)c1cccc(-c2nnn(Cc3cc(OC(F)(F)F)ccc3F)n2)n1)S(N)(=O)=O]

The enantiomer pair B obtained in step 3b was subjected to the same procedures as in step 4a to provide the enantiomer pair B of the title compound. Total yield of 24% over steps 3b and 4b.

ESI-MS m/z: $[M+H]^+$ 477.2 (Rt: 0.94 min., LCMS Method 2).

Chiral separation of the product from Step 4b (43 mg) provided Example 50 as the first eluting peak (6 mg, 14% yield) and Example 49 as the second eluting peak (5.5 mg, 13% yield).

Chiral Prep HPLC:
Instrument: Waters SFC MS100 system;
Column: Chiralpak AD-H (21×250 mm, 5 μm);
Mobile phase: 15-35% MeOH:IPA (1:1)/$CO_2$,
Flow rate: 80 g/min.
Detection: UV @274 nm Peak 1 (Example 50): ESI-MS m/z: $[M+H]^+$ 477.1 (Rt: 0.96 min., LCMS Method 2); $^1$H NMR (400 MHz, DMSO-$d_6$) δ 8.11-7.99 (m, 2H), 7.73-7.62 (m, 2H), 7.55 (dt, J=7.7, 3.8 Hz, 1H), 7.47 (t, J=9.2 Hz, 1H), 6.61 (s, 2H), 6.15 (s, 3H), 5.00 (d, J=6.0 Hz, 1H), 3.54 (p, J=7.0 Hz, 1H), 1.08 (d, J=7.1 Hz, 3H); e.e. >99%.

Peak 2 (Example 49): ESI-MS m/z: $[M+H]^+$ 477.1 (Rt: 0.95 min., LCMS Method 2); $^1$H NMR (400 MHz, DMSO-$d_6$) δ 8.13-7.96 (m, 2H), 7.74-7.63 (m, 2H), 7.55 (dt, J=7.6, 3.8 Hz, 1H), 7.47 (t, J=9.2 Hz, 1H), 6.63 (s, 2H), 6.14 (d, J=15.1 Hz, 3H), 5.00 (d, J=6.2 Hz, 1H), 3.55 (p, J=6.9 Hz, 1H), 1.08 (d, J=7.2 Hz, 3H); HRMS: M+H, found 477.0977, calc. 477.0968 (HRMS Method 10); e.e. =98.4%.

Enantiomeric excess was determined using the following conditions:
Instrument: Waters UPC$^2$ system
Column: Chiralpak AD-3 (3 μm, 3×100 mm)
Mobile phase: MeOH:IPA (1:1) with 0.1% ammonium hydroxide (modifier)/$CO_2$;
Gradient: 5% modifier for 0.2 minutes, increase to 55% modifier over 3.0
minutes, and hold at 55% modifier for 0.4 minutes
Flow rate: 2.5 g/min.
Detection: PDA detector (210-400 nm)

Example 53: 1-(6-(1-(2-fluoro-5-(trifluoromethoxy)benzyl)-1H-pyrazol-3-yl)pyridin-2-yl)-1-hydroxy-2-methylpropane-2-sulfonamide Prepared according to Scheme 7.

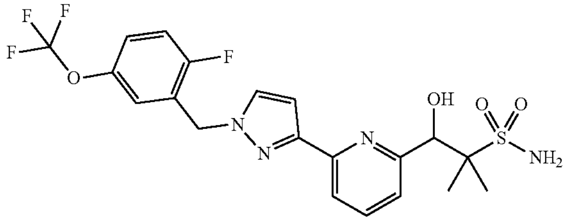 [SMILES: CC(C)(C(O)c1cccc(-c2ccn(Cc3cc(OC(F)(F)F)ccc3F)n2)n1)S(N)(=O)=O]

Step 1: 2-(6-bromopyridin-2-yl)-N,N-bis(4-methoxybenzyl)-2-oxoethane-1-sulfonamide

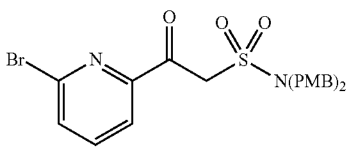

To a solution of 2-(6-bromopyridin-2-yl)-2-hydroxy-N,N-bis(4-methoxybenzyl)ethane-1-sulfonamide (2.20 g, 4.22 mmol) in DCM (100 mL) was added 1,1,1-Tris(acetyloxy)-1,1-dihydro-1,2-benziodoxol-3-(1H)-one (Dess-Martin reagent, 3.58 g, 8.44 mmol) and the mixture was stirred at room temperature for 4 h. Then the reaction mixture was quenched with saturated aqueous $NaHCO_3$ solution and extracted with DCM (3×). The DCM layers were combined, concentrated under reduced pressure and the residue was purified with silica gel column chromatography (10-30% ethyl acetate in heptane) to afford the title compound as a sticky solid (2.01 g, 92% yield).

ESI-MS m/z: 519.0 [M−H]—(Rt: 1.18 min., LCMS Method 2).

$^1$H NMR (400 MHz, Chloroform-d) δ 8.03 (dd, J=6.5, 1.9 Hz, 1H), 7.77-7.71 (m, 2H), 7.31-7.26 (m, 4H), 6.92-6.85 (m, 4H), 4.79 (s, 2H), 4.40 (s, 4H), 3.82 (s, 6H).

Step 2: 1-(6-bromopyridin-2-yl)-N,N-bis(4-methoxybenzyl)-2-methyl-1-oxopropane-2-sulfonamide

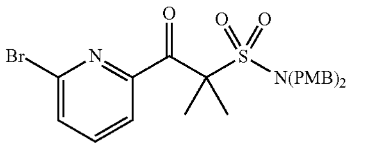

To a mixture of 2-(6-bromopyridin-2-yl)-N,N-bis(4-methoxybenzyl)-2-oxoethane-1-sulfonamide (505 mg, 0.97 mmol) and potassium carbonate (296 mg, 2.1 mmol) in DMF (12 mL) was added iodomethane (414 mg, 2.9 mmol). The mixture was stirred at room temperature for 14 h. Then another batch of potassium carbonate (50 mg, 0.83 mmol) was added. The mixture was stirred at 45° C. for 12 h, then at 60° C. for 5 h. The solid was filtered out and volatiles in filtrate were removed under high vacuum. The residue was purified with silica gel column chromatography (10-20% ethyl acetate in heptane) to afford the title compound (260 mg, 49% yield).

$^1$H NMR (400 MHz, Chloroform-d) δ 7.94-7.87 (m, 1H), 7.76-7.63 (m, 2H), 7.13-7.03 (m, 4H), 6.81-6.75 (m, 4H), 4.40 (s, 4H), 3.80 (s, 6H), 2.07 (s, 6H).

Step 3: 1-(6-(1-(2-fluoro-5-(trifluoromethoxy)benzyl)-1H-pyrazol-3-yl)pyridin-2-yl)-N,N-bis(4-methoxybenzyl)-2-methyl-1-oxopropane-2-sulfonamide

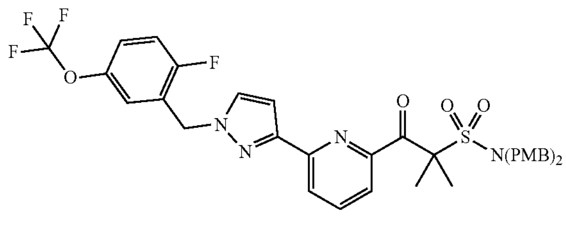

A mixture of 1-(6-bromopyridin-2-yl)-N,N-bis(4-methoxybenzyl)-2-methyl-1-oxopropane-2-sulfonamide (100 mg, 0.18 mmol), 1-(2-fluoro-5-(trifluoromethoxy)benzyl)-3-(4,4,5,5-tetramethyl-1,3,2-dioxaborolan-2-yl)-1H-pyrazole (85 mg, 0.22 mmol), chloro(2-dicyclohexylphosphino-2',4',6'-triisopropyl-1,1'-biphenyl)[2-(2'-amino-1,1'-biphenyl)]palladium(II) (Xphos-Pd-G2, 21 mg, 0.027 mmol) and potassium carbonate (76 mg, 0.55 mmol) in 1,4-dioxane/water (3 mL/0.5 mL) was heated with microwave at 110° C. for 12 min. The reaction mixture was purified directly with silica gel column chromatography (10-20% ethyl acetate in heptane) to afford the title compound as a sticky solid (96 mg, 72% yield).

ESI-MS m/z: 727.2 [M+H]$^+$ (Rt: 1.41 min., LCMS Method 2).

Step 4: 1-(6-(1-(2-fluoro-5-(trifluoromethoxy)benzyl)-1H-pyrazol-3-yl)pyridin-2-yl)-1-hydroxy-N,N-bis(4-methoxybenzyl)-2-methylpropane-2-sulfonamide

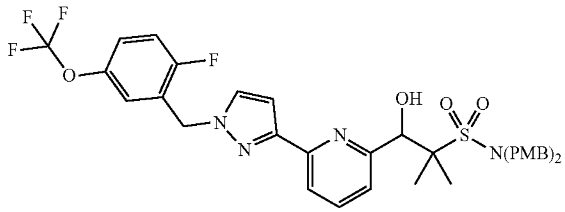

To a solution of 1-(6-(1-(2-fluoro-5-(trifluoromethoxy)benzyl)-1H-pyrazol-3-yl)pyridin-2-yl)-N,N-bis(4-methoxybenzyl)-2-methyl-1-oxopropane-2-sulfonamide (45 mg, 0.062 mmol) in MeOH (1 mL) and triethylamine (2 mL) was added $NaBH_4$ (23 mg, 0.62 mmol) and the mixture was stirred at room temperature for 20 min. Excess water was then added to quench the reaction mixture. Volatiles were removed under reduced pressure and the residue was used directly in the next step.

ESI-MS m/z: 729.3 [M+H]$^+$ (Rt: 1.41 min., LCMS Method 2).

Step 5: 1-(6-(1-(2-fluoro-5-(trifluoromethoxy)benzyl)-1H-pyrazol-3-yl)pyridin-2-yl)-1-hydroxy-2-methylpropane-2-sulfonamide

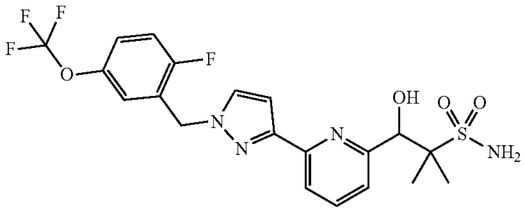 [SMILES: CC(C)(C(O)c1cccc(-c2ccn(Cc3cc(OC(F)(F)F)ccc3F)n2)n1)S(N)(=O)=O]

To a solution of 1-(6-(1-(2-fluoro-5-(trifluoromethoxy)benzyl)-1H-pyrazol-3-yl)pyridin-2-yl)-1-hydroxy-N,N-bis(4-methoxybenzyl)-2-methylpropane-2-sulfonamide from previous step in DCM (3 mL) was added TFA (2 mL) and the mixture was stirred at room temperature for 12 h. All volatiles were removed under reduced pressure and to the residue was added excess triethylamine. Volatiles were removed under reduced pressure again and the residue was purified with preparative HPLC to afford the racemic title compound as a white solid (13 mg, 43% total yield calculated over steps 4 and 5).

Conditions for Preparative HPLC:

Instrument: Waters AutoPurification System (equipped with 2545/515 pumps and 2998 detector)

Column: Waters Xbridge BEH C18, 5 μm, 30×50 mm

Mobile Phase: water (375 mM ammonium hydroxide)/acetonitrile (375 mM ammonium hydroxide) with a gradient of 75/25 held for 1 min., ramp to 50/50 over 3.2 min., then ramp to 5/95 over 0.5 min. followed by hold at 5/95 for 1.3 min.

Flow rate: 75 mL/min.

Detection: UV 210-400 nm

ESI-MS m/z: 488.9 $[M+H]^+$ (Rt: 1.03 min., LCMS Method 2); $^1H$ NMR (400 MHz, DMSO-$d_6$) δ 7.96 (d, J=2.4 Hz, 1H), 7.83 (t, J=7.6 Hz, 1H), 7.77 (d, J=7.6 Hz, 1H), 7.42 (t, J=7.8 Hz, 3H), 7.32-7.25 (m, 1H), 6.86 (d, J=2.4 Hz, 1H), 6.49 (s, 2H), 5.93 (s, 1H), 5.52 (s, 2H), 5.03 (s, 1H), 1.28 (s, 3H), 1.11 (s, 3H); HRMS: M+H, found 489.1212, calc. 489.1220 (HRMS Method 10).

Example 54: 3-(6-(1-(2-fluoro-5-(trifluoromethoxy)benzyl)-1H-pyrazol-3-yl)pyridin-2-yl)-3-hydroxy-2-methylbutane-2-sulfonamide Prepared according to Scheme 7.

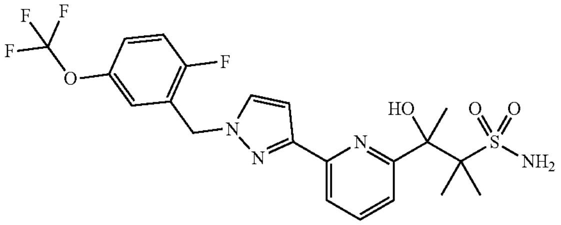 [SMILES: CC(O)(c1cccc(-c2ccn(Cc3cc(OC(F)(F)F)ccc3F)n2)n1)C(C)(C)S(N)(=O)=O]

Step 1: 3-(6-(1-(2-fluoro-5-(trifluoromethoxy)benzyl)-1H-pyrazol-3-yl)pyridin-2-yl)-3-hydroxy-N,N-bis(4-methoxybenzyl)-2-methylbutane-2-sulfonamide

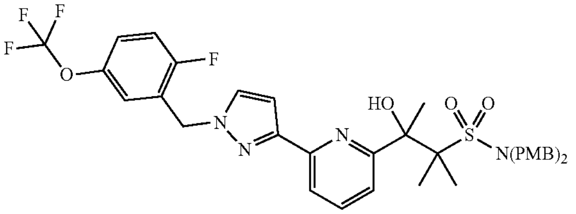

To a mixture of 1-(6-(1-(2-fluoro-5-(trifluoromethoxy)benzyl)-1H-pyrazol-3-yl)pyridin-2-yl)-N,N-bis(4-methoxybenzyl)-2-methyl-1-oxopropane-2-sulfonamide (45 mg, 0.062 mmol) in triethylamine (2 mL), from Example 53 Step 3, was added methyl magnesium bromide (3.4 M in 2-methyl-THF, 73 μL, 0.25 mmol) and the mixture was stirred at room temperature for 10 min. Water was added to quench the reaction. Volatiles were removed under reduced pressure and the residue was purified with silica gel column chromatography (10-30% ethyl acetate in heptane) to afford the title compound (25 mg, 54% yield).

ESI-MS m/z: 743.2 $[M+H]^+$ (Rt: 1.42 min., LCMS Method 2).

Step 2: 3-(6-(1-(2-fluoro-5-(trifluoromethoxy)benzyl)-1H-pyrazol-3-yl)pyridin-2-yl)-3-hydroxy-2-methylbutane-2-sulfonamide

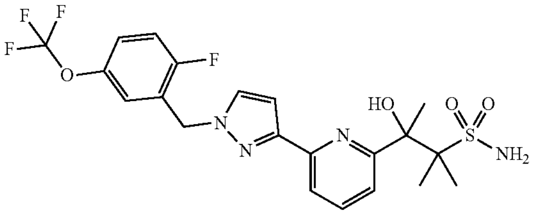 [SMILES: CC(O)(c1cccc(-c2ccn(Cc3cc(OC(F)(F)F)ccc3F)n2)n1)C(C)(C)S(N)(=O)=O]

To a solution of 3-(6-(1-(2-fluoro-5-(trifluoromethoxy)benzyl)-1H-pyrazol-3-yl)pyridin-2-yl)-3-hydroxy-N,N-bis(4-methoxybenzyl)-2-methylbutane-2-sulfonamide (25 mg, 0.034 mmol) in DCM (2 mL) was added TFA (3 mL) and the mixture was stirred at room temperature for 2 days. Volatiles were removed under reduced pressure and to the residue was added excess triethylamine. Volatiles were removed under reduced pressure again and the residue was purified with preparative HPLC to afford the racemic title compound (5 mg, 28% yield).

Conditions for Preparative HPLC:

Instrument: Waters AutoPurification System (equipped with 2545/515 pumps and 2998 detector)

Column: Waters Xbridge BEH C18, 5 μm, 30×50 mm

Mobile Phase: water (375 mM ammonium hydroxide)/acetonitrile (375 mM ammonium hydroxide) with a gradient of 65/35 held for 1 min., ramp to 40/60 over 3.2 min., then ramp to 5/95 over 0.5 min. followed by hold at 5/95 for 1.3 min.

Flow rate: 75 mL/min.

Detection: UV 210-400 nm

ESI-MS m/z: 503.1 $[M+H]^+$ (Rt: 1.07 min., LCMS Method 2); $^1H$ NMR (400 MHz, DMSO-$d_6$) δ 7.96 (d, J=2.4 Hz, 1H), 7.81 (t, J=7.8 Hz, 1H), 7.73 (d, J=7.5 Hz, 1H), 7.61 (d, J=7.8 Hz, 1H), 7.47-7.39 (m, 2H), 7.35-7.28 (m, 1H), 6.88 (d, J=2.4 Hz, 1H), 6.52 (bs, 2H), 5.80 (bs, 1H), 5.52 (s, 2H), 1.79 (s, 3H), 1.48 (s, 3H), 1.13 (s, 3H); HRMS: M+H, found 503.1375, calc. 503.1376 (HRMS Method 10).

Example 55: (R or S)-2-(6-(1-(2-fluoro-5-(trifluoromethoxy)benzyl)-1H-1,2,4-triazol-3-yl)pyridin-2-yl)-2-hydroxypropane-1-sulfonamide and Example 56: (R or S)-2-(6-(1-(2-fluoro-5-(trifluoromethoxy)benzyl)-1H-1,2,4-triazol-3-yl)pyridin-2-yl)-2-hydroxypropane-1-sulfonamide Prepared according to Scheme 8.

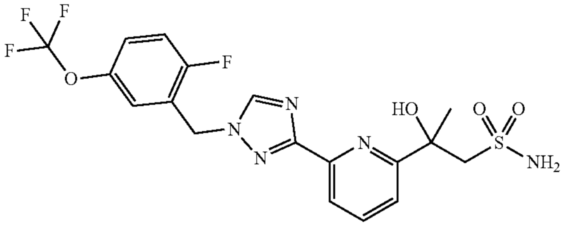 [SMILES: CC(O)(CS(N)(=O)=O)c1cccc(-c2ncn(Cc3cc(OC(F)(F)F)ccc3F)n2)n1]

Step 1: 6-cyanopicolinimidohydrazide

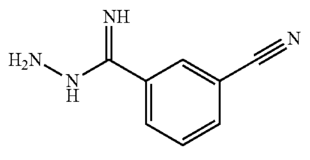 [SMILES: N#Cc1cccc(C(=N)NN)c1]

A mixture of pyridine-2,6-dicarbonitrile (50 g, 39 mmol) and hydrazine hydrate (30.8 mL, 41 mmol) in 1550 mL of EtOH was stirred at room temperature overnight. The next day the white precipitate was filtered off and dried under vacuum to afford the desired product (59.7 g, 370 mmol, 96% yield) as a white solid which was used for the next step without further purification. ESI-MS m/z: 162.1 $[M+H]^+$ (Rt: 0.16 min., LCMS Method 1)$^1$H NMR (400 MHz, DMSO-$d_6$) δ 8.18 (dd, J=7.2, 2.1 Hz, 1H), 8.01-7.88 (m, 2H), 5.76 (s, 2H), 5.63 (s, 2H).

Step 2: 6-(1H-1,2,4-triazol-3-yl)picolinonitrile

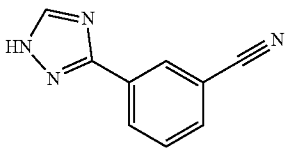 [SMILES: N#Cc1cccc(-c2nc[nH]n2)c1]

This reaction was carried out in 2 reaction batches. In one batch a solution of 6-cyanopicolinimidohydrazide (15.4 g, 95 mmol) in formic acid (132 g, 2860 mmol) was heated to 110° C. for 2.5 h. In another batch a solution of 6-cyanopicolinimidohydrazide (9.81 g, 60.9 mmol) in formic acid (84 g, 1830 mmol) was heated to 110° C. for 2.5 h. Both batches were removed from heat, cooled to room temperature, then concentrated under reduced pressure and combined. The resulting gray solid was triturated with a 5% heptane solution in EtOAc. The solids were collected by vacuum filtration and the resulting filter cake was rinsed with EtOAc and dried under vacuum to afford the title product as a formate salt (24.2 g, 106 mmol, 68% yield).

Step 3: 6-(1-(2-fluoro-5-(trifluoromethoxy)benzyl)-1H-1,2,4-triazol-3-yl)picolinonitrile

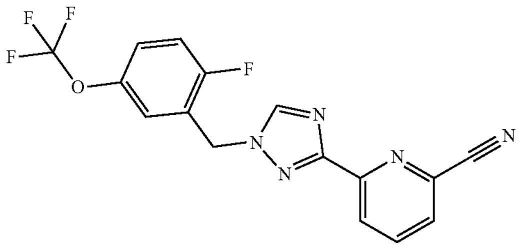 [SMILES: N#Cc1cccc(-c2ncn(Cc3cc(OC(F)(F)F)ccc3F)n2)n1]

To a solution of the 6-(1H-1,2,4-triazol-3-yl)picolinonitrile (4 g, 18.4 mmol) in 92 mL of THF, DBU (8.41 g, 55.3 mmol) and 2-(bromomethyl)-1-fluoro-4-(trifluoromethoxy)benzene (6.03 g, 22.1 mmol) were added. The resulting mixture was stirred at room temperature for 3 hours. The solids were filtered out and the resulting mixture was concentrated under vacuum. Water was added and the aqueous mixture was extracted with EtOAc three times. The organic layers were combined, washed with brine, dried over sodium sulfate, filtered and concentrated. The crude was purified by chromatography on silica eluting with 0-100% ethyl acetate in heptane to afford N2-regioisomer (3.5 g, 9.63 mmol, 52% yield) and N1-regioisomer (1.66 g, 4.57 mmol, 25% yield).

N2-regioisomer: ESI-MS m/z: 364.1 $[M+H]^+$ (Rt: 1.02 min., LCMS Method 1). $^1$H NMR (400 MHz, DMSO-$d_6$) δ 8.89 (s, 1H), 8.31 (d, J=8.2 Hz, 1H), 8.17 (t, J=8.0 Hz, 1H), 8.08 (d, J=7.9 Hz, 1H), 7.56-7.39 (m, 3H), 5.64 (s, 2H).

N1-regioisomer: ESI-MS m/z: 364.1 $[M+H]^+$ (Rt: 1.1 min., LCMS Method 1). $^1$H NMR (400 MHz, DMSO-$d_6$) δ 8.49-8.38 (m, 1H), 8.30-8.12 (m, 3H), 7.42-7.29 (m, 2H), 7.22-7.16 (m, 1H), 6.03 (s, 2H).

Step 4. 1-(6-(1-(2-fluoro-5-(trifluoromethoxy)benzyl)-1H-1,2,4-triazol-3-yl)pyridin-2-yl)ethan-1-one

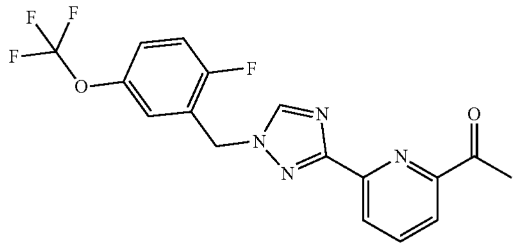 [SMILES: CC(=O)c1cccc(-c2ncn(Cc3cc(OC(F)(F)F)ccc3F)n2)n1]

6-(1-(2-fluoro-5-(trifluoromethoxy)benzyl)-1H-1,2,4-triazol-3-yl)picolinonitrile (597 mg, 1.6 mmol) was taken up in THF (8 mL) under nitrogen and it was cooled to 0° C. A dropping funnel was charged with methyl magnesium bromide (3.4 M in THF) (1.5 mL, 5.1 mmol) and it was added dropwise at this temperature. The mixture was allowed to come to room temperature. Then the dropping funnel was swapped for a reflux condenser. The mixture was lowered onto a heating block set to 70° C., then allowed to stir for one hour. The mixture was removed from heat. LCMS showed conversion to desired product. The mixture was cooled to 0° C. The reflux condenser was removed, and a vent bubbler was attached as a precaution. A 6N aqueous HCl solution was added in portions. Some effervescence was observed. The mixture was allowed to come to room temperature overnight. The mixture was partitioned between EtOAc/water in a separatory funnel. The layers were separated. The aqueous layer was extracted with EtOAc twice. The aqueous layer remained highly colored after extraction. LCMS indicated remaining product, likely as the aqueous layer was acidic and the product was protonated. The pH of the aqueous layer was adjusted to pH 12 using 1M NaOH. The now basic aqueous layer was extracted with EtOAc two times after which no color remained. The combined set of organic layers were dried over anhydrous magnesium sulfate, filtered then concentrated under reduced pressure. The crude product was purified with silica gel column chromatography (30%-70% ethyl acetate in heptane) to provide the title compound (209 mg, 33% yield).

ESI-MS m/z: 381.2 $[M+H]^+$ (Rt: 1.02 min., LCMS Method 1). $^1$H NMR (400 MHz, DMSO-$d_6$) d 8.85 (s, 1H), 8.27-8.23 (m, 1H), 8.09 (t, J=7.8 Hz, 1H), 7.97 (dd, J=7.8, 1.4 Hz, 1H), 7.54-7.40 (m, 3H), 5.66 (s, 2H), 2.67 (s, 3H).

Step 5: 2-(6-(1-(2-fluoro-5-(trifluoromethoxy)benzyl)-1H-1,2,4-triazol-3-yl)pyridin-2-yl)-2-hydroxy-N,N-bis(4-methoxybenzyl)propane-1-sulfonamide

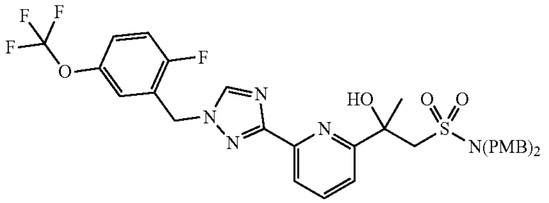

To a suspension of N,N-bis(4-methoxybenzyl)methanesulfonamide (980 mg, 2.9 mmol) in tetrahydrofuran (15 mL) cooled to −78° C. was added n-BuLi (1.6 M in hexanes, 2 mL, 3.2 mmol) drop-wise. The mixture was stirred at −78° C. for 30 min., to which was added a solution of 1-(6-(1-(2-fluoro-5-(trifluoromethoxy)benzyl)-1H-1,2,4-triazol-3-yl)pyridin-2-yl)ethan-1-one (549 mg, 1.4 mmol) in tetrahydrofuran (5 mL, then wash with 2×5 mL) via dropping funnel. The reaction mixture was allowed to stir and warm to room temperature and was then stirred for 15 h. The reaction mixture was quenched by addition of saturate aqueous ammonium chloride solution, partitioned with DCM and transferred to a separatory funnel. The pH was adjusted to pH-2 using 1N HCl and the aqueous layer was extracted 2× with DCM. The combined organic layers were dried over MgSO4, filtered and concentrated by rotary evaporation under reduced pressure to afford crude product. The crude material was purified by silica gel column chromatography (30%-100% ethyl acetate in heptane) to afford the title compound as a colorless oil (163 mg, 11% yield). Recovered starting material was resubjected to the reaction conditions to obtain an additional 70 mg of title product for a total yield of 233 mg (23% yield).

ESI-MS m/z: 716.2 $[M+H]^+$ (Rt: 1.23 min., LCMS Method 1).

Step 6: 2-(6-(1-(2-fluoro-5-(trifluoromethoxy)benzyl)-1H-1,2,4-triazol-3-yl)pyridin-2-yl)-2-hydroxypropane-1-sulfonamide

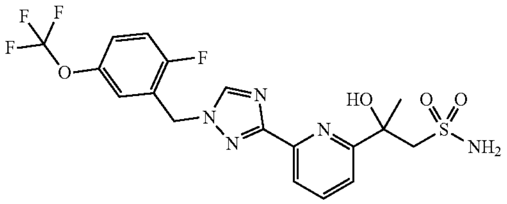 [SMILES: CC(O)(CS(N)(=O)=O)c1cccc(-c2ncn(Cc3cc(OC(F)(F)F)ccc3F)n2)n1]

To a solution of 2-(6-(1-(2-fluoro-5-(trifluoromethoxy)benzyl)-1H-1,2,4-triazol-3-yl)pyridin-2-yl)-2-hydroxy-N,N-bis(4-methoxybenzyl)propane-1-sulfonamide (233 mg, 0.33 mmol) in DCM (3 mL) was added TFA (1.3 mL, 17 mmol) and the mixture was stirred at room temperature for 18 h. The reaction mixture was quenched with a saturate aqueous solution of sodium bicarbonate and partitioned with EtOAc. The aqueous layer was extracted with EtOAc three times. The combined organic phases were dried over MgSO4, filtered and concentrated by rotary evaporation under reduced pressure to afford a crude product. The crude material was purified by preparative HPLC to afford the racemate of the title compound (Rac-55+56) (98 mg).

Instrument: Waters $UPC^2$ system

Column: Xbridge C18 OBD (5 μm, 30×50 mm)

Mobile phase: Gradient of 25-50% acetonitrile in 0.1% aqueous formic acid over 3.5 min.

and then hold 50% acetonitrile for 3 min.

Flow rate: 75 mL g/min.

Detection: PDA detector (210-400 nm)

Chiral separation of the racemate (98 mg) provided Example 55 as the first eluting peak (43 mg, 44% yield, e.e. >99%, Rt: 2.14 min.) and Example 56 as the second eluting peak (39 mg, 40% yield, e.e. >99%, Rt: 2.85 min.) as white solids.

Chiral Prep SFC:

Instrument: Waters Thar 80

Column: Chiralcel OD-H (30×250 mm, 5 μm)

Mobile phase: isopropanol with 10 mM ammonia in methanol/$CO_2$ (30/70)

Flow rate: 80 g/min.

Detection: UV @272 nm

Peak 1 (Example 55): ESI-MS m/z: 476.1 $[M+H]^+$ (Rt: 1.87 min., LCMS Method 8); $^1H$ NMR (400 MHz, DMSO-$d_6$) δ 8.78 (s, 1H), 7.93-7.86 (m, 2H), 7.70 (dd, J=6.7, 2.3 Hz, 1H), 7.53-7.36 (m, 3H), 6.72 (s, 2H), 5.74 (s, 1H), 5.62 (s, 2H), 3.70 (d, J=14.2 Hz, 1H), 3.60 (d, J=14.2 Hz, 1H), 1.60 (s, 3H).

Peak 2 (Example 56): ESI-MS m/z: 476.0 $[M+H]^+$ (Rt: 1.91 min., LCMS Method 8); $^1H$ NMR (400 MHz, DMSO-$d_6$) δ 8.78 (s, 1H), 7.93-7.86 (m, 2H), 7.70 (dd, J=6.8, 2.4 Hz, 1H), 7.55-7.38 (m, 3H), 6.66 (s, 2H), 5.62 (s, 2H), 3.69 (d, J=14.4 Hz, 1H), 3.60 (d, J=14.4 Hz, 1H), 1.60 (s, 3H).

Enantiomeric excess was determined using the following conditions:

Instrument: Waters $UPC^2$ system

Column: Chiralpak OD-3 (3 μm, 3×100 mm) @40° C.

Mobile phase: methanol/$CO_2$ (30/70); Gradient of 5% modifier for 0.2 min., increase to 55% modifier over 3.0 min., and hold at 55% modifier for 0.4 min.

Flow rate: 2.5 g/min.

Detection: PDA detector (210-400 nm)

Example 57: (R or S)-2-(6-(3-(2-fluoro-5-(trifluoromethoxy)benzyl)-1,2,4-oxadiazol-5-yl)pyridin-2-yl)-2-hydroxypropane-1-sulfonamide and Example 58: (R or S)-2-(6-(3-(2-fluoro-5-(trifluoromethoxy)benzyl)-1,2,4-oxadiazol-5-yl)pyridin-2-yl)-2-hydroxypropane-1-sulfonamide Prepared according to Scheme 9.

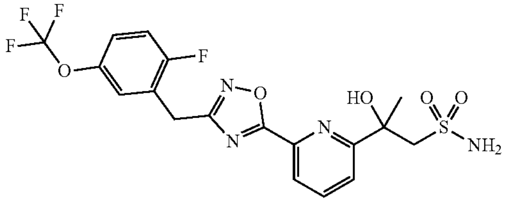 [SMILES: CC(O)(CS(N)(=O)=O)c1cccc(-c2nc(Cc3cc(OC(F)(F)F)ccc3F)no2)n1]

Step 1: 2-(2-fluoro-5-(trifluoromethoxy)phenyl)-N'-hydroxyacetimidamide

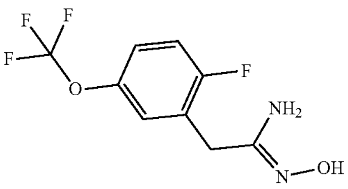 [SMILES: N/C(Cc1cc(OC(F)(F)F)ccc1F)=N\O]

To a solution of 2-(2-fluoro-5-(trifluoromethoxy)phenyl) acetonitrile (2.0 g, 9.1 mmol) in ethanol (91 mL) was added hydroxylamine (50% in water) (1.1 mL, 18.3 mmol). The result mixture was stirred at 85° C. for 3 hours. The reaction mixture was then concentrated under reduced pressure and it was used in the next step without further purification (2.3 g, 100% yield).

ESI-MS m/z: 253.1 $[M+H]^+$ (Rt: 0.77 min., LCMS Method 2). $^1$H NMR (400 MHz, DMSO-$d_6$) δ 9.04 (s, 1H), 7.38 (d, J=6.5 Hz, 1H), 7.34-7.26 (m, 2H), 5.54 (s, 2H), 3.38 (s, 2H).

Step 2: 1-(6-(3-(2-fluoro-5-(trifluoromethoxy)benzyl)-1,2,4-oxadiazol-5-yl)pyridin-2-yl)ethan-1-one

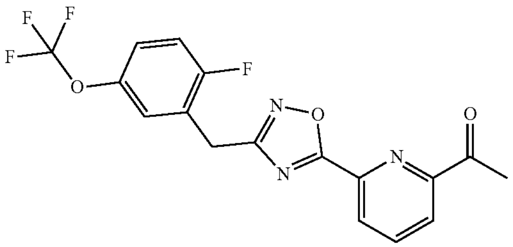 [SMILES: CC(=O)c1cccc(-c2nc(Cc3cc(OC(F)(F)F)ccc3F)no2)n1]

To a mixture of 2-(2-fluoro-5-(trifluoromethoxy)phenyl)-N'-hydroxyacetimidamide (1.53 g, 6.1 mmol) and 6-acetylpicolinic acid (1 g, 6.1 mmol) in 3 mL of EtOAc was added triethylamine (2.53 mL, 18.2 mmol) followed by T3P (50% solution in EtOAc) (9.0 mL, 15 mmol) in drops. The resulting mixture was heated at 80° C. under nitrogen for 4 hours. The completion of reaction was confirmed with LCMS. The mixture was cooled to room temperature and poured onto ice-water. The product was extracted with ethyl acetate three times. The combined organic phase was washed sequentially with a saturated sodium hydrogen carbonate solution twice followed by brine. The organic phase was dried over anhydrous magnesium sulfate, filtered and the solvent was removed under reduced pressure. The crude product was purified with silica gel column chromatography (0%-100% ethyl acetate in heptane) to provide the title compound (891 mg, 39% yield).

ESI-MS m/z: 382.2 $[M+H]^+$ (Rt: 1.18 min., LCMS Method 2).

Steps 3 and 4: 2-(6-(3-(2-fluoro-5-(trifluoromethoxy)benzyl)-1,2,4-oxadiazol-5-yl)pyridin-2-yl)-2-hydroxypropane-1-sulfonamide Prepared by analogy to Steps 4 and 5 from Examples 27 and 28 starting from 1-(6-(3-(2-fluoro-5-(trifluoromethoxy) benzyl)-1,2,4-oxadiazol-5-yl)pyridin-2-yl)ethan-1-one from Step 2 in this example to afford the racemate of the title compound (Rac-57+58) (470 mg).

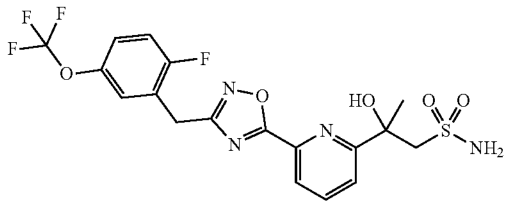 [SMILES: CC(O)(CS(N)(=O)=O)c1cccc(-c2nc(Cc3cc(OC(F)(F)F)ccc3F)no2)n1]

Chiral separation of the racemate (470 mg) provided Example 57 as the first eluting peak (151 mg, 32% yield, chiral HPLC: e.e. >99%, Rt: 1.71 min.) and Example 58 as the second eluting peak (152 mg, 32% yield, chiral HPLC: e.e. >99%, Rt: 1.91 min.) as white solids.

Chiral Prep HPLC:

Instrument: Thar 80

Column: Chiralpak IH (21×250 mm, 5 μm) @35° C.

Mobile phase: 25% methanol/isopropanol (1/1) with 10 mM ammonia/$CO_2$

Flow rate: 80 g/min.

Detection: UV @275 nm

Peak 1 (Example 57): ESI-MS m/z: 477.0 $[M+H]^+$ (Rt: 2.21 min., LCMS Method 3); $^1$H NMR (400 MHz, DMSO-$d_6$) δ 8.10-8.00 (m, 2H), 7.95 (dd, J=5.9, 3.0 Hz, 1H), 7.59-7.53 (m, 1H), 7.45-7.33 (m, 2H), 6.65 (s, 2H), 5.89 (s, 1H), 4.32 (s, 2H), 3.75-3.61 (m, 2H), 1.61 (s, 3H).

Peak 2 (Example 58): ESI-MS m/z: 477.0 $[M+H]^+$ (Rt: 2.23 min., LCMS Method 3); $^1$H NMR (400 MHz, DMSO-$d_6$) δ 8.11-8.02 (m, 2H), 7.96 (dd, J=5.9, 3.0 Hz, 1H), 7.60-7.54 (m, 1H), 7.45-7.35 (m, 2H), 6.66 (s, 2H), 5.90 (s, 1H), 4.33 (s, 2H), 3.77-3.62 (m, 2H), 1.62 (s, 3H).

Enantiomeric excess was determined using the following conditions:

Instrument: Waters UPC$^2$ system

Column: Chiralpak IH-3 (3 μm, 3×100 mm) @40° C.

Mobile phase: methanol/isopropanol (1/1) with 0.1% ammonium hydroxide/$CO_2$;

gradient method was 5% modifier for 0.2 min., increase to 55% modifier over 3.0 min., and hold at 55% modifier for 0.4 min.

Flow rate: 2.5 g/min.

Detection: PDA detector (210-400 nm)

Example 59: (R or S)-2-(6-(1-(2-fluoro-5-(trifluoromethoxy)benzyl)-1H-1,2,3-triazol-4-yl)pyridin-2-yl)-2-hydroxypropane-1-sulfonamide and Example 60: (R or S)-2-(6-(1-(2-fluoro-5-(trifluoromethoxy)benzyl)-1H-1,2,3-triazol-4-yl)pyridin-2-yl)-2-hydroxypropane-1-sulfonamide and Example 61: (R or S)-2-(6-(2-(2-fluoro-5-(trifluoromethoxy)benzyl)-2H-1,2,3-triazol-4-yl)pyridin-2-yl)-2-hydroxypropane-1-sulfonamide and Example 62: (R or S)-2-(6-(2-(2-fluoro-5-(trifluoromethoxy)benzyl)-2H-1,2,3-triazol-4-yl)pyridin-2-yl)-2-hydroxypropane-1-sulfonamide Prepared according to Scheme 10.

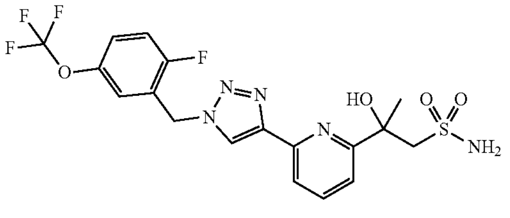

Example 59
Example 60

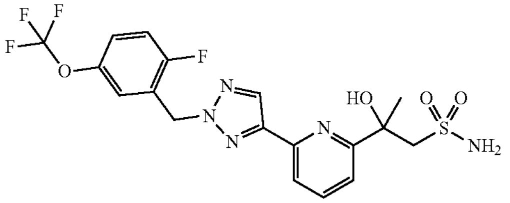

Example 61
Example 62

Step 1: 1-(6-((trimethylsilyl)ethynyl)pyridin-2-yl)ethan-1-one

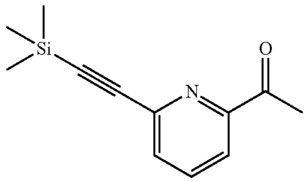

To a solution of 1-(6-bromopyridin-2-yl)ethan-1-one (10.0 g, 50 mmol) in DMF (50 mL) was added copper(I) iodide (0.48 g, 2.5 mmol), $Pd(PPh_3)_2Cl_2$(2.1 g, 3.0 mmol) and triethylamine (35 mL, 250 mmol). The mixture was purged with nitrogen gas for 5 minutes and to this degassed mixture was added ethynyltrimethylsilane (7.86 g, 80 mmol). The reaction was stirred at room temperature overnight. The resulting reaction mixture was diluted with water and extracted with EtOAc three times. The combined organic phase was washed with water, dried over anhydrous magnesium sulfate, filtered and concentrated under reduced pressure. The resulting crude product was purified with silica gel column chromatography (0%-60% ethyl acetate in heptane) to provide the title compound (7 g, 64.4% yield).

ESI-MS m/z: 218.1 $[M+H]^+$ (Rt: 1.18 min., LCMS Method 1).

Step 2: 1-(6-ethynylpyridin-2-yl)ethan-1-one

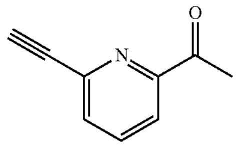

To a solution of 1-(6-((trimethylsilyl)ethynyl)pyridin-2-yl)ethan-1-one (7 g, 32 mmol) in 32 mL of MeOH (32 mL) at room temperature was added potassium carbonate (8.9 g, 64 mmol). The reaction mixture was stirred for 2 hours at room temperature and then quenched by slow addition of a saturated aqueous $NH_4Cl$ solution. The resulting mixture was extracted with DCM three times. The combined organic layers were dried over $Na_2SO_4$, filtered and concentrated. The crude product was purified with silica gel column chromatography (0%-100% ethyl acetate in heptane) to provide the title compound (3.69 g, 79% yield).

ESI-MS m/z: 146.1 $[M+H]^+$ (Rt: 0.72 min., LCMS Method 1). $^1$H NMR (400 MHz, DMSO-$d_6$) δ 7.91 (t, J=7.8 Hz, 1H), 7.83 (dd, J=7.9, 1.3 Hz, 1H), 7.70 (dd, J=7.9, 1.4 Hz, 1H), 4.36 (s, 1H), 2.50 (s, 3H).

Step 3: (4-(6-acetylpyridin-2-yl)-1H-1,2,3-triazol-1-yl)methyl pivalate

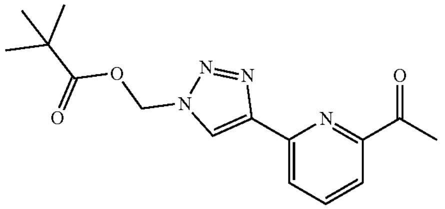 [SMILES: CC(=O)c1cccc(-c2cn(COC(=O)C(C)(C)C)nn2)n1]

1-(6-ethynylpyridin-2-yl)ethan-1-one (1.0 g, 6.9 mmol) was dissolved in tert-butanol (17 mL). To this was added azidomethyl pivalate (2.16 g, 13.8 mmol), copper(II) sulfate pentahydrate (0.172 g, 0.69 mmol), sodium ascorbate (0.273 g, 1.38 mmol) and water (17 mL). The reaction mixture was stirred at room temperature overnight. The reaction mixture was diluted with water and extracted with EtOAc three times. The combined organic layers were washed with brine, dried over sodium sulfate, filtered and concentrated. The crude was purified by column chromatography on silica gel (0-100% ethyl acetate in heptane) to afford the title compound (1.79 g, 86% yield).

ESI-MS m/z: 303.6 $[M+H]^+$ (Rt: 0.98 min., LCMS Method 2). $^1$H NMR (400 MHz, DMSO-$d_6$) δ 8.90 (s, 1H), 8.32-8.26 (m, 1H), 8.12 (t, J=7.7 Hz, 1H), 7.92 (dd, J=7.8, 0.9 Hz, 1H), 6.43 (s, 2H), 2.72 (s, 3H), 1.15 (s, 9H).

Step 4: 1-(6-(1H-1,2,3-triazol-4-yl)pyridin-2-yl) ethan-1-one

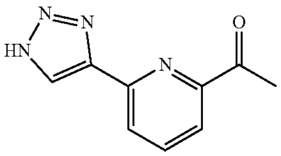

(4-(6-acetylpyridin-2-yl)-1H-1,2,3-triazol-1-yl)methyl pivalate (0.24 g, 0.6 mmol) was dissolved in MeOH (12 mL) and 1N aqueous sodium hydroxide solution (12.0 mL, 12 mmol) was added. The resulting mixture was stirred for 10 minutes and to it was added a 1N aqueous HCl solution (12 mL, 12 mmol). The mixture was extracted with EtOAc three times and the combined organic layers were washed with brine, dried over $Na_2SO_4$, filtered and concentrated to provide the title compound (1.1 g, 99% yield), which was used in the next step without further purification.

ESI-MS m/z: 189.1 $[M+H]^+$ (Rt: 0.62 min., LCMS Method 1).

Step 5: 1-(6-(2-(2-fluoro-5-(trifluoromethoxy)benzyl)-2H-1,2,3-triazol-4-yl)pyridin-2-yl)ethan-1-one, and 1-(6-(1-(2-fluoro-5-(trifluoromethoxy)benzyl)-1H-1,2,3-triazol-4-yl)pyridin-2-yl)ethan-1-one

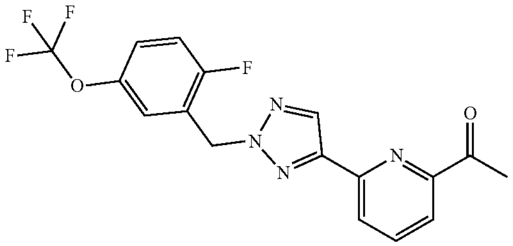

First eluting peak

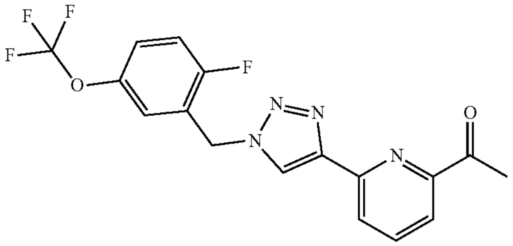

Second eluting peak

To a solution of 1-(6-(1H-1,2,3-triazol-4-yl)pyridin-2-yl) ethan-1-one(1.1 g, 5.9 mmol) in 2-butanone (30 mL) was added potassium carbonate (2.42 g, 5.9 mmol) and 2-(bromomethyl)-1-fluoro-4-(trifluoromethoxy)benzene (1.59 g, 5.9 mmol). The resulting mixture was stirred at room temperature overnight. The resulting suspension was filtered and the filter cake was rinsed with DCM. The combined filtrate was concentrated under reduced pressure and the resulting residue was purified with silica gel column chromatography (0%-60% ethyl acetate in heptane) to provide first eluting isomer (0.514 g, 23% yield) and second eluting isomer (0.614 g, 28% yield).

First Eluting Isomer: N2-Substituted 1,2,3-Triazole

ESI-MS m/z: 381.2 $[M+H]^+$ (Rt: 1.22 min., LCMS Method 2). $^1H$ NMR (400 MHz, DMSO-$d_6$) δ 8.45 (s, 1H), 8.15-8.05 (m, 2H), 7.93 (dd, J=6.7, 2.2 Hz, 1H), 7.54-7.39 (m, 3H), 5.87 (s, 2H), 2.71 (s, 3H).

Second Eluting Isomer: N1-Substituted 1,2,3-Triazole

ESI-MS m/z: 381.1 $[M+H]^+$ (Rt: 1.08 min., LCMS Method 2). $^1H$ NMR (400 MHz, DMSO-$d_6$) δ 8.88 (s, 1H), 8.26 (dd, J=7.8, 1.3 Hz, 1H), 8.10 (t, J=7.8 Hz, 1H), 7.90 (d, J=7.9 Hz, 1H), 7.58-7.41 (m, 3H), 5.83 (s, 2H), 2.71 (s, 3H).

Example 59: (R or S)-2-(6-(1-(2-fluoro-5-(trifluoromethoxy)benzyl)-1H-1,2,3-triazol-4-yl)pyridin-2-yl)-2-hydroxypropane-1-sulfonamide and Example 60: (R or S)-2-(6-(1-(2-fluoro-5-(trifluoromethoxy) benzyl)-1H-1,2,3-triazol-4-yl)pyridin-2-yl)-2-hydroxypropane-1-sulfonamide Prepared by analogy to Steps 4 and 5 from Examples 27 and 28 starting from the Second eluting isomer from Step 5 in this example to afford the racemate of the title compound (Rac-59+60) (395 mg).

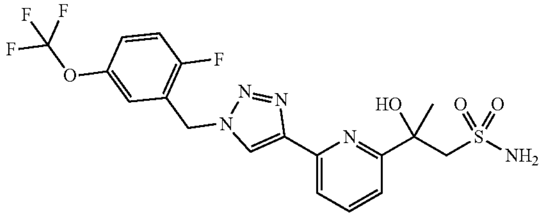 [SMILES: CC(O)(CS(N)(=O)=O)c1cccc(-c2cn(Cc3cc(OC(F)(F)F)ccc3F)nn2)n1]

Chiral separation of the racemate (395 mg) provided Example 59 as the first eluting peak (91 mg, 23% yield, chiral HPLC: e.e. 96.4%, Rt: 1.94 min.) and Example 60 as the second eluting peak (81 mg, 21% yield, chiral HPLC: e.e. 98.9%, Rt: 2.08 min.) as white solids.

Chiral Prep HPLC:

Instrument: Waters Thar 80

Column: RegisPack (30×250 mm, 5 μm)

Mobile phase: ethanol with 0.25% isopropylamine/$CO_2$ (20/80)

Flow rate: 80 g/min.

Detection: UV @280 nm

Peak 1 (Example 59): ESI-MS m/z: 476.1 $[M+H]^+$ (Rt: 1.95 min., LCMS Method 3); $^1H$ NMR (400 MHz, DMSO-$d_6$) δ 8.75 (s, 1H), 7.93-7.84 (m, 2H), 7.61 (dd, J=6.8, 2.4 Hz, 1H), 7.57-7.40 (m, 3H), 6.61 (s, 2H), 5.78 (d, J=8.8 Hz, 3H), 3.65 (d, J=2.6 Hz, 2H), 1.62 (s, 3H).

Peak 2 (Example 60): ESI-MS m/z: 476.7 $[M+H]^+$ (Rt: 1.97 min., LCMS Method 3); $^1H$ NMR (400 MHz, DMSO-$d_6$) δ 8.76 (s, 1H), 7.94-7.84 (m, 2H), 7.62 (dd, J=6.6, 2.2 Hz, 1H), 7.57-7.40 (m, 3H), 6.61 (s, 2H), 5.78 (d, J=8.8 Hz, 3H), 3.72-3.59 (m, 2H), 1.62 (s, 3H).

Enantiomeric excess was determined using the following conditions:

Instrument: Waters UPC$^2$ system

Column: Chiralpak AD-H (5 μm, 4.6×100 mm)

Mobile phase: ethanol with 0.1% isopropylamine/$C_{02}$ (20/80); gradient method was starting at 5% modifier, increased to 65% modifier over 4 min., and hold at 65% modifier for 1 min.

Flow rate: 3.5 g/min.

Detection: PDA detector (210-400 nm)

Example 61: (R or S)-2-(6-(2-(2-fluoro-5-(trifluoromethoxy)benzyl)-2H-1,2,3-triazol-4-yl)pyridin-2-yl)-2-hydroxypropane-1-sulfonamide and Example 62: (R or S)-2-(6-(2-(2-fluoro-5-(trifluoromethoxy) benzyl)-2H-1,2,3-triazol-4-yl)pyridin-2-yl)-2-hydroxypropane-1-sulfonamide Prepared by analogy to Steps 4 and 5 from Examples 27 and 28 starting from the First eluting isomer from Step 5 in this example to afford the racemate of the title compound (Rac-61+62) (190 mg).

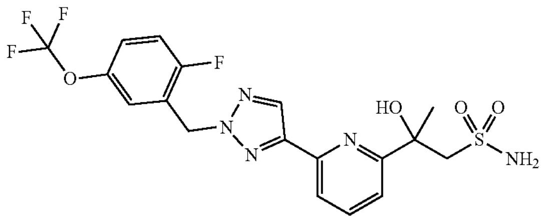 [SMILES: CC(O)(CS(N)(=O)=O)c1cccc(-c2cnn(Cc3cc(OC(F)(F)F)ccc3F)n2)n1]

Chiral separation of the racemate (190 mg) provided Example 61 as the first eluting peak (72 mg, 38% yield, chiral HPLC: e.e. >99%, Rt: 1.32 min.) and Example 62 as the second eluting peak (66 mg, 35% yield, chiral HPLC: e.e. >99%, Rt: 1.57 min.) as white solids.

Chiral Prep SFC:

Instrument: Waters Preparative SFC80

Column: Chiralpak IG (21×250 mm, 5 μm) @35° C.

Mobile phase: methanol/$C_{02}$ (30/70)

Flow rate: 80 g/min.

Detection: UV @252 nm

Peak 1 (Example 61): ESI-MS m/z: 476.1 $[M+H]^+$ (Rt: 2.23 min., LCMS Method 3); $^1H$ NMR (400 MHz, DMSO-$d_6$) δ 8.35 (s, 1H), 7.87 (t, J=7.8 Hz, 1H), 7.72 (d, J=7.9 Hz, 1H), 7.64 (d, J=7.9 Hz, 1H), 7.52-7.37 (m, 3H), 6.59 (s, 2H), 5.82 (s, 2H), 5.75 (d, J=2.7 Hz, 1H), 3.66 (s, 2H), 1.60 (s, 3H).

Peak 2 (Example 62): ESI-MS m/z: 476.0 $[M+H]^+$ (Rt: 2.26 min., LCMS Method 3); $^1H$ NMR (400 MHz, DMSO-$d_6$) δ 8.37 (s, 1H), 7.89 (t, J=7.8 Hz, 1H), 7.73 (d, J=7.8 Hz, 1H), 7.65 (d, J=7.8 Hz, 1H), 7.53-7.39 (m, 3H), 6.61 (s, 2H), 5.84 (s, 2H), 5.77 (s, 1H), 3.68 (s, 2H), 1.62 (s, 3H).

Enantiomeric excess was determined using the following conditions:

Instrument: Waters $UPC^2$ system

Column: Chiralpak IG-3(3 μm, 3×100 mm)

Mobile phase: methanol/$CO_2$; gradient method was 5% modifier for 0.2 min., increase to 55% modifier over 3.0 min., and hold at 55% modifier for 0.4 min.

Flow rate: 2.5 g/min.

Detection: PDA detector (210-400 nm)

Synthesis of Examples 63 to 90

Chiral intermediate: (R)-2-(6-(2H-tetrazol-5-yl)pyridin-2-yl)-2-hydroxy-N,N-bis(4-methoxybenzyl)propane-1-sulfonamide

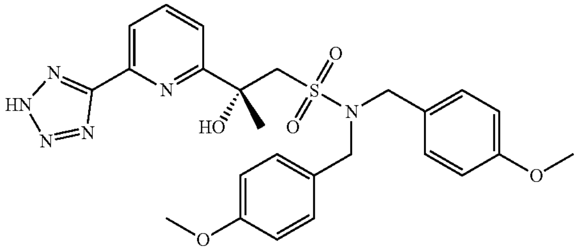 [SMILES: COc1ccc(CN(Cc2ccc(OC)cc2)S(=O)(=O)C[C@](C)(O)c2cccc(-c3nn[nH]n3)n2)cc1]

racemic-2-(6-(2H-tetrazol-5-yl)pyridin-2-yl)-2-hydroxy-N,N-bis(4-methoxybenzyl)propane-1-sulfonamide (Example-1, step-3, 0.88 Kg) was subjected to chiral separation under the condition described below to give two fractions with retention time of 4.90, and 6.35 min, respectively. Concentration of the fractions with retention time 6.35 min afforded R-enantiomer (42.4%, >98% e.e.).

| | | |
|---|---|---|
| Equipment: | SMB Licosep | |
| Column: | CHIRALPAK IG-20 | |
| Size: | 50 mm I.D. * 100 mm L | |
| Batch size | 0.88 kg/batch | |
| Eluent: | MeOH/ACN/TFA = 90/10/0.1 (V/V) | |
| Temperature: | 42° C. | |
| Flow rate: | Recycling: | 224 ml/min |
| | Extract: | 102 ml/min |
| | Feed: | 17.50 ml/min |
| | Raffinate: | 23.30 ml/min |
| | Eluent: | 107.8 ml/min |

The selected chiral compounds (structures of Example 63 to 90 shown in Table 6) were prepared using the chiral intermediate above according to the general procedures described for racemic synthesis of Example of 1 (steps 4-5).

Biological Assays and Data

The Nav1.5 modulating activity of the compounds, in free form or in pharmaceutically acceptable salt form, according to the present disclosure can be assessed by the following in vitro methods. As such the compounds of the present disclosure, exhibit valuable pharmacological properties, and are therefore indicated for therapy related to modulation of Nav1.5, or for use as research chemicals, e.g., as tool compounds.

Electrophysiology was used to measure the ionic currents in isolated living cells using automated patch-clamp recording, performed using an automated patch-clamp machine called Qpatch (Sophion Bioscience). Two different assay conditions were used to identify compounds with atrial-selective potential. The 5-Hz AF-like assay has more depolarized holding potential at −85 mV to mimic atrial resting membrane potential (RMP) and was used to identify compounds of strong rate-dependence. Active, rate-dependent compounds were then screened at 1 Hz (i.e., sinus rate) at the holding potential of −100 mV to mimic the ventricular scenario and help identify compounds with the largest potency separation or attenuation from the 5-Hz AF-like assay. Such compounds have the potential for treating AF without the QRS liability inherent to Class Ic drugs.

The sodium current conducted through a cell (via Nav1.5) or electrical signals were processed through a low-pass filter at 5 KHz, re-digitalized and acquired at 20 kHz. Series resistance was not compensated and leak subtraction was performed.

1 to 3 million Chinese Hamster Ovary cells (also known as CHO-K1) stably expressing human Nav1.5 were seeded into 175-mm culture flasks with 25 mL medium (consisting of Gibco Dulbecco's Modified Eagle Medium as a base medium with 1% MEM non-essential amino acids, 400 µg/mL Geneticin, 5 µg/mL puromycin and 10% fetal bovine serum) 48-72 hours prior to the experiments. On the day of the experiment, cells were washed once with phosphate-buffered saline (also known as PBS; Gibco) detached with Detachin™ (Genlantis), and re-suspended in CHO-S-SFM II media (Gibco) at 200,000 cells/mL. The CHO-S-SFM II was replaced with assay solutions prior to the assays. Whole-cell currents were recorded at room temperature in the whole-cell configuration. The external aqueous assay solution (pH=7.4; Osm=307-315) contained the following (the concentration for each component is expressed in parentheses in mM): NaCl (140 mM), KCl (4 mM), $CaCl_2$) (2 mM), $MgCl_2$ (1 mM), 4-(2-hydroxyethyl)-1-piperazineethanesulfonic acid, also known as HEPES (10 mM), and glucose (5 mM). The internal aqueous assay solution (pH=7.2; Osm=292-295) contained the following (the concentration for each component is expressed in parentheses in mM): CsF (110 mM), CsCl (10 mM), NaCl (10 mM), HEPES (10 mM), and ethylene glycol-bis(β-aminoethyl ether)-N,N,N',N'-tetraacetic acid, also known as EGTA (10 mM).

To assess peak Nav1.5 current inhibition in an atrial fibrillation-mimicking condition (Nav1.5 $IC_{50}$ (5 Hz, AF-like rate) (µM)), compounds were first prepared at 10 mM in DMSO, and cells were pre-incubated with test compounds at each concentration for 3 min. in an ascending order of 0, 0.37, 1.1, 3.3, 10 and 30 µM. An atrial action potential-like protocol consisting of a voltage ramp (+10 mV to −85 mV for a 150 ms duration and a holding potential at −85 mV) was then applied to cells at 5 Hz for 12 s until no further current change or inhibition was observed. The percent inhibition (expressed as ($[I_{after\ compound\ treatment}/I_{before\ compound\ treatment}]\times 100\%$) is calculated by normalizing the peak current amplitude at the last pulse of each of the 6 compound concentrations by the amplitude before exposure to the test compound. The compiled data was further normalized by vehicle control (DMSO) to account for Nav1.5 current run-down, and $IC_{50}$ was calculated by Matlab (MathWorks, USA).

To assess peak Nav1.5 current inhibition mimicking a ventricular condition at sinus rate with or without ATX-II (Nav1.5 $IC_{50}$ (1 Hz, ATXII) (µM) or (1 Hz, Sinus Rate) (µM)), compounds were first prepared at 10 mM in DMSO, and cells were pre-incubated with test compounds at each concentration for 3 min. in an ascending order of 0, 0.37, 1.1, 3.3, 10 and 30 uM. In the assay with ATX-II (Alomone Labs), 50 nM ATX-II was included during the 3-min. compound incubation. A square pulse (−10 mV; 400 ms and a holding potential at −100 mV) was run at 1 Hz for 25 s until no further inhibition or Nav1.5 current change was observed. The percent inhibition (expressed as ($[I_{after\ compound\ treatment}/I_{before\ compound\ treatment}]\times 100\%$) is calculated by normalizing the peak current amplitude at the last pulse of each of the 6 compound concentrations by the amplitude before exposure to the test compound. The compiled data was further normalized by vehicle control (DMSO) to account for Nav1.5 current run-down, and IC50 was calculated by Matlab (MathWorks, USA).

TABLE 5

| Example | Structure | Nav1.5 $IC_{50}$ (5 Hz, AF Rate) (µM) | Nav1.5 $IC_{50}$ (1 Hz, Sinus Rate) (µM ) | Nav1.5 $IC_{50}$ (1 Hz, ATXII) (µM) |
|---|---|---|---|---|
| Representative data for Nav1.5 blockade | | | | |
| Rac-1 + 2 | 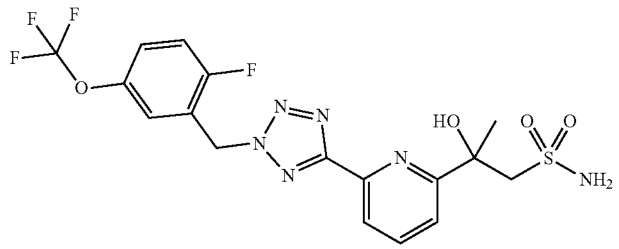 [SMILES: CC(O)(CS(N)(=O)=O)c1cccc(-c2nnn(Cc3cc(OC(F)(F)F)ccc3F)n2)n1] | 3.6 | ND | ND |
| 1 | 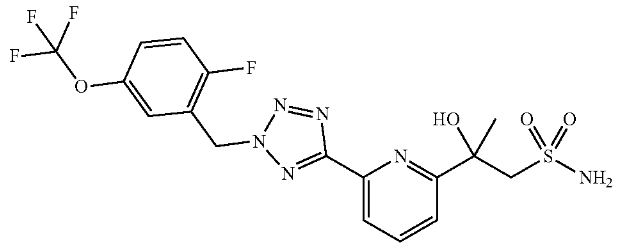 [SMILES: CC(O)(CS(N)(=O)=O)c1cccc(-c2nnn(Cc3cc(OC(F)(F)F)ccc3F)n2)n1] (Example 1) | 3.1 (n = 2) | 22 | 19 (n = 3) |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| | 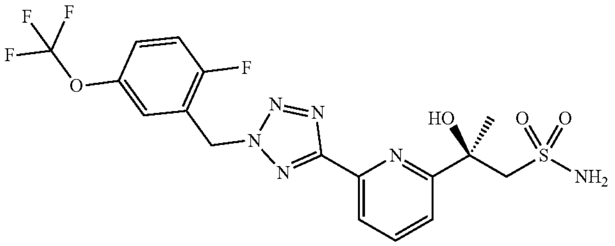 [SMILES: C[C@](O)(CS(N)(=O)=O)c1cccc(-c2nnn(Cc3cc(OC(F)(F)F)ccc3F)n2)n1] | | | |
| 2 | 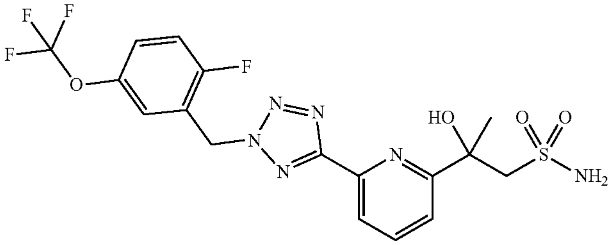 [SMILES: CC(O)(CS(N)(=O)=O)c1cccc(-c2nnn(Cc3cc(OC(F)(F)F)ccc3F)n2)n1] (Example 2) | 4.7 | ND | >30 |
| | 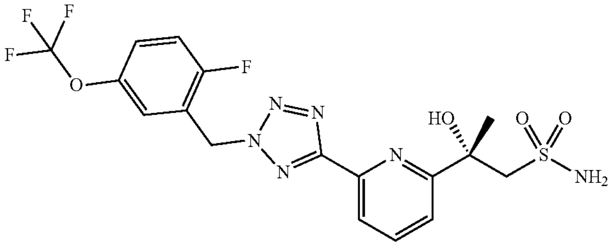 [SMILES: C[C@@](O)(CS(N)(=O)=O)c1cccc(-c2nnn(Cc3cc(OC(F)(F)F)ccc3F)n2)n1] | | | |
| Rac-3 + 4 | 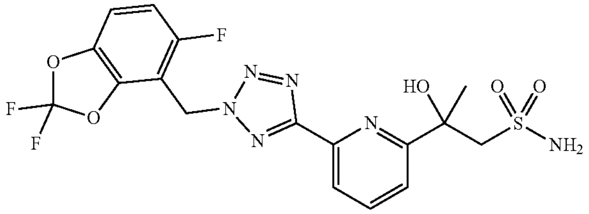 [SMILES: CC(O)(CS(N)(=O)=O)c1cccc(-c2nnn(Cc3c(F)ccc4c3OC(F)(F)O4)n2)n1] | 7.0 | ND | ND |
| 3 | 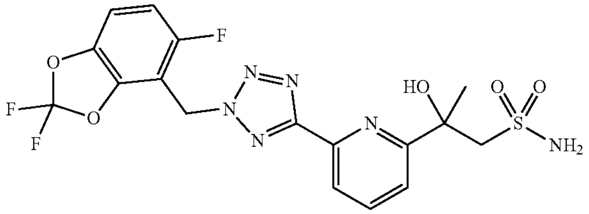 [SMILES: CC(O)(CS(N)(=O)=O)c1cccc(-c2nnn(Cc3c(F)ccc4c3OC(F)(F)O4)n2)n1] | 7.5 | >30 | ND |
| 4 | 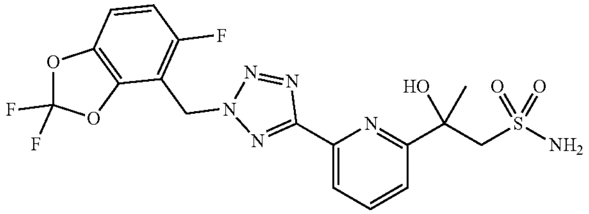 [SMILES: CC(O)(CS(N)(=O)=O)c1cccc(-c2nnn(Cc3c(F)ccc4c3OC(F)(F)O4)n2)n1] | 6.7 | >30 | ND |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 5 | 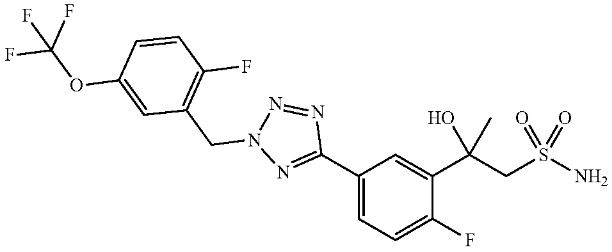 [SMILES: CC(O)(CS(N)(=O)=O)c1cc(-c2nnn(Cc3cc(OC(F)(F)F)ccc3F)n2)ccc1F] | 7.9 | >30 | ND |
| 6 | 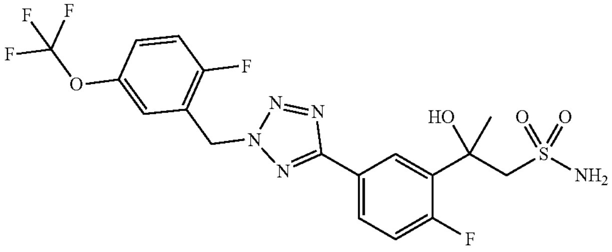 [SMILES: CC(O)(CS(N)(=O)=O)c1cc(-c2nnn(Cc3cc(OC(F)(F)F)ccc3F)n2)ccc1F] | 7.9 | >30 | ND |
| 7 | 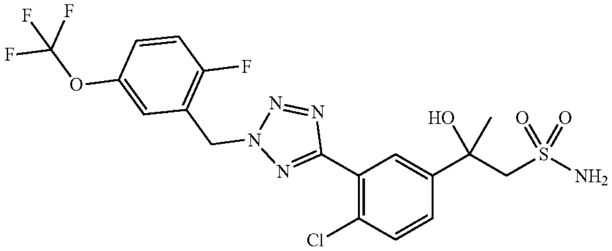 [SMILES: CC(O)(CS(N)(=O)=O)c1ccc(Cl)c(-c2nnn(Cc3cc(OC(F)(F)F)ccc3F)n2)c1] | 1.3 | 28 | 15 |
| 8 | 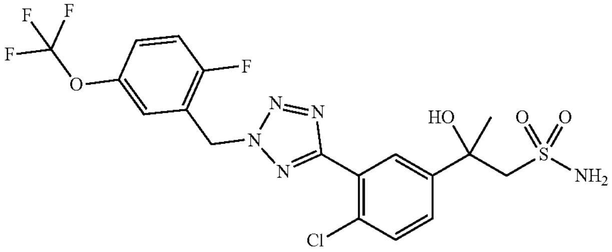 [SMILES: CC(O)(CS(N)(=O)=O)c1ccc(Cl)c(-c2nnn(Cc3cc(OC(F)(F)F)ccc3F)n2)c1] | 1.3 | >30 | 28 |
| 9 | 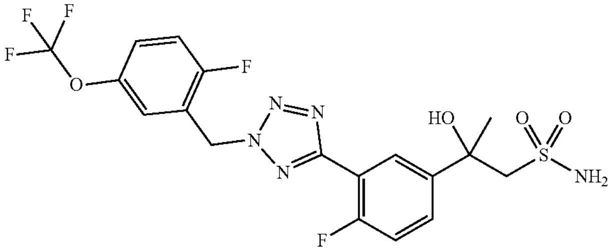 [SMILES: CC(O)(CS(N)(=O)=O)c1ccc(F)c(-c2nnn(Cc3cc(OC(F)(F)F)ccc3F)n2)c1] | 4.1 | >30 | >30 |

TABLE 5-continued
Representative data for Nav1.5 blockade
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
|---|---|---|---|---|
| 10 | 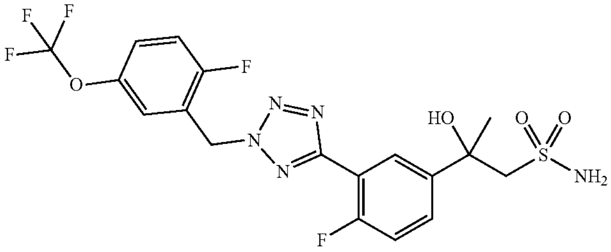 | 1.0 | >30 | 11 |
| 11 | 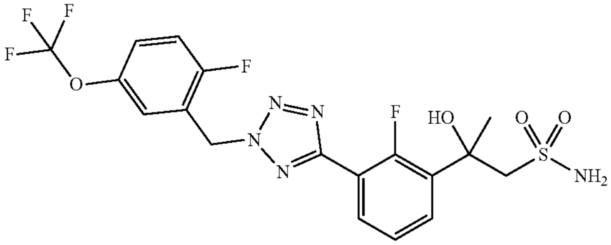 [SMILES: CC(O)(CS(N)(=O)=O)c1cccc(-c2nnn(Cc3cc(OC(F)(F)F)ccc3F)n2)c1F] | 1.7 | 8.9 | 5.6 |
| 12 | 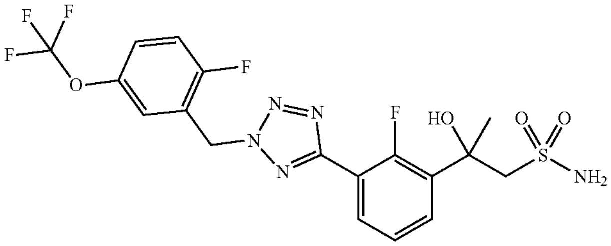 [SMILES: CC(O)(CS(N)(=O)=O)c1cccc(-c2nnn(Cc3cc(OC(F)(F)F)ccc3F)n2)c1F] | 4.2 | 10 | 5.2 |
| 13 | 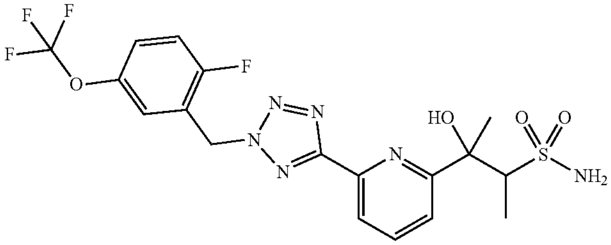 [SMILES: CC(C(C)(O)c1cccc(-c2nnn(Cc3cc(OC(F)(F)F)ccc3F)n2)n1)S(N)(=O)=O] | 4.3 (n = 2) | 12 (n = 2) | >30 |
| 14 | 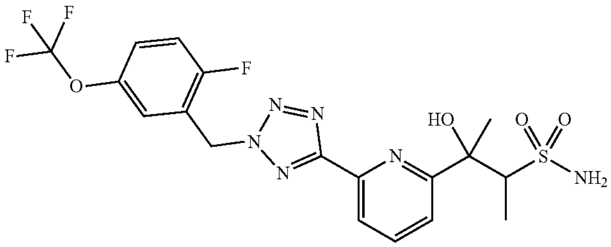 [SMILES: CC(C(C)(O)c1cccc(-c2nnn(Cc3cc(OC(F)(F)F)ccc3F)n2)n1)S(N)(=O)=O] | 4.0 (n = 2) | >30 (n = 2) | 15 (n = 2) |

TABLE 5-continued
Representative data for Nav1.5 blockade
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
|---|---|---|---|---|
| 15 | 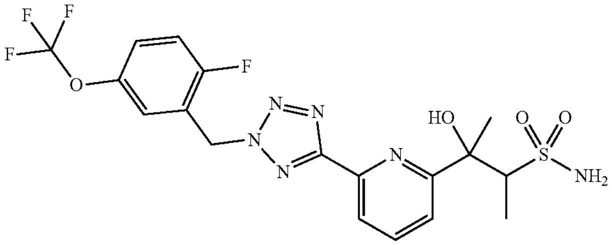 [SMILES: CC(C(C)(O)c1cccc(-c2nnn(Cc3cc(OC(F)(F)F)ccc3F)n2)n1)S(N)(=O)=O] | 4.1 (n = 2) | >30 (n = 2) | 24 |
| 16 | 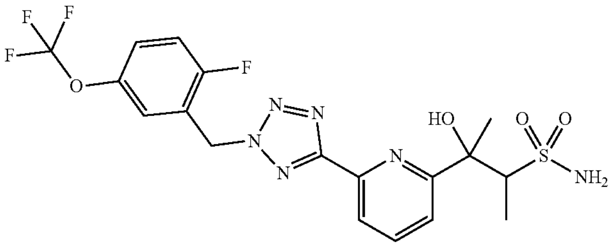 [SMILES: CC(C(C)(O)c1cccc(-c2nnn(Cc3cc(OC(F)(F)F)ccc3F)n2)n1)S(N)(=O)=O] | 2.8 (n = 2) | 16 (n = 2) | 4.8 (n = 2) |
| 17 | 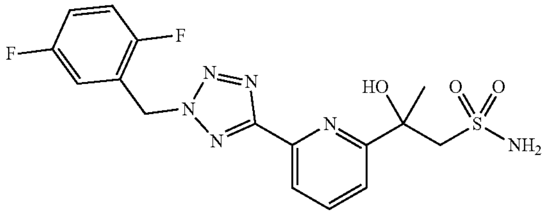 [SMILES: CC(O)(CS(N)(=O)=O)c1cccc(-c2nnn(Cc3cc(F)ccc3F)n2)n1] | 24 (n = 2) | ND | ND |
| 18 | 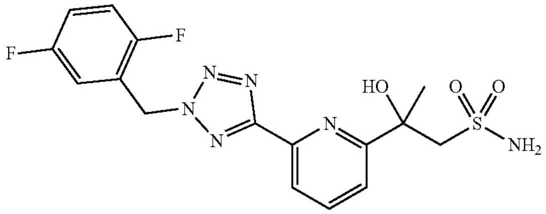 [SMILES: CC(O)(CS(N)(=O)=O)c1cccc(-c2nnn(Cc3cc(F)ccc3F)n2)n1] | 20 (n = 2) | ND | ND |
| 19 | 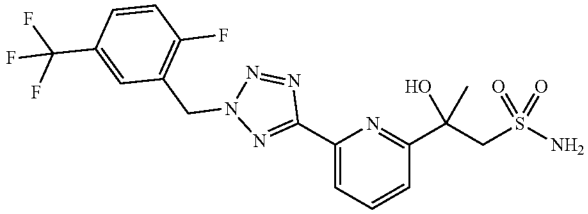 [SMILES: CC(O)(CS(N)(=O)=O)c1cccc(-c2nnn(Cc3cc(C(F)(F)F)ccc3F)n2)n1] | 5.0 (n = 3) | ND | 14 |
| 20 | 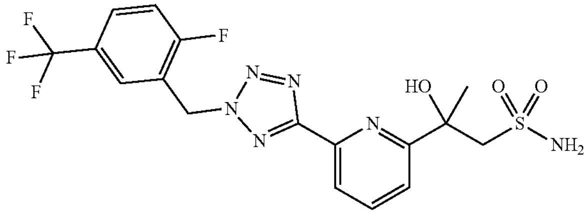 [SMILES: CC(O)(CS(N)(=O)=O)c1cccc(-c2nnn(Cc3cc(C(F)(F)F)ccc3F)n2)n1] | 7.9 (n = 3) | ND | 23 |

TABLE 5-continued
| Example | Structure | Nav1.5 IC50 (5 Hz, AF Rate) (μM) | Nav1.5 IC50 (1 Hz, Sinus Rate) (μM ) | Nav1.5 IC50 (1 Hz, ATXII) (μM) |
|---|---|---|---|---|
| Representative data for Nav1.5 blockade | | | | |
| 21 | 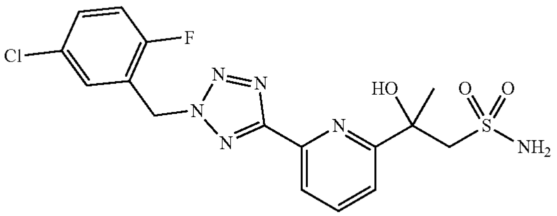 [SMILES: CC(O)(CS(N)(=O)=O)c1cccc(-c2nnn(Cc3cc(Cl)ccc3F)n2)n1] | 6.3 (n = 3) | ND | >30 |
| 22 | 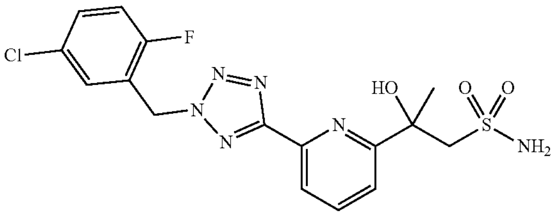 [SMILES: CC(O)(CS(N)(=O)=O)c1cccc(-c2nnn(Cc3cc(Cl)ccc3F)n2)n1] | 8.4 (n = 3) | ND | 22 |
| 23 | 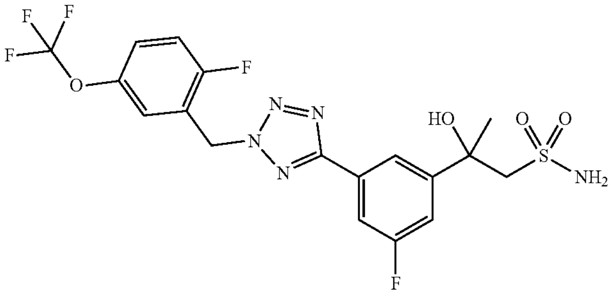 [SMILES: CC(O)(CS(N)(=O)=O)c1cc(F)cc(-c2nnn(Cc3cc(OC(F)(F)F)ccc3F)n2)c1] | 5.6 | >30 | >30 |
| 24 | 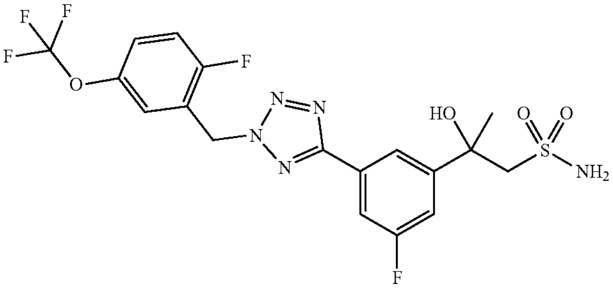 [SMILES: CC(O)(CS(N)(=O)=O)c1cc(F)cc(-c2nnn(Cc3cc(OC(F)(F)F)ccc3F)n2)c1] | 2.0 | >30 | 7.8 |
| Rac-25 + 26 | 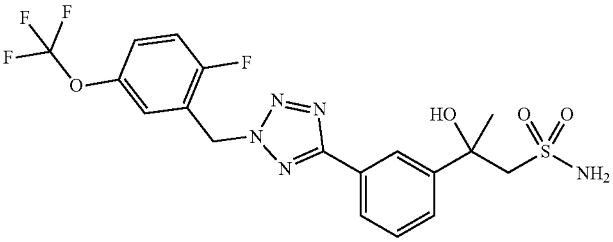 [SMILES: CC(O)(CS(N)(=O)=O)c1cccc(-c2nnn(Cc3cc(OC(F)(F)F)ccc3F)n2)c1] | 2.2 | ND | >30 |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 25 | 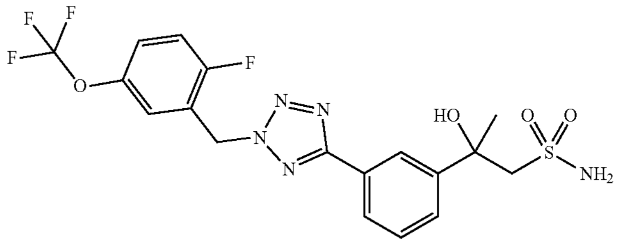 [SMILES: CC(O)(CS(N)(=O)=O)c1cccc(-c2nnn(Cc3cc(OC(F)(F)F)ccc3F)n2)c1] | 5.5 | ND | ND |
| 26 | 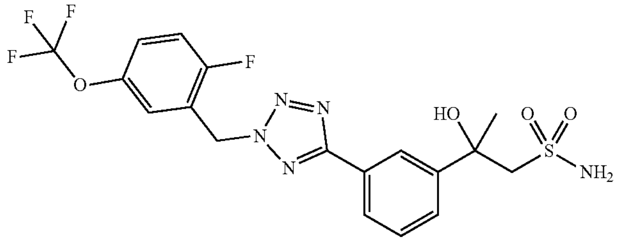 [SMILES: CC(O)(CS(N)(=O)=O)c1cccc(-c2nnn(Cc3cc(OC(F)(F)F)ccc3F)n2)c1] | 1.8 | ND | ND |
| Rac-27 + 28 | 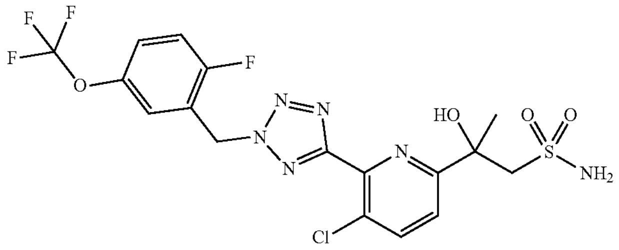 [SMILES: CC(O)(CS(N)(=O)=O)c1ccc(Cl)c(-c2nnn(Cc3cc(OC(F)(F)F)ccc3F)n2)n1] | 1.1 | ND | 16 |
| 27 | 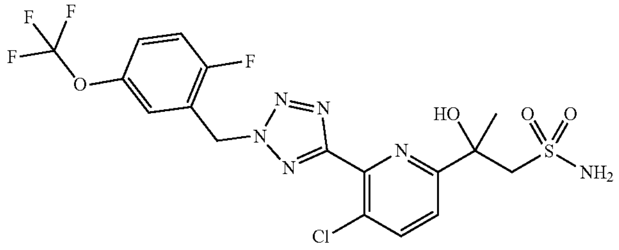 [SMILES: CC(O)(CS(N)(=O)=O)c1ccc(Cl)c(-c2nnn(Cc3cc(OC(F)(F)F)ccc3F)n2)n1] | 0.8 | ND | 4.1 |
| 28 | 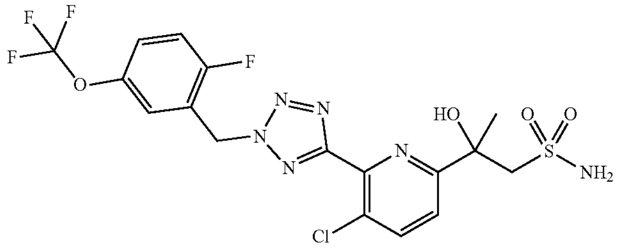 [SMILES: CC(O)(CS(N)(=O)=O)c1ccc(Cl)c(-c2nnn(Cc3cc(OC(F)(F)F)ccc3F)n2)n1] | 0.7 | ND | 3.2 |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| Rac-29+30 | 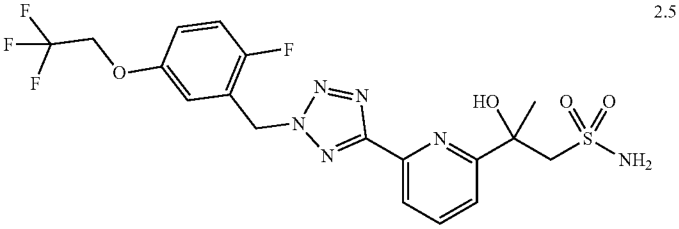 | 2.5 | ND | 3.0 |
| 29 | 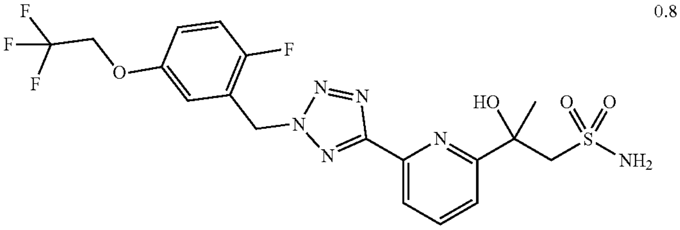 | 0.8 | ND | ND |
| 30 | 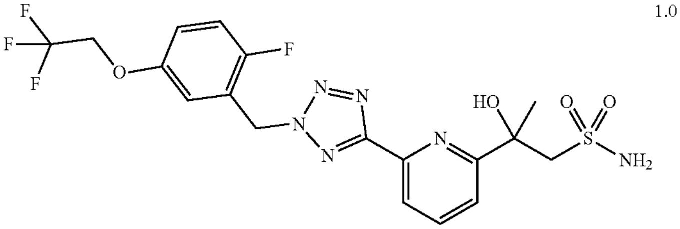 | 1.0 | ND | ND |
| 31 | 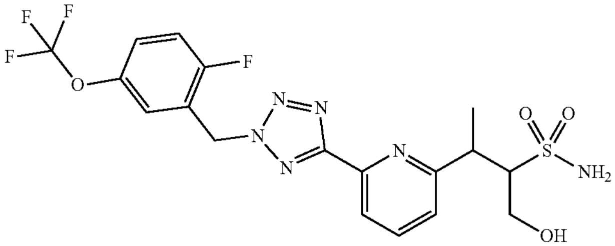 [SMILES: CC(c1cccc(-c2nnn(Cc3cc(OC(F)(F)F)ccc3F)n2)n1)C(CO)S(N)(=O)=O] | 1.1 | 7.8 | ND |
| 32 | 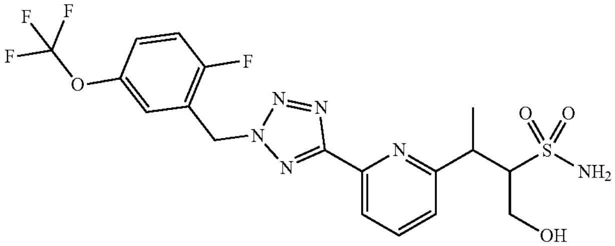 [SMILES: CC(c1cccc(-c2nnn(Cc3cc(OC(F)(F)F)ccc3F)n2)n1)C(CO)S(N)(=O)=O] | 2.7 | 28 | ND |
| 33 | 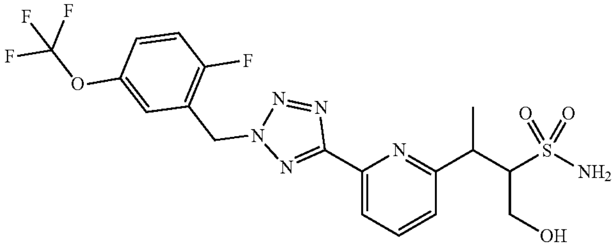 [SMILES: CC(c1cccc(-c2nnn(Cc3cc(OC(F)(F)F)ccc3F)n2)n1)C(CO)S(N)(=O)=O] | 1.3 | 6.7 | ND |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 34 | 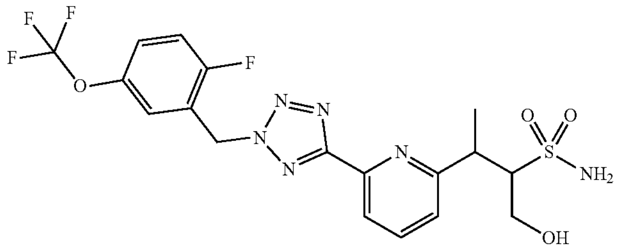 [SMILES: CC(c1cccc(-c2nnn(Cc3cc(OC(F)(F)F)ccc3F)n2)n1)C(CO)S(N)(=O)=O] | 2.2 | >30 | ND |
| 35 | 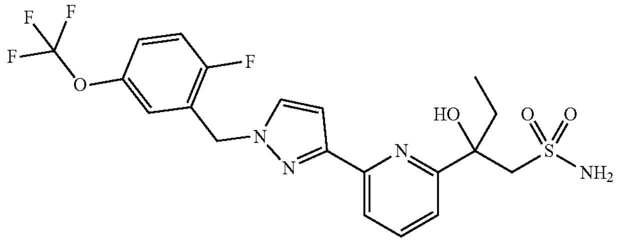 [SMILES: CCC(O)(CS(N)(=O)=O)c1cccc(-c2ccn(Cc3cc(OC(F)(F)F)ccc3F)n2)n1] | 4.0 | ND | ND |
| 36 | 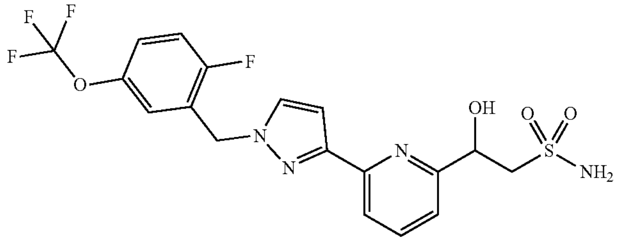 [SMILES: NS(=O)(=O)CC(O)c1cccc(-c2ccn(Cc3cc(OC(F)(F)F)ccc3F)n2)n1] | 3.7 (n = 3) | ND | >30 |
| Rac-37 + 38 | 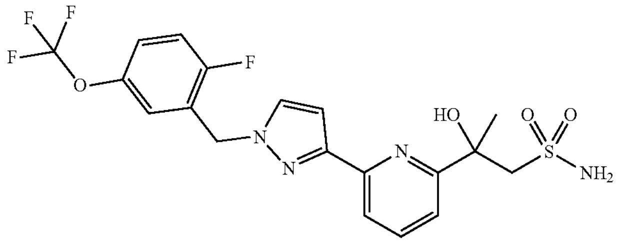 [SMILES: CC(O)(CS(N)(=O)=O)c1cccc(-c2ccn(Cc3cc(OC(F)(F)F)ccc3F)n2)n1] | 2.3 | ND | >30 |
| 37 | 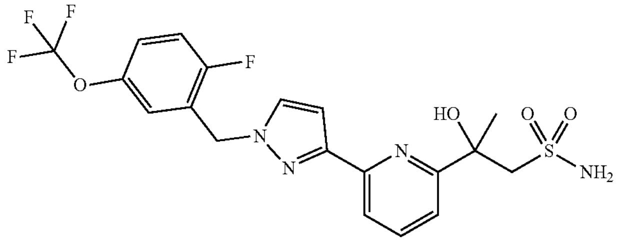 [SMILES: CC(O)(CS(N)(=O)=O)c1cccc(-c2ccn(Cc3cc(OC(F)(F)F)ccc3F)n2)n1] | 1.3 | ND | 14 |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 38 | 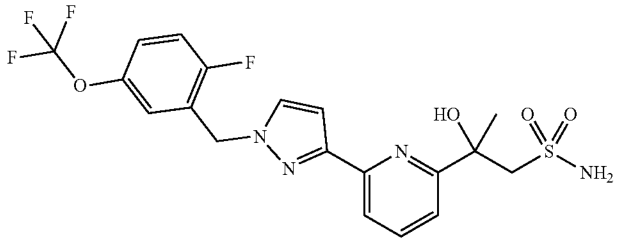 [SMILES: CC(O)(CS(N)(=O)=O)c1cccc(-c2ccn(Cc3cc(OC(F)(F)F)ccc3F)n2)n1] | 4.3 | ND | >30 |
| 39 | 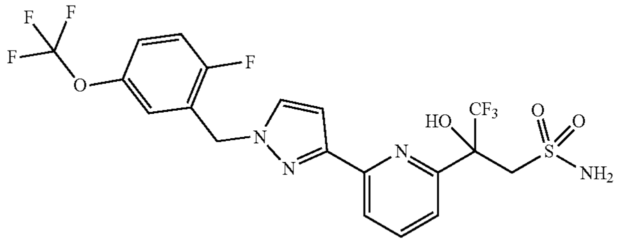 [SMILES: NS(=O)(=O)CC(O)(c1cccc(-c2ccn(Cc3cc(OC(F)(F)F)ccc3F)n2)n1)C(F)(F)F] | 4.4 (n = 3) | ND | >30 |
| 40 | 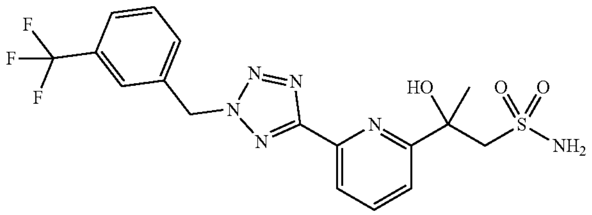 [SMILES: CC(O)(CS(N)(=O)=O)c1cccc(-c2nnn(Cc3cccc(C(F)(F)F)c3)n2)n1] | 21 | >30 | ND |
| 41 | 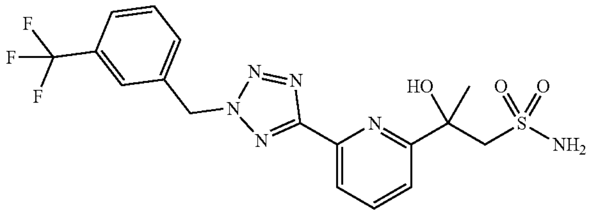 [SMILES: CC(O)(CS(N)(=O)=O)c1cccc(-c2nnn(Cc3cccc(C(F)(F)F)c3)n2)n1] | >30 | >30 | ND |
| 42 | 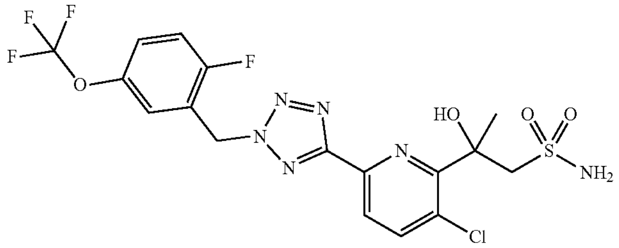 [SMILES: CC(O)(CS(N)(=O)=O)c1nc(-c2nnn(Cc3cc(OC(F)(F)F)ccc3F)n2)ccc1Cl] | 12 | ND | ND |
| 43 | 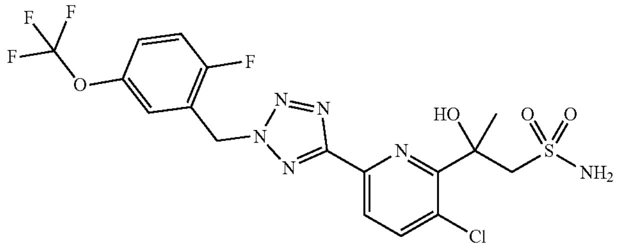 [SMILES: CC(O)(CS(N)(=O)=O)c1nc(-c2nnn(Cc3cc(OC(F)(F)F)ccc3F)n2)ccc1Cl] | 8.2 (n = 2) | ND | ND |

TABLE 5-continued
| Representative data for Nav1.5 blockade | | | | |
|---|---|---|---|---|
| Example | Structure | Nav1.5 $IC_{50}$ (5 Hz, AF Rate) (µM) | Nav1.5 $IC_{50}$ (1 Hz, Sinus Rate) (µM ) | Nav1.5 $IC_{50}$ (1 Hz, ATXII) (µM) |
| 44 | 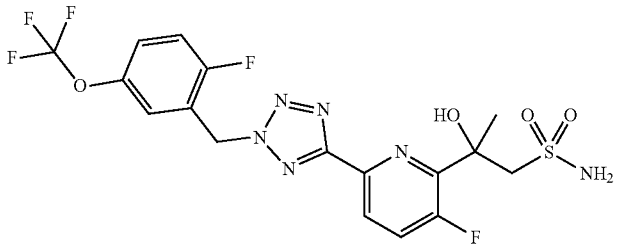 [SMILES: CC(O)(CS(N)(=O)=O)c1nc(-c2nnn(Cc3cc(OC(F)(F)F)ccc3F)n2)ccc1F] | 4.6 | >30 | 19 |
| 45 | 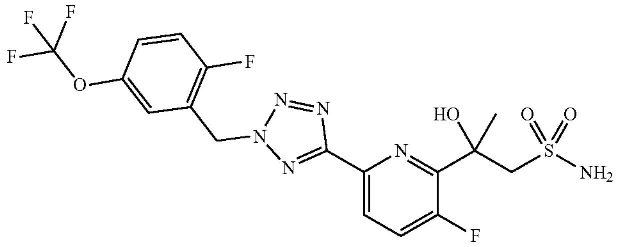 [SMILES: CC(O)(CS(N)(=O)=O)c1nc(-c2nnn(Cc3cc(OC(F)(F)F)ccc3F)n2)ccc1F] | 4.8 | >30 | >30 |
| 46 | 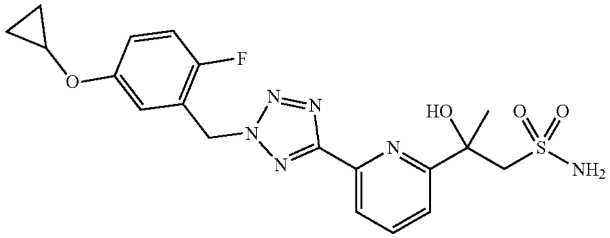 [SMILES: CC(O)(CS(N)(=O)=O)c1cccc(-c2nnn(Cc3cc(OC4CC4)ccc3F)n2)n1] | 8.3 | >30 | >30 |
| 47 | 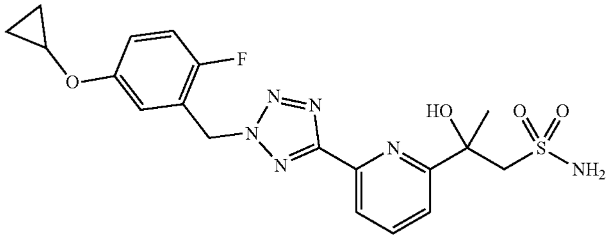 [SMILES: CC(O)(CS(N)(=O)=O)c1cccc(-c2nnn(Cc3cc(OC4CC4)ccc3F)n2)n1] | 3.9 | 27 | 13 |
| 48 | 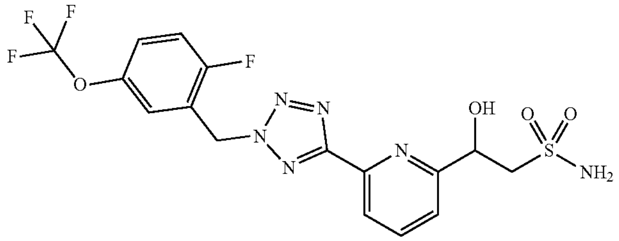 [SMILES: NS(=O)(=O)CC(O)c1cccc(-c2nnn(Cc3cc(OC(F)(F)F)ccc3F)n2)n1] | 5.5 | ND | ND |

TABLE 5-continued
| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 49 | 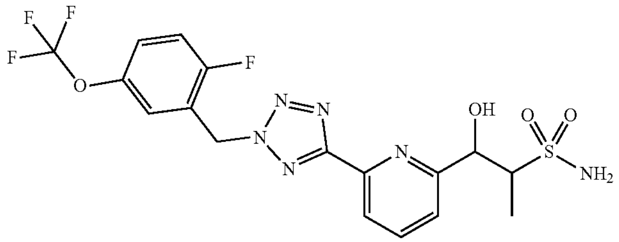 [SMILES: CC(C(O)c1cccc(-c2nnn(Cc3cc(OC(F)(F)F)ccc3F)n2)n1)S(N)(=O)=O] | 5.7 | ND | ND |
| 50 | 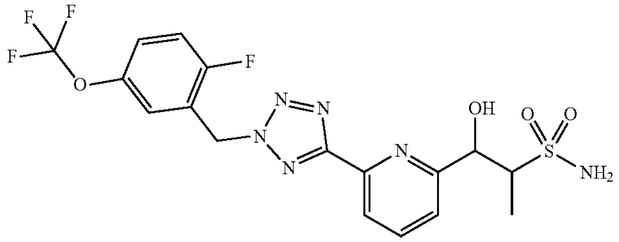 [SMILES: CC(C(O)c1cccc(-c2nnn(Cc3cc(OC(F)(F)F)ccc3F)n2)n1)S(N)(=O)=O] | 6.6 | ND | ND |
| 51 | 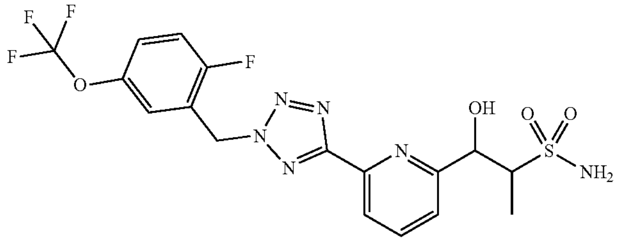 [SMILES: CC(C(O)c1cccc(-c2nnn(Cc3cc(OC(F)(F)F)ccc3F)n2)n1)S(N)(=O)=O] | 25 (n = 2) | >30 | ND |
| 52 | 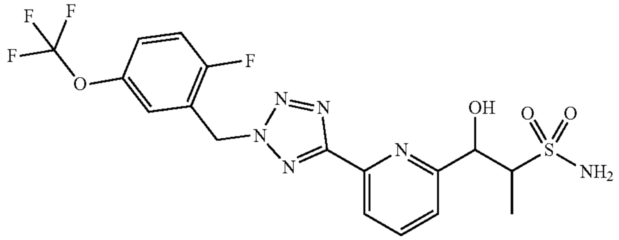 [SMILES: CC(C(O)c1cccc(-c2nnn(Cc3cc(OC(F)(F)F)ccc3F)n2)n1)S(N)(=O)=O] | 2.9 (n = 4) | 49 (n = 3) | 22 (n = 4) |
| 53 | 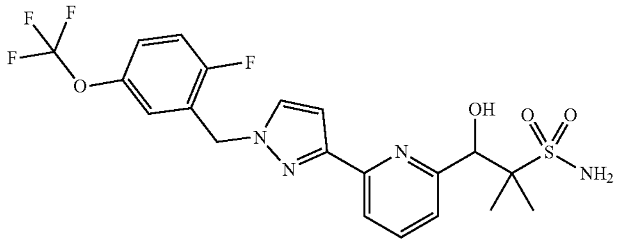 [SMILES: CC(C)(C(O)c1cccc(-c2ccn(Cc3cc(OC(F)(F)F)ccc3F)n2)n1)S(N)(=O)=O] | 12 | ND | ND |
| 54 | 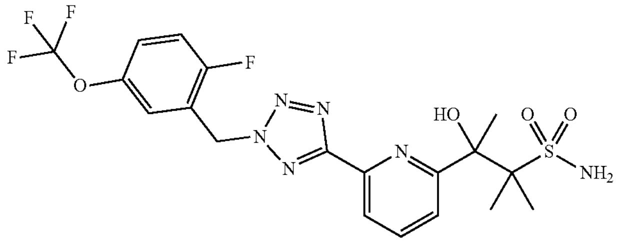 [SMILES: CC(O)(c1cccc(-c2nnn(Cc3cc(OC(F)(F)F)ccc3F)n2)n1)C(C)(C)S(N)(=O)=O] | 4.2 | ND | ND |

TABLE 5-continued
Representative data for Nav1.5 blockade
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
|---|---|---|---|---|
| Rac-55 + 56 | 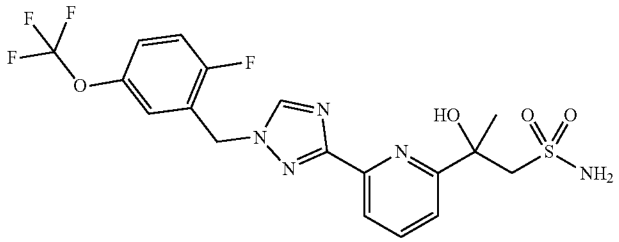 [SMILES: CC(O)(CS(N)(=O)=O)c1cccc(-c2ncn(Cc3cc(OC(F)(F)F)ccc3F)n2)n1] | 4.5 (n = 4) | >30 | 17 |
| 55 | 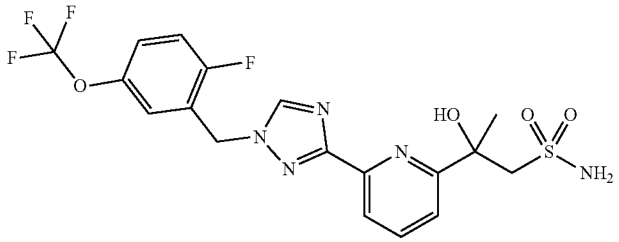 [SMILES: CC(O)(CS(N)(=O)=O)c1cccc(-c2ncn(Cc3cc(OC(F)(F)F)ccc3F)n2)n1] | 19 (n = 3) | >30 (n = 2) | ND |
| 56 | 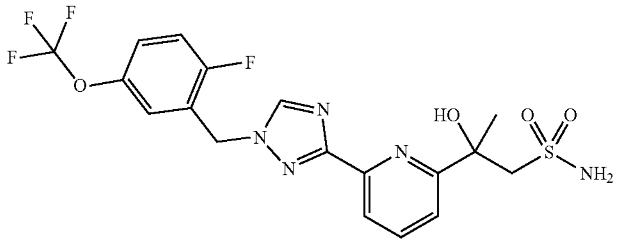 [SMILES: CC(O)(CS(N)(=O)=O)c1cccc(-c2ncn(Cc3cc(OC(F)(F)F)ccc3F)n2)n1] | 16 (n = 3) | >30 (n = 2) | ND |
| Rac-57 + 58 | 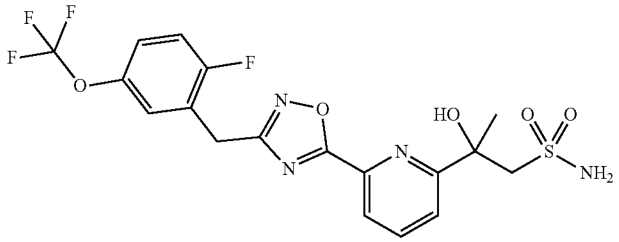 [SMILES: CC(O)(CS(N)(=O)=O)c1cccc(-c2nc(Cc3cc(OC(F)(F)F)ccc3F)no2)n1] | 3.7 | ND | ND |
| 57 | 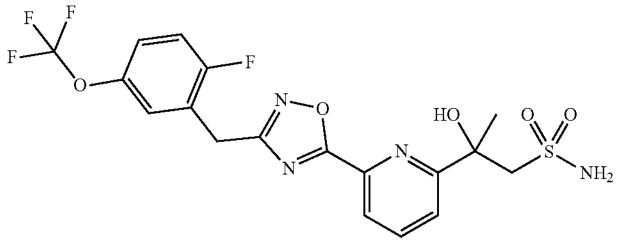 [SMILES: CC(O)(CS(N)(=O)=O)c1cccc(-c2nc(Cc3cc(OC(F)(F)F)ccc3F)no2)n1] | 3.6 (n = 2) | ND | 27 |

TABLE 5-continued
Representative data for Nav1.5 blockade
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
|---|---|---|---|---|
| 58 | 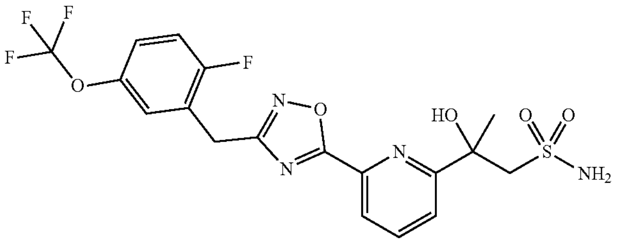 [SMILES: CC(O)(CS(N)(=O)=O)c1cccc(-c2nc(Cc3cc(OC(F)(F)F)ccc3F)no2)n1] | 5.0 (n = 2) | ND | >30 |
| Rac-59 + 60 | 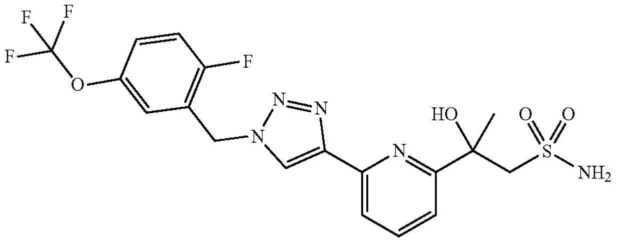 [SMILES: CC(O)(CS(N)(=O)=O)c1cccc(-c2cn(Cc3cc(OC(F)(F)F)ccc3F)nn2)n1] | 5.2 (n = 3) | ND | 15 |
| 59 | 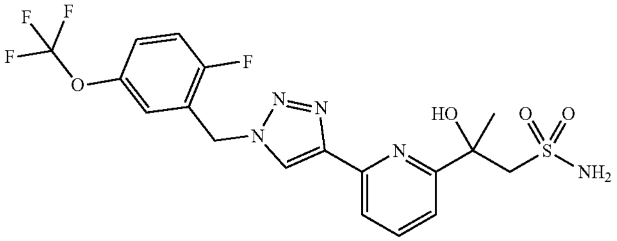 [SMILES: CC(O)(CS(N)(=O)=O)c1cccc(-c2cn(Cc3cc(OC(F)(F)F)ccc3F)nn2)n1] | 3.4 (n = 2) | ND | 8.6 |
| 60 | 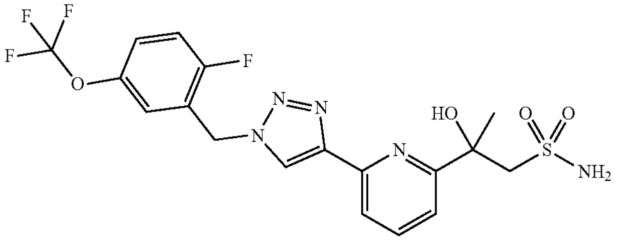 [SMILES: CC(O)(CS(N)(=O)=O)c1cccc(-c2cn(Cc3cc(OC(F)(F)F)ccc3F)nn2)n1] | 7.0 | ND | 16 |
| Rac-61 + 62 | 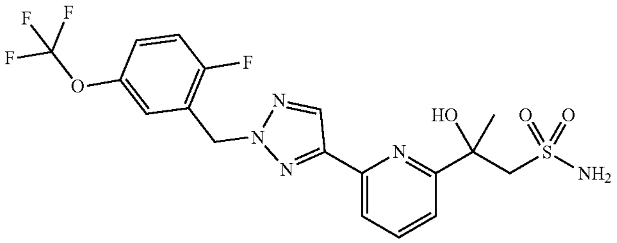 [SMILES: CC(O)(CS(N)(=O)=O)c1cccc(-c2cnn(Cc3cc(OC(F)(F)F)ccc3F)n2)n1] | 3.4 (n = 3) | ND | >30 |
| 61 | 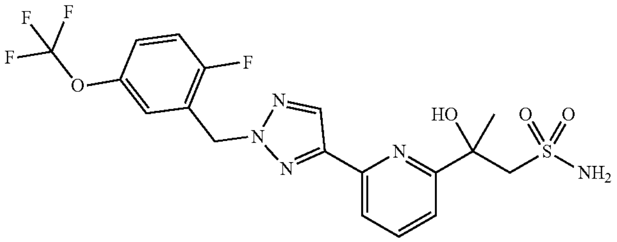 [SMILES: CC(O)(CS(N)(=O)=O)c1cccc(-c2cnn(Cc3cc(OC(F)(F)F)ccc3F)n2)n1] | 5.0 | ND | >30 |

TABLE 5-continued

| Representative data for Nav1.5 blockade | | | | |
|---|---|---|---|---|
| Example | Structure | Nav1.5 $IC_{50}$ (5 Hz, AF Rate) (μM) | Nav1.5 $IC_{50}$ (1 Hz, Sinus Rate) (μM ) | Nav1.5 $IC_{50}$ (1 Hz, ATXII) (μM) |
| 62 | 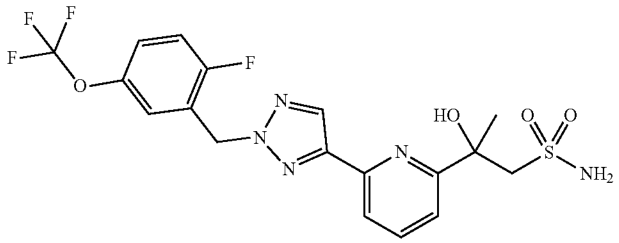 [SMILES: CC(O)(CS(N)(=O)=O)c1cccc(-c2cnn(Cc3cc(OC(F)(F)F)ccc3F)n2)n1] | 3.4 (n = 2) | ND | ND |

$IC_{50}$ data are reported as an average when multiple tests were undertaken (number of data points is expressed by "n" in parentheses). If not specified, n = 1.
ND = Not determined.

TABLE 6

Compounds from Examples 63 to 90 and Nav1.5 blockade results
Additional Compounds of Formula (I), Examples 63-90, were tested as described above and Nav1.5 blockade results are shown in Table 6.

| Example | Structure | MS | Nav1.5 $IC_{50}$ (5 Hz, AF Rate) (μM) |
|---|---|---|---|
| 63 | 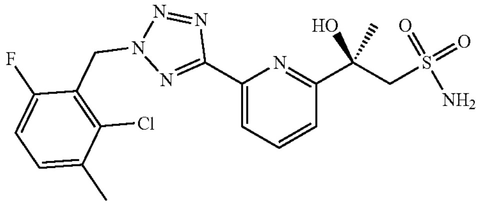 [SMILES: Cc1ccc(F)c(Cn2nnc(-c3cccc([C@@](C)(O)CS(N)(=O)=O)n3)n2)c1Cl] | m/z: $[M + Na]^+$ 463.1 | 3.80 |
| 64 | 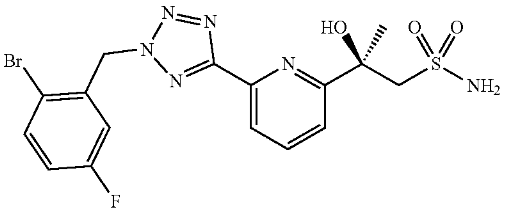 [SMILES: C[C@](O)(CS(N)(=O)=O)c1cccc(-c2nnn(Cc3cc(F)ccc3Br)n2)n1] | m/z: $[M + H]^+$ 473.3 | 13.00 |
| 65 | 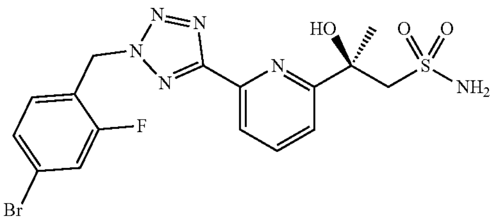 [SMILES: C[C@](O)(CS(N)(=O)=O)c1cccc(-c2nnn(Cc3ccc(Br)cc3F)n2)n1] | m/z: $[M + H]^+$ 473.2 | 17.00 |
| 66 | 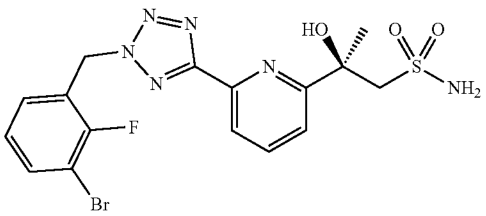 [SMILES: C[C@](O)(CS(N)(=O)=O)c1cccc(-c2nnn(Cc3cccc(Br)c3F)n2)n1] | m/z: $[M + H]^+$ 473.1 | 28.00 |

TABLE 6-continued
Compounds from Examples 63 to 90 and Nav1.5 blockade results
Additional Compounds of Formula (I), Examples 63-90, were tested as described above and Nav1.5 blockade results are shown in Table 6.
| Example | Structure | MS | Nav1.5 $IC_{50}$ (5 Hz, AF Rate) (μM) |
|---|---|---|---|
| 67 | 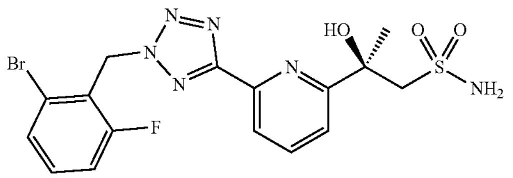 [SMILES: C[C@](O)(CS(N)(=O)=O)c1cccc(-c2nnn(Cc3c(F)cccc3Br)n2)n1] | m/z: $[M + H]^+$ 473.2 | 8.10 |
| 68 | 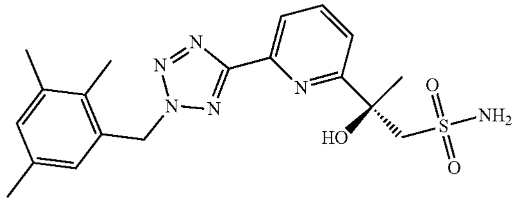 [SMILES: Cc1cc(C)c(C)c(Cn2nnc(-c3cccc([C@@](C)(O)CS(N)(=O)=O)n3)n2)c1] | m/z: $[M + H]^+$ 417.2 | 16.00 |
| 69 | 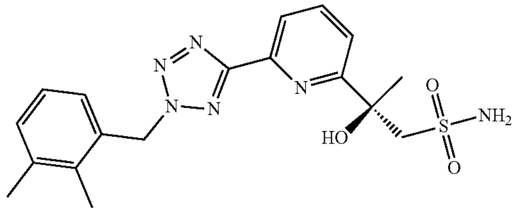 [SMILES: Cc1cccc(Cn2nnc(-c3cccc([C@@](C)(O)CS(N)(=O)=O)n3)n2)c1C] | m/z: $[M + H]^+$ 403.2 | 11.00 |
| 70 | 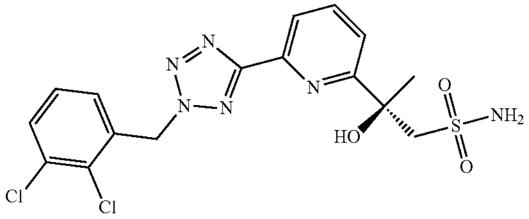 [SMILES: C[C@](O)(CS(N)(=O)=O)c1cccc(-c2nnn(Cc3cccc(Cl)c3Cl)n2)n1] | m/z: $[M + H]^+$ 443.0 | 22.00 |
| 71 | 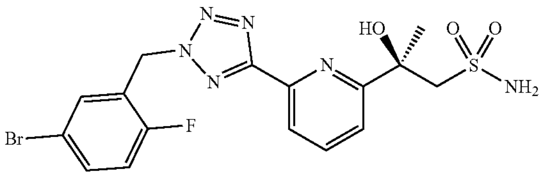 [SMILES: C[C@](O)(CS(N)(=O)=O)c1cccc(-c2nnn(Cc3cc(Br)ccc3F)n2)n1] | m/z: $[M + H]^+$ 473.1 | — |
| 72 | 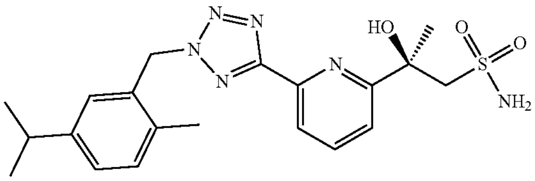 [SMILES: Cc1ccc(C(C)C)cc1Cn1nnc(-c2cccc([C@@](C)(O)CS(N)(=O)=O)n2)n1] | m/z: $[M + H]^+$ 431.4 | 7.30 |

TABLE 6-continued
Compounds from Examples 63 to 90 and Nav1.5 blockade results
Additional Compounds of Formula (I), Examples 63-90, were tested as described above and Nav1.5 blockade results are shown in Table 6.
| Example | Structure | MS | Nav1.5 $IC_{50}$ (5 Hz, AF Rate) (μM) |
|---|---|---|---|
| 73 | 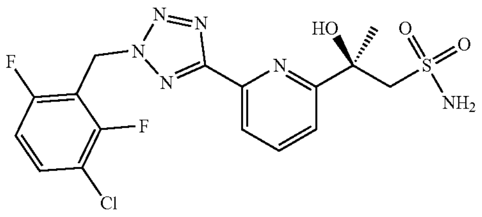 [SMILES: C[C@](O)(CS(N)(=O)=O)c1cccc(-c2nnn(Cc3c(F)ccc(Cl)c3F)n2)n1] | m/z: $[M + Na]^+$ 466.9 | 19.00 |
| 74 | 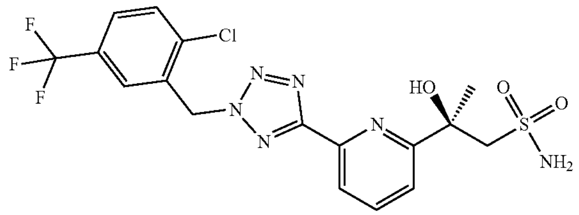 [SMILES: C[C@](O)(CS(N)(=O)=O)c1cccc(-c2nnn(Cc3cc(C(F)(F)F)ccc3Cl)n2)n1] | m/z: $[M + Na]^+$ 499.3 | 21.00 |
| 75 | 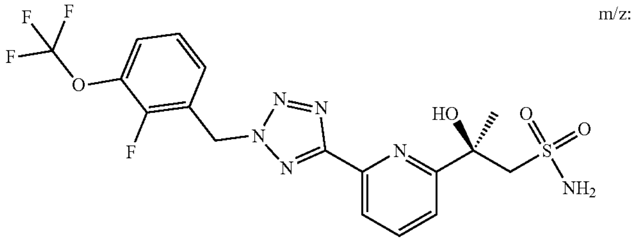 | m/z: $[M + H]^+$ 477.3 | 4.80 |
| 76 | 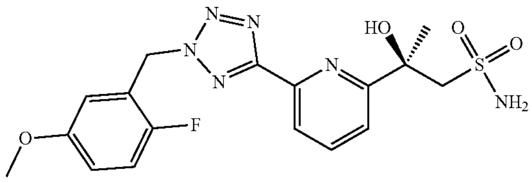 [SMILES: COc1ccc(F)c(Cn2nnc(-c3cccc([C@@](C)(O)CS(N)(=O)=O)n3)n2)c1] | m/z: $[M + Na]^+$ 445.1 | 17.00 |
| 77 | 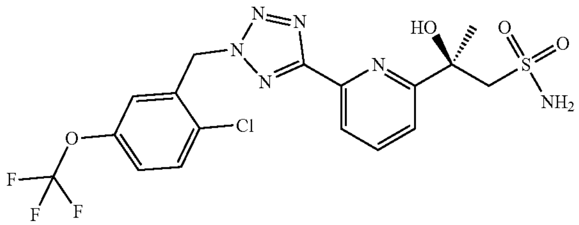 [SMILES: C[C@](O)(CS(N)(=O)=O)c1cccc(-c2nnn(Cc3cc(OC(F)(F)F)ccc3Cl)n2)n1] | m/z: $[M + H]^+$ 493.3 | 13.00 |
| 78 | 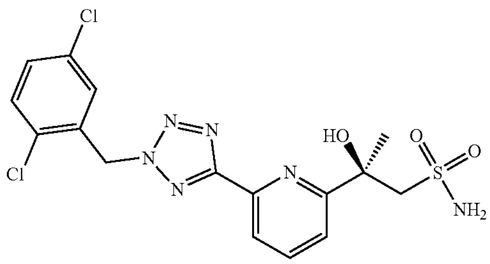 [SMILES: C[C@](O)(CS(N)(=O)=O)c1cccc(-c2nnn(Cc3cc(Cl)ccc3Cl)n2)n1] | m/z: $[M + Na]^+$ 465.0 | 10.00 |

TABLE 6-continued
| Compounds from Examples 63 to 90 and Nav1.5 blockade results Additional Compounds of Formula (I), Examples 63-90, were tested as described above and Nav1.5 blockade results are shown in Table 6. | | | |
|---|---|---|---|
| Example | Structure | MS | Nav1.5 $IC_{50}$ (5 Hz, AF Rate) (μM) |
| 79 | 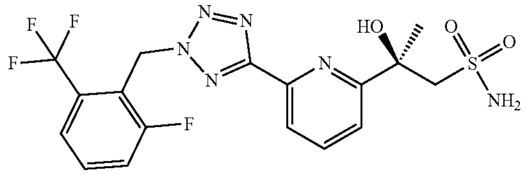 [SMILES: C[C@](O)(CS(N)(=O)=O)c1cccc(-c2nnn(Cc3c(F)cccc3C(F)(F)F)n2)n1] | m/z: $[M + Na]^+$ 483.2 | 13.00 |
| 80 | 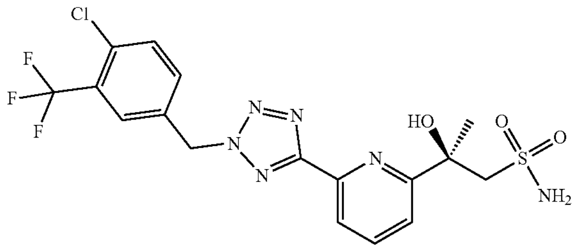 [SMILES: C[C@](O)(CS(N)(=O)=O)c1cccc(-c2nnn(Cc3ccc(Cl)c(C(F)(F)F)c3)n2)n1] | m/z: $[M + Na]^+$ 499.2 | 14.00 |
| 81 | 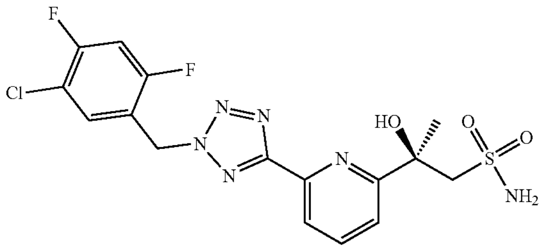 [SMILES: C[C@](O)(CS(N)(=O)=O)c1cccc(-c2nnn(Cc3cc(Cl)c(F)cc3F)n2)n1] | m/z: $[M + Na]^+$ 467.0 | 21.00 |
| 82 | 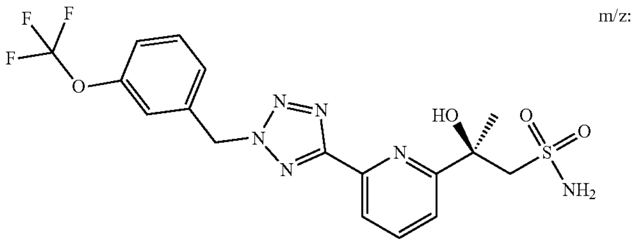 | m/z: $[M + H]^+$ 459.3 | 7.30 |
| 83 | 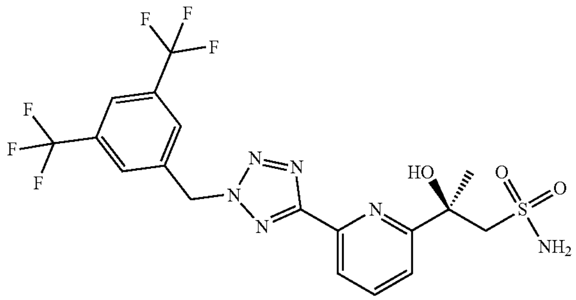 [SMILES: C[C@](O)(CS(N)(=O)=O)c1cccc(-c2nnn(Cc3cc(C(F)(F)F)cc(C(F)(F)F)c3)n2)n1] | m/z: $[M + H]^+$ 511.2 | 18.00 |

TABLE 6-continued
Compounds from Examples 63 to 90 and Nav1.5 blockade results
Additional Compounds of Formula (I), Examples 63-90, were tested as described above and Nav1.5 blockade results are shown in Table 6.
| Example | Structure | MS | Nav1.5 $IC_{50}$ (5 Hz, AF Rate) (μM) |
|---|---|---|---|
| 84 | 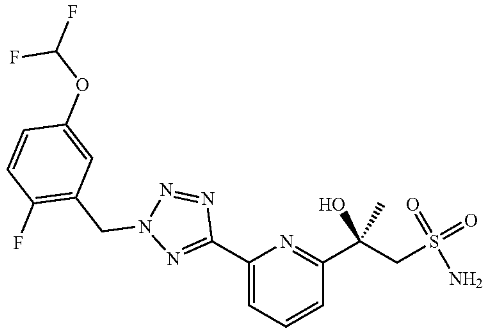 [SMILES: C[C@](O)(CS(N)(=O)=O)c1cccc(-c2nnn(Cc3cc(OC(F)F)ccc3F)n2)n1] | m/z: $[M + H]^+$ 459.3 | 14.00 |
| 85 | 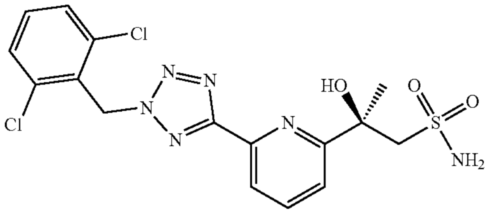 [SMILES: C[C@](O)(CS(N)(=O)=O)c1cccc(-c2nnn(Cc3c(Cl)cccc3Cl)n2)n1] | m/z: $[M + H]^+$ 443.2 | 5.20 |
| 86 | 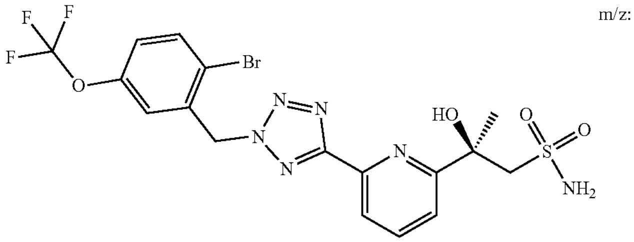 | m/z: $[M + H]^+$ 539.1 | 6.30 |
| 87 | 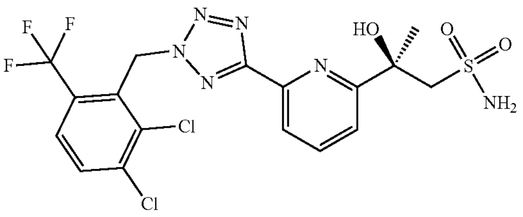 [SMILES: C[C@](O)(CS(N)(=O)=O)c1cccc(-c2nnn(Cc3c(C(F)(F)F)ccc(Cl)c3Cl)n2)n1] | m/z: $[M + H]^+$ 511.3 | 9.30 |
| 88 | 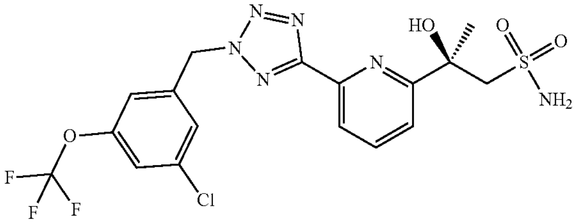 [SMILES: C[C@](O)(CS(N)(=O)=O)c1cccc(-c2nnn(Cc3cc(Cl)cc(OC(F)(F)F)c3)n2)n1] | m/z: $[M + H]^+$ 493.3 | 28.00 |

TABLE 6-continued

Compounds from Examples 63 to 90 and Nav1.5 blockade results
Additional Compounds of Formula (I), Examples 63-90, were tested as described above and Nav1.5 blockade results are shown in Table 6.

| Example | Structure | MS | Nav1.5 $IC_{50}$ (5 Hz, AF Rate) (μM) |
|---|---|---|---|
| 89 | 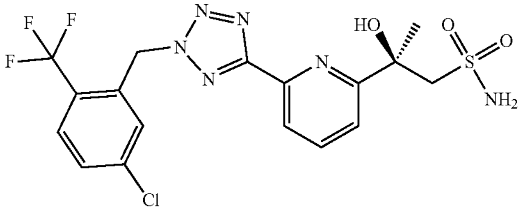 [SMILES: C[C@](O)(CS(N)(=O)=O)c1cccc(-c2nnn(Cc3cc(Cl)ccc3C(F)(F)F)n2)n1] | m/z: $[M + H]^+$ 477.3 | 27.00 |
| 90 | 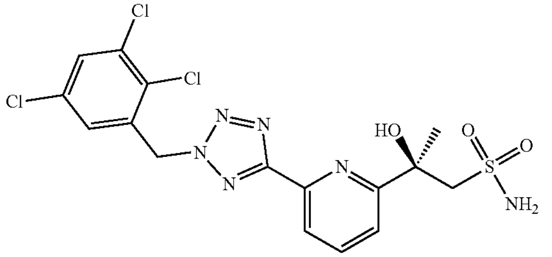 [SMILES: C[C@](O)(CS(N)(=O)=O)c1cccc(-c2nnn(Cc3cc(Cl)cc(Cl)c3Cl)n2)n1] | m/z: $[M + H]^+$ 479.1 | 8.90 |

*Some MS data reported in Table 6 were produced by different LCMS instruments and methods from Method 1-9, and HRMS method-10.

The invention claimed is:

1. A compound of formula (I):

(I)

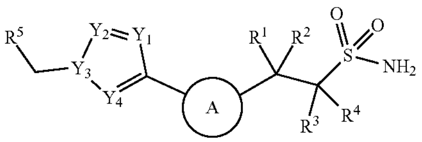

or a pharmaceutically acceptable salt thereof, wherein ring A is:

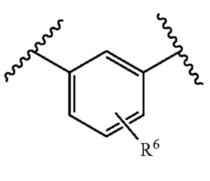

;

$R^1$ is selected from —OH and $C_{1-4}$-alkyl;

$R^2$ is selected from H and $C_{1-4}$-alkyl optionally substituted with one or more halogen atoms;

$R^3$ is selected from H and $C_{1-4}$-alkyl;

$R^4$ is selected from H and $C_{1-4}$-alkyl optionally substituted with —OH;

$R^5$ is phenyl substituted with (i) at least one group selected from halogen, $C_{1-4}$-alkyl, —O—$C_{1-4}$-alkyl, and O—$C_{3-6}$-cycloalkyl, wherein the $C_{1-4}$-alkyl is optionally substituted with one or more halogen atoms, or (ii) two adjacent groups bonded together to form a 4- to 7-membered heterocyclyl containing two or more heteroatoms selected from O, S and N, wherein the 4- to 7-membered heterocyclyl is optionally substituted with one or more halogen atoms;

$R^6$ is H or a halogen atom;

$Y_1$ is selected from CH, N and O;

$Y_2$ is CH or N;

$Y_3$ is CH or N; and $Y_4$ is CH or N, wherein at least one of $Y_1$, $Y_2$, $Y_3$ and $Y_4$ is N.

2. The compound according to claim 1, wherein $R^1$ is —OH or —$CH_3$;

$R^2$ is selected from H, —$CH_3$, —$CH_2CH_3$ and —$CF_3$;

$R^3$ is H or —$CH_3$;

$R^4$ is selected from H, —$CH_3$ and —$CH_2OH$;

$R^5$ is phenyl substituted with (i) at least one group selected from F, Cl, —$CF_3$, —$OCF_3$, —$OCH_2CF_3$, and —O-cyclopropyl, or (ii) two adjacent groups bonded together to form

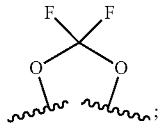 [SMILES: *OC(F)(F)O*]

;

and $R^6$ is selected from H, F and Cl.

3. The compound according to claim 1, or a pharmaceutically acceptable salt thereof, wherein $R^6$ is H.

4. The compound according to claim 1, said compound being of formula (II-B):

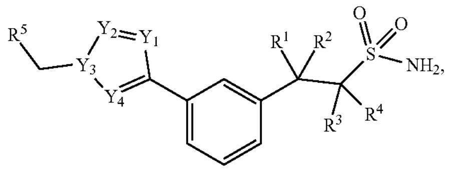

or a pharmaceutically acceptable salt thereof.

5. The compound according to claim 1, or a pharmaceutically acceptable salt thereof, wherein each of $Y_1$, $Y_2$, $Y_3$ and $Y_4$ are N; or $Y_2$ is CH and each of $Y_1$, $Y_3$ and $Y_4$ are N; or each of $Y_1$ and $Y_2$ are CH and each of $Y_3$ and $Y_4$ are N.

6. The compound according to claim 1, said compound being of formula (III-B):

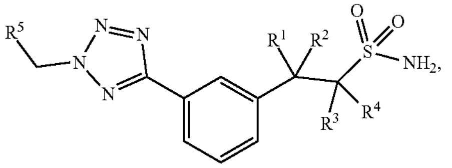

or a pharmaceutically acceptable salt thereof.

7. The compound according to claim 1, or a pharmaceutically acceptable salt thereof, wherein $R^3$ is H and $R^4$ is H.

8. The compound according to claim 1, or a pharmaceutically acceptable salt thereof, wherein $R^1$ is —OH.

9. The compound according to claim 1, or a pharmaceutically acceptable salt thereof, wherein $R^2$ is selected from H, $—CH_3$ and $—CH_2CH_3$.

10. The compound according to claim 1, or a pharmaceutically acceptable salt thereof, wherein $R^1$ is —OH and $R^2$ is $—CH_3$.

11. The compound according to claim 1, or a pharmaceutically acceptable salt thereof, wherein $R^5$ is phenyl substituted with at least two groups selected from F, Cl, $—CF_3$, $—OCF_3$ and $—OCH_2CF_3$.

12. The compound according to claim 1, or a pharmaceutically acceptable salt thereof, wherein $R^5$ is:

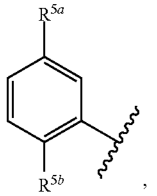

wherein, $R^{5a}$ and $R^{5b}$ are independently selected from F, Cl, $—CF_3$, $—OCF_3$ and $—OCH_2CF_3$.

13. The compound according to claim 1, or a pharmaceutically acceptable salt thereof, wherein $R^5$ is:

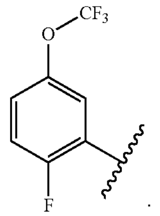 [SMILES: *c1cc(OC(F)(F)F)ccc1F]

14. The compound according to claim 1, said compound being of formula (IV-B):

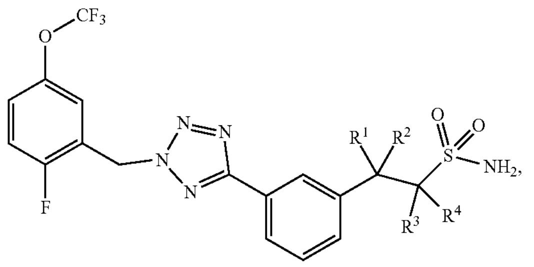

or a pharmaceutically acceptable salt thereof.

15. The compound of formula (I) according to claim 1, or a pharmaceutically acceptable salt thereof, wherein the compound is selected from the group consisting of:

2-(2-fluoro-5-(2-(2-fluoro-5-(trifluoromethoxy)benzyl)-2H-tetrazol-5-yl)phenyl)-2-hydroxypropane-1-sulfonamide;

2-(4-chloro-3-(2-(2-fluoro-5-(trifluoromethoxy)benzyl)-2H-tetrazol-5-yl)phenyl)-2-hydroxypropane-1-sulfonamide;

2-(4-fluoro-3-(2-(2-fluoro-5-(trifluoromethoxy)benzyl)-2H-tetrazol-5-yl)phenyl)-2-hydroxypropane-1-sulfonamide;

2-(2-fluoro-3-(2-(2-fluoro-5-(trifluoromethoxy)benzyl)-2H-tetrazol-5-yl)phenyl)-2-hydroxypropane-1-sulfonamide;

2-(3-fluoro-5-(2-(2-fluoro-5-(trifluoromethoxy)benzyl)-2H-tetrazol-5-yl)phenyl)-2-hydroxypropane-1-sulfonamide; and 2-(3-(2-(2-fluro-5-(trifluoromethoxy)benzyl)-2H-tetrazol-5-yl)phenyl)-2-hydroxypropane-1-sulfonamide.

16. A pharmaceutical composition comprising the compound according to claim 1, or a pharmaceutically acceptable salt thereof, and one or more pharmaceutically acceptable carriers.

17. A combination comprising of the compound according to claim 1, or a pharmaceutically acceptable salt thereof, and one or more therapeutically active agents.

18. A method of modulating Nav1.5 activity in a subject, wherein the method comprises administering to the subject a therapeutically effective amount of the compound according to claim 1, or a pharmaceutically acceptable salt thereof.

19. A method of treating a disease, disorder, or condition selected from a long QT syndrome LQTS1, LQTS2, LQTS3, LQTS4, LQTS5, LQTS6, LQTS7, LQTS8, LQTS9, LQTS10, LQTS11, LQTS12, LQTS13, LQTS14, or LQTS15, atrial fibrillation, ventricular fibrillation, ventricular tachycardia, LQT-associated ventricular arrhythmias, hypertrophic cardiomyopathy, angina, heart failure, peripheral pain, and myotonia, wherein the method comprises administering to the subject a therapeutically effective amount of the compound according to claim 1, or a pharmaceutically acceptable salt thereof.

* * * * *